(12) United States Patent
Rikimaru et al.

(10) Patent No.: US 8,410,089 B2
(45) Date of Patent: Apr. 2, 2013

(54) FUSED HETEROCYCLIC RING COMPOUND

(75) Inventors: Kentaro Rikimaru, Osaka (JP); Hiroshi Imoto, Osaka (JP); Masahiro Kamaura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 42 days.

(21) Appl. No.: 13/201,536

(22) PCT Filed: Feb. 17, 2010

(86) PCT No.: PCT/JP2010/052374
§ 371 (c)(1),
(2), (4) Date: Aug. 15, 2011

(87) PCT Pub. No.: WO2010/095663
PCT Pub. Date: Aug. 26, 2010

(65) Prior Publication Data
US 2012/0028962 A1    Feb. 2, 2012

Related U.S. Application Data

(60) Provisional application No. 61/202,321, filed on Feb. 18, 2009.

(51) Int. Cl.
*A01N 43/00* (2006.01)
*A61K 31/55* (2006.01)

(52) U.S. Cl. .......... 514/217.06; 544/280; 544/296; 544/324; 546/199; 514/265.1; 514/322; 514/269; 514/256

(58) Field of Classification Search .......... 514/217.06, 514/265.1, 322, 269, 256; 544/280, 296, 544/324; 546/199
See application file for complete search history.

(56) References Cited

U.S. PATENT DOCUMENTS

| | | | |
|---|---|---|---|
| 8,232,287 B2 * | 7/2012 | Kaneko et al. ............ 514/269 |
| 2005/0059650 A1 | 3/2005 | Jones et al. |
| 2005/0070562 A1 | 3/2005 | Jones et al. |
| 2006/0142262 A1 | 6/2006 | Jones et al. |
| 2006/0155128 A1 | 7/2006 | Jones et al. |
| 2006/0161001 A1 | 7/2006 | Hong et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0155763 A1 | 7/2007 | Jones et al. |
| 2007/0167473 A1 | 7/2007 | Jones et al. |
| 2008/0293690 A1 | 11/2008 | Fevig et al. |
| 2009/0018055 A1 | 1/2009 | Fevig et al. |
| 2009/0036434 A1 | 2/2009 | Jones et al. |
| 2009/0286812 A1 | 11/2009 | Erickson et al. |
| 2009/0286816 A1 | 11/2009 | Jones et al. |
| 2009/0318477 A1 | 12/2009 | Katamreddy |
| 2010/0004272 A1 | 1/2010 | Jones et al. |
| 2010/0093761 A1 | 4/2010 | Jones et al. |
| 2010/0160359 A1 | 6/2010 | Jones et al. |
| 2010/0292259 A1 | 11/2010 | Kaneko et al. |
| 2011/0059942 A1 | 3/2011 | Fyfe et al. |
| 2011/0112060 A1 | 5/2011 | Jones et al. |
| 2011/0136783 A1 | 6/2011 | Fevig et al. |

FOREIGN PATENT DOCUMENTS

| | | |
|---|---|---|
| WO | 2005/007647 | 1/2005 |
| WO | 2005/007658 | 1/2005 |
| WO | 2005/121121 | 12/2005 |
| WO | 2006/038001 | 4/2006 |
| WO | 2006/069258 | 6/2006 |
| WO | 2006/083491 | 8/2006 |
| WO | 2007/035355 | 3/2007 |
| WO | 2008/005569 | 1/2008 |
| WO | 2008/005576 | 1/2008 |
| WO | 2008/008895 | 1/2008 |
| WO | 2008/137435 | 11/2008 |
| WO | 2008/137436 | 11/2008 |
| WO | 2009/050522 | 4/2009 |
| WO | 2009/051119 | 4/2009 |
| WO | 2009/106565 | 9/2009 |
| WO | 2009/141238 | 11/2009 |
| WO | 2011/055770 | 5/2011 |

OTHER PUBLICATIONS

English translation of International Preliminary Report on Patentability and Written Opinion dated Sep. 13, 2011.
International Search Report issued Mar. 16, 2010 in International (PCT) Application No. PCT/JP2010/052374.
Supplementary European Search Report dated Jul. 27, 2012 in EP Application No. 10743789.9.
Search Results CAS Nos. 888878-65-7; 888132-65-8, 884925-24-0; 884921-27-1; 884913-05-7, 884299-50-7; 883476-76-4 and 883470-09-5, 2006.

* cited by examiner

*Primary Examiner* — James O Wilson
*Assistant Examiner* — Alexander R Pagano
(74) *Attorney, Agent, or Firm* — Wenderoth, Lind & Ponack, L.L.P.

(57) ABSTRACT

A compound represented by the following formula or a salt thereof, which has an GPR119 agonist action, is useful for the prophylaxis or treatment of diabetes, obesity and the like, and shows superior efficacy:

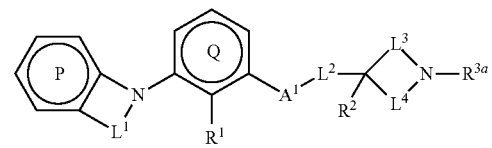

wherein
P: substituted 6-membered aromatic ring,
Q: (substituted) 6-membered aromatic ring,
$A^1$: $CR^{4a}R^{4b}$, $NR^{4c}$, O, S, SO or $SO_2$ {$R^{4a-4c}$: H etc.},
$L^1$: (substituted) $C_{1-5}$ alkylene,
$L^2$: a bond or (substituted) $C_{1-3}$ alkylene,
$L^{3-4}$: (substituted) $C_{1-3}$ alkylene,
$R^1$: H, X, CN, (substituted) hydrocarbon, (substituted) heterocycle or (substituted) OH, or (substituted) 4- to 8-membered (heterocyclic) ring together with $A^1$,
$R^2$: H, CN, (substituted) hydrocarbon, and
$R^{3a}$: $—COSR^{41}$, (substituted) 5- or 6-membered aromatic ring {$R^{41}$: (substituted) hydrocarbon or (substituted) heterocycle}.

14 Claims, No Drawings

FUSED HETEROCYCLIC RING COMPOUND

This application is a U.S. national stage of International Application No. PCT/JP2010/052374 filed Feb. 17, 2010, which claims the benefit of U.S. provisional application Ser. No. 61/202,321 filed Feb. 18, 2009.

TECHNICAL FIELD

The present invention relates to a fused heterocyclic compound having a GPR119 agonist action, which is useful for the prophylaxis or treatment of diabetes, obesity and the like.

BACKGROUND OF THE INVENTION

Diabetes is one of the metabolic diseases characterized by high blood glucose level caused by abnormal glucose metabolism. This disease is largely classified into type 1 diabetes also called insulin dependency diabetes or IDDM, and type 2 diabetes also called non-insulin dependent diabetes or NIDDM. Diabetes not only causes microvascular complications (e.g., diabetic retinopathy, diabetic neuropathy, diabetic nephropathy) but also is a risk factor of macroangiopathy (e.g., arteriosclerosis, cardiovascular disease, myocardial infarction).

GPR119 is a G protein-coupled receptor strongly expressed in pancreatic B cells, and has been reported in recent years to function as a blood glucose sensor that promotes insulin secretion in a blood glucose level-dependent manner (see non-patent document 1). Therefore, GPR119 is drawing attention as a new target molecule for diabetes treatment.

It has also been reported that GPR119 is expressed in human or mouse intestine, and a GPR119 agonist promotes GLP-1 and GIP secretion in mouse (see non-patent document 2), and that a GPR119 agonist promotes PYY or glucagon secretion in mouse (see non-patent document 3).

Accordingly, a compound having a GPR119 agonist action is useful for the prophylaxis or treatment of diabetes, obesity and the like.

In the meantime, the following compounds have been reported.

(1) A compound represented by the formula:

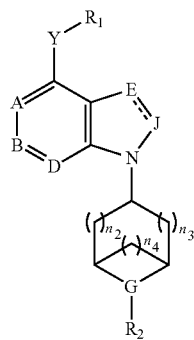

wherein
A, B and D are each independently $CR_{4b}$ or N wherein at least one of A, B and D is N,
E is $CR_9R_9$, $CR_9$, O, N or NH,
G is CH or N,
J is $CR_9R_9$, $CR_9$, CO, CS or N,
Y is $NR_3$, O or S,
$n_2$ and $n_3$ are each independently an integer of 0 to 2,
$n_4$ is an integer of 0 to 3, $R_1$ is optionally substituted aryl or optionally substituted heteroaryl,
$R_2$ is optionally substituted aryl, optionally substituted heteroaryl, $-COR_5$, $-COOR_5$ or the like, and
$R_3$ is a hydrogen atom, alkyl, alkoxy, cycloalkyl, heteroaryl, heterocyclyl or the like
(see patent document 1).

(2) A compound represented by the formula:

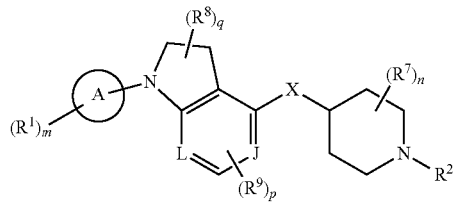

wherein
ring A is aryl or heteroaryl,
m is an integer of 1 to 3,
$R^1$ is acyl, acylsulfonamide, $C_{1-6}$ alkylsulfonyl or the like,
L and J are each independently CH or N,
n is an integer of 0 to 4,
$R^7$ is $C_{1-6}$ alkyl,
q is an integer of 0 to 2,
$R^8$ is $C_{1-6}$ alkyl, amino or the like,
p is an integer of 0 to 2,
$R^9$ is $C_{1-6}$ alkyl, $C_{1-6}$ alkoxy or the like,
X is $NR^4$, O, S, S(O) or S(O)$_2$,
$R^4$ is a hydrogen atom or $C_{1-6}$ alkyl,
$R^2$ is $-Y_t-R^5$,
Y is C(O), C(O)O, C(S), C(S)S, C(S)O or C(O)S,
t is an integer of 0 to 1, and
$R^5$ is a hydrogen atom, optionally substituted acylalkylene, $C_{1-6}$ alkyl or the like
(see patent document 2).

(3) A compound represented by the formula:

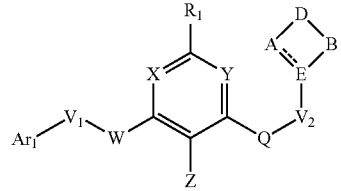

wherein
A and B are each independently an optionally substituted $C_{1-3}$ alkylene,
D is O, S, S(O), S(O)$_2$, $CR_2R_3$ or $NR_2$,
E is N, C or $CR_4$,
$V_1$ is a bond, optionally substituted $C_{1-3}$ alkylene or the like,
$V_2$ is a bond, optionally substituted $C_{3-6}$ cycloalkylene or optionally substituted $C_{1-3}$ alkylene,
W is $NR_5$, O, S, S(O) or S(O)$_2$, or absent,
Q is $NR_6$, O, S, S(O) or S(O)$_2$.
X is N or $CR_7$,
Y is N or $CR_8$,
$Ar_1$ is optionally substituted aryl or optionally substituted heteroaryl, and
$R_2$ is aryl, heteroaryl, carboxy, -G-$R_{22}$ wherein G is $-C(O)-$, $-COO-$ or the like, or the like
(see patent document 3).

(4) A compound represented by the formula:

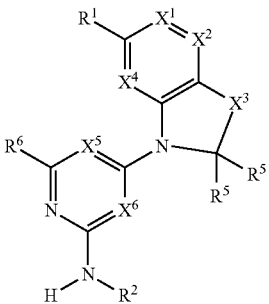

wherein
X¹ is N or CR³,
X² and X⁴ are each independently N or CR⁴,
X⁵ and X⁶ are each independently N or CR⁶,
X³ is

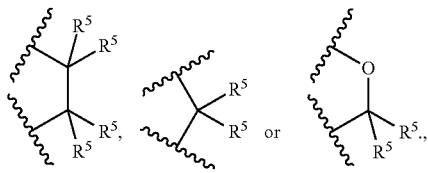

R¹ is optionally substituted 5- to 7-membered ring,
R² is optionally substituted $C_{1-6}$ alkyl, optionally substituted 5- to 7-membered monocycle or optionally substituted 6- to 11-membered bicycle,
R³, R⁴ and R⁵ are each independently a hydrogen atom, a halogen atom, $C_{1-4}$ haloalkyl or the like, and
R⁶ is a hydrogen atom, $C_{1-6}$ alkyl, $C_{1-4}$ haloalkyl or the like
(see patent document 4).

(5) A compound represented by the formula:

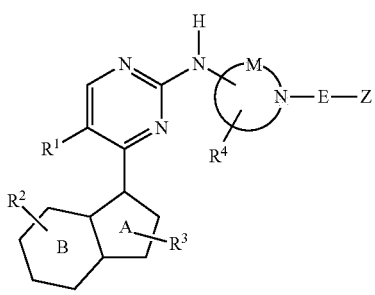

wherein
ring A is pyrrole, pyrazole, imidazole or triazole,
ring B is benzene, pyridine or pyrimidine,
ring M is azetidine, pyrrolidine or piperidine,
E is a bond or optionally substituted $C_{1-4}$ alkylene,
Z is a hydrogen atom, —COR$^a$, —CO₂R$^a$, optionally substituted phenyl, optionally substituted heteroaryl or the like,
R¹ and R² are each independently a hydrogen atom, a halogen atom, cyano, $C_{1-6}$ alkyl or the like,
R³ is a hydrogen atom, $C_{1-6}$ alkyl or the like,
R⁴ is a hydrogen atom, $C_{1-6}$ alkoxy, oxo or the like,
R$^a$ is a hydrogen atom, optionally substituted $C_{1-6}$ alkyl, optionally substituted aryl, optionally substituted heteroaryl or the like
(see patent document 5).

(6) A compound represented by the formula:

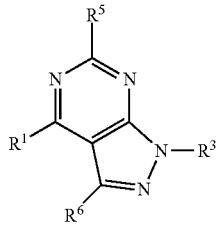

wherein
R¹ is indolin-1-yl mono-substituted by —OR², —NHR² or SO₂CH₃,
R² is aryl optionally substituted by halogen, lower alkyl, alkoxy or the like, monocyclic heteroaryl optionally substituted by halogen, SO₂CH₃, lower alkyl or the like, or the like,
R³ is cyclohexane substituted by oxadiazole substituted by lower alkyl, or piperidine wherein the nitrogen is substituted by R⁴,
R⁴ is benzyl optionally substituted by cyano, alkoxy or the like, —C(O)—O-lower alkyl, or the like,
R⁵ is hydrogen, NH₂, alkoxy, halogen or lower alkyl, and
R⁶ is hydrogen or lower alkyl
(see patent document 6).

(7) A compound represented by the formula:

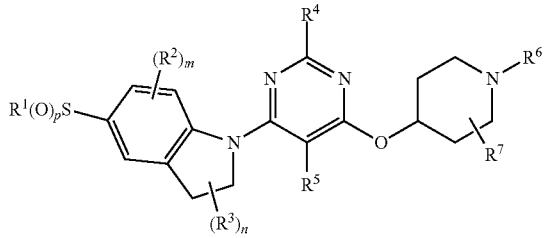

wherein
p is 1 or 2,
R¹ is a C1-C6 alkyl group optionally having 1 to 3 substituents selected from substituent group α, a C3-C7 cycloalkyl group optionally having 1 to 3 substituents selected from substituent group β, a C2-C6 alkynyl group optionally having 1 to 3 substituents selected from substituent group β, a $C_2$-$C_6$ alkenyl group optionally having 1 to 3 substituents selected from substituent group β, an amino group or a mono- or di-(C1-C6 alkyl)amino group,
substituent group α is the group consisting of a halogen atom, a hydroxyl group, a C1-C6 alkoxy group, a C3-C7 cycloalkyl group optionally having 1 to 3 substituents selected from substituent group β, an amino group, a mono- or di-(C1-C6 alkyl)amino group, an aryl group optionally having 1 to 3 substituents selected from substituent group β, and a heteroaryl group optionally having 1 to 3 substituents selected from substituent group β,
substituent group β is the group consisting of a halogen atom, a hydroxyl group, a C1-C6 alkyl group and a $C_1$-$C_6$ alkoxy group, m is an integer of 0 to 3,
R² are the same or different and each is a halogen atom, a C1-C6 alkyl group, a C1-C6 alkoxy group or a C1-C6 alkoxy $C_1$-$C_6$ alkyl group,
n is an integer of 0 to 4,
R³ are the same or different and each is a halogen atom, a C1-C6 alkyl group, a C1-C6 alkoxy group or a C1-C6 alkoxy C1-C6 alkyl group,
R⁴ and R⁵ are each independently a hydrogen atom, a halogen atom, a C1-C6 alkyl group, a C1-C6 alkoxy group or a C1-C6 alkoxy C1-C6 alkyl group, $R^6$ is —C(O)OR$^{6a}$, —C(O)—R$^{6b}$ or —S(O)$_2$—R$^{6c}$, $R^{6a}$ is a C1-C6 alkyl group optionally having 1 to 3 substituents selected from substituent group α, a C3-C7 cycloalkyl group optionally having 1 to 3 substituents selected from substituent group β, a C2-C6 alkynyl group optionally having 1 to 3 substituents selected from substituent group β, a C2-C6 alkenyl group optionally having 1 to 3 substituents selected from substituent group β, an aryl group optionally having 1 to 3 substituents selected from substituent group β, or a heteroaryl group optionally having 1 to 3 substituents selected from substituent group β, $R^{6b}$ is a C1-C6 alkyl group optionally having 1 to 3 substituents selected from substituent group α, a C3-C7 cycloalkyl group optionally having 1 to 3 substituents selected from substituent group β, a C2-C6 alkynyl group optionally having 1 to 3 substituents selected from substituent group β, a C2-C6 alkenyl group optionally having 1 to 3 substituents selected from substituent group β, an amino group, a mono- or di-(C1-C6 alkyl)amino group, an aryl group optionally having 1 to 3 substituents selected from substituent group β, or a heteroaryl group optionally having 1 to 3 substituents selected from substituent group β, $R^{6c}$ is a C1-C6 alkyl group, and $R^7$ is a hydrogen atom, a halogen atom or a C1-C6 alkyl group (see patent document 7).

However, none of the documents report on the fused heterocyclic compound of the present invention.

DOCUMENT LIST

Patent Documents patent document 1: WO 2008/137436
patent document 2: WO 2008/008895
patent document 3: WO 2005/007647
patent document 4: WO 2006/069258
patent document 5: WO 2006/038001
patent document 6: WO 2009/141238
patent document 7: WO 2009/051119

Non-Patent Documents non-patent document 1: Endocrinology, 148(6), 2601-2609, 2007
non-patent document 2: Endocrinology, 149(5), 2038-47, 2008
non-patent document 3: Keystone Symposium 2008, Islet and Beta Cell Biology, Poster Abstract, 102, P. 58

SUMMARY OF THE INVENTION

Problems to be Solved by the Invention

The development of a compound having GPR119 agonist action, is useful for the prophylaxis or treatment of diabetes, obesity and the like and shows superior efficacy has been desired.

Means of Solving the Problems

The present inventors have found for the first time that a compound represented by the formula:

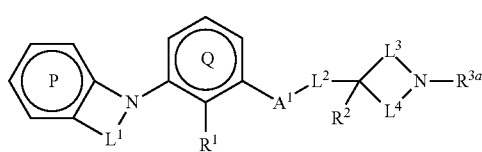

(I)

wherein ring P is a further substituted 6-membered aromatic ring;
ring Q is a further optionally substituted 6-membered aromatic ring;
$A^1$ is CR$^{4a}$R$^{4b}$ wherein R$^{4a}$ and R$^{4b}$ are each independently a hydrogen atom, an optionally substituted hydrocarbon group, an optionally substituted heterocyclic group or an optionally substituted hydroxy group, NR$^{4c}$ wherein R$^{4c}$ is a hydrogen atom or an optionally substituted hydrocarbon group, O, S, SO or SO$_2$;
$L^1$ is an optionally substituted C$_{1-5}$ alkylene group;
$L^2$ is a bond or an optionally substituted C$_{1-3}$ alkylene group;
$L^3$ and $L^4$ are each independently an optionally substituted C$_{1-3}$ alkylene group;
$R^1$ is (1) a hydrogen atom, a halogen atom, a cyano group, an optionally substituted hydrocarbon group, an optionally substituted heterocyclic group or an optionally substituted hydroxy group, or (2) when $A^1$ is CR$^{4a}$R$^{4b}$, R$^1$ and R$^{4a}$ and/or R$^{4b}$ in combination optionally form, together with the adjacent carbon atoms, an optionally substituted 4- to 8-membered ring, or (3) when $A^1$ is NR$^{4c}$, R$^1$ and R$^{4c}$ in combination optionally form, together with the adjacent carbon atom and nitrogen atom, an optionally substituted 4- to 8-membered nitrogen-containing heterocycle;

$R^2$ is a hydrogen atom, a cyano group or an optionally substituted hydrocarbon group; and $R^3$ is an acyl group or an optionally substituted 5- or 6-membered aromatic ring group, provided that tert-butyl 4-[4-(5-methanesulfonyl-2,3-dihydroindol-1-yl)pyrazolo[3,4-d]pyrimidin-1-yl]piperidine-1-carboxylate is excluded, or a salt thereof

[hereinafter sometimes to be referred to as compound (I)] or a prodrug thereof has a superior GPR119 agonist action, is useful for the prophylaxis or treatment of diabetes, obesity and the like and shows superior efficacy. Based on such findings, the present inventors have conducted intensive studies and completed the present invention.

Accordingly, the present invention relates to

[1] a compound represented by the formula:

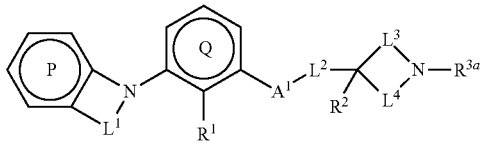

(Ia)

wherein ring P is a further substituted 6-membered aromatic ring;
ring Q is a further optionally substituted 6-membered aromatic ring;
$A^1$ is CR$^{4a}$R$^{4b}$ wherein R$^{4a}$ and R$^{4b}$ are each independently a hydrogen atom, an optionally substituted hydrocarbon group, an optionally substituted heterocyclic group or an optionally substituted hydroxy group, NR$^{4c}$ wherein R$^{4c}$ is a hydrogen atom or an optionally substituted hydrocarbon group, O, S, SO or SO$_2$;
$L^1$ is an optionally substituted C$_{1-5}$ alkylene group;
$L^2$ is a bond or an optionally substituted C$_{1-3}$ alkylene group;
$L^3$ and $L^4$ are each independently an optionally substituted C$_{1-3}$ alkylene group;

R¹ is
(1) a hydrogen atom, a halogen atom, a cyano group, an optionally substituted hydrocarbon group, an optionally substituted heterocyclic group or an optionally substituted hydroxy group, or
(2) when $A^1$ is $CR^{4a}R^{4b}$, $R^1$ and $R^{4a}$ and/or $R^{4b}$ in combination optionally form, together with the adjacent carbon atoms, an optionally substituted 4- to 8-membered ring, or
(3) when $A^1$ is $NR^{4c}$, $R^1$ and $R^{4c}$ in combination optionally form, together with the adjacent carbon atom and nitrogen atom, an optionally substituted 4- to 8-membered nitrogen-containing heterocycle;
$R^2$ is a hydrogen atom, a cyano group or an optionally substituted hydrocarbon group; and
$R^{3a}$ is a group represented by the formula: —CO—$SR^{41}$ wherein $R^{41}$ is an optionally substituted hydrocarbon group or an optionally substituted heterocyclic group, or an optionally substituted 5- or 6-membered aromatic ring group, or a salt thereof;
[2] the compound of the above-mentioned [1], wherein $R^{3a}$ is an optionally substituted 5- or 6-membered aromatic ring group;
[3] the compound of the above-mentioned [1] or [2], wherein ring P is a benzene ring substituted by 1 to 3 substituents selected from
(1) a halogen atom,
(2) a $C_{1-6}$ alkylsulfonyl group,
(3) a $C_{1-6}$ alkyl-carbonylamino group optionally substituted by 1 to 3 substituents selected from
  (i) a hydroxy group, and
  (ii) a $C_{1-6}$ alkoxy group,
(4) a carbamoyl group optionally mono- or di-substituted by $C_{1-6}$ alkyl group(s) optionally substituted by hydroxy group(s),
(5) a 5- or 6-membered non-aromatic heterocyclic group optionally substituted by 1 to 3 oxo groups, and
(6) a 5- or 6-membered non-aromatic heterocyclylcarbonyl group;
[4] the compound of any of the above-mentioned [1] to [3], wherein ring Q is a pyrimidine ring;
[5] the compound of any of the above-mentioned [1] to [4], wherein $A^1$ is $NR^{4c}$ wherein $R^{4c}$ is a hydrogen atom or a $C_{1-6}$ alkyl group optionally substituted by 1 to 3 halogen atoms, or O;
[6] the compound of any of the above-mentioned [1] to [5], wherein $L^1$ is an ethylene group;
[7] the compound of any of the above-mentioned [1] to [6], wherein $L^3$ and $L^4$ are each independently an ethylene group;
[8] the compound of any of the above-mentioned [1] to [7], wherein $R^{3a}$ is
(1) a $C_{1-6}$ alkylthio-carbonyl group, or
(2) a 5- or 6-membered aromatic heterocyclic group optionally substituted by 1 to 3 substituents selected from
  (i) a halogen atom,
  (ii) a $C_{1-6}$ alkyl group,
  (iii) a $C_{1-6}$ alkoxy group, and
  (iv) a $C_{3-10}$ cycloalkyl group;
[9] the compound of any of the above-mentioned [1] to [8], wherein
ring P is a benzene ring substituted by 1 to 3 substituents selected from
(1) a halogen atom,
(2) a $C_{1-6}$ alkylsulfonyl group,
(3) a $C_{1-6}$ alkyl-carbonylamino group optionally substituted by 1 to 3 substituents selected from
  (i) a hydroxy group, and
  (ii) a $C_{1-6}$ alkoxy group,
(4) a carbamoyl group optionally mono- or di-substituted by $C_{1-6}$ alkyl group(s) optionally substituted by hydroxy group(s),
(5) a 5- or 6-membered non-aromatic heterocyclic group optionally substituted by 1 to 3 oxo groups, and
(6) a 5- or 6-membered non-aromatic heterocyclylcarbonyl group;
ring Q is a pyrimidine ring;
$A^1$ is $NR^{4c}$ wherein $R^{4c}$ is a hydrogen atom or a $C_{1-6}$ alkyl group optionally substituted by 1 to 3 halogen atoms, or O;
$L^1$ is an ethylene group;
$L^2$ is a bond;
$L^3$ and $L^4$ are each independently an ethylene group;
$R^1$ is a hydrogen atom;
$R^2$ is a hydrogen atom; and
$R^{3a}$ is
(1) a $C_{1-6}$ alkylthio-carbonyl group, or
(2) a 5- or 6-membered aromatic heterocyclic group optionally substituted by 1 to 3 substituents selected from
  (i) a halogen atom,
  (ii) a $C_{1-6}$ alkyl group,
  (iii) a $C_{1-6}$ alkoxy group, and
  (iv) a $C_{3-10}$ cycloalkyl group;
[10] 1-[6-({1-[3-(1-methylethyl)-1,2,4-oxadiazol-5-yl]piperidin-4-yl}oxy)pyrimidin-4-yl]-5-(methylsulfonyl)-2,3-dihydro-1H-indole or a salt thereof;
[11] S-(1-methylethyl)4-[(6-{5-[(hydroxyacetyl)amino]-2,3-dihydro-1H-indol-1-yl}pyrimidin-4-yl)oxy]piperidine-1-carbothioate or a salt thereof;
[12] 1-(6-{[1-(5-ethylpyrimidin-2-yl)piperidin-4-yl]oxy}pyrimidin-4-yl)-5-(methylsulfonyl)-2,3-dihydro-1H-indole or a salt thereof;
[13] a GPR119 agonist comprising compound (I) or a prodrug thereof;
[13A] a method of activating GPR119 in a mammal, which comprises administering an effective amount of compound (I) or a prodrug thereof to the mammal;
[13B] use of compound (I) or a prodrug thereof, for the production of a GPR119 agonist;
[14] the GPR119 agonist of the above-mentioned [13], wherein $R^3$ is a group represented by the formula: —CO—$SR^{41}$ wherein $R^{41}$ is an optionally substituted hydrocarbon group or an optionally substituted heterocyclic group, or an optionally substituted 5- or 6-membered aromatic ring group;
[15] the GPR119 agonist of the above-mentioned [13], wherein $R^3$ is an optionally substituted 5- or 6-membered aromatic ring group;
[16] a prodrug of the compound of the above-mentioned [1];
[17] a medicament comprising the compound of the above-mentioned [1] or a prodrug thereof;
[18] the medicament of the above-mentioned [17], which is an insulin secretagogue;
[19] the medicament of the above-mentioned [17], which is a glucagon-like peptide-1 secretion promoter;
[20] the medicament of the above-mentioned [17], which is an agent for the prophylaxis or treatment of diabetes;
[21] the medicament of the above-mentioned [17], which is an agent for the prophylaxis or treatment of obesity;
[22] a method for the prophylaxis or treatment of diabetes in a mammal, which comprises administering an effective amount of the compound of the above-mentioned [1] or a prodrug thereof to the mammal;
[23] a method for the prophylaxis or treatment of obesity in a mammal, which comprises administering an effective amount of the compound of the above-mentioned [1] or a prodrug thereof to the mammal;

[24] use of the compound of the above-mentioned [1] or a prodrug thereof, for the production of an agent for the prophylaxis or treatment of diabetes;

[25] use of the compound of the above-mentioned [1] or a prodrug thereof, for the production of an agent for the prophylaxis or treatment of obesity;

[26] a compound represented by the formula:

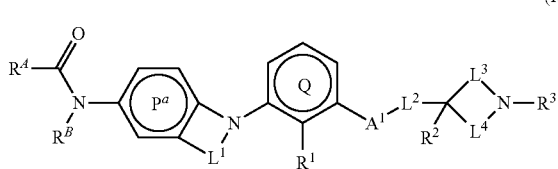

(Ib)

wherein
ring $P^a$ is a further optionally substituted 6-membered aromatic ring;
ring Q is a further optionally substituted 6-membered aromatic ring;
$A^1$ is $CR^{4a}R^{4b}$ wherein $R^{4a}$ and $R^{4b}$ are each independently a hydrogen atom, an optionally substituted hydrocarbon group, an optionally substituted heterocyclic group or an optionally substituted hydroxy group, $NR^{4c}$ wherein $R^{4c}$ is a hydrogen atom or an optionally substituted hydrocarbon group, O, S, SO or $SO_2$;
$L^1$ is an optionally substituted $C_{1-5}$ alkylene group;
$L^2$ is a bond or an optionally substituted $C_{1-3}$ alkylene group;
$L^3$ and $L^4$ are each independently an optionally substituted $C_{1-3}$ alkylene group;
$R^1$ is
(1) a hydrogen atom, a halogen atom, a cyano group, an optionally substituted hydrocarbon group, an optionally substituted heterocyclic group or an optionally substituted hydroxy group, or
(2) when $A^1$ is $CR^{4a}R^{4b}$, $R^1$ and $R^{4a}$ and/or $R^{4b}$ in combination optionally form, together with the adjacent carbon atoms, an optionally substituted 4- to 8-membered ring, or
(3) when $A^1$ is $NR^{4c}$, $R^1$ and $R^{4c}$ in combination optionally form, together with the adjacent carbon atom and nitrogen atom, an optionally substituted 4- to 8-membered nitrogen-containing heterocycle;
$R^2$ is a hydrogen atom, a cyano group or an optionally substituted hydrocarbon group;
$R^3$ is an acyl group or an optionally substituted 5- or 6-23 membered aromatic ring group;
$R^4$ is a hydrogen atom, an optionally substituted hydrocarbon group or an optionally substituted heterocyclic group; and
$R^B$ is a hydrogen atom or a $C_{1-6}$ alkyl group, or a salt thereof; and the like.

Effect of the Invention

Compound (I) has a GPR119 agonist action, is useful for the prophylaxis or treatment of diabetes, obesity and the like and shows superior efficacy.

DETAILED DESCRIPTION OF THE INVENTION

Hereinafter, the definition of each symbol in the formula (I), the formula (Ia) and the formula (Ib) is explained in detail.

The "halogen atom" in the present specification means, unless otherwise specified, a fluorine atom, a chlorine atom, a bromine atom or an iodine atom.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, isopropoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

Ring P is a further substituted 6-membered aromatic ring.

Examples of the "6-membered aromatic ring" of the "substituted 6-membered aromatic ring" for ring P include benzene, pyridine, pyridazine, pyrimidine, pyrazine, triazine and the like. The 6-membered aromatic ring is preferably benzene, pyridine, pyridazine, pyrimidine, pyrazine or the like, more preferably benzene, pyridine, pyrimidine or the like, particularly preferably benzene.

The "6-membered aromatic ring" of the "substituted 6-membered aromatic ring" for ring P has, besides $L^1$ and N, 1 to 3 substituents at substitutable positions.

Examples of the substituent include (1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 substituents selected from a halogen atom, a hydroxy group and a $C_{1-6}$ alkoxy group, (c) a $C_{1-6}$ alkoxy-carbonyl group optionally substituted by 1 to 3 halogen atoms,
(d) a $C_{1-6}$ alkylsulfonyl group (e.g., methylsulfonyl) optionally substituted by 1 to 3 halogen atoms,
(e) a carbamoyl group optionally mono- or di-substituted by $C_{1-6}$ alkyl group(s) optionally substituted by 1 to 3 halogen atoms,
(f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and
(g) an non-aromatic heterocyclylcarbonyl group (e.g., tetrahydrofurylcarbonyl);
(6) a $C_{1-6}$ alkyl-carbonyl group optionally substituted by 1 to 3 halogen atoms;
(7) a $C_{1-6}$ alkoxy-carbonyl group (e.g., methoxycarbonyl) optionally substituted by 1 to 3 substituents selected from
    (a) a halogen atom,
    (b) a $C_{1-6}$ alkoxy group,
    (c) a $C_{6-14}$ aryl group (e.g., phenyl), and
    (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by substituent(s) selected from
    (a) a $C_{1-6}$ alkyl group optionally substituted by 1 to 3 substituents selected from a halogen atom, a hydroxy group and a $C_{1-6}$ alkoxy group, and
    (b) a non-aromatic heterocyclic group (e.g., tetrahydrofuryl);
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
    (a) a halogen atom,
    (b) a carboxy group,
    (c) a $C_{1-6}$ alkoxy group,
    (d) a $C_{1-6}$ alkoxy-carbonyl group optionally substituted by 1 to 3 $C_{6-14}$ aryl groups (e.g., phenyl),
    (e) an amino group optionally mono- or di-substituted by substituent(s) selected from a $C_{1-6}$ alkyl group and a $C_{1-6}$ alkoxy-carbonyl group,
    (f) a heterocyclic group (e.g., tetrahydrofuryl), and
    (g) a $C_{3-10}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
    (a) a halogen atom, and
    (b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
    (a) a halogen atom, and
    (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom (e.g., a fluorine atom, a chlorine atom, a bromine atom);
(28) a $C_{1-3}$ alkylenedioxy group;
(29) a $C_{1-3}$ alkyleneoxy group (e.g., methyleneoxy, ethyleneoxy);
(30) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
    (a) a halogen atom (e.g., a fluorine atom), and
    (b) a $C_{1-6}$ alkoxy group (e.g., methoxy);
(32) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
(33) a $C_{2-6}$ alkenyl group (e.g., ethenyl, 1-propenyl) optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
(34) a $C_{7-13}$ aralkyl group (e.g., benzyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group, and
    (d) a halogen atom;
and the like. When the number of the substituents is not less than 2, the respective substituents may be the same or is different.

Ring P is preferably a benzene ring, a pyridine ring, a pyridazine ring, a pyrimidine ring, a pyrazine ring or the like, each of which is substituted by 1 to 3 substituents selected from
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;

(2) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;
(3) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 substituents selected from a halogen atom, a hydroxy group and a $C_{1-6}$ alkoxy group,
    (c) a $C_{1-6}$ alkoxy-carbonyl group optionally substituted by 1 to 3 halogen atoms,
    (d) a $C_{1-6}$ alkylsulfonyl group (e.g., methylsulfonyl) optionally substituted by 1 to 3 halogen atoms,
    (e) a carbamoyl group optionally mono- or di-substituted by $C_{1-6}$ alkyl group(s) optionally substituted by 1 to 3 halogen atoms,
    (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and
    (g) an non-aromatic heterocyclylcarbonyl group (e.g., tetrahydrofurylcarbonyl);
(4) a $C_{1-6}$ alkyl-carbonyl group optionally substituted by 1 to 3 halogen atoms;
(5) a $C_{1-6}$ alkoxy-carbonyl group (e.g., methoxycarbonyl) optionally substituted by 1 to 3 substituents selected from
    (a) a halogen atom,
    (b) a $C_{1-6}$ alkoxy group,
    (c) a $C_{6-14}$ aryl group (e.g., phenyl), and
    (d) a heterocyclic group (e.g., tetrahydrofuryl);
(6) a $C_{1-6}$ alkylsulfonyl group (e.g., methylsulfonyl, ethylsulfonyl, isopropylsulfonyl) optionally substituted by 1 to 3 halogen atoms;
(7) a carbamoyl group optionally mono- or di-substituted by substituent(s) selected from
    (a) a $C_{1-6}$ alkyl group optionally substituted by 1 to 3 substituents selected from a halogen atom, a hydroxy group and a $C_{1-6}$ alkoxy group, and
    (b) a non-aromatic heterocyclic group (e.g., tetrahydrofuryl);
(8) a carboxy group;
(9) a hydroxy group;
(10) an non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(11) a mercapto group;
(12) a cyano group;
(13) a nitro group;
(14) a halogen atom (e.g., a fluorine atom, a chlorine atom, a bromine atom);
(15) a $C_{3-10}$ cycloalkoxy group (e.g., cyclopropoxy, cyclopentyloxy) optionally substituted by 1 to 3 substituents selected from
    (a) a halogen atom (e.g., a fluorine atom), and
    (b) a $C_{1-6}$ alkoxy group (e.g., methoxy);
(16) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
and the like.

Ring P is more preferably a benzene ring, a pyridine ring, a pyrimidine ring or the like, each of which is substituted by 1 to 3 substituents selected from
(1) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;
(2) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 substituents selected from a halogen atom, a hydroxy group and a $C_{1-6}$ alkoxy group,
    (c) a $C_{1-6}$ alkoxy-carbonyl group optionally substituted by 1 to 3 halogen atoms,
    (d) a $C_{1-6}$ alkylsulfonyl group (e.g., methylsulfonyl) optionally substituted by 1 to 3 halogen atoms,
    (e) a carbamoyl group optionally mono- or di-substituted by $C_{1-6}$ alkyl group(s) optionally substituted by 1 to 3 halogen atoms,
    (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and
    (g) an non-aromatic heterocyclylcarbonyl group (e.g., tetrahydrofurylcarbonyl);
(3) a $C_{1-6}$ alkyl-carbonyl group optionally substituted by 1 to 3 halogen atoms;
(4) a $C_{1-6}$ alkoxy-carbonyl group (e.g., methoxycarbonyl) optionally substituted by 1 to 3 substituents selected from
    (a) a halogen atom,
    (b) a $C_{1-6}$ alkoxy group,
    (c) a $C_{6-14}$ aryl group (e.g., phenyl), and
    (d) a heterocyclic group (e.g., tetrahydrofuryl);
(5) a $C_{1-6}$ alkylsulfonyl group (e.g., methylsulfonyl, ethylsulfonyl, isopropylsulfonyl) optionally substituted by 1 to 3 halogen atoms;
(6) a carbamoyl group optionally mono- or di-substituted by substituent(s) selected from
    (a) a $C_{1-6}$ alkyl group optionally substituted by 1 to 3 substituents selected from a halogen atom, a hydroxy group and a $C_{1-6}$ alkoxy group, and
    (b) a non-aromatic heterocyclic group (e.g., tetrahydrofuryl);
(7) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;

(8) a carboxy group;
(9) a cyano group;
(10) a nitro group;
(11) a halogen atom (e.g., a fluorine atom, a chlorine atom, a bromine atom);
and the like.

Ring P is still more preferably a benzene ring substituted by 1 to 3 substituents selected from
(1) a halogen atom,
(2) a $C_{1-6}$ alkylsulfonyl group,
(3) a $C_{1-6}$ alkyl-carbonylamino group optionally substituted by 1 to 3 substituents selected from
  (i) a hydroxy group, and
  (ii) a $C_{1-6}$ alkoxy group,
(4) a carbamoyl group optionally mono- or di-substituted by $C_{1-6}$ alkyl group(s) optionally substituted by hydroxy group(s),
(5) a 5- or 6-membered non-aromatic heterocyclic group optionally substituted by 1 to 3 oxo groups,
(6) a 5- or 6-membered non-aromatic heterocyclylcarbonyl group and the like.

Ring $P^a$ is a further optionally substituted 6-membered aromatic ring.

Examples of the "6-membered aromatic ring" of the "optionally substituted 6-membered aromatic ring" for ring $P^a$ include those similar to the "6-membered aromatic ring" of the "substituted 6-membered aromatic ring" for ring P. The 6-membered aromatic ring is preferably benzene, pyridine, pyridazine, pyrimidine, pyrazine or the like, more preferably benzene, pyridine, pyrimidine or the like, particularly preferably benzene.

The "6-membered aromatic ring" of the "optionally substituted 6-membered aromatic ring" for ring $P^a$ has, besides $L^1$, N and —N($R^B$)—CO—$R^A$, 1 to 3 substituents at substitutable positions. Examples of the substituent include those similar to the substituent that the "6-membered aromatic ring" of the "substituted 6-membered aromatic ring" for ring P has. When the number of the substituents is not less than 2, the respective substituents may be the same or different.

Ring $P^a$ is preferably a benzene ring, a pyridine ring, a pyrimidine ring or the like (preferably benzene ring), each of which is optionally substituted by 1 to 3 substituents selected from
(1) a halogen atom (e.g., a fluorine atom, a chlorine atom, a bromine atom);
(2) a $C_{1-6}$ alkyl group optionally substituted by 1 to 3 halogen atoms;
and the like.

Ring $P^a$ is more preferably a benzene ring having no additional substituent, besides $L^1$, N and —N($R^B$)—CO—$R^a$.

Ring Q is a further optionally substituted 6-membered aromatic ring.

Examples of the "6-membered aromatic ring" of the "optionally substituted 6-membered aromatic ring" for ring Q include benzene, pyridine, pyridazine, pyrimidine, triazine and the like. The 6-membered aromatic ring is preferably benzene, pyridine, pyridazine, pyrimidine or the like, more preferably benzene, pyridine, pyrimidine or the like, particularly preferably pyrimidine.

The "6-membered aromatic ring" of the "optionally substituted 6-membered aromatic ring" for ring Q has, besides $R^1$, $A^1$ and N, 1 to 3 substituents at substitutable positions. Examples of the substituent include those similar to the substituent that the "6-membered aromatic ring" of the "substituted 6-membered aromatic ring" for ring P has. When the number of the substituents is not less than 2, the respective substituents may be the same or different.

Ring Q is preferably a benzene ring, a pyridine ring, a pyridazine ring, a pyrimidine ring or the like, each of which is optionally substituted by 1 to 3 substituents selected from
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(2) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 so halogen atoms,
  (b) a hydroxy group,
  (c) a $C_{1-6}$ alkoxy group optionally substituted by 1 to 3 halogen atoms,
  (d) a halogen atom, and
  (e) an oxo group;
(3) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 substituents selected from a halogen atom, a hydroxy group and a $C_{1-6}$ alkoxy group,
  (c) a $C_{1-6}$ alkoxy-carbonyl group optionally substituted by 1 to 3 halogen atoms,
  (d) a $C_{1-6}$ alkylsulfonyl group (e.g., methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms,
  (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and
  (g) an non-aromatic heterocyclylcarbonyl group (e.g., tetrahydrofurylcarbonyl);
(4) a $C_{1-6}$ alkyl-carbonyl group optionally substituted by 1 to 3 halogen atoms;
(5) a $C_{1-6}$ alkoxy-carbonyl group (e.g., methoxycarbonyl) optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(6) a $C_{1-6}$ alkylsulfonyl group (e.g., methylsulfonyl, ethylsulfonyl, isopropylsulfonyl) optionally substituted by 1% to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a hydroxy group and a $C_{1-6}$ alkoxy group, and
  (b) a non-aromatic heterocyclic group (e.g., tetrahydrofuryl);
(8) a carboxy group;
(9) a hydroxy group;
(10) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;

(11) a mercapto group;
(12) a cyano group;
(13) a nitro group;
(14) a halogen atom (e.g., a fluorine atom, a chlorine atom, a bromine atom);
(15) a $C_{3-10}$ cycloalkoxy group (e.g., cyclopropoxy, cyclopentyloxy) optionally substituted by 1 to 3 substituents selected from
  (a) a halogen atom (e.g., a fluorine atom), and
  (b) a $C_{1-6}$ alkoxy group (e.g., methoxy);
(16) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);
and the like.

Ring Q is more preferably a benzene ring, a pyridine ring, a pyrimidine ring or the like, each of which is optionally substituted by 1 to 3 substituents selected from
(1) a halogen atom (e.g., a fluorine atom, a chlorine atom, a bromine atom);
(2) a $C_{1-6}$ alkyl group optionally substituted by 1 to 3 halogen atoms;
and the like.

Ring Q is still more preferably a pyrimidine ring having no additional substituent besides $R^1$, $A^1$ and N.

$A^1$ is $CR^{4a}R^{4b}$ wherein $R^{4a}$ and $R^{4b}$ are each independently a hydrogen atom, an optionally substituted hydrocarbon group, an optionally substituted heterocyclic group or an optionally substituted hydroxy group, $NR^{4c}$ wherein $R^{4c}$ is a hydrogen atom or an optionally substituted hydrocarbon group, O, S, SO or $SO_2$.

Examples of the "hydrocarbon group" of the "optionally substituted hydrocarbon group" for $R^{4a}$, $R^{4b}$ or $R^{4c}$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

Examples of the "$C_{1-10}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Examples of the "$C_{2-10}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Examples of the "$C_{2-10}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl, 1-heptynyl, 1-octynyl and the like.

Examples of the $C_{3-10}$ cycloalkyl group include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Examples of the $C_{3-10}$ cycloalkenyl group include 2-cyclopenten-1-yl, 3-cyclopenten-1-yl, 2-cyclohexen-1-yl, 3-cyclohexen-1-yl and the like.

Examples of the $C_{4-10}$ cycloalkadienyl group include 2,4-cyclopentadien-1-yl, 2,4-cyclohexadien-1-yl, cyclohexadien-1-yl and the like.

The above-mentioned $C_{3-10}$ cycloalkyl group, $C_{3-10}$ cycloalkenyl group and $C_{4-10}$ cycloalkadienyl group optionally condense with a benzene ring to form a fused ring group. Examples of the fused ring group include indanyl, dihydronaphthyl, tetrahydronaphthyl, fluorenyl and the like.

Examples of the $C_{6-14}$ aryl group include phenyl, naphthyl, anthryl, phenanthryl, acenaphthyl, biphenylyl and the like.

Examples of the $C_{7-13}$ aralkyl group include benzyl, phenethyl, naphthylmethyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group, which are exemplified as the "hydrocarbon group" of the "optionally substituted hydrocarbon group" for $R^{4a}$, $R^{4b}$ or $R^{4c}$, optionally have 1 to 3 substituents at substitutable positions.

Examples of the substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 substituents selected from a halogen atom, a hydroxy group and a $C_{1-6}$ alkoxy group,
  (c) a $C_{1-6}$ alkoxy-carbonyl group optionally substituted by 1 to 3 halogen atoms,
  (d) a $C_{1-6}$ alkylsulfonyl group (e.g., methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms,
  (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and (g) an non-aromatic heterocyclylcarbonyl group (e.g., tetrahydrofurylcarbonyl);

(6) a $C_{1-6}$ alkyl-carbonyl group optionally substituted by 1 to 3 halogen atoms;

(7) a $C_{1-6}$ alkoxy-carbonyl group (e.g., methoxycarbonyl) optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);

(8) a $C_{1-6}$ alkylsulfonyl group (e.g., methylsulfonyl, ethylsulfonyl, isopropylsulfonyl) optionally substituted by 1 to 3 halogen atoms;

(9) a carbamoyl group optionally mono- or di-substituted by substituent(s) selected from
  (a) a $C_{1-6}$ alkyl group optionally substituted by 1 to 3 substituents selected from a halogen atom, a hydroxy group and a $C_{1-6}$ alkoxy group, and
  (b) a non-aromatic heterocyclic group (e.g., tetrahydrofuryl);

(10) a thiocarbamoyl group optionally mono- or di-substituted by $C_{1-6}$ alkyl group(s) optionally substituted by 1 to 3 halogen atoms;

(11) a sulfamoyl group optionally mono- or di-substituted by $C_{1-6}$ alkyl group(s) optionally substituted by 1 to 3 halogen atoms;

(12) a carboxy group;

(13) a hydroxy group;

(14) a $C_{1-6}$ alkoxy group optionally substituted by 1 to 3 substituents selected from
  (a) a halogen atom,
  (b) a carboxy group,
  (c) a $C_{1-6}$ alkoxy group,
  (d) a $C_{1-6}$ alkoxy-carbonyl group optionally substituted by 1 to 3 $C_{6-14}$ aryl groups (e.g., phenyl),
  (e) an amino group optionally mono- or di-substituted by substituent(s) selected from a $C_{1-6}$ alkyl group and a $C_{1-6}$ alkoxy-carbonyl group,
  (f) a heterocyclic group (e.g., tetrahydrofuryl), and
  (g) a $C_{3-10}$ cycloalkyl group;

(15) a $C_{2-6}$ alkenyloxy group (e.g., ethenyloxy) optionally substituted by 1 to 3 halogen atoms;

(16) a $C_{7-13}$ aralkyloxy group (e.g., benzyloxy);

(17) a $C_{6-14}$ aryloxy group (e.g., phenyloxy, naphthyloxy);

(18) a $C_{1-6}$ alkyl-carbonyloxy group (e.g., acetyloxy, tert-butylcarbonyloxy);

(19) a $C_{6-14}$ aryl-carbonyl group (e.g., benzoyl) optionally substituted by 1 to 3 substituents selected from
  (a) a halogen atom, and
  (b) a $C_{1-6}$ alkyl group optionally substituted by 1 to 3 halogen atoms;

(20) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;

(21) a mercapto group;

(22) a $C_{1-6}$ alkylthio group (e.g., methylthio, ethylthio) optionally substituted by 1 to 3 substituents selected from
  (a) a halogen atom, and
  (b) a $C_{1-6}$ alkoxy-carbonyl group;

(23) a $C_{7-13}$ aralkylthio group (e.g., benzylthio);

(24) a $C_{6-14}$ arylthio group (e.g., phenylthio, naphthylthio);

(25) a cyano group;

(26) a nitro group;

(27) a halogen atom (e.g., a fluorine atom, a chlorine atom, a bromine atom);

(28) a $C_{1-3}$ alkylenedioxy group;

(29) a $C_{1-3}$ alkyleneoxy group (e.g., methyleneoxy, ethyleneoxy);

(30) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;

(31) a $C_{3-10}$ cycloalkoxy group (e.g., cyclopropoxy, cyclopentyloxy) optionally substituted by 1 to 3 substituents selected from
  (a) a halogen atom (e.g., a fluorine atom), and
  (b) a $C_{1-6}$ alkoxy group (e.g., methoxy);

and the like. When the number of the substituents is not less than 2, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group, which are exemplified as the "hydrocarbon group" of the "optionally substituted hydrocarbon group" for $R^{4a}$, $R^{4b}$ or $R^{4c}$, optionally have 1 to 3 substituents at substitutable positions. Examples of the substituent include those similar to the substituent that the "6-membered aromatic ring" of the "substituted 6-membered aromatic ring" for ring P has. When the number of the substituents is not less than 2, the respective substituents may be the same or different.

The "optionally substituted hydrocarbon group" for $R^{4a}$, $R^{4b}$ or $R^{4c}$ is preferably (1) a $C_{3-10}$ cycloalkyl group (e.g., cyclopropyl, cyclohexyl);

(2) a $C_{6-14}$ aryl group (e.g., phenyl, naphthyl);

(3) a $C_{1-6}$ alkyl group optionally substituted by 1 to 3 halogen atoms;

(4) a $C_{7-13}$ aralkyl group (e.g., benzyl);

or the like.

Examples of the "heterocyclic group" of the "optionally substituted heterocyclic group" for $R^{4a}$ or $R^{4b}$ include an aromatic heterocyclic group and a non-aromatic heterocyclic group.

Examples of the aromatic heterocyclic group include a 4- to 7-membered (preferably a 5- or 6-membered) monocyclic aromatic heterocyclic group containing, as a ring constituting atom besides carbon atom, 1 to 4 hetero atoms selected from an oxygen atom, a sulfur atom and a nitrogen atom and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and the like.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;

fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl), pyridopyridinyl (e.g., pyrido[2,3-b]pyridin-3-yl), thienopyridyl (e.g., thieno[2,3-b]pyridin-3-yl) and the like; and the like.

Examples of the non-aromatic heterocyclic group include a 4- to 7-membered (preferably a 5- or 6-membered) monocyclic non-aromatic heterocyclic group containing, as a ring constituting atom besides carbon atom, 1 to 4 hetero atoms selected from an oxygen atom, a sulfur atom and a nitrogen atom and fused non-aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, a group wherein the above-mentioned group is partially saturated, and the like.

Preferable examples of the non-aromatic heterocyclic group include
monocyclic non-aromatic heterocyclic groups such as pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;

fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like;
and the like.

The "heterocyclic group" of the "optionally substituted heterocyclic group" for $R^{4a}$ or $R^{4b}$ optionally has 1 to 3 substituents at substitutable positions. Examples of the substituent include those similar to the substituent that the "6-membered aromatic ring" of the "substituted 6-membered aromatic ring" for ring P has. When the heterocyclic group is a "non-aromatic heterocyclic group", the substituent further includes an oxo group. When the number of the substituents is not less than 2, the respective substituents may be the same or different.

The "optionally substituted heterocyclic group" for $R^{4a}$ or $R^{4b}$ is preferably
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(2) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
or the like.

Examples of the "optionally substituted hydroxy group" for $R^{4a}$ or $R^{4b}$ include a hydroxy group optionally substituted by a substituent selected from a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the $C_{1-10}$ alkyl group, $C_{2-10}$ alkenyl group, $C_{2-10}$ alkynyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group, which are exemplified as the "substituent" of the above-mentioned "optionally substituted hydroxy group", include those exemplified as the "hydrocarbon group" of the "optionally substituted hydrocarbon group" for $R^{4a}$, $R^{4b}$ or $R^{4c}$.

Examples of the heterocyclic group, which is exemplified as the "substituent" of the above-mentioned "optionally substituted hydroxy group", include those similar to the "heterocyclic group" of the "optionally substituted heterocyclic group" for $R^{4a}$ or $R^{4b}$.

The $C_{1-10}$ alkyl group, $C_{2-10}$ alkenyl group, $C_{2-10}$ alkynyl group and $C_{1-6}$ alkyl-carbonyl group, which are exemplified as the "substituent" of the above-mentioned "optionally substituted hydroxy group", optionally have 1 to 3 substituents at substitutable positions. Examples of the substituent include those similar to the substituent that the $C_{1-10}$ alkyl group and the like, which are exemplified as the "hydrocarbon group" of the "optionally substituted hydrocarbon group" for $R^{4a}$, $R^{4b}$ or $R^{4c}$, optionally has.

The $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group, which are exemplified as the "substituent" of the above-mentioned "optionally substituted hydroxy group", optionally have 1 to 3 substituents at substitutable positions. Examples of the substituent include those similar to the substituent that the "6-membered aromatic ring" of the "substituted 6-membered aromatic ring" for ring P has. When the heterocyclic group is a "non-aromatic heterocyclic group", the substituent further includes an oxo group. When the number of the substituents is not less than 2, the respective substituents may be the same or different.

The "optionally substituted hydroxy group" for $R^{4a}$ or $R^{4b}$ is preferably a hydroxy group optionally substituted by substituent(s) selected from (1) a $C_{3-10}$ cycloalkyl group (e.g., cyclopropyl, cyclohexyl);
(2) a $C_{6-14}$ aryl group (e.g., phenyl, naphthyl);
(3) a $C_{1-6}$ alkyl group;
(4) a $C_{7-13}$ aralkyl group (e.g., benzyl);
and the like,
or the like.

$R^{4a}$ and $R^{4c}$ is preferably each independently
(1) a hydrogen atom;
(2) a $C_{1-6}$ alkyl group;
(3) a hydroxy group;
(4) a $C_{1-6}$ alkoxy group;
or the like.

$R^{4a}$ and $R^{4b}$ is more preferably each independently
(1) a hydrogen atom;
(2) a $C_{1-6}$ alkyl group;
or the like.

$R^{4a}$ and $R^{4b}$ are particularly preferably each independently a hydrogen atom.

$R^{4c}$ is preferably
(1) a hydrogen atom;
(2) a $C_{1-6}$ alkyl group optionally substituted by 1 to 3 halogen atoms;
(3) a $C_{3-10}$ cycloalkyl group;
or the like.

$R^{4c}$ is more preferably
(1) a hydrogen atom;
(2) a $C_{1-6}$ alkyl group optionally substituted by 1 to 3 halogen atoms;
or the like.

$A^1$ is preferably
(1) $CR^{4a}R^{4b}$ wherein $R^{4a}$ and $R^{4b}$ are each independently a hydrogen atom, a $C_{1-6}$ alkyl group, a hydroxy group, a $C_{1-6}$ alkoxy group or the like;

(2) $NR^{4c}$ wherein $R^{4c}$ is a hydrogen atom, a $C_{1-6}$ alkyl group optionally substituted by 1 to 3 halogen atoms, a $C_{3-10}$ cycloalkyl group or the like;
(3) O;
(4) S;
or the like.

$A^1$ is more preferably
(1) $CR^{4a}R^{4b}$ wherein $R^{4a}$ and $R^{4b}$ are each independently a hydrogen atom, a $C_{1-6}$ alkyl group or the like;
(2) $NR^{4c}$ wherein $R^{4c}$ is a hydrogen atom, a $C_{1-6}$ alkyl group optionally substituted by 1 to 3 halogen atoms, or the like;
(3) O;
or the like.

$A^1$ is more preferably
(1) $NR^{4c}$ wherein $R^{4c}$ is a hydrogen atom, a $C_{1-5}$ alkyl group optionally substituted by 1 to 3 halogen atoms, or the like;
(2) O;
or the like.

$L^1$ is an optionally substituted $C_{1-5}$ alkylene group.

The "$C_{1-5}$ alkylene group" of the "optionally substituted $C_{1-5}$ alkylene group" for $L^1$ may be linear or branched, and examples thereof include methylene, ethylene, trimethylene, tetramethylene, pentamethylene and the like. The $C_{1-5}$ alkylene group is preferably ethylene, trimethylene, tetramethylene or the like, more preferably ethylene, trimethylene or the like, particularly preferably ethylene.

The "$C_{1-5}$ alkylene group" of the "optionally substituted $C_{1-5}$ alkylene group" for $L^1$ optionally has 1 to 3 substituents at substitutable positions. Examples of the substituent include those similar to the substituent that the "6-membered aromatic ring" of the "substituted 6-membered aromatic ring" for ring P has. When the number of the substituents is not less than 2, the respective substituents may be the same or different.

$L^1$ is preferably ethylene, trimethylene, tetramethylene or the like, each of which is optionally substituted by 1 to 3 substituents selected from (1) a halogen atom;
(2) a hydroxy group;
(3) a $C_{1-6}$ alkoxy group;
(4) a $C_{1-6}$ alkyl-carbonyl group optionally substituted by 1 to 3 halogen atoms;
(5) a $C_{1-6}$ alkoxy-carbonyl group optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl);
(6) a $C_{1-6}$ alkylsulfonyl group (e.g., methylsulfonyl, ethylsulfonyl, isopropylsulfonyl) optionally substituted by 1 to 3 halogen atoms;
(7) a cyano, group;
(8) a nitro group;
and the like.

$L^1$ is more preferably ethylene, trimethylene, tetramethylene or the like.

$L^1$ is still more preferably ethylene, trimethylene or the like, particularly preferably ethylene.

$L^2$ is a bond or an optionally substituted $C_{1-3}$ alkylene group.

The "$C_{1-3}$ alkylene group" of the "optionally substituted $C_{1-3}$ alkylene group" for $L^2$ may be linear or branched, and examples thereof include methylene, ethylene, trimethylene and the like. The $C_{1-3}$ alkylene group is preferably methylene, ethylene or the like.

The "$C_{1-3}$ alkylene group" of the "optionally substituted $C_{1-3}$ alkylene group" for $L^2$ optionally has 1 to 3 substituents at substitutable positions. Examples of the substituent include those similar to the substituent that the "6-membered aromatic ring" of the "substituted 6-membered aromatic ring" for ring P has. When the number of the substituents is not less than 2, the respective substituents may be the same or different.

$L^2$ is preferably
(1) a bond;
(2) methylene or ethylene, each of which is optionally substituted by 1 to 3 substituents selected from
  (a) a halogen atom,
  (b) a hydroxy group,
  (c) a $C_{1-6}$ alkoxy group
  and the like;
or the like.

$L^2$ is more preferably a bond, methylene, ethylene or the like, particularly preferably a bond.

$L^3$ and $L^4$ are each independently an optionally substituted $C_{1-3}$ alkylene group.

The "$C_{1-3}$ alkylene group" of the "optionally substituted $C_{1-3}$ alkylene group" for $L^3$ or $L^4$ may be linear or branched, and examples thereof include methylene, ethylene, trimethylene and the like.

The "$C_{1-3}$ alkylene group" of the "optionally substituted $C_{1-3}$ alkylene group" for $L^3$ or $L^4$ optionally has 1 to 3 substituents at substitutable positions. Examples of the substituent include those similar to the substituent that the "6-membered aromatic ring" of the "substituted 6-membered aromatic ring" for ring P has. When the number of the substituents is not less than 2, the respective substituents may be the same or different.

$L^3$ and $L^4$ is preferably each independently methylene, ethylene, trimethylene or the like, each of which is optionally substituted by 1 to 3 substituents selected from
(1) a halogen atom;
(2) a hydroxy group;
(3) a $C_{1-6}$ alkoxy group;
(4) a $C_{1-6}$ alkyl-carbonyl group optionally substituted by 1 to 3 halogen atoms;
(5) a $C_{1-6}$ alkoxy-carbonyl group optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
and the like.

$L^3$ and $L^4$ is more preferably each independently methylene, ethylene, trimethylene or the like, particularly preferably each independently ethylene.

$R^1$ is
(1) a hydrogen atom, a halogen atom, a cyano group, an optionally substituted hydrocarbon group, an optionally substituted heterocyclic group or an optionally substituted hydroxy group, or
(2) when $A^1$ is $CR^{4a}R^{4b}$, $R^1$ and $R^{4a}$ and/or $R^{4b}$ in combination optionally form, together with the adjacent carbon atoms, an optionally substituted 4- to 8-membered ring, or
(3) when $A^1$ is $NR^{4c}$, $R^1$ and $R^{4c}$ in combination optionally form, together with the adjacent carbon atom and nitrogen atom, an optionally substituted 4- to 8-membered nitrogen-containing heterocycle.

Examples of the "hydrocarbon group" of the "optionally substituted hydrocarbon group" for $R^1$ include those similar to the "hydrocarbon group" of the "optionally substituted hydrocarbon group" for $R^{4a}$, $R^{4b}$ or $R^{4c}$.

The "hydrocarbon group" of the "optionally substituted hydrocarbon group" for $R^1$ optionally has 1 to 3 substituents at substitutable positions. Examples of the substituent include those similar to the substituent that the "hydrocarbon group" of the "optionally substituted hydrocarbon group" for $R^{4a}$, $R^{4b}$ or $R^{4c}$ optionally has. When the number of the substituents is not less than 2, the respective substituents may be the same or different.

The "optionally substituted hydrocarbon group" for $R^1$ is preferably
(1) a $C_{3-10}$ cycloalkyl group (e.g., cyclopropyl, cyclohexyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);
(4) a $C_{2-6}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);
(5) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
or the like.

Examples of the "heterocyclic group" of the "optionally substituted heterocyclic group" for $R^1$ include those similar to the "heterocyclic group" of the "optionally substituted heterocyclic group" for $R^{4a}$ or $R^{4b}$.

The "heterocyclic group" of the "optionally substituted heterocyclic group" for $R^1$ optionally has 1 to 3 substituents at substitutable positions. Examples of the substituent include those similar to the substituent that the "heterocyclic group" of the "optionally substituted heterocyclic group" for $R^{4a}$ or $R^{4b}$ optionally has. When the number of the substituents is not less than 2, the respective substituents may be the same or different.

The "optionally substituted heterocyclic group" for $R^1$ is preferably
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(2) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
or the like.

Examples of the "optionally substituted hydroxy group" for $R^1$ include those similar to the "optionally substituted hydroxy group" for $R^{4a}$ or $R^{4b}$.

The "optionally substituted hydroxy group" for $R^1$ is preferably a hydroxy group optionally substituted by a substituent selected from
(1) a $C_{3-10}$ cycloalkyl group (e.g., cyclopropyl, cyclohexyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);
(4) a $C_{2-6}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);
(5) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
and the like,
or the like.

Examples of the "4- to 8-membered ring" of the "optionally substituted 4- to 8-membered ring" formed by $R^1$ and $R^{4a}$ and/or $R^{4b}$ in combination together with the adjacent carbon atoms when $A^1$ is $CR^{4a}R^{4b}$ include a "4- to 8-membered hydrocarbon ring" and a "4- to 8-membered heterocycle".

Examples of the "4- to 8-membered hydrocarbon ring" include a 4- to 8-membered ring, from among the rings corresponding to the $C_{3-10}$ cycloalkenyl group, $C_{4-10}$ cycloalkadienyl group and $C_{6-14}$ aryl group, which are exemplified as the "hydrocarbon group" of the "optionally substituted hydrocarbon group" for $R^{4a}$, $R^{4b}$ or $R^{4c}$. Specific examples thereof include benzene, cyclobutene, cyclopentene, cyclohexene, cycloheptene, cyclooctene, cyclopentadiene, cyclohexadiene, cycloheptadiene and the like. The 4- to 8-membered hydrocarbon ring is preferably a 5- or 6-membered hydrocarbon ring, more preferably cyclopentadiene, cyclopentene, cyclohexene, benzene or the like.

Examples of the "4- to 8-membered heterocycle" include a 4- to 8-membered ring, from among the rings corresponding to the monocyclic aromatic heterocyclic group and partially saturated group thereof, which are exemplified as the "heterocyclic group" of the "optionally substituted heterocyclic group" for $R^{4a}$ or $R^{4b}$. Specific examples thereof include dihydroazete, pyrrole, pyrazole, isoxazole, isothiazole, pyridine, pyrimidine, pyridazine, tetrahydroazepine, hexahydroazocine, dihydropyrrole, dihydropyrazole, dihydroisoxazole, dihydroisothiazole, dihydropyridine, dihydropyrimidine, dihydropyridazine and the like. The 4- to 8-membered heterocycle is preferably a 5- or 6-membered heterocycle (preferably a 5- or 6-membered aromatic heterocycle), more preferably pyrrole, pyrazole, pyridine, pyrimidine or the like.

When $A^1$ is $CR^{4a}R^{4b}$, and $R^1$ and $R^{4a}$ and/or $R^{4b}$ in combination form, together with the adjacent carbon atoms, an optionally substituted 4- to 8-membered ring, ring Q and the "4- to 8-membered ring" commonly have one bond of each ring (i.e., they are condensed) to form a bicycle. The bond of ring Q and the bond of the "4- to 8-membered ring", which are involved in the formation of bicycle, have the same multiplicity.

For example, when the bicycle is the ring represented by (A)

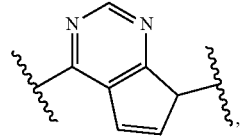

then ring Q is pyrimidine and the "4- to 8-membered ring" is cyclopentadiene. When the bicycle is the ring represented by (B)

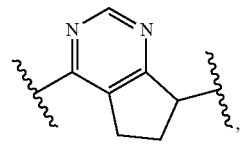 [SMILES: *c1ncnc2c1CCC2*]

then the ring Q is pyrimidine, and the "4- to 8-membered ring" is cyclopentene.

The "4- to 8-membered ring" optionally has 1 to 3 substituents at substitutable positions. Examples of the substituent include those similar to the substituent that the "heterocyclic group" of the "optionally substituted heterocyclic group" for $R^{4a}$ or $R^{4b}$ optionally has. When the number of the substituents is not less than 2, the respective substituents may be the same or different.

The "optionally substituted 4- to 8-membered ring" formed by $R^1$ and $R^{4a}$ and/or $R^{4b}$ in combination together with the adjacent carbon atoms is preferably a 5- or 6-membered ring (e.g., cyclopentadiene, cyclopentene, cyclohexene, benzene, pyrrole, pyrazole, pyridine, pyrimidine) optionally substituted by 1 to 3 substituents selected from
(1) a halogen atom;
(2) a hydroxy group;
(3) a $C_{1-6}$ alkoxy group;
(4) a $C_{1-6}$ alkyl group;
and the like,
or the like.

Examples of the "4- to 8-membered nitrogen-containing heterocycle" of the "optionally substituted 4- to 8-membered nitrogen-containing heterocycle" formed by $R^1$ and $R^{4c}$ in combination together with the adjacent carbon atom and nitrogen atom when $A^1$ is $NR^{4c}$ include a 4- to 8-membered nitrogen-containing heterocycle containing at least one nitrogen atom and further optionally containing 1 or 2 hetero atoms selected from an oxygen atom, a sulfur atom and a nitrogen atom, as a ring constituting atom besides carbon atom. Specific examples thereof include dihydroazete, pyrrole, pyrazole, imidazole, triazole, tetrahydroazepine, hexahydroazocine, dihydropyrrole, dihydropyrazole, dihydroimidazole, dihydrooxazole, dihydrothiazole, dihydroisoxazole, dihydroisothiazole, dihydropyridine, dihydropyrimidine, dihydropyridazine and the like. The 4- to 8-membered nitrogen-containing heterocycle is preferably a 5- or 6-membered nitrogen-containing heterocycle, more preferably pyrrole, pyrazole, imidazole, dihydropyrrole or the like.

When $A^1$ is $NR^{4c}$, and $R^1$ and $R^{4c}$ in combination form, together with the adjacent carbon atom and nitrogen atom, an optionally substituted 4- to 8-membered nitrogen-containing heterocycle, ring Q and the "nitrogen-containing heterocycle" commonly have one bond of each ring (i.e., they are condensed) to form a bicycle. The bond of ring Q and the bond of the "nitrogen-containing heterocycle", which are involved in the formation of bicycle, have the same multiplicity.

For example, when the bicycle is the ring represented by (A)

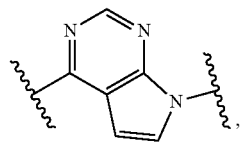 [SMILES: *c1ncnc2c1ccn2*]

then ring Q is pyrimidine and the "nitrogen-containing heterocycle" is pyrrole. When the bicycle is the ring represented by (B)

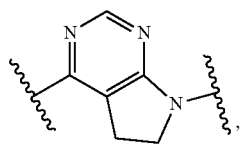 [SMILES: *c1ncnc2c1CCN2*]

then ring Q is pyrimidine, and the "nitrogen-containing heterocycle" is dihydropyrrole.

The "nitrogen-containing heterocycle" optionally has 1 to 3 substituents at substitutable positions. Examples of the substituent include those similar to the substituent that the "heterocyclic group" of the "optionally substituted heterocyclic group" for $R^{4a}$ or $R^{4b}$ optionally has. When the number of the substituents is not less than 2, the respective substituents may be the same or different.

The "optionally substituted 4- to 8-membered nitrogen-containing heterocycle" formed by $R^1$ and $R^{4c}$ in combination together with the adjacent carbon atom and nitrogen atom is preferably a 5- or 6-membered nitrogen-containing heterocycle (e.g., pyrrole, pyrazole, imidazole, dihydropyrrole, tetrahydropyridine) optionally substituted by 1 to 3 substituents selected from
(1) a halogen atom;
(2) a hydroxy group;
(3) a $C_{1-6}$ alkoxy group;
(4) a $C_{1-6}$ alkyl group;
and the like,
or the like.

$R^1$ is preferably
(1) (a) a hydrogen atom,
    (b) a halogen atom,
    (c) a hydroxy group,
    (d) a $C_{1-6}$ alkoxy group,
    (e) a $C_{1-6}$ alkyl group
    or the like; or,
(2) when $A^1$ $CR^{4a}R^{4b}$, $R^1$ and $R^{4a}$ and/or $R^{4b}$ in combination form, together with the adjacent carbon atoms, a 5- or 6-membered ring (e.g., cyclopentadiene, cyclopentene, cyclohexene, benzene, pyrrole, pyrazole, pyridine, pyrimidine) optionally substituted by 1 to 3 substituents selected from
    (a) a halogen atom,
    (b) a hydroxy group,
    (c) a $C_{1-6}$ alkoxy group,
    (d) a $C_{1-6}$ alkyl group
    and the like
or the like; or
(3) when $A^1$ is $NR^{4c}$, $R^1$ and $R^{4c}$ in combination form, together with the adjacent carbon atom and nitrogen atom, a 5- or 6-membered nitrogen-containing heterocycle (e.g., pyrrole, pyrazole, imidazole, dihydropyrrole, tetrahydropyridine) optionally substituted by 1 to 3 substituents selected from
    (a) a halogen atom,
    (b) a hydroxy group,
    (c) a $C_{1-6}$ alkoxy group,
    (d) a $C_{1-6}$ alkyl group
    and the like
or the like.

$R^1$ is more preferably a hydrogen atom.

$R^2$ is a hydrogen atom, a cyano group or an optionally substituted hydrocarbon group.

Examples of the "hydrocarbon group" of the "optionally substituted hydrocarbon group" for $R^2$ include those similar to the "hydrocarbon group" of the "optionally substituted hydrocarbon group" for $R^{4a}$, $R^{4b}$ or $R^{4c}$.

The "hydrocarbon group" of the "optionally substituted hydrocarbon group" for $R^2$ optionally has 1 to 3 substituents at substitutable positions. Examples of the substituent include those similar to the substituent that the "hydrocarbon group" of the "optionally substituted hydrocarbon group" for $R^{4a}$, $R^{4b}$ or $R^{4c}$ optionally has. When the number of the substituents is not less than 2, the respective substituents may be the same or different.

$R^2$ is preferably
(1) a hydrogen atom;
(2) a cyano group;
(3) a $C_{1-6}$ alkyl group
or the like.

$R^2$ is more preferably a hydrogen atom.

$R^3$ is an acyl group or an optionally substituted 5- or 6-membered aromatic ring group.

Examples of the "acyl group" for $R^3$ include a group represented by the formula: $-COR^{A1}$, $-CO-OR^{A1}$, $-CO-SR^{A1}$, $-CS-OR^{A1}$, $-CS-SR^{A1}$, $-SO_2R^{A1}$, $-SOR^{A1}$, $-CO-NR^{A2}R^{B2}$, $-CS-NR^{A2}R^{B2}$ or $-SO_2NR^{A2}R^{B2}$ wherein $R^{A1}$ is a hydrogen atom, an optionally substituted hydrocarbon group or an optionally substituted heterocyclic group, $R^{A2}$ and $R^{B2}$ are each independently a hydrogen atom, an optionally substituted hydrocarbon group or an optionally substituted heterocyclic group, or $R^{A2}$ and $R^{B2}$ in combination, together with the adjacent nitrogen atom, form an optionally substituted nitrogen-containing heterocycle, and the like.

Examples of the "hydrocarbon group" of the "optionally substituted hydrocarbon group" for $R^{A1}$, $R^{A2}$ or $R^{B2}$ include those similar to the "hydrocarbon group" of the "optionally substituted hydrocarbon group" for $R^{4a}$, $R^{4b}$ or $R^{ic}$.

The "hydrocarbon group" of the "optionally substituted hydrocarbon group" for $R^{A1}$, $R^{A2}$ or $R^{B2}$ optionally has 1 to 3 substituents at substitutable positions. Examples of the substituent include those similar to the substituent that the "hydrocarbon group" of the "optionally substituted hydrocarbon group" for $R^{4a}$, $R^{4b}$ or $R^{4c}$ optionally has. When the number of the substituents is not less than 2, the respective substituents may be the same or different.

Examples of the "heterocyclic group" of the "optionally substituted heterocyclic group" for $R^{A1}$, $R^{A2}$ or $R^{B2}$ include those similar to the "heterocyclic group" of the "optionally substituted heterocyclic group" for $R^{4a}$ or $R^{4b}$.

The "heterocyclic group" of the "optionally substituted heterocyclic group" for $R^{A1}$, $R^{A2}$ or $R^{B2}$ optionally has 1 to 3 substituents at substitutable positions. Examples of the substituent include those similar to the substituent that the "heterocyclic group" of the "optionally substituted heterocyclic group" for $R^{4a}$ or $R^{4b}$ optionally has. When the number of the substituents is not less than 2, the respective substituents may be the same or different.

Examples of the "nitrogen-containing heterocycle" of the "optionally substituted nitrogen-containing heterocycle" formed by $R^{A2}$ and $R^{B2}$ together with the adjacent nitrogen atom include a 5- to 7-membered nitrogen-containing heterocycle containing at least one nitrogen atom and further optionally containing 1 or 2 hetero atoms selected from an oxygen atom, a sulfur atom and a nitrogen atom, as a ring constituting atom besides carbon atom. Specific examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 3 substituents at substitutable positions. Examples of the substituent include those similar to the substituent that the "heterocyclic group" of the "optionally substituted heterocyclic group" for $R^{4a}$ or $R^{4b}$ optionally has. When the number of the substituents is not less than 2, the respective substituents may be the same or different.

The "acyl group" for $R^3$ is preferably
(1) a formyl group;
(2) a $C_{1-6}$ alkyl-carbonyl group optionally substituted by 1 to 3 substituents selected from
    (i) a halogen atom,
    (ii) an amino group,
    (iii) a carboxyl group,
    (iv) a $C_{1-6}$ alkoxy-carbonyl group,
    (v) a $C_{6-14}$ aryl group (e.g., phenyl), and
    (vi) a $C_{1-6}$ alkoxy group;
(3) a $C_{1-6}$ alkoxy-carbonyl group optionally substituted by 1 to 3 substituents selected from
    (i) a halogen atom,
    (ii) a $C_{6-14}$ aryl group (e.g., phenyl),
    (iii) a $C_{1-6}$ alkoxy group, and
    (iv) a heterocyclic group (e.g., tetrahydrofuryl);
(4) a $C_{3-10}$ cycloalkyl-carbonyl group (e.g., cyclopropylcarbonyl, cyclopentylcarbonyl, cyclohexylcarbonyl);
(5) a $C_{6-14}$ aryl-carbonyl group (e.g., benzoyl) optionally substituted by 1 to 3 halogen atoms;
(6) a carbamoyl group optionally mono- or di-substituted by substituent(s) selected from
    (i) a $C_{1-6}$ alkyl group optionally substituted by 1 to 3 substituents selected from
        (a) a halogen atom,
        (b) a $C_{1-6}$ alkoxy-carbonyl group,
        (c) a $C_{6-14}$ aryl group (e.g., phenyl),
        (d) a $C_{1-6}$ alkoxy group, and
        (e) an aromatic heterocyclic group (e.g., furyl),
    (ii) a $C_{3-10}$ cycloalkyl group (e.g., cyclopentyl, cyclohexyl),
    (iii) a $C_{6-14}$ aryl group (e.g., phenyl) optionally substituted by 1 to 3 substituents selected from
        (a) a halogen atom,
        (b) a $C_{1-6}$ alkyl group optionally substituted by 1 to 3 halogen atoms, and
        (c) a $C_{1-6}$ alkoxy group,
    (iv) a $C_{1-6}$ alkylsulfonyl group (e.g., methylsulfonyl), and
    (v) an aromatic heterocyclic group (e.g., pyridyl) optionally substituted by 1 to 3 $C_{1-6}$ alkyl groups;
(7) a $C_{1-6}$ alkylsulfonyl group (e.g., methylsulfonyl, ethylsulfonyl, isopropylsulfonyl) optionally substituted by 1 to 3 substituents selected from
    (i) a halogen atom, and
    (ii) a $C_{6-14}$ aryl group (e.g., phenyl);
(8) a $C_{6-14}$ arylsulfonyl group (e.g., benzenesulfonyl) optionally substituted by 1 to 3 substituents selected from
    (i) a halogen atom, and
    (ii) a $C_{1-6}$ alkyl group;
(9) a $C_{3-10}$ cycloalkylsulfonyl group (e.g., cyclopropylsulfonyl);
(10) a sulfamoyl group optionally mono- or di-substituted by substituent(s) selected from
    (i) a $C_{1-6}$ alkyl group optionally substituted by 1 to 3 substituents selected from
        (a) a halogen atom, and
        (b) a non-aromatic heterocyclic group (e.g., pyrrolidinyl) optionally substituted by oxo group(s);
(11) a thiocarbamoyl group optionally mono- or di-substituted by substituent(s) selected from a $C_{1-6}$ alkyl group optionally substituted by 1 to 3 halogen atoms;
(12) an aromatic heterocyclylcarbonyl group (e.g., furylcarbonyl, thienylcarbonyl, pyrazolylcarbonyl, pyridylcarbonyl, isoxazolylcarbonyl, thiazolylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, tetrahydropyranylcarbonyl) optionally substituted by 1 to 3 substituents selected from a $C_{1-6}$ alkyl group optionally substituted by 1 to 3 halogen atoms;
(14) a $C_{1-6}$ alkylthio-carbonyl group optionally substituted by 1 to 3 substituents selected from
    (i) a halogen atom,
    (ii) a $C_{6-14}$ aryl group,
    (iii) a $C_{1-6}$ alkoxy group, and
    (iv) a heterocyclic group;
and the like.

Examples of the "5- or 6-membered aromatic ring group" of the "optionally substituted 5- or 6-membered aromatic ring group" for $R^3$ include phenyl; pyrrolyl, pyrazolyl, imidazolyl, triazolyl (1,2,3-triazolyl, 1,2,4-triazolyl, 1,3,4-triazolyl), tetrazolyl, oxazolyl, isoxazolyl, thiazolyl, isothiazolyl, oxadiazolyl, thiadiazolyl, furyl, thienyl, pyridyl, pyrazinyl, pyridazinyl, pyrimidinyl, pyrazinyl, triazinyl and the like.

The "5- or 6-membered aromatic ring group" of the "optionally substituted 5- or 6-membered aromatic ring group" for $R^3$ optionally has 1 to 3 substituents at substitutable positions. Examples of the substituent include those similar to the substituent that the "6-membered aromatic ring" of the "substituted 6-membered aromatic ring" for ring P has. When the number of the substituents is not less than 2, the respective substituents may be the same or different.

The "5- or 6-membered aromatic ring group" of the "optionally substituted 5- or 6-membered aromatic ring group" for $R^3$ is preferably oxadiazolyl, thiadiazolyl, phenyl, pyridyl, pyrazinyl, pyrimidinyl or the like, more preferably oxadiazolyl, pyrimidinyl or the like.

The "optionally substituted 5- or 6-membered aromatic ring group" for $R^3$ is preferably oxadiazolyl, thiadiazolyl, phenyl, pyridyl, pyrazinyl, pyrimidinyl or the like (preferably oxadiazolyl, pyrimidinyl), each of which is optionally substituted by 1 to 3 substituents selected from
(1) a $C_{1-6}$ alkyl-carbonyl group optionally substituted by 1 to 3 halogen atoms;
(2) a $C_{1-6}$ alkoxy-carbonyl group optionally substituted by 1 to 3 substituents selected from
  (a) a halogen atom,
  (b) a $C_{1-6}$ alkoxy group, and
  (c) a $C_{6-14}$ aryl group (e.g., phenyl);
(3) a carbamoyl group optionally mono- or di-substituted by substituent(s) selected from
  (a) a $C_{1-6}$ alkyl group optionally substituted by 1 to 3 substituents selected from a halogen atom, a hydroxy group and a $C_{1-6}$ alkoxy group, and
  (b) a non-aromatic heterocyclic group (e.g., tetrahydrofuryl);
(4) a carboxy group;
(5) a hydroxy group;
(6) a halogen atom;
(7) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group, and
  (e) a $C_{1-6}$ alkoxy group;
(8) a $C_{1-6}$ alkoxy group;
(9) a $C_{3-10}$ cycloalkyl group (e.g., cyclopropyl);
(10) a non-aromatic heterocyclic group (e.g., tetrahydrofuryl);
and the like.

$R^3$ is preferably
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., methoxycarbonyl, tert-butoxycarbonyl, isopropoxycarbonyl) optionally substituted by 1 to 3 substituents selected from
  (i) a halogen atom,
  (ii) a $C_{1-6}$ alkoxy group,
  (iii) a $C_{6-14}$ aryl group (e.g., phenyl), and
  (iv) a heterocyclic group (e.g., tetrahydrofuryl);
(3) a $C_{3-10}$ cycloalkyl-carbonyl group (e.g., cyclopropylcarbonyl, cyclopentylcarbonyl);
(4) a $C_{6-14}$ aryl-carbonyl group (e.g., benzoyl);
(5) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(6) a $C_{1-6}$ alkylsulfonyl group (e.g., methylsulfonyl) optionally substituted by 1 to 3 $C_{6-14}$ aryl groups (e.g., phenyl);
(7) a $C_{6-14}$ arylsulfonyl group (e.g., benzenesulfonyl) optionally substituted by 1 to 3 $C_{1-6}$ alkyl groups (e.g., methyl);
(8) a $C_{3-10}$ cycloalkylsulfonyl group (e.g., cyclopropylsulfonyl);
(9) an aromatic heterocyclylcarbonyl group (e.g., furylcarbonyl, pyrazolylcarbonyl, pyridylcarbonyl, isoxazolylcarbonyl, thiazolylcarbonyl) optionally substituted by 1 to 3 substituents selected from a $C_{1-6}$ alkyl group optionally substituted by 1 to 3 halogen atoms (e.g., a fluorine atom);
(10) an non-aromatic heterocyclylcarbonyl group (e.g., tetrahydropyranylcarbonyl);
(11) a $C_{1-6}$ alkylthio-carbonyl group optionally substituted by 1 to 3 substituents selected from
  (i) a halogen atom,
  (ii) a $C_{6-14}$ aryl group,
  (iii) a $C_{1-6}$ alkoxy group, and
  (iv) a heterocyclic group;
(12) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a $C_{1-6}$ alkyl-carbonyl group optionally substituted by 1 to 3 halogen atoms,
  (ii) a $C_{1-6}$ alkoxy-carbonyl group optionally substituted by 1 to 3 substituents selected from
    (a) a halogen atom,
    (b) a $C_{1-6}$ alkoxy group, and
    (c) a $C_{6-14}$ aryl group (e.g., phenyl),
  (iii) a carbamoyl group optionally mono- or di-substituted by substituent(s) selected from
    (a) a $C_{1-6}$ alkyl group optionally substituted by 1 to 3 substituents selected from a halogen atom, a hydroxy group and a $C_{1-6}$ alkoxy group, and
    (b) a non-aromatic heterocyclic group (e.g., tetrahydrofuryl),
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy,
  (viii) a $C_{1-6}$ alkoxy group,
  (ix) a $C_{3-10}$ cycloalkyl group (e.g., cyclopropyl), and
  (x) a non-aromatic heterocyclic group (e.g., tetrahydrofuryl);
or the like.

$R^3$ is more preferably
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., methoxycarbonyl, tert-butoxycarbonyl, isopropoxycarbonyl) optionally substituted by 1 to 3 substituents selected from
  (i) a halogen atom,
  (ii) a $C_{1-6}$ alkoxy group,
  (iii) a $C_{6-14}$ aryl group (e.g., phenyl), and
  (iv) a heterocyclic group (e.g., tetrahydrofuryl);
(3) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(4) a $C_{1-6}$ alkylsulfonyl group (e.g., methylsulfonyl) optionally substituted by 1 to 3 $C_{6-14}$ aryl groups (e.g., phenyl);
(5) a $C_{1-6}$ alkylthio-carbonyl group;
(6) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a $C_{1-6}$ alkyl-carbonyl group,
  (ii) a $C_{1-6}$ alkoxy-carbonyl group,
  (iii) a carbamoyl group optionally mono- or di-substituted by $C_{1-6}$ alkyl group(s),
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group,
  (viii) a $C_{1-6}$ alkoxy group,
  (ix) a $C_{3-10}$ cycloalkyl group (e.g., cyclopropyl), and
  (x) a non-aromatic heterocyclic group (e.g., tetrahydrofuryl);
or the like.

$R^3$ is still more preferably
(1) a $C_{1-6}$ alkylthio-carbonyl group;
(2) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a $C_{1-6}$ alkyl-carbonyl group,
  (ii) a $C_{1-6}$ alkoxy-carbonyl group,
  (iii) a carbamoyl group optionally mono- or di-substituted by $C_{1-6}$ alkyl group(s),
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group,
  (viii) a $C_{1-6}$ alkoxy group,
  (ix) a $C_{3-10}$ cycloalkyl group (e.g., cyclopropyl), and
  (x) a non-aromatic heterocyclic group (e.g., tetrahydrofuryl);
or the like.

$R^3$ is particularly preferably
(1) a $C_{1-6}$ alkylthio-carbonyl group;
(2) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a halogen atom,
  (ii) a $C_{1-6}$ alkyl group
  (iii) a $C_{1-6}$ alkoxy group, and
  (iv) a $C_{3-10}$ cycloalkyl group (e.g., cyclopropyl);
or the like.

$R^{3a}$ is a group represented by the formula: —CO—SR$^{41}$ wherein R$^{41}$ is as defined above, or an optionally substituted 5- or 6-membered aromatic ring group.

$R^{3a}$ is another preferable embodiment of $R^3$.

Examples of the "optionally substituted 5- or 6-membered aromatic ring group" include for $R^{3a}$ include those similar to the "optionally substituted 5- or 6-membered aromatic ring group" include for $R^3$.

$R^{3a}$ is preferably
(1) a $C_{1-6}$ alkylthio-carbonyl group;
(2) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a $C_{1-6}$ alkyl-carbonyl group,
  (ii) a $C_{1-6}$ alkoxy-carbonyl group,
  (iii) a carbamoyl group optionally mono- or di-substituted by $C_{1-6}$ alkyl group(s),
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group,
  (viii) a $C_{1-6}$ alkoxy group,
  (ix) a $C_{3-10}$ cycloalkyl group (e.g., cyclopropyl), and
  (x) a non-aromatic heterocyclic group (e.g., tetrahydrofuryl);
or the like.

$R^{3a}$ is more preferably
(1) a $C_{1-6}$ alkylthio-carbonyl group;
(2) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a halogen atom,
  (ii) a $C_{1-6}$ alkyl group
  (iii) a $C_{1-6}$ alkoxy group, and
  (iv) a $C_{3-10}$ cycloalkyl group (e.g., cyclopropyl);
or the like.

$R^A$ is a hydrogen atom, an optionally substituted hydrocarbon group or an optionally substituted heterocyclic group.

Examples of the "hydrocarbon group" of the "optionally substituted hydrocarbon group" for $R^A$ include those similar to the "hydrocarbon group" of the "optionally substituted hydrocarbon group" for $R^{4a}$, $R^{4b}$ or $R^{4c}$.

The "hydrocarbon group" of the "optionally substituted hydrocarbon group" for $R^A$ optionally has 1 to 3 substituents at substitutable positions. Examples of the substituent include those similar to the substituent that the "hydrocarbon group" of the "optionally substituted hydrocarbon group" for $R^{4a}$, $R^{4b}$ or $R^{4c}$ optionally has. When the number of the substituents is not less than 2, the respective substituents may be the same or different.

Examples of the "heterocyclic group" of the "optionally substituted heterocyclic group" for $R^A$ include those similar to the "heterocyclic group" of the "optionally substituted heterocyclic group" for $R^{4a}$ or $R^{4b}$.

The "heterocyclic group" of the "optionally substituted heterocyclic group" for $R^A$ optionally has 1 to 3 substituents at substitutable positions. Examples of the substituent include those similar to the substituent that the "heterocyclic group" of the "optionally substituted heterocyclic group" for $R^{4a}$ or $R^{4b}$ optionally has. When the number of the substituents is not less than 2, the respective substituents may be the same or different.

$R^A$ is preferably (1) a hydrogen atom;
(2) a $C_{3-10}$ cycloalkyl group (e.g., cyclopropyl, cyclohexyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(3) a $C_{6-14}$ aryl group (e.g., phenyl, naphthyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(4) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
(5) a $C_{2-6}$ alkenyl group (e.g., ethenyl, 1-propenyl) optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
(6) a $C_{7-13}$ aralkyl group (e.g., benzyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group, and
    (d) a halogen atom;
(7) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(8) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;
or the like.

$R^A$ is more preferably (1) a hydrogen atom;
(2) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
(3) an aromatic heterocyclic group (e.g., thienyl, furyl, is pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(4) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;
or the like.

$R^A$ is still more preferably (1) a $C_{1-6}$ alkyl group optionally substituted by 1 to 3 substituents selected from
    (a) a halogen atom,
    (b) a hydroxy group, and
    (c) a $C_{1-6}$ alkoxy group;
(2) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
- (a) a $C_{1-6}$ alkyl group optionally substituted by 1 to 3 halogen atoms,
- (b) a hydroxy group,
- (c) a $C_{1-6}$ alkoxy group,
- (d) a halogen atom, and
- (e) an oxo group;

or the like.

$R^B$ is a hydrogen atom or a $C_{1-6}$ alkyl group. $R^B$ is preferably a hydrogen atom, a methyl group or the like.

Preferable embodiment of compound (I) is a compound represented by the formula (Ia) or a salt thereof. Another preferable embodiment of compound (I) is a compound represented by the formula (Ib) or a salt thereof.

Preferable examples of compound (I) include the following compounds.

[Compound A-1]

Compound (I) wherein
ring P is a benzene ring, a pyridine ring, a pyridazine ring, a pyrimidine ring or a pyrazine ring, each of which is substituted by 1 to 3 substituents selected from
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
- (a) a $C_{1-6}$ alkyl group optionally substituted by 1 to 3 halogen atoms,
- (b) a hydroxy group,
- (c) a $C_{1-6}$ alkoxy group optionally substituted by 1 to 3 halogen atoms, and
- (d) a halogen atom, (2) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
- (a) a $C_{1-6}$ alkyl group optionally substituted by 1 to 3 halogen atoms,
- (b) a hydroxy group,
- (c) a $C_{1-6}$ alkoxy group optionally substituted by 1 to 3 halogen atoms,
- (d) a halogen atom, and
- (e) an oxo group, (3) an amino group optionally mono- or di-substituted by substituent(s) selected from
- (a) a $C_{1-6}$ alkyl group optionally substituted by 1 to 3 halogen atoms,
- (b) a $C_{1-6}$ alkyl-carbonyl group optionally substituted by 1 to 3 halogen atoms,
- (c) a $C_{1-6}$ alkoxy-carbonyl group optionally substituted by 1 to 3 halogen atoms,
- (d) a $C_{1-6}$ alkylsulfonyl group (e.g., methylsulfonyl) optionally substituted by 1 to 3 halogen atoms,
- (e) a carbamoyl group optionally mono- or di-substituted by $C_{1-6}$ alkyl group(s) optionally substituted by 1 to 3 halogen atoms, and
- (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), (4) a $C_{1-6}$ alkyl-carbonyl group optionally substituted by 1 to 3 halogen atoms, (5) a $C_{1-6}$ alkoxy-carbonyl group (e.g., methoxycarbonyl) optionally substituted by 1 to 3 substituents selected from
- (a) a halogen atom,
- (b) a $C_{1-6}$ alkoxy group,
- (c) a $C_{6-14}$ aryl group (e.g., phenyl), and
- (d) a heterocyclic group (e.g., tetrahydrofuryl), (6) a $C_{1-6}$ alkylsulfonyl group (e.g., methylsulfonyl, ethylsulfonyl, isopropylsulfonyl) optionally substituted by 1 to 3 halogen atoms, (7) a carbamoyl group optionally mono- or di-substituted by $C_{1-6}$ alkyl group(s) optionally substituted by 1 to 3 halogen atoms, (8) a carboxy group, (9) a hydroxy group,

(10) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms,

(11) a mercapto group,

(12) a cyano group,

(13) a nitro group,

(14) a halogen atom (e.g., a fluorine atom, a chlorine atom, a bromine atom),

(15) a $C_{3-10}$ cycloalkoxy group (e.g., cyclopropoxy, cyclopentyloxy) optionally substituted by 1 to 3 substituents selected from
- (a) a halogen atom (e.g., a fluorine atom), and
- (b) a $C_{1-6}$ alkoxy group (e.g., methoxy), and

(16) a $C_{1-6}$ alkyl group optionally substituted by 1 to 3 substituents selected from
- (a) a halogen atom,
- (b) a carboxy group,
- (c) a hydroxy group,
- (d) a $C_{1-6}$ alkoxy-carbonyl group,
- (e) a $C_{1-6}$ alkoxy group, and
- (f) an amino group optionally mono- or di-substituted by $C_{1-6}$ alkyl group(s);

ring Q is a benzene ring, a pyridine ring, a pyridazine ring or a pyrimidine ring, each of which is optionally substituted by 1 to 3 substituents selected from
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
- (a) a $C_{1-6}$ alkyl group optionally substituted by 1 to 3 halogen atoms,
- (b) a hydroxy group,
- (c) a $C_{1-6}$ alkoxy group optionally substituted by 1 to 3 halogen atoms, and
- (d) a halogen atom, (2) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
- (a) a $C_{1-6}$ alkyl group optionally substituted by 1 to 3 halogen atoms,
- (b) a hydroxy group,
- (c) a $C_{1-6}$ alkoxy group optionally substituted by 1 to 3 halogen atoms,
- (d) a halogen atom, and
- (e) an oxo group, (3) an amino group optionally mono- or di-substituted by substituent(s) selected from
- (a) a $C_{1-6}$ alkyl group optionally substituted by 1 to 3 halogen atoms,
- (b) a $C_{1-6}$ alkyl-carbonyl group optionally substituted by 1 to 3 halogen atoms,
- (c) a $C_{1-6}$ alkoxy-carbonyl group optionally substituted by 1 to 3 halogen atoms,
- (d) a $C_{1-6}$ alkylsulfonyl group (e.g., methylsulfonyl) optionally substituted by 1 to 3 halogen atoms, (e) a carbamoyl group optionally mono- or di-substituted by $C_{1-6}$ alkyl group(s) optionally substituted by 1 to 3 halogen atoms, and (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), (4) a $C_{1-6}$ alkyl-carbonyl group optionally substituted by 1 to 3 halogen atoms, (5) a $C_{1-6}$ alkoxy-carbonyl group (e.g., methoxycarbonyl) optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl), (6) a $C_{1-6}$ alkylsulfonyl group (e.g., methylsulfonyl, ethylsulfonyl, isopropylsulfonyl) optionally substituted by 1 to 3 halogen atoms, (7) a carbamoyl group optionally mono- or di-substituted by $C_{1-6}$ alkyl group(s) optionally substituted by 1 to 3 halogen atoms, (8) a carboxy group, (9) a hydroxy group,

(10) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms,

(11) a mercapto group,

(12) a cyano group,

(13) a nitro group,

(14) a halogen atom (e.g., a fluorine atom, a chlorine atom, a bromine atom),

(15) a $C_{3-10}$ cycloalkoxy group (e.g., cyclopropoxy, cyclopentyloxy) optionally substituted by 1 to 3 substituents selected from
   (a) a halogen atom (e.g., a fluorine atom), and
   (b) a $C_{1-6}$ alkoxy group (e.g., methoxy), and

(16) a $C_{1-6}$ alkyl group optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);

$A^1$ is (1) $CR^{4a}R^{4b}$ wherein $R^{4a}$ and $R^{4b}$ are each independently a hydrogen atom, a $C_{1-6}$ alkyl group, a hydroxy group or a $C_{1-6}$ alkoxy group, (2) $NR^{4c}$ wherein $R^{4c}$ is a hydrogen atom, a $C_{1-6}$ alkyl group or a $C_{3-10}$ cycloalkyl group, (3) O, or (4) S;

$L^1$ is ethylene, trimethylene or tetramethylene, each of which is optionally substituted by 1 to 3 substituents selected from (1) a halogen atom, (2) a hydroxy group, (3) a $C_{1-6}$ alkoxy group, (4) a $C_{1-6}$ alkyl-carbonyl group optionally substituted by 1 to 3 halogen atoms, (5) a $C_{1-6}$ alkoxy-carbonyl group optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl), (6) a $C_{1-6}$ alkylsulfonyl group (e.g., methylsulfonyl, ethylsulfonyl, isopropylsulfonyl) optionally substituted by 1 to 3 halogen atoms, (7) a cyano group, and (8) a nitro group;

$L^2$ is (1) a bond, or (2) methylene or ethylene, each of which is optionally substituted by 1 to 3 substituents selected from
   (a) a halogen atom,
   (b) a hydroxy group, and
   (c) a $C_{1-6}$ alkoxy group;

$L^3$ and $L^4$ are each independently methylene, ethylene or trimethylene, each of which is optionally substituted by 1 to 3 substituents selected from (1) a halogen atom, (2) a hydroxy group, (3) a $C_{1-6}$ alkoxy group, (4) a $C_{1-6}$ alkyl-carbonyl group optionally substituted by 1 to 3 halogen atoms, and (5) a $C_{1-6}$ alkoxy-carbonyl group optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl);

$R^1$ is (1)(a) a hydrogen atom,
   (b) a halogen atom,
   (c) a hydroxy group,
   (d) a $C_{1-6}$ alkoxy group, or
   (e) a $C_{1-6}$ alkyl group, or, (2) when $A^1$ is $CR^{4a}R^{4b}$, $R^1$ and $R^{4a}$ and/or $R^{4b}$ in combination optionally form, together with the adjacent carbon atoms, a 5- or 6-membered ring (e.g., cyclopentadiene, cyclopentene, cyclohexene, benzene, pyrrole, pyrazole, pyridine, pyrimidine) optionally substituted by 1 to 3 substituents selected from
   (a) a halogen atom,
   (b) a hydroxy group,
   (c) a $C_{1-6}$ alkoxy group, and
   (d) a $C_{1-6}$ alkyl group, or (3) when $A^1$ is $NR^{4c}$, $R^1$ and $R^{4c}$ in combination optionally form, together with the adjacent carbon atom and nitrogen atom, a 5- or 6-membered nitrogen-containing heterocycle (e.g., pyrrole, pyrazole, imidazole, dihydropyrrole, tetrahydropyridine) optionally substituted by 1 to 3 substituents selected from
   (a) a halogen atom,
   (b) a hydroxy group,
   (c) a $C_{1-6}$ alkoxy group, and
   (d) a $C_{1-6}$ alkyl group;

$R^2$ is (1) a hydrogen atom, (2) a cyano group, or (3) a $C_{1-6}$ alkyl group; and $R^3$ is (1) a $C_{1-6}$ alkyl-carbonyl group (e.g., acetyl, propionyl, butyryl, isobutyryl, isoamyl) optionally substituted by 1 to 3 substituents selected from
   (i) an amino group,
   (ii) a carboxyl group,
   (iii) a $C_{1-6}$ alkoxy-carbonyl group (e.g., methoxycarbonyl, ethoxycarbonyl),
   (iv) a $C_{6-14}$ aryl group (e.g., phenyl), and
   (v) a $C_{1-6}$ alkoxy group (e.g., methoxy), (2) a $C_{1-6}$ alkoxy-carbonyl group (e.g., methoxycarbonyl, tert-butoxycarbonyl, isopropoxycarbonyl) optionally substituted by 1 to 3 substituents selected from
  (i) a halogen atom,
  (ii) a $C_{1-6}$ alkoxy group,
  (iii) a $C_{6-14}$ aryl group (e.g., phenyl), and
  (iv) a heterocyclic group (e.g., tetrahydrofuryl),
(3) a $C_{3-10}$ cycloalkyl-carbonyl group (e.g., cyclopropylcarbonyl, cyclopentylcarbonyl),
(4) a $C_{6-14}$ aryl-carbonyl group (e.g., benzoyl),
(5) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl),
(6) a $C_{1-6}$ alkylsulfonyl group (e.g., methylsulfonyl) optionally substituted by 1 to 3 $C_{6-14}$ aryl groups (e.g., phenyl),
(7) a $C_{6-14}$ arylsulfonyl group (e.g., benzenesulfonyl) optionally substituted by 1 to 3 $C_{1-6}$ alkyl groups (e.g., methyl),
(8) a $C_{3-10}$ cycloalkylsulfonyl group (e.g., cyclopropylsulfonyl),
(9) an aromatic heterocyclylcarbonyl group (e.g., furylcarbonyl, pyrazolylcarbonyl, pyridylcarbonyl, isoxazolylcarbonyl, thiazolylcarbonyl) optionally substituted by 1 to 3 substituents selected from a $C_{1-6}$ alkyl group optionally substituted by 1 to 3 halogen atoms (e.g., a fluorine atom),
(10) an non-aromatic heterocyclylcarbonyl group (e.g., tetrahydropyranylcarbonyl), or
(11) a 5- or 6-membered aromatic ring group (e.g., oxadiazolyl, thiadiazolyl, phenyl, pyridyl, pyrazinyl, pyrimidinyl) optionally substituted by 1 to 3 substituents selected from
  (i) a $C_{1-6}$ alkyl-carbonyl group optionally substituted by 1 to 3 halogen atoms,
  (ii) a $C_{1-6}$ alkoxy-carbonyl group optionally substituted by 1 to 3 substituents selected from
    (a) a halogen atom,
    (b) a $C_{1-6}$ alkoxy group, and
    (c) a $C_{6-14}$ aryl group (e.g., phenyl),
  (iii) a carbamoyl group optionally mono- or di-substituted by $C_{1-6}$ alkyl group(s) optionally substituted by 1 to 3 halogen atoms,
  (iv) a carboxy group,
  (v) a hydroxy group,
  (vi) a halogen atom, and
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group.

[Compound B-1]
Compound (I) wherein
ring P is a benzene ring, a pyridine ring or a pyrimidine ring, each of which is substituted by 1 to 3 substituents selected from
(1) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
(2) a $C_{1-6}$ alkyl-carbonyl group optionally substituted by 1 to 3 halogen atoms;
(3) a $C_{1-6}$ alkoxy-carbonyl group (e.g., methoxycarbonyl) optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(4) a $C_{1-6}$ alkylsulfonyl group (e.g., methylsulfonyl, ethylsulfonyl, isopropylsulfonyl) optionally substituted by 1 to 3 halogen atoms;
(5) a carboxy group;
(6) a cyano group;
(7) a nitro group; and
(8) a halogen atom (e.g., a fluorine atom, a chlorine atom, a bromine atom);
ring Q is a benzene ring, a pyridine ring or a pyrimidine ring, each of which is optionally substituted by 1 to 3 substituents selected from
(1) a halogen atom (e.g., a fluorine atom, a chlorine atom, a bromine atom); and
(2) a $C_{1-6}$ alkyl group optionally substituted by 1 to 3 halogen atoms;
$A^1$ is
(1) $CR^{4a}R^{4b}$ wherein $R^{4a}$ and $R^{4b}$ are each independently a hydrogen atom or a $C_{1-6}$ alkyl group;
(2) $NR^{4c}$ wherein $R^{4c}$ is a hydrogen atom or a $C_{1-6}$ alkyl group; or
(3) O;
$L^1$ is ethylene, trimethylene or tetramethylene;
$L^2$ is a bond, methylene or ethylene;
$L^3$ and $L^4$ are each independently methylene, ethylene or trimethylene;
$R^1$ is
(1)(a) a hydrogen atom,
  (b) a halogen atom,
  (c) a hydroxy group,
  (d) a $C_{1-6}$ alkoxy group, or
  (e) a $C_{1-6}$ alkyl group; or,
(2) when $A^1$ is $CR^{4a}R^{4b}$, $R^1$ and $R^{4a}$ and/or $R^{4b}$ in combination optionally form, together with the adjacent carbon atoms, a 5- or 6-membered ring (e.g., cyclopentadiene, cyclopentene, cyclohexene, benzene, pyrrole, pyrazole, pyridine, pyrimidine) optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group; or
(3) when $A^1$ is $NR^{4c}$, $R^1$ and $R^{4c}$ in combination optionally form, together with the adjacent carbon atom and nitrogen atom, a 5- or 6-membered nitrogen-containing heterocycle (e.g., pyrrole, pyrazole, imidazole, dihydropyrrole, tetrahydropyridine) optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group;

R² is a hydrogen atom; and
R³ is
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., methoxycarbonyl, tert-butoxycarbonyl, isopropoxycarbonyl) optionally substituted by 1 to 3 substituents selected from
  (i) a halogen atom,
  (ii) a $C_{1-6}$ alkoxy group,
  (iii) a $C_{6-14}$ aryl group (e.g., phenyl), and
  (iv) a heterocyclic group (e.g., tetrahydrofuryl);
(3) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(4) a $C_{1-6}$ alkylsulfonyl group (e.g., methylsulfonyl) optionally substituted by 1 to 3 $C_{6-14}$ aryl groups (e.g., phenyl); or
(5) a 5- or 6-membered aromatic ring group (e.g., oxadiazolyl, thiadiazolyl, phenyl, pyridyl, pyrazinyl, pyrimidinyl) optionally substituted by 1 to 3 substituents selected from
  (i) a $C_{1-6}$ alkyl-carbonyl group,
  (ii) a $C_{1-6}$ alkoxy-carbonyl group,
  (iii) a carbamoyl group optionally mono- or di-substituted by $C_{1-6}$ alkyl group(s),
  (iv) a carboxy group,
  (v) a hydroxy group,
  (vi) a halogen atom, and
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group.

[Compound A-2]
A compound represented by the formula:

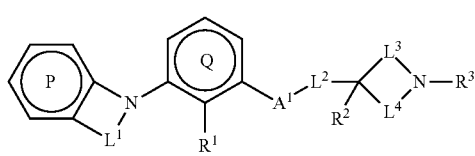

(I)

wherein
ring P is a benzene ring, a pyridine ring, a pyridazine ring, a pyrimidine ring or a pyrazine ring, each of which is substituted by 1 to 3 substituents selected from
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(2) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
(3) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 substituents selected from a halogen atom, a hydroxy group and a $C_{1-6}$ alkoxy group,
  (c) a $C_{1-6}$ alkoxy-carbonyl group optionally substituted by 1 to 3 halogen atoms,
  (d) a $C_{1-6}$ alkylsulfonyl group (e.g., methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms,
  (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and
  (g) an non-aromatic heterocyclylcarbonyl group (e.g., tetrahydrofurylcarbonyl);
(4) a $C_{1-6}$ alkyl-carbonyl group optionally substituted by 1 to 3 halogen atoms;
(5) a $C_{1-6}$ alkoxy-carbonyl group (e.g., methoxycarbonyl) optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(6) a $C_{1-5}$ alkylsulfonyl group (e.g., methylsulfonyl, ethylsulfonyl, isopropylsulfonyl) optionally substituted by 1 to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a hydroxy group and a $C_{1-6}$ alkoxy group, and
  (b) a non-aromatic heterocyclic group (e.g., tetrahydrofuryl);
(8) a carboxy group;
(9) a hydroxy group;
(10) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(11) a mercapto group;
(12) a cyano group;
(13) a nitro group;
(14) a halogen atom (e.g., a fluorine atom, a chlorine atom, a bromine atom);

(15) a $C_{3-10}$ cycloalkoxy group (e.g., cyclopropoxy, cyclopentyloxy) optionally substituted by 1 to 3 substituents selected from
   (a) a halogen atom (e.g., a fluorine atom), and
   (b) a $C_{1-6}$ alkoxy group (e.g., methoxy); and
(16) a $C_{1-6}$ alkyl group optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);
ring Q is a benzene ring, a pyridine ring, a pyridazine ring or a pyrimidine ring, each of which is optionally substituted by 1 to 3 substituents selected from
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom;
(2) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom, and
   (e) an oxo group;
(3) an amino group optionally mono- or di-substituted by substituent(s) selected from
   (a) a $C_{1-6}$ alkyl group optionally substituted by 1 to 3 halogen atoms,
   (b) a $C_{1-6}$ alkyl-carbonyl group optionally substituted by 1 to 3 substituents selected from a halogen atom, a hydroxy group and a $C_{1-6}$ alkoxy group,
   (c) a $C_{1-6}$ alkoxy-carbonyl group optionally substituted by 1 to 3 halogen atoms,
   (d) a $C_{1-6}$ alkylsulfonyl group (e.g., methylsulfonyl) optionally substituted by 1 to 3 halogen atoms,
   (e) a carbamoyl group optionally mono- or di-substituted by $C_{1-6}$ alkyl group(s) optionally substituted by 1 to 3 halogen atoms,
   (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and
   (g) an non-aromatic heterocyclylcarbonyl group (e.g., tetrahydrofurylcarbonyl);
(4) a $C_{1-6}$ alkyl-carbonyl group optionally substituted by 1 to 3 halogen atoms;
(5) a $C_{1-6}$ alkoxy-carbonyl group (e.g., methoxycarbonyl) optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl);
(6) a $C_{1-6}$ alkylsulfonyl group (e.g., methylsulfonyl, ethylsulfonyl, isopropylsulfonyl) optionally substituted by 1 to 3 halogen atoms;
(7) a carbamoyl group optionally mono- or di-substituted by substituent(s) selected from
   (a) a $C_{1-6}$ alkyl group optionally substituted by 1 to 3 substituents selected from a halogen atom, a hydroxy group and a $C_{1-6}$ alkoxy group, and
   (b) a non-aromatic heterocyclic group (e.g., tetrahydrofuryl);
(8) a carboxy group;
(9) a hydroxy group;
(10) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(11) a mercapto group;
(12) a cyano group;
(13) a nitro group;
(14) a halogen atom (e.g., a fluorine atom, a chlorine atom, a bromine atom);
(15) a $C_{3-10}$ cycloalkoxy group (e.g., cyclopropoxy, cyclopentyloxy) optionally substituted by 1 to 3 substituents selected from
   (a) a halogen atom (e.g., a fluorine atom), and
   (b) a $C_{1-6}$ alkoxy group (e.g., methoxy); and
(16) a $C_{1-6}$ alkyl group optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);
$A^1$ is
(1) $CR^{4a}R^{4b}$ wherein $R^{4a}$ and $R^{4b}$ are each independently a hydrogen atom, a $C_{1-6}$ alkyl group, a hydroxy group or a $C_{1-6}$ alkoxy group;
(2) $NR^{4c}$ wherein $R^4$ is a hydrogen atom, a $C_{1-6}$ alkyl group optionally substituted by 1 to 3 halogen atoms, or a $C_{3-10}$ cycloalkyl group;
(3) O; or
(4) S;
$L^1$ is ethylene, trimethylene or tetramethylene, each of is which is optionally substituted by 1 to 3 substituents selected from
(1) a halogen atom;
(2) a hydroxy group;
(3) a $C_{1-6}$ alkoxy group;
(4) a $C_{1-6}$ alkyl-carbonyl group optionally substituted by 1 to 3 halogen atoms;
(5) a $C_{1-6}$ alkoxy-carbonyl group optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl);
(6) a $C_{1-6}$ alkylsulfonyl group (e.g., methylsulfonyl, ethylsulfonyl, isopropylsulfonyl) optionally substituted by 1 to 3 halogen atoms;
(7) a cyano group; and
(8) a nitro group;

L² is
(1) a bond; or
(2) methylene or ethylene, each of which is optionally substituted by 1 to 3 substituents selected from
   (a) a halogen atom,
   (b) a hydroxy group, and
   (c) a $C_{1-6}$ alkoxy group;

L³ and L⁴ are each independently methylene, ethylene or trimethylene, each of which is optionally substituted by 1 to 3 substituents selected from
(1) a halogen atom;
(2) a hydroxy group;
(3) a $C_{1-6}$ alkoxy group;
(4) a $C_{1-6}$ alkyl-carbonyl group optionally substituted by 1 to 3 halogen atoms; and
(5) a $C_{1-6}$ alkoxy-carbonyl group optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl);

R¹ is
(1) a hydrogen atom,
(2) a halogen atom,
(3) a hydroxy group,
(4) a $C_{1-6}$ alkoxy group, or
(5) a $C_{1-6}$ alkyl group;

R² is
(1) a hydrogen atom;
(2) a cyano group; or
(3) a $C_{1-6}$ alkyl group; and R³ is
(1) a $C_{1-6}$ alkyl-carbonyl group (e.g., acetyl, propionyl, butyryl, isobutyryl, isoamyl) optionally substituted by 1 to 3 substituents selected from
   (i) an amino group,
   (ii) a carboxyl group,
   (iii) a $C_{1-6}$ alkoxy-carbonyl group (e.g., methoxycarbonyl, ethoxycarbonyl),
   (iv) a $C_{6-14}$ aryl group (e.g., phenyl), and
   (v) a $C_{1-6}$ alkoxy group (e.g., methoxy);
(2) a $C_{1-6}$ alkoxy-carbonyl group (e.g., methoxycarbonyl, tert-butoxycarbonyl, isopropoxycarbonyl) optionally substituted by 1 to 3 substituents selected from
   (i) a halogen atom,
   (ii) a $C_{1-6}$ alkoxy group,
   (iii) a $C_{6-14}$ aryl group (e.g., phenyl), and
   (iv) a heterocyclic group (e.g., tetrahydrofuryl);
(3) a $C_{3-10}$ cycloalkyl-carbonyl group (e.g., cyclopropylcarbonyl, cyclopentylcarbonyl);
(4) a $C_{6-14}$ aryl-carbonyl group (e.g., benzoyl);
(5) a carbamoyl group optionally mono- or di-substituted by substituent(s) selected from
   (i) a $C_{1-6}$ alkyl group (e.g., methyl, ethyl, propyl, isopropyl) optionally substituted by 1 to 3 $C_{6-14}$ aryl groups (e.g., phenyl),
   (ii) a $C_{6-14}$ aryl group (e.g., phenyl),
   (iii) a $C_{3-10}$ cycloalkyl group (e.g., cyclopentyl, cyclohexyl),
   (iv) a $C_{1-6}$ alkylsulfonyl group (e.g., methylsulfonyl), and
   (v) an aromatic heterocyclic group (e.g., pyridyl) optionally substituted by 1 to 3 $C_{1-6}$ alkyl groups (e.g., methyl);
(6) a $C_{1-6}$ alkylsulfonyl group (e.g., methylsulfonyl) optionally substituted by 1 to 3 $C_{6-14}$ aryl groups (e.g., phenyl);
(7) a $C_{6-14}$ arylsulfonyl group (e.g., benzenesulfonyl) optionally substituted by 1 to 3 $C_{1-6}$ alkyl groups (e.g., methyl);
(8) a $C_{3-10}$ cycloalkylsulfonyl group (e.g., cyclopropylsulfonyl);
(9) an aromatic heterocyclylcarbonyl group (e.g., furylcarbonyl, pyrazolylcarbonyl, pyridylcarbonyl, isoxazolylcarbonyl, thiazolylcarbonyl) optionally substituted by 1 to 3 substituents selected from a $C_{1-6}$ alkyl group optionally substituted by 1 to 3 halogen atoms (e.g., a fluorine atom);
(10) an non-aromatic heterocyclylcarbonyl group (e.g., tetrahydropyranylcarbonyl);
(11) a $C_{1-6}$ alkylthio-carbonyl group optionally substituted by 1 to 3 substituents selected from
   (i) a halogen atom,
   (ii) a $C_{6-14}$ aryl group,
   (iii) a $C_{1-6}$ alkoxy group, and
   (iv) a heterocyclic group; or
(12) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
   (i) a $C_{1-6}$ alkyl-carbonyl group optionally substituted by 1 to 3 halogen atoms,
   (ii) a $C_{1-6}$ alkoxy-carbonyl group optionally substituted by 1 to 3 substituents selected from
      (a) a halogen atom,
      (b) a $C_{1-6}$ alkoxy group, and
      (c) a $C_{6-14}$ aryl group (e.g., phenyl),
   (iii) a carbamoyl group optionally mono- or di-substituted by substituent(s) selected from
      (a) a $C_{1-6}$ alkyl group optionally substituted by 1 to 3 substituents selected from a halogen atom, a hydroxy group and a $C_{1-6}$ alkoxy group, and
      (b) a non-aromatic heterocyclic group (e.g., tetrahydrofuryl),
   (iv) a carboxy group,
   (v) a hydroxy group,
   (vi) a halogen atom,
   (vii) a $C_{1-6}$ alkyl group optionally substituted by 1 to 3 substituents selected from
      (a) a halogen atom,
      (b) a carboxy group,
      (c) a hydroxy group,
      (d) a $C_{1-6}$ alkoxy-carbonyl group, and
      (e) a $C_{1-6}$ alkoxy,
   (viii) a $C_{1-6}$ alkoxy group,
   (ix) a $C_{3-10}$ cycloalkyl group (e.g., cyclopropyl), and
   (x) a non-aromatic heterocyclic group (e.g., tetrahydrofuryl);
or a salt thereof.

[Compound B-2]
A compound represented by the formula:

$$\text{(I)}$$

wherein
ring P is a benzene ring, a pyridine ring or a pyrimidine ring, each of which is substituted by 1 to 3 substituents selected from (1) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
(2) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 substituents selected from a halogen atom, a hydroxy group and a $C_{1-6}$ alkoxy group,
  (c) a $C_{1-6}$ alkoxy-carbonyl group optionally substituted by 1 to 3 halogen atoms,
  (d) a $C_{1-6}$ alkylsulfonyl group (e.g., methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms,
  (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and
  (g) an non-aromatic heterocyclylcarbonyl group (e.g., tetrahydrofurylcarbonyl);
(3) a $C_{1-6}$ alkyl-carbonyl group optionally substituted by 1 to 3 halogen atoms;
(4) a $C_{1-6}$ alkoxy-carbonyl group (e.g., methoxycarbonyl) optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(5) a $C_{1-6}$ alkylsulfonyl group (e.g., methylsulfonyl, ethylsulfonyl, isopropylsulfonyl) optionally substituted by 1 to 3 halogen atoms;
(6) a carbamoyl group optionally mono- or di-substituted by substituent(s) selected from
  (a) a $C_{1-6}$ alkyl group optionally substituted by 1 to 3 substituents selected from a halogen atom, a hydroxy group and a $C_{1-6}$ alkoxy group, and
  (b) a non-aromatic heterocyclic group (e.g., tetrahydrofuryl);
(7) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(8) a carboxy group;
(9) a cyano group;
(10) a nitro group; and
(11) a halogen atom (e.g., a fluorine atom, a chlorine atom, bromine atom);
ring Q is a benzene ring, a pyridine ring or a pyrimidine ring, each of which is optionally substituted by 1 to 3 substituents selected from
(1) a halogen atom (e.g., a fluorine atom, a chlorine atom, a bromine atom); and
(2) a $C_{1-6}$ alkyl group optionally substituted by 1 to 3 halogen atoms;
$A^1$ is
(1) $CR^{4a}R^{4b}$ wherein $R^{4a}$ and $R^{4b}$ are each independently a hydrogen atom or a $C_{1-6}$ alkyl group;
(2) $NR^{4c}$ wherein $R^{4c}$ is a hydrogen atom, or a $C_{1-6}$ alkyl group optionally substituted by 1 to 3 halogen atoms; or
(3) O;
  $L^1$ is ethylene, trimethylene or tetramethylene;
  $L^2$ is a bond, methylene or ethylene;
  $L^3$ and $L^4$ are each independently methylene, ethylene or trimethylene;
  $R^1$ is
(1) a hydrogen atom,
(2) a halogen atom,
(3) a hydroxy group,
(4) a $C_{1-6}$ alkoxy group, or
(5) a $C_{1-6}$ alkyl group;
  $R^2$ is a hydrogen atom; and
  $R^3$ is
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., methoxycarbonyl, tert-butoxycarbonyl, isopropoxycarbonyl) optionally substituted by 1 to 3 substituents selected from
  (i) a halogen atom,
  (ii) a $C_{1-6}$ alkoxy group,
  (iii) a $C_{6-14}$ aryl group (e.g., phenyl), and
  (iv) a heterocyclic group (e.g., tetrahydrofuryl);
(3) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(4) a $C_{1-6}$ alkylsulfonyl group (e.g., methylsulfonyl) optionally substituted by 1 to 3 $C_{6-14}$ aryl groups (e.g., phenyl);
(5) a $C_{1-6}$ alkylthio-carbonyl group; or
(6) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a $C_{1-6}$ alkyl-carbonyl group,
  (ii) a $C_{1-6}$ alkoxy-carbonyl group,
  (iii) a carbamoyl group optionally mono- or di-substituted by $C_{1-6}$ alkyl group(s),
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group,
  (viii) a $C_{1-6}$ alkoxy group,
  (ix) a $C_{3-10}$ cycloalkyl group (e.g., cyclopropyl), and
  (x) a non-aromatic heterocyclic group (e.g., tetrahydrofuryl),
or a salt thereof.

[Compound C-1]
A compound represented by the formula:

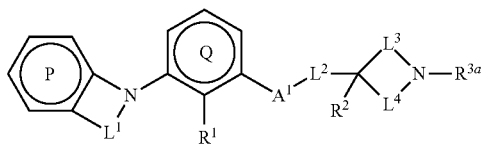

(Ia)

wherein
ring P is a benzene ring, a pyridine ring or a pyrimidine ring, each of which is substituted by 1 to 3 substituents selected from
(1) a non-aromatic heterocyclic group (preferably tetrahydrofuryl, morpholinyl, thiomorpholinyl, piperidinyl, pyrrolidinyl, piperazinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom, and
   (e) an oxo group,
(2) an amino group optionally mono- or di-substituted by substituent(s) selected from
   (a) a $C_{1-6}$ alkyl group optionally substituted by 1 to 3 halogen atoms,
   (b) a $C_{1-6}$ alkyl-carbonyl group optionally substituted by 1 to 3 substituents selected from a halogen atom, a hydroxy group and a $C_{1-6}$ alkoxy group,
   (c) a $C_{1-6}$ alkoxy-carbonyl group optionally substituted by 1 to 3 halogen atoms,
   (d) a $C_{1-6}$ alkylsulfonyl group (preferably methylsulfonyl) optionally substituted by 1 to 3 halogen atoms,
   (e) a carbamoyl group optionally mono- or di-substituted by $C_{1-6}$ alkyl group(s) optionally substituted by 1 to 3 halogen atoms,
   (f) an aromatic heterocyclic group (preferably thienyl, furyl, pyridyl, pyrazolyl, imidazolyl, tetrazolyl, oxazolyl, thiazolyl, oxadiazolyl, thiadiazolyl), and
   (g) an non-aromatic heterocyclylcarbonyl group (preferably tetrahydrofurylcarbonyl),
(3) a $C_{1-6}$ alkyl-carbonyl group optionally substituted by 1 to 3 halogen atoms,
(4) a $C_{1-6}$ alkoxy-carbonyl group (preferably methoxycarbonyl) optionally substituted by 1 to 3 substituents selected from
   (a) a halogen atom,
   (b) a $C_{1-6}$ alkoxy group,
   (c) a $C_{6-14}$ aryl group (preferably phenyl), and
   (d) a heterocyclic group (preferably tetrahydrofuryl),
(5) a $C_{1-6}$ alkylsulfonyl group (preferably methylsulfonyl, ethylsulfonyl, isopropylsulfonyl) optionally substituted by 1 to 3 halogen atoms,
(6) a carbamoyl group optionally mono- or di-substituted by substituent(s) selected from
   (a) a $C_{1-6}$ alkyl group optionally substituted by 1 to 3 substituents selected from a halogen atom, a hydroxy group and a $C_{1-6}$ alkoxy group, and
   (b) a non-aromatic heterocyclic group (preferably tetrahydrofuryl),
(7) a non-aromatic heterocyclylcarbonyl group (preferably pyrrolidinylcarbonyl, morpholinylcarbonyl) optionally substituted by 1 to 3 substituents selected from a $C_{1-6}$ alkyl group optionally substituted by 1 to 3 halogen atoms,
(8) a carboxy group,
(9) a cyano group,
(10) a nitro group, and
(11) a halogen atom (preferably fluorine atom, a chlorine atom, a bromine atom);
ring Q is a benzene ring, a pyridine ring or a pyrimidine ring, each of which is optionally substituted by 1 to 3 substituents selected from
(1) a halogen atom (preferably fluorine atom, a chlorine atom, a bromine atom), and
(2) a $C_{1-6}$ alkyl group optionally substituted by 1 to 3 halogen atoms;
$A^1$ is
(1) $CR^{4a}R^{4b}$ wherein $R^{4a}$ and $R^{4b}$ are each independently a hydrogen atom, a $C_{1-6}$ alkyl group, a hydroxy group or a $C_{1-6}$ alkoxy group,
(2) $NR^{4c}$ wherein $R^{4c}$ is a hydrogen atom, a $C_{1-6}$ alkyl group optionally substituted by 1 to 3 halogen atoms, or a $C_{3-10}$ cycloalkyl group,
(3) O, or
(4) S;
$L^1$ is ethylene, trimethylene or tetramethylene;
$L^2$ is a bond, methylene or ethylene;
$L^3$ and $L^4$ are each independently methylene, ethylene or trimethylene;
$R^1$ is
(1)(a) a hydrogen atom,
   (b) a halogen atom,
   (c) a hydroxy group,
   (d) a $C_{1-6}$ alkoxy group, or
   (e) a $C_{1-6}$ alkyl group; or,
(2) when $A^1$ is $CR^{4a}R^{4b}$, $R^1$ and $R^{4a}$ and/or $R^{4b}$ in combination optionally form, together with the adjacent carbon atoms, a 5- or 6-membered ring (preferably cyclopentadiene, cyclopentene, cyclohexene, benzene, pyrrole, pyrazole, pyridine, pyrimidine) optionally substituted by 1 to 3 substituents selected from
   (a) a halogen atom,
   (b) a hydroxy group,
   (c) a $C_{1-6}$ alkoxy group, and
   (d) a $C_{1-6}$ alkyl group; or
(3) when $A^1$ is $NR^{4c}$, $R^1$ and $R^{4c}$ in combination optionally form, together with the adjacent carbon atom and nitrogen atom, a 5- or 6-membered nitrogen-containing heterocycle (preferably pyrrole, pyrazole, imidazole, dihydropyrrole, tetrahydropyridine) optionally substituted by 1 to 3 substituents selected from
   (a) a halogen atom,
   (b) a hydroxy group,
   (c) a $C_{1-6}$ alkoxy group, and
   (d) a $C_{1-6}$ alkyl group;
$R^2$ is
(1) a hydrogen atom,
(2) a cyano group, or
(3) a $C_{1-6}$ alkyl group; and
$R^{3a}$ is
(1) a $C_{1-6}$ alkylthio-carbonyl group, or
(2) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
   (i) a $C_{1-6}$ alkyl-carbonyl group,
   (ii) a $C_{1-6}$ alkoxy-carbonyl group,
   (iii) a carbamoyl group optionally mono- or di-substituted by $C_{1-6}$ alkyl group(s), (iv) a carboxy group,
(v) a hydroxy group,
(vi) a halogen atom,
(vii) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group, and
  (e) a $C_{1-6}$ alkoxy group,
(viii) a $C_{1-6}$ alkoxy group,
(ix) a $C_{3-10}$ cycloalkyl group (preferably cyclopropyl), and
(x) a non-aromatic heterocyclic group (preferably tetrahydrofuryl),
or a salt thereof.
[Compound C-2]
A compound represented by the formula:

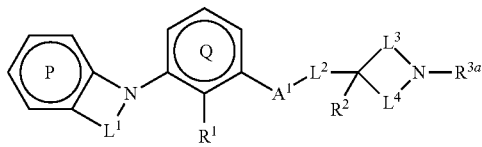

(Ia)

wherein
ring P is a benzene ring, a pyridine ring, a pyrimidine ring, each of which is substituted by 1 to 3 substituents selected from
(1) a non-aromatic heterocyclic group (preferably tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group,
(2) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 substituents selected from a halogen atom, a hydroxy group and a $C_{1-6}$ alkoxy group,
  (c) a $C_{1-6}$ alkoxy-carbonyl group optionally substituted by 1 to 3 halogen atoms,
  (d) a $C_{1-6}$ alkylsulfonyl group (preferably methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms,
  (f) an aromatic heterocyclic group (preferably thienyl, furyl, pyridyl, pyrazolyl, imidazolyl, tetrazolyl, oxazolyl, thiazolyl, oxadiazolyl, thiadiazolyl), and
  (g) an non-aromatic heterocyclylcarbonyl group (preferably tetrahydrofurylcarbonyl),
(3) a $C_{1-6}$ alkyl-carbonyl group optionally substituted by 1 to 3 halogen atoms,
(4) a $C_{1-6}$ alkoxy-carbonyl group (preferably methoxycarbonyl) optionally substituted by 1 to 3 substituents selected from
  (a) a halogen atom,
  (b) a $C_{1-6}$ alkoxy group,
  (c) a $C_{6-14}$ aryl group (preferably phenyl), and
  (d) a heterocyclic group (preferably tetrahydrofuryl), (5) a $C_{1-6}$ alkylsulfonyl group (preferably methylsulfonyl, ethylsulfonyl, isopropylsulfonyl) optionally substituted by 1 to 3 halogen atoms,
(6) a carbamoyl group optionally mono- or di-substituted by substituent(s) selected from
  (a) a $C_{1-6}$ alkyl group optionally substituted by 1 to 3 substituents selected from a halogen atom, a hydroxy group and a $C_{1-6}$ alkoxy group, and
  (b) a non-aromatic heterocyclic group (preferably tetrahydrofuryl),
(7) a non-aromatic heterocyclylcarbonyl group (preferably pyrrolidinylcarbonyl, morpholinylcarbonyl) optionally substituted by 1 to 3 substituents selected from a $C_{1-6}$ alkyl group optionally substituted by 1 to 3 halogen atoms,
(8) a carboxy group,
(9) a cyano group,
(10) a nitro group, and
(11) a halogen atom (preferably fluorine atom, a chlorine atom, a bromine atom);
ring Q is a pyrimidine ring having no additional substituent;
$A^1$ is
(1) $NR^{4c}$ wherein $R^{4c}$ is a hydrogen atom, or a $C_{1-6}$ alkyl group optionally substituted by 1 to 3 halogen atoms; or
(2) O;
$L^1$ is ethylene;
$L^2$ is a bond;
$L^3$ and $L^4$ are each independently ethylene;
$R^1$ is a hydrogen atom;
$R^2$ is a hydrogen atom; and
$R^{3a}$ is
(1) a $C_{1-6}$ alkylthio-carbonyl group, or
(2) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a $C_{1-6}$ alkyl-carbonyl group,
  (ii) a $C_{1-6}$ alkoxy-carbonyl group,
  (iii) a carbamoyl group optionally mono- or di-substituted by $C_{1-6}$ alkyl group(s),
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group,
  (viii) a $C_{1-6}$ alkoxy group,
  (ix) a $C_{3-10}$ cycloalkyl group (preferably cyclopropyl), and
  (x) a non-aromatic heterocyclic group (preferably tetrahydrofuryl),
or a salt thereof.
[Compound C-3]
A compound represented by the formula:

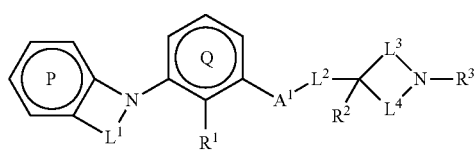

(Ia)

wherein
ring P is a benzene ring substituted by 1 to 3 substituents selected from
(1) a halogen atom,
(2) a $C_{1-6}$ alkylsulfonyl group,
(3) a $C_{1-6}$ alkyl-carbonylamino group optionally substituted by 1 to 3 substituents selected from
  (i) a hydroxy group, and
  (ii) a $C_{1-6}$ alkoxy group,
(4) a carbamoyl group optionally mono- or di-substituted by $C_{1-6}$ alkyl group(s) optionally substituted by hydroxy group(s),
(5) a 5- or 6-membered non-aromatic heterocyclic group optionally substituted by 1 to 3 oxo groups, or
(6) a 5- or 6-membered non-aromatic heterocyclylcarbonyl group;
ring Q is a pyrimidine ring having no additional substituent;
$A^1$ is
(1) $NR^{4c}$ wherein $R^{4c}$ is a hydrogen atom, a $C_{1-6}$ alkyl group optionally substituted by 1 to 3 halogen atoms, or the like; or
(2) O;
$L^1$ is ethylene;
$L^2$ is a bond;
$L^3$ and $L^4$ are each independently ethylene;
$R^1$ is a hydrogen atom;
$R^2$ is a hydrogen atom; and
$R^{1a}$ is
(1) a $C_{1-6}$ alkylthio-carbonyl group; or
(2) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a halogen atom,
  (ii) a $C_{1-6}$ alkyl group
  (iii) a $C_{1-6}$ alkoxy group, and
  (iv) a $C_{3-10}$ cycloalkyl group (e.g., cyclopropyl),
or a salt thereof.

[Compound D-1]
A compound represented by the formula:

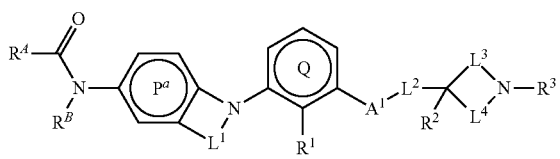

(Ib)

wherein
ring $P^a$ is a benzene ring, a pyridine ring or a pyrimidine ring, each of which is optionally substituted by 1 to 3 substituents selected from
(1) a halogen atom (e.g., a fluorine atom, a chlorine atom, a bromine atom); and
(2) a $C_{1-6}$ alkyl group optionally substituted by 1 to 3 halogen atoms;
ring Q is a benzene ring, a pyridine ring, a pyridazine ring or a pyrimidine ring, each of which is optionally substituted by 1 to 3 substituents selected from
(1) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(2) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
(3) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 substituents selected from a halogen atom, a hydroxy group and a $C_{1-6}$ alkoxy group,
  (c) a $C_{1-6}$ alkoxy-carbonyl group optionally substituted by 1 to 3 halogen atoms,
  (d) a $C_{1-6}$ alkylsulfonyl group (e.g., methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms,
  (f) an aromatic heterocyclic group (e.g., thienyl, furyl, pyridyl, pyrazolyl, imidazolyl, tetrazolyl, oxazolyl, thiazolyl, oxadiazolyl, thiadiazolyl), and
  (g) an non-aromatic heterocyclylcarbonyl group (e.g., tetrahydrofurylcarbonyl);
(4) a $C_{1-6}$ alkyl-carbonyl group optionally substituted by 1 to 3 halogen atoms;
(5) a $C_{1-6}$ alkoxy-carbonyl group (e.g., methoxycarbonyl) optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(6) a $C_{1-6}$ alkylsulfonyl group (e.g., methylsulfonyl, ethylsulfonyl, isopropylsulfonyl) optionally substituted by 1 to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a hydroxy group and a $C_{1-6}$ alkoxy group, and
  (b) a non-aromatic heterocyclic group (e.g., tetrahydrofuryl);
(8) a carboxy group;
(9) a hydroxy group;
(10) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(11) a mercapto group;
(12) a cyano group;
(13) a nitro group;
(14) a halogen atom (e.g., a fluorine atom, a chlorine atom, a bromine atom);
(15) a $C_{3-10}$ cycloalkoxy group (e.g., cyclopropoxy, cyclopentyloxy) optionally substituted by 1 to 3 substituents selected from
  (a) a halogen atom (e.g., a fluorine atom), and
  (b) a $C_{1-6}$ alkoxy group (e.g., methoxy); and
(16) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group, (e) a $C_{1-6}$ alkoxy group, and
(f) an amino group optionally mono- or di-substituted by $C_{1-6}$ alkyl group(s);

$A^1$ is
(1) $CR^{4a}R^{4b}$ wherein $R^{4a}$ and $R^{4b}$ are each independently a hydrogen atom, a $C_{1-6}$ alkyl group, a hydroxy group or a $C_{1-6}$ alkoxy group;
(2) $NR^{4c}$ wherein $R^{4c}$ is a hydrogen atom, a $C_{1-6}$ alkyl group optionally substituted by 1 to 3 halogen atoms, or a $C_{3-10}$ cycloalkyl group;
(3) O; or
(4) S;

$L^1$ is ethylene, trimethylene or tetramethylene, each of which is optionally substituted by 1 to 3 substituents selected from
(1) a halogen atom;
(2) a hydroxy group;
(3) a $C_{1-6}$ alkoxy group;
(4) a $C_{1-6}$ alkyl-carbonyl group optionally substituted by 1 to 3 halogen atoms;
(5) a $C_{1-6}$ alkoxy-carbonyl group optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(6) a $C_{1-6}$ alkylsulfonyl group (e.g., methylsulfonyl, ethylsulfonyl, isopropylsulfonyl) optionally substituted by 1 to 3 halogen atoms;
(7) a cyano group; and
(8) a nitro group;

$L^2$ is
(1) a bond; or
(2) methylene or ethylene, each of which is optionally substituted by 1 to 3 substituents selected from
  (a) a halogen atom,
  (b) a hydroxy group, and
  (c) a $C_{1-6}$ alkoxy group;

$L^3$ and $L^4$ are each independently methylene, ethylene or trimethylene, each of which is optionally substituted by 1 to 3 substituents selected from
(1) a halogen atom;
(2) a hydroxy group;
(3) a $C_{1-6}$ alkoxy group;
(4) a $C_{1-6}$ alkyl-carbonyl group optionally substituted by 1 to 3 halogen atoms; and
(5) a $C_{1-6}$ alkoxy-carbonyl group optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);

$R^1$ is
(1) a hydrogen atom,
(2) a halogen atom,
(3) a hydroxy group,
(4) a $C_{1-6}$ alkoxy group, or
(5) a $C_{1-6}$ alkyl group;

$R^2$ is
(1) a hydrogen atom;
(2) a cyano group; or
(3) a $C_{1-6}$ alkyl group;

$R^3$ is
(1) a $C_{1-6}$ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a $C_{1-6}$ alkoxy-carbonyl group (e.g., methoxycarbonyl, ethoxycarbonyl),
  (iv) a $C_{6-14}$ aryl group (e.g., phenyl), and
  (v) a $C_{1-6}$ alkoxy group (e.g., methoxy);
(2) a $C_{1-6}$ alkoxy-carbonyl group (e.g., methoxycarbonyl, tert-butoxycarbonyl, isopropoxycarbonyl) optionally substituted by 1 to 3 substituents selected from
  (i) a halogen atom,
  (ii) a $C_{1-6}$ alkoxy group,
  (iii) a $C_{6-14}$ aryl group (e.g., phenyl), and
  (iv) a heterocyclic group (e.g., tetrahydrofuryl);
(3) a $C_{3-10}$ cycloalkyl-carbonyl group (e.g., cyclopropylcarbonyl, cyclopentylcarbonyl);
(4) a $C_{6-14}$ aryl-carbonyl group (e.g., benzoyl);
(5) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 $C_{6-14}$ aryl groups (e.g., phenyl),
  (ii) a $C_{6-14}$ aryl group (e.g., phenyl),
  (iii) a $C_{3-10}$ cycloalkyl group (e.g., cyclopentyl, cyclohexyl),
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups (e.g., methyl);
(6) a $C_{1-6}$ alkylsulfonyl group (e.g., methylsulfonyl) optionally substituted by 1 to 3 $C_{6-14}$ aryl groups (e.g., phenyl);
(7) a $C_{6-14}$ arylsulfonyl group (e.g., benzenesulfonyl) optionally substituted by 1 to 3 $C_{1-6}$ alkyl groups (e.g., methyl);
(8) a $C_{3-10}$ cycloalkylsulfonyl group (e.g., cyclopropylsulfonyl);
(9) an aromatic heterocyclylcarbonyl group (e.g., furylcarbonyl, pyrazolylcarbonyl, pyridylcarbonyl, isoxazolylcarbonyl, thiazolylcarbonyl) optionally substituted by 1 to 3 substituents selected from a $C_{1-6}$ alkyl group optionally substituted by 1 to 3 halogen atoms (e.g., a fluorine atom);
(10) an non-aromatic heterocyclylcarbonyl group (e.g., tetrahydropyranylcarbonyl);
(11) a $C_{1-6}$ alkylthio-carbonyl group optionally substituted by 1 to 3 substituents selected from
  (i) a halogen atom,
  (ii) a $C_{6-14}$ aryl group,
  (iii) a $C_{1-6}$ alkoxy group, and
  (iv) a heterocyclic group; or
(12) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a $C_{1-6}$ alkyl-carbonyl group optionally substituted by 1 to 3 halogen atoms,
  (ii) a $C_{1-6}$ alkoxy-carbonyl group optionally substituted by 1 to 3 substituents selected from
    (a) a halogen atom,
    (b) a $C_{1-6}$ alkoxy group, and
    (c) a $C_{6-14}$ aryl group (e.g., phenyl),
  (iii) a carbamoyl group optionally mono- or di-substituted by substituent(s) selected from
    (a) a $C_{1-6}$ alkyl group optionally substituted by 1 to 3 substituents selected from a halogen atom, a hydroxy group and a $C_{1-6}$ alkoxy group, and
    (b) a non-aromatic heterocyclic group (e.g., tetrahydrofuryl),
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy, (viii) a $C_{1-6}$ alkoxy group,
(ix) a $C_{3-10}$ cycloalkyl group (e.g., cyclopropyl), and
(x) a non-aromatic heterocyclic group (e.g., tetrahydrofuryl);
$R^A$ is
(1) a hydrogen atom,
(2) a $C_{3-10}$ cycloalkyl group (e.g., cyclopropyl, cyclohexyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom,
(3) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom,
(4) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s),
(5) a $C_{2-6}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s),
(6) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom,
(7) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom, or
(8) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group; and
$R^B$ is a hydrogen atom or a $C_{1-6}$ alkyl group,
or a salt thereof.

[Compound D-2]
A compound represented by the formula:

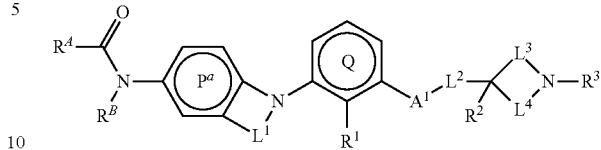

(Ib)

wherein
ring $P^a$ is a benzene ring optionally substituted by 1 to 3 substituents selected from
(1) a halogen atom (e.g., a fluorine atom, a chlorine atom, a bromine atom); and
(2) a $C_{1-6}$ alkyl group optionally substituted by 1 to 3 halogen atoms;
ring Q is a benzene ring, a pyridine ring or a pyrimidine ring, each of which is optionally substituted by 1 to 3 substituents selected from
(1) a halogen atom (preferably fluorine atom, a chlorine atom, a bromine atom), and
(2) a $C_{1-6}$ alkyl group optionally substituted by 1 to 3 halogen atoms;
$A^1$ is
(1) $CR^{4a}R^{4b}$ wherein $R^{4a}$ and $R^{4b}$ are each independently a hydrogen atom, a $C_{1-6}$ alkyl group, a hydroxy group or a $C_{1-6}$ alkoxy group,
(2) $NR^{4c}$ wherein $R^{4c}$ is a hydrogen atom, a $C_{1-6}$ alkyl group optionally substituted by 1 to 3 halogen atoms, or a $C_{3-10}$ cycloalkyl group,
(3) O, or
(4) S
$L^1$ is ethylene, trimethylene or tetramethylene;
$L^2$ is a bond, methylene or ethylene;
$L^3$ and $L^4$ are each independently methylene, ethylene or trimethylene;
$R^1$ is
(1)(a) a hydrogen atom,
  (b) a halogen atom,
  (c) a hydroxy group,
  (d) a $C_{1-6}$ alkoxy group, or
  (e) a $C_{1-6}$ alkyl group; or,
(2) when $A^1$ is $CR^{4a}R^{4b}$, $R^1$ and $R^{4a}$ and/or $R^{4b}$ in combination optionally form, together with the adjacent carbon atoms, a 5- or 6-membered ring (preferably cyclopentadiene, cyclopentene, cyclohexene, benzene, pyrrole, pyrazole, pyridine, pyrimidine) optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group; or
(3) when $A^1$ is $NR^{4c}$, $R^1$ and $R^{4c}$ in combination optionally form, together with the adjacent carbon atom and nitrogen atom, a 5- or 6-membered nitrogen-containing heterocycle (preferably pyrrole, pyrazole, imidazole, dihydropyrrole, tetrahydropyridine) optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group;
$R^2$ is
(1) a hydrogen atom,
(2) a cyano group, or
(3) a $C_{1-6}$ alkyl group;

R³ is
(1) a C₁₋₆ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a C₁₋₆ alkoxy-carbonyl group (e.g., methoxycarbonyl, ethoxycarbonyl),
  (iv) a C₆₋₁₄ aryl group (e.g., phenyl), and
  (v) a C₁₋₆ alkoxy group (e.g., methoxy);
(2) a C₁₋₆ alkoxy-carbonyl group (e.g., methoxycarbonyl, tert-butoxycarbonyl, isopropoxycarbonyl) optionally substituted by 1 to 3 substituents selected from
  (i) a halogen atom,
  (ii) a C₁₋₆ alkoxy group,
  (iii) a C₆₋₁₄ aryl group (e.g., phenyl), and
  (iv) a heterocyclic group (e.g., tetrahydrofuryl);
(3) a carbamoyl group optionally mono- or di-substituted by substituent(s) selected from
  (i) a C₁₋₆ alkyl group (e.g., methyl, ethyl, propyl, isopropyl) optionally substituted by 1 to 3 C₆₋₁₄ aryl groups (e.g., phenyl),
  (ii) a C₆₋₁₄ aryl group (e.g., phenyl),
  (iii) a C₃₋₁₀ cycloalkyl group (e.g., cyclopentyl, cyclohexyl),
  (iv) a C₁₋₆ alkylsulfonyl group (e.g., methylsulfonyl), and
  (v) an aromatic heterocyclic group (e.g., pyridyl) optionally substituted by 1 to 3 C₁₋₆ alkyl groups (e.g., methyl);
(4) a C₁₋₆ alkylsulfonyl group (e.g., methylsulfonyl) optionally substituted by 1 to 3 C₆₋₁₄ aryl groups (e.g., phenyl);
(5) a C₁₋₆ alkylthio-carbonyl group; or
(6) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a C₁₋₆ alkyl-carbonyl group,
  (ii) a C₁₋₆ alkoxy-carbonyl group,
  (iii) a carbamoyl group optionally mono- or di-substituted by C₁₋₆ alkyl group(s),
  (iv) a carboxy group,
  (v) a hydroxy group,
  (vi) a halogen atom,
  (vii) a C₁₋₆ alkyl group optionally substituted by 1 to 3 substituents selected from
    (a) a halogen atom,
    (b) a carboxy group,
    (c) a hydroxy group,
    (d) a C₁₋₆ alkoxy-carbonyl group, and
    (e) a C₁₋₆ alkoxy group,
  (viii) a C₁₋₆ alkoxy group,
  (ix) a C₃₋₁₀ cycloalkyl group (e.g., cyclopropyl), and
  (x) a non-aromatic heterocyclic group (e.g., tetrahydrofuryl);
R^A is
(1) a hydrogen atom,
(2) a C₁₋₆ alkyl group optionally substituted by 1 to 3 substituents selected from
  (a) a halogen atom,
  (b) a carboxy group,
  (c) a hydroxy group,
  (d) a C₁₋₆ alkoxy-carbonyl group,
  (e) a C₁₋₆ alkoxy group, and
  (f) an amino group optionally mono- or di-substituted by C₁₋₆ alkyl group(s),
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a C₁₋₆ alkyl group optionally substituted by 1 to 3 halogen atoms,
  (b) a hydroxy group,
  (c) a C₁₋₆ alkoxy group optionally substituted by 1 to 3 halogen atoms, and
  (d) a halogen atom, or
(4) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a C₁₋₆ alkyl group optionally substituted by 1 to 3 halogen atoms,
  (b) a hydroxy group,
  (c) a C₁₋₆ alkoxy group optionally substituted by 1 to 3 halogen atoms,
  (d) a halogen atom, and
  (e) an oxo group; and
R^B is a hydrogen atom or a C₁₋₆ alkyl group,
or a salt thereof.

[Compound D-3]
a compound represented by the formula:

$$R^A \underset{R^B}{\overset{O}{\underset{N}{\parallel}}} \!\!-\!\! \overset{P^a}{\bigcirc} \!\!-\!\! \underset{L^1}{N} \!\!-\!\! \overset{Q}{\bigcirc} \!\!-\!\! \underset{R^1}{A^1} \!\!-\!\! L^2 \!\!-\!\! \underset{R^2}{\overset{L^3}{\underset{L^4}{\rangle}}} N \!\!-\!\! R^3 \quad (Ib)$$

wherein
ring P^a is a benzene ring having no additional substituent;
ring Q is a pyrimidine ring having no additional substituent;
A¹ is
(1) NR^{4c} wherein R^{4c} is a hydrogen atom, or a C₁₋₆ alkyl group optionally substituted by 1 to 3 halogen atoms; or
(2) O;
L¹ is ethylene;
L² is a bond;
L³ and L⁴ are each independently ethylene;
R¹ is a hydrogen atom;
R² is a hydrogen atom; and
R³ is
(1) a C₁₋₆ alkyl-carbonyl group (e.g., acetyl, propionyl, butyryl, isobutyryl, isoamyl) optionally substituted by 1 to 3 substituents selected from
  (i) an amino group,
  (ii) a carboxyl group,
  (iii) a C₁₋₆ alkoxy-carbonyl group (e.g., methoxycarbonyl, ethoxycarbonyl),
  (iv) a C₆₋₁₄ aryl group (e.g., phenyl), and
  (v) a C₁₋₆ alkoxy group (e.g., methoxy);
(2) a C₁₋₆ alkoxy-carbonyl group (e.g., methoxycarbonyl, tert-butoxycarbonyl, isopropoxycarbonyl) optionally substituted by 1 to 3 substituents selected from
  (i) a halogen atom,
  (ii) a C₁₋₆ alkoxy group,
  (iii) a C₆₋₁₄ aryl group (e.g., phenyl), and
  (iv) a heterocyclic group (e.g., tetrahydrofuryl);
(3) a carbamoyl group optionally mono- or di-substituted by substituent(s) selected from
  (i) a C₁₋₆ alkyl group (e.g., methyl, ethyl, propyl, isopropyl) optionally substituted by 1 to 3 C₆₋₁₄ aryl groups (e.g., phenyl),
  (ii) a C₆₋₁₄ aryl group (e.g., phenyl),
  (iii) a C₃₋₁₀ cycloalkyl group (e.g., cyclopentyl, cyclohexyl),
  (iv) a C₁₋₆ alkylsulfonyl group (e.g., methylsulfonyl), and
  (v) an aromatic heterocyclic group (e.g., pyridyl) optionally substituted by 1 to 3 C₁₋₆ alkyl groups (e.g., methyl);

(4) a $C_{1-6}$ alkylsulfonyl group (e.g., methylsulfonyl) optionally substituted by 1 to 3 $C_{6-14}$ aryl groups (e.g., phenyl);
(5) a $C_{1-6}$ alkylthio-carbonyl group; or
(6) a 5- or 6-membered aromatic ring group (preferably oxadiazolyl, thiadiazolyl, phenyl, pyridyl, pyrazinyl, pyrimidinyl, more preferably oxadiazolyl, pyrimidinyl) optionally substituted by 1 to 3 substituents selected from
  (i) a $C_{1-6}$ alkyl-carbonyl group,
  (ii) a $C_{1-6}$ alkoxy-carbonyl group,
  (iii) a carbamoyl group optionally mono- or di-substituted by $C_{1-6}$ alkyl group(s),
  (iv) a carboxy group,
  (v) a hydroxy group,
  (vi) a halogen atom,
  (vii) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group, and
    (e) a $C_{1-6}$ alkoxy group,
  (viii) a $C_{1-6}$ alkoxy group,
  (ix) a $C_{3-10}$ cycloalkyl group (e.g., cyclopropyl), and
  (x) a non-aromatic heterocyclic group (e.g., tetrahydrofuryl);
$R^A$ is
(1) a $C_{1-6}$ alkyl group optionally substituted by 1 to 3 substituents selected from
  (a) a halogen atom,
  (b) a hydroxy group, and
  (c) a $C_{1-6}$ alkoxy group, or
(2) an non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group,
  (d) a halogen atom, and
  (e) an oxo group; and
$R^B$ is a hydrogen atom or a $C_{1-6}$ alkyl group,
or a salt thereof.
[Compound E-1]
1-[6-({1-[3-(1-methylethyl)-1,2,4-oxadiazol-5-yl]piperidin-4-yl}oxy)pyrimidin-4-yl]-5-(methylsulfonyl)-2,3-dihydro-1H-indole or a salt thereof;
S-(1-methylethyl) 4-[(6-{5-[(hydroxyacetyl)amino]-2,3-dihydro-1H-indol-1-yl}pyrimidin-4-yl)oxy]piperidine-1-carbothioate or a salt thereof;
1-(6-{[1-(5-ethylpyrimidin-2-yl)piperidin-4-yl]oxy}pyrimidin-4-yl)-5-(methylsulfonyl)-2,3-dihydro-1H-indole or a salt thereof.

A salt of the compound represented by the formula (I), (Ia) or (Ib) is preferably a pharmacologically acceptable salt. Examples of such salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Compound (I) may be labeled with an isotope (e.g., $^3$H, $^{14}$C, $^{35}$S, $^{125}$I etc.) and the like.

Compound (I) may be a non-solvate (e.g., anhydride) or a solvate (e.g., hydrate).

A deuterium converter wherein $^1$H has been converted to $^2$H(D) is also encompassed in compound (I).

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc.

Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

The production methods of compound (I) are explained in the following.

Compound (I) can be produced according to a method known per se, for example, Method A-Method E and Method G-Method J, shown below, or a method analogous thereto. In the following each production method, the starting compounds may be in the form of salts. As such salts, those exemplified as the above-mentioned salts of compound (I) can be used.

Compound (I-2), which is compound (I) wherein $A^1$ is $NR^{4c}$ and compound (I-3) wherein $A^1$ is $NR^{4c}$ and $L^1$ is $CH_2CH_2$, can be produced, for example, by the following Method A.

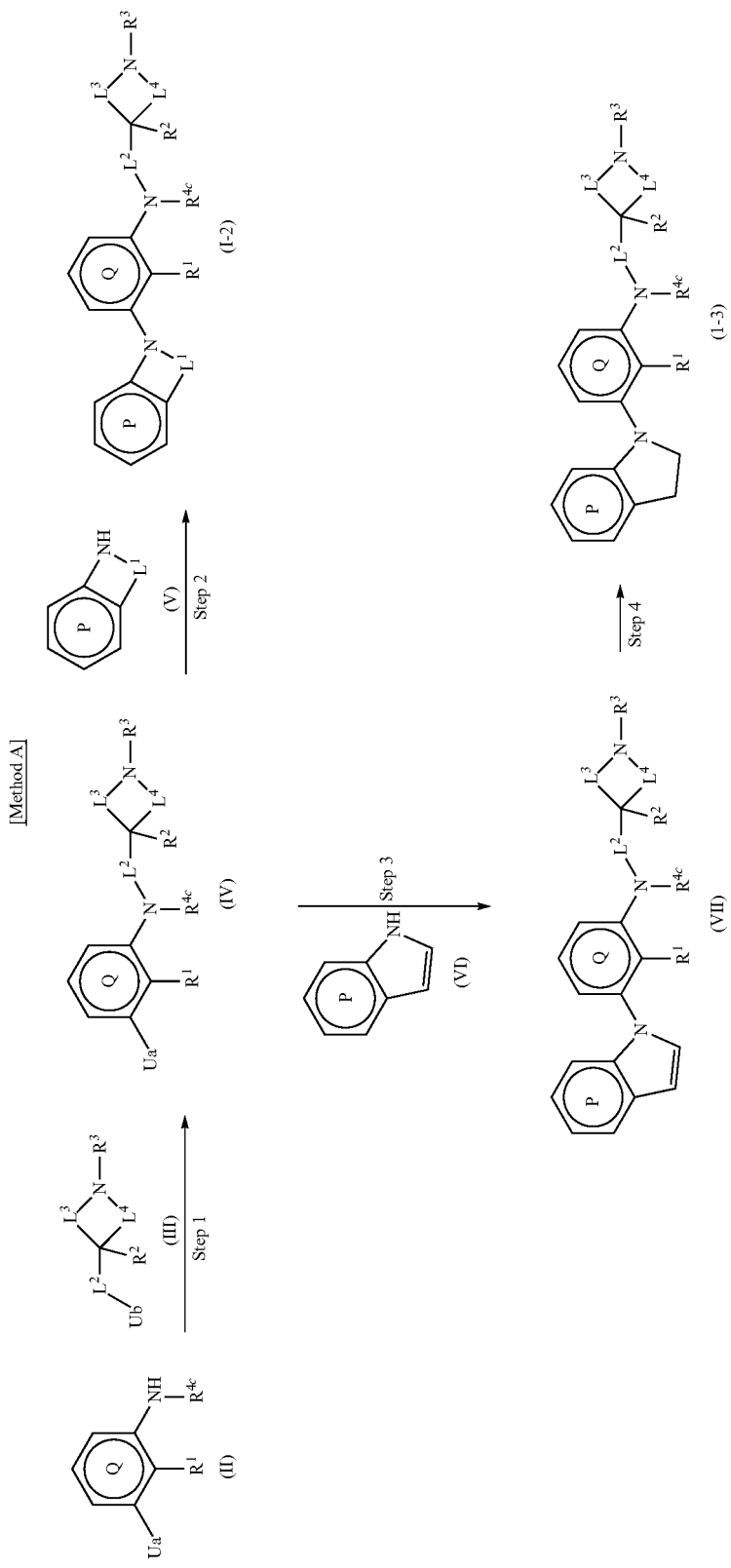

wherein Ua is a halogen atom, Ub is a leaving group or a hydroxy group, and other symbols are as defined above.

Examples of the halogen atom for Ua include a fluorine atom, a chlorine atom, a bromine atom and an iodine atom.

Examples of the "leaving group" for Ua include a chlorine atom, a bromine atom, an iodine atom, a benzenesulfonyloxy group, a p-toluenesulfonyloxy group, a methanesulfonyloxy group, a trifluoromethanesulfonyloxy group and the like.

[Step 1]

In this step, compound (IV) can be produced from compound (II) and compound (III).

When Ub is a leaving group, this reaction is carried out according to a method known per se, for example, a method to be performed in the presence of a base and the like.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, cesium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide, sodium tert-butoxide and the like, and the like.

The amount of the base to be used is preferably about 1 to about 5 mol per 1 mol of compound (II).

The amount of compound (III) to be used is preferably about 1 to about 5 mol per 1 mol of compound (II).

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethylsulfoxide and the like; ketones such as acetone, 2-butanone and the like, and the like. These solvents may be used in a mixture at an appropriate ratio.

The reaction temperature is generally about −80 to about 150° C., preferably about −10 to about 100° C.

The reaction time is generally about 0.5 to about 40 hr.

When Ub is a hydroxy group, this reaction is carried out according to a method known per se, for example, the method described in Synthesis, page 1 (1981), or a method analogous thereto. That is, this reaction is generally carried out in the presence of an organic phosphorus compound and an electrophile, in a solvent that does not adversely influence the reaction.

Examples of the organic phosphorus compound include triphenylphosphine, tributylphosphine and the like.

Examples of the electrophile include diethyl azodicarboxylate, diisopropyl azodicarboxylate, 1,1'-azodicarbonyldipiperidine and the like.

The amount of the organic phosphorus compound and electrophile to be used is preferably about 1 to about 5 mol per 1 mol of compound (II), respectively.

The amount of compound (III) to be used is preferably about 1 to about 5 mol per 1 mol of compound (II).

Examples of the solvent that does not adversely influence the reaction include those similar to the solvents mentioned above.

The reaction temperature is generally about −80 to about 150° C., preferably about −10 to about 100° C.

The reaction time is generally about 0.5 to about 40 hr

[Step 2]

In this step, compound (I-2) can be produced from compound (IV) and compound (V).

This reaction is carried out in the presence of a base, in a solvent that does not adversely influence the reaction.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, cesium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide, sodium tert-butoxide and the like, and the like.

The amount of the base to be used is preferably about 1 to about 5 mol per 1 mol of compound (IV).

The amount of compound (V) to be used is preferably about 1 to about 5 mol per 1 mol of compound (IV).

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethylsulfoxide and the like; ketones such as acetone, 2-butanone and the like, and the like. These solvents may be used in a mixture at an appropriate ratio.

The reaction temperature is generally about −80 to about 150° C., preferably about −10 to about 100° C.

The reaction time is generally about 0.5 to about 40 hr.

Alternatively, this reaction can be carried out in the presence of a transition metal catalyst under inert gas atmosphere, in a solvent that does not adversely influence the reaction. In addition, this reaction can be carried out in the presence of a base.

Examples of the inert gas include argon, nitrogen and the like.

Examples of the transition metal catalyst include a mixture of tris(dibenzylideneacetone)dipalladium(O) with 2 mol equivalents of 2-dicyclohexylphosphino-2',4',6'-triisopropyl-1,1'-biphenyl, a mixture of tris(dibenzylideneacetone)dipalladium(O) with 3 mol equivalents of (9,9-dimethyl-9H-xanthene-4,5-diyl)bis(diphenylphosphane), a mixture of palladium acetate (II) with 1 mol equivalents of 2,8,9-tris(2-methylpropyl)-2,5,8,9-tetraaza-1-phosphabicyclo[3.3.3]undecane, and the like.

The amount of the transition metal catalyst to be used is generally 0.001 to 2 mol, preferably 0.01 to 0.1 mol, per 1 mol of compound (IV).

Examples of the solvent that does not adversely influence the reaction include ethers such as diethyl ether, tetrahydrofuran, dioxane and the like; aliphatic hydrocarbons such as hexane, heptane and the like; aromatic hydrocarbons such as benzene, toluene, xylene and the like; amides such as N,N-dimethylformamide, N,N-dimethylacetamide, N-methylpyrrolidone and the like; halogenated hydrocarbons such as dichloromethane, chloroform, 1,2-dichloroethane, 1,1,2,2-tetrachloroethane and the like; nitriles such as acetonitrile and the like; sulfoxides such as dimethylsulfoxide and the like; alcohols such as methanol, ethanol, tert-butanol and the like; water and the like. These solvents may be used in a mixture at an appropriate ratio.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, cesium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide, sodium tert-butoxide and the like, and the like.

The amount of the base to be used is preferably about 0 to about 10 mol per 1 mol of compound (IV).

The amount of compound (V) to be used is preferably about 1 to about 5 mol per 1 mol of compound (IV).

The reaction temperature is generally about −80 to about 150° C., preferably about 0 to about 120° C.

The reaction time is generally about 0.5 to about 20 hr.

[Step 3]

In this step, compound (VII) can be produced form compound (IV) and compound (VI).

This reaction is carried out according to the above-mentioned Method A, Step 2.

[Step 4]

In this step, compound (I-3) can be produced by reducing compound (VII).

This reaction is carried out in the presence of a metal catalyst and a hydrogen source, in a solvent that does not adversely influence the reaction, according to a conventional method.

Examples of the metal catalyst include palladium-carbon, palladium-carbonethylenediamine complex, palladium black, palladium chloride, platinum oxide, platinum black, platinum-palladium, Raney-nickel, Raney-cobalt and the like.

The amount of the metal catalyst to be used is generally 0.001 to 1000 mol, preferably 0.01 to 100 mol, per 1 mol of compound (VII).

Examples of the hydrogen source include hydrogen gas, formic acid, formic acid amine salts, phosphinates, hydrazine and the like.

Examples of the solvent that does not adversely influence the reaction include aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, dimethoxyethane and the like; halogenated hydrocarbons such as chloroform, dichloromethane and the like, alcohols such as methanol, ethanol and the like, water and the like. These solvents may be used in a mixture at an appropriate ratio.

The reaction temperature is generally about −100 to about 150° C., preferably about −10 to about 100° C.

The reaction time is generally about 0.5 to about 20 hr.

Compound (II), compound (III), compound (V) and compound (VI), which are used as a starting material compound in the above-mentioned Method A, can be produced according to a method known per se, for example, the below-mentioned Method F or a method analogous thereto.

Compound (I) can also be produced, for example, according to the following Method B.

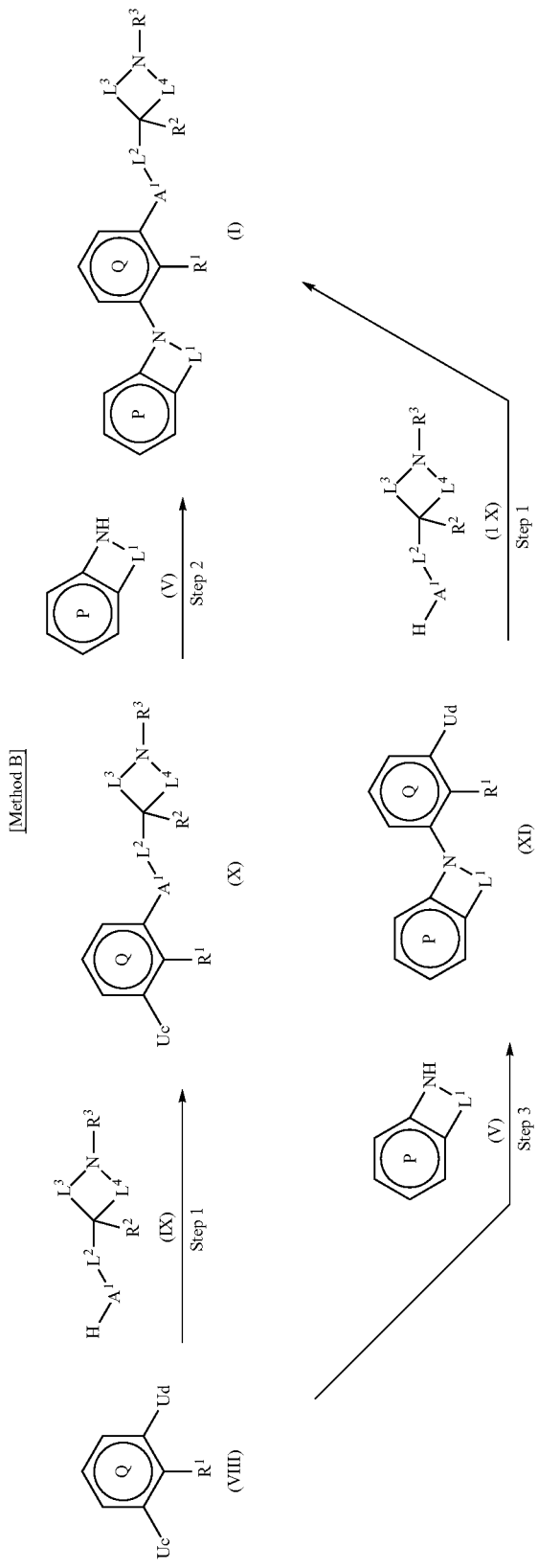

wherein Uc and Ud are each independently a halogen atom, and other symbols are as defined above.

Examples of the halogen atom for Uc or Ud include a fluorine atom, a chlorine atom, a bromine atom and an iodine atom.

[Step 1]

In this step, compound (X) can be produced from compound (VIII) and compound (IX).

This reaction can be carried out in the presence of a base, in a solvent that does not adversely influence the reaction.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, cesium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide, sodium tert-butoxide and the like, and the like.

The amount of the base to be used is preferably about 1 to about 5 mol per 1 mol of compound (VIII).

The amount of compound (IX) to be used is preferably about 1 to about 5 mol per 1 mol of compound (VIII).

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethylsulfoxide and the like; ketones such as acetone, 2-butanone and the like, and the like. These solvents may be used in a mixture at an appropriate ratio.

The reaction temperature is generally about −80 to about 150° C., preferably about −10 to about 100° C.

The reaction time is generally about 0.5 to about 40 hr.

Alternatively, this reaction can also be carried out in the presence of a transition metal catalyst under inert gas atmosphere, in a solvent that does not adversely influence the reaction. In addition, this reaction can also be carried out in the presence of a base.

Examples of the inert gas include argon, nitrogen and the like.

Examples of the transition metal catalyst include a mixture of tris(dibenzylideneacetone)dipalladium(O) with 2 mol equivalents of 2-dicyclohexylphosphino-2',4',6'-triisopropyl-1,1'-biphenyl, a mixture of tris(dibenzylideneacetone)dipalladium(O) with 3 mol equivalents of (9,9-dimethyl-9H-xanthene-4,5-diyl)bis(diphenylphosphane), a mixture of palladium acetate (II) with 1 mol equivalents of 2,8,9-tris(2-methylpropyl)-2,5,8,9-tetraaza-1-phosphabicyclo[3.3.3]undecane, and the like.

The amount of the transition metal catalyst to be used is generally 0.001 to 2 mol, preferably 0.01 to 0.1 mol, per 1 mol of compound (VIII).

Examples of the solvent that does not adversely influence the reaction include ethers such as diethyl ether, tetrahydrofuran, dioxane and the like; aliphatic hydrocarbons such as hexane, heptane and the like; aromatic hydrocarbons such as benzene, toluene, xylene and the like; amides such as N,N-dimethylformamide, N,N-dimethylacetamide, N-methylpyrrolidone and the like; halogenated hydrocarbons such as dichloromethane, chloroform, 1,2-dichloroethane, 1,1,2,2-tetrachloroethane and the like; nitriles such as acetonitrile and the like; sulfoxides such as dimethylsulfoxide and the like; alcohols such as methanol, ethanol, tert-butanol and the like; water and the like. These solvents may be used in a mixture at an appropriate ratio.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, cesium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide, sodium tert-butoxide and the like, and the like.

The amount of the base to be used is preferably 0 to about 10 mol per 1 mol of compound (VIII).

The amount of compound (IX) to be used is preferably about 1 to about 5 mol per 1 mol of compound (VIII).

The reaction temperature is generally about −80 to about 150° C., preferably about 0 to about 120° C.

The reaction time is generally about 0.5 to about 20 hr.

[Step 2]

In this step, compound (I) can be produced by reacting compound (X) with compound (V).

This reaction can be carried out in the presence of a base, in a solvent that does not adversely influence the reaction.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, cesium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide, sodium tert-butoxide and the like, and the like.

The amount of the base to be used is preferably about 1 to about 5 mol per 1 mol of compound (X).

The amount of compound (V) to be used is preferably about 1 to about 5 mol per 1 mol of compound (X).

Examples of the solvent that does not adversely influence the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethylsulfoxide and the like; ketones such as acetone, 2-butanone and the like, and the like. These solvents may be used in a mixture at an appropriate ratio.

The reaction temperature is generally about −80 to about 150° C., preferably about −10 to about 100° C.

The reaction time is generally about 0.5 to about 40 hr.

Alternatively, this reaction can also be carried out in the presence of a transition metal catalyst under inert gas atmosphere, in a solvent that does not adversely influence the reaction. In addition, this reaction can also be carried out in the presence of a base.

Examples of the inert gas include argon, nitrogen and the like.

Examples of the transition metal catalyst include a mixture of tris(dibenzylideneacetone)dipalladium(O) with 2 mol equivalents of 2-dicyclohexylphosphino-2',4',6'-triisopropyl-1,1'-biphenyl, a mixture of tris(dibenzylideneacetone)dipalladium(O) with 3 mol equivalents of (9,9-dimethyl-9H-xanthene-4,5-diyl)bis(diphenylphosphane), a mixture of palladium acetate (II) with 1 mol equivalents of 2,8,9-tris(2-methylpropyl)-2,5,8,9-tetraaza-1-phosphabicyclo[3.3.3]undecane, and the like.

The amount of the transition metal catalyst to be used is generally 0.001 to 2 mol, preferably 0.01 to 0.1 mol, per 1 mol of compound (X).

Examples of the solvent that does not adversely influence the reaction include ethers such as diethyl ether, tetrahydrofuran, dioxane and the like; aliphatic hydrocarbons such as hexane, heptane and the like; aromatic hydrocarbons such as benzene, toluene, xylene and the like; amides such as N,N-dimethylformamide, N,N-dimethylacetamide, N-methylpyrrolidone and the like; halogenated hydrocarbons such as dichloromethane, chloroform, 1,2-dichloroethane, 1,1,2,2-tetrachloroethane and the like; nitriles such as acetonitrile and the like; sulfoxides such as dimethylsulfoxide and the like; alcohols such as methanol, ethanol, tert-butanol and the like; water and the like. These solvents may be used in a mixture at an appropriate ratio.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, cesium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide, sodium tert-butoxide and the like, and the like.

The amount of the base to be used is preferably 0 to about 10 mol per 1 mol of compound (X).

The amount of compound (V) to be used is preferably about 1 to about 5 mol per 1 mol of compound (X).

The reaction temperature is generally about −80 to about 150° C., preferably about 0 to about 120° C.

The reaction time is generally about 0.5 to about 20 hr.

[Step 3]

In this step, compound (XI) can be produced from compound (VIII) and compound (V).

This reaction is carried out according to the above-mentioned Method B, Step 2.

[Step 4]

In this step, compound (I) can be produced from compound (XI) and compound (IX).

This reaction is carried out according to the above-mentioned Method B, Step 1.

Compound (VIII) and compound (IX), which are used as a starting material compound in the above-mentioned Method, can be produced according to a method known per se.

Compound (I-5), which is compound (I) wherein $R^3$ is a tert-butoxycarbonyl group, can be produced, for example, according to the following Method C.

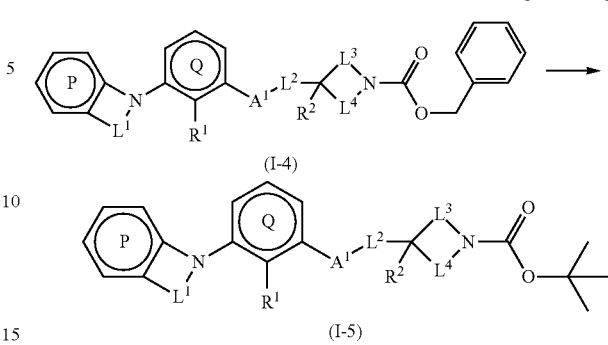

wherein each symbol is as defined above.

In this step, compound (I-5) can be produced from compound (I-4).

This reaction is carried out in the presence of di-tert-butyl dicarbonate, a metal catalyst and a hydrogen source, in a solvent that does not adversely influence the reaction.

The amount of the di-tert-butyl dicarbonate to be used is preferably about 1 to about 10 mol per 1 mol of compound (I-4).

Examples of the metal catalyst include palladium-carbon, palladium-carbonethylenediamine complex, palladium black, palladium chloride, platinum oxide, platinum black, platinum-palladium, Raney-nickel, Raney-cobalt and the like.

The amount of the metal catalyst to be used is generally 0.001 to 1000 mol, preferably 0.01 to 100 mol, per 1 mol of compound (I-4).

Examples of the hydrogen source include hydrogen gas, formic acid, formic acid amine salts, phosphinates, hydrazine and the like.

Examples of the solvent that does not adversely influence the reaction include aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, dimethoxyethane and the like; halogenated hydrocarbons such as chloroform, dichloromethane and the like, alcohols such as methanol, ethanol and the like, water and the like. These solvents may be used in a mixture at an appropriate ratio.

The reaction temperature is generally about −100 to about 150° C., preferably about −10 to about 100° C.

The reaction time is generally about 0.5 to about 20 hr.

Compound (I-4) used as a starting material compound in the above-mentioned Method C can be produced, for example, according to the above-mentioned Method A, Method B, the below-mentioned Method D, or a method analogous thereto.

Compound (I-7) which is compound (I) having the substituent $NR^5R^6$ on ring P can be produced, for example, according to the following Method D.

[Method D]

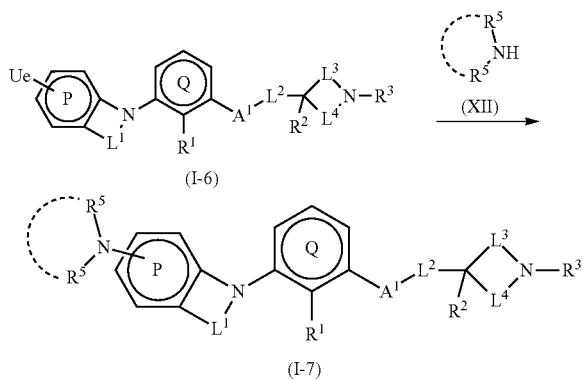

wherein Ue is a halogen atom or a trifluoromethanesulfonyloxy group, $R^5$ and $R^6$ are each independently (1)
  (i) a hydrogen atom,
  (ii) a $C_{1-6}$ alkyl group optionally substituted by 1 to 3 halogen atoms,
  (iii) a $C_{1-6}$ alkyl-carbonyl group optionally substituted by 1 to 3 halogen atoms,
  (iv) a $C_{1-6}$ alkoxy-carbonyl group optionally substituted by 1 to 3 halogen atoms,
  (v) a $C_{1-6}$ alkylsulfonyl group (e.g., methylsulfonyl) optionally substituted by 1 to 3 halogen atoms,
  (vi) a carbamoyl group optionally mono- or di-substituted by $C_{1-6}$ alkyl group(s) optionally substituted by 1 to 3 halogen atoms, or
  (vii) an aromatic heterocyclic group (e.g., thienyl, furyl, pyridyl, pyrazolyl, imidazolyl, tetrazolyl, oxazolyl, thiazolyl, oxadiazolyl, thiadiazolyl), or;
(2) $R^5$ and $R^6$ in combination optionally form, together with the adjacent nitrogen atom, an optionally substituted nitrogen-containing heterocycle,
and other symbols are as defined above.

Examples of the halogen atom for Ue include a chlorine atom, a bromine atom, an iodine atom and the like.

Examples of the "optionally substituted nitrogen-containing heterocycle" formed by $R^5$ and $R^6$ in combination include
(1) an aromatic nitrogen-containing heterocycle optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(2) a non-aromatic nitrogen-containing heterocycle optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
and the like.

$R^5$ and $R^6$ is preferably each independently a hydrogen atom, methyl, ethyl, propyl, cyclopropyl, cyclopropylmethyl, 2-methoxyethyl, phenyl, methoxy, ethoxy, phenoxy or the like, or $R^5$ and $R^6$ in combination form, together with the adjacent nitrogen atom, pyrrolidine, piperidine, hexamethylenimine, morpholine or the like.

In this step, compound (I-7) can be produced from compound (I-6) and compound (XII).

This reaction is carried out in the presence of a transition metal catalyst under inert gas atmosphere, in a solvent that does not adversely influence the reaction. In addition, this reaction can be carried out in the presence of a base.

Examples of the inert gas include argon, nitrogen and the like.

Examples of the transition metal catalyst include a mixture of tris(dibenzylideneacetone)dipalladium(O) with 2 mol equivalents of 2-dicyclohexylphosphino-2',4',6'-triisopropyl-1,1'-biphenyl, a mixture of tris(dibenzylideneacetone)dipalladium(O) with 3 mol equivalents of (9,9-dimethyl-9H-xanthene-4,5-diyl)bis(diphenylphosphane), a mixture of palladium acetate (II) with 1 mol equivalents of 2,8,9-tris(2-methylpropyl)-2,5,8,9-tetraaza-1-phosphabicyclo[3.3.3]undecane, and the like.

The amount of the transition metal catalyst to be used is generally 0.001 to 2 mol, preferably 0.01 to 0.1 mol, per 1 mol of compound (I-6).

Examples of the solvent that does not adversely influence the reaction include ethers such as diethyl ether, tetrahydrofuran, dioxane and the like; aliphatic hydrocarbons such as hexane, heptane and the like; aromatic hydrocarbons such as benzene, toluene, xylene and the like; amides such as N,N-dimethylformamide, N,N-dimethylacetamide, N methylpyrrolidone and the like; halogenated hydrocarbons such as dichloromethane, chloroform, 1,2-dichloroethane, 1,1,2,2-tetrachloroethane and the like; nitriles such as acetonitrile and the like; sulfoxides such as dimethylsulfoxide and the like; alcohols such as methanol, ethanol, tert-butanol and the like; water and the like. These solvents may be used in a mixture at an appropriate ratio.

Examples of the base include amines such as triethylamine, N,N-diisopropylethylamine, N-methylmorpholine, N,N-dimethylaniline, 4-dimethylaminopyridine and the like; alkali metal salts such as sodium hydrogen carbonate, sodium carbonate, potassium carbonate, cesium carbonate and the like; alkali metal hydroxides such as sodium hydroxide, potassium hydroxide, lithium hydroxide and the like; alkaline earth metal hydroxides such as magnesium hydroxide, calcium hydroxide, barium hydroxide and the like; metal hydrides such as potassium hydride, sodium hydride and the like; alkali metal $C_{1-6}$ alkoxides such as sodium methoxide, sodium ethoxide, potassium tert-butoxide, sodium tert-butoxide and the like, and the like.

The amount of the base to be used is preferably 0 to about 10 mol per 1 mol of compound (I-6).

The amount of compound (XII) to be used is preferably about 1 to about 5 mol per 1 mol of compound (I-6).

The reaction temperature is generally about −80 to about 150° C., preferably about 0 to about 120° C.

The reaction time is generally about 0.5 to about 40 hr.

Compound (I-6) used as a starting material compound in the above-mentioned Method D can be produced, for example, according to the above-mentioned Method A, Method B, Method C, or a method analogous thereto.

Compound (I-9), which is compound (I) wherein $A^1$ is O, and having the substituent $CONR^5R^6$ on ring P can be produced, for example, according to the following Method E.

[Method E]

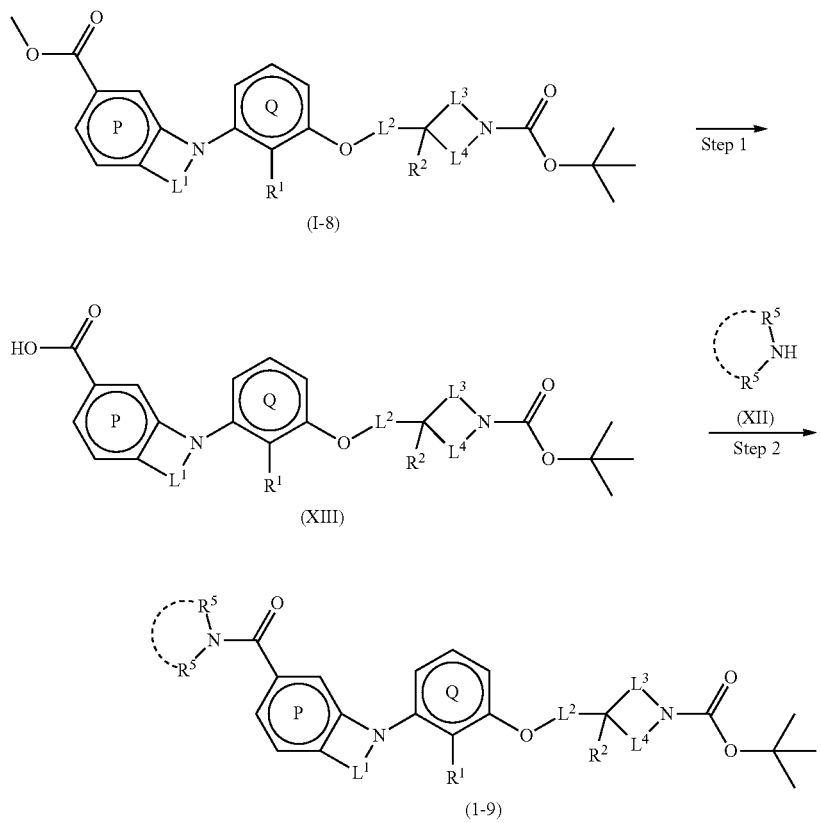

wherein each symbol is as defined above.

[Step 1]

In this step, compound (XIII) can be produced from compound (I-8).

This reaction is carried out according to a method known per se, for example, in the presence of a base, in a solvent that does not adversely influence the reaction.

Examples of the base include alkali metal hydroxides such as sodium hydroxide, potassium hydroxide, lithium hydroxide and the like, and the like. These bases may be used in the form of an aqueous solution having an appropriate concentration.

The amount of the base to be used is preferably about 1 to about 20 mol per 1 mol of compound (I-8).

Examples of the solvent that does not adversely influence the reaction include ethers such as tetrahydrofuran, dioxane and the like; alcohols such as ethanol, methanol and the like; water and the like. These solvents may be used in a mixture at an appropriate ratio.

The reaction temperature is generally about −80 to about 150° C., preferably about 0 to about 120° C.

The reaction time is generally about 0.5 to about 40 hr.

[Step 2]

In this step, compound (I-9) can be produced from compound (XIII) and compound (XII).

This reaction is carried out according to a method known per se, for example, in the presence of a condensing agent, in a solvent that does not adversely influence the reaction.

The amount of compound (XII) to be used is preferably about 1 to about 10 mol per 1 mol of compound (XIII).

Examples of the condensing agent include 2-(7-aza-1H-benzotriazol-1-yl)-1,1,3,3-tetramethyluronium hexafluorophosphate, 1-ethyl-3-(3-dimethylaminopropyl)-carbodiimide hydrochloride, 4-(4,6-dimethoxy-1,3,5-triazin-2-yl)-4-methylmorpholinium chloride hydrate and the like.

The amount of the condensing agent to be used is preferably about 1 to about 20 mol per 1 mol of compound (XIII).

Examples of the solvent that does not adversely influence the reaction include ethers such as tetrahydrofuran, dioxane and the like; amides such as N,N-dimethylformamide and the like; acetonitrile and the like. These solvents may be used in a mixture at an appropriate ratio.

The reaction temperature is generally about −80 to about 150° C., preferably about 0 to about 120° C.

The reaction time is generally about 0.5 to about 40 hr.

Compound (I-8) used as a starting material compound in the above-mentioned Method E can be carried out, for example, according to the above-mentioned Method B, Method C, or a method analogous thereto.

Compound (V-2) can be produced, for example, according to the following Method F.

[Method F]

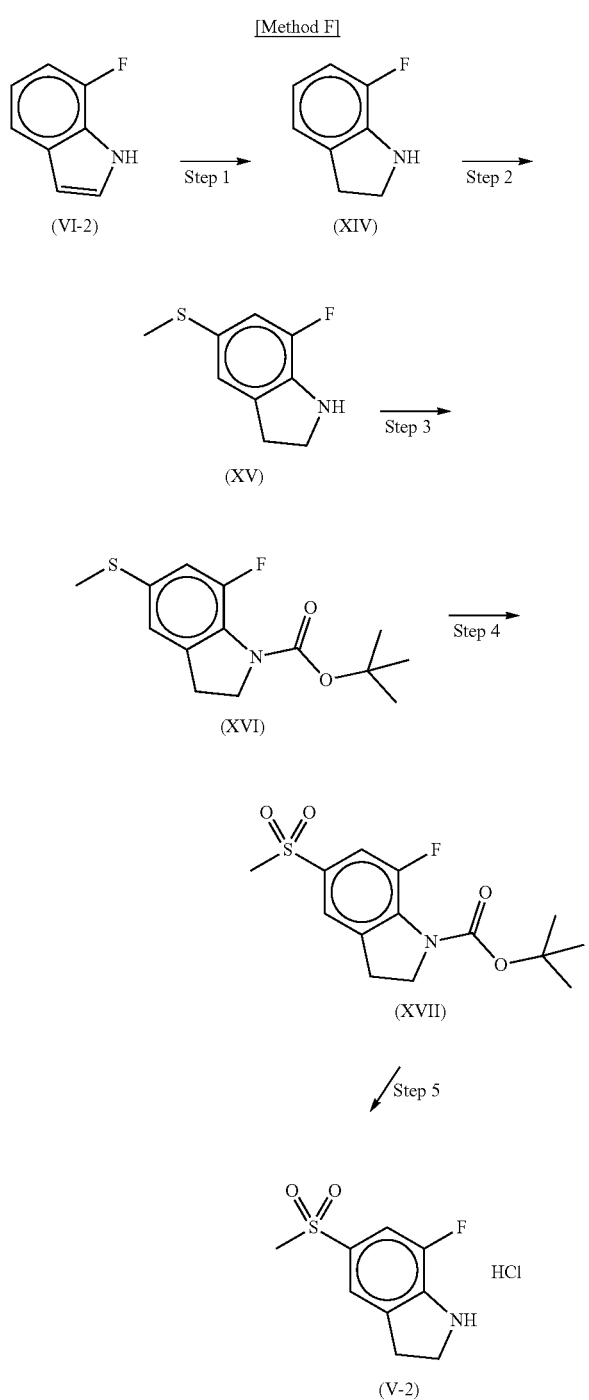

[Step 1]

In this step, compound (XIV) can be produced from compound (VI-2).

This reaction is carried out according to a method known per se, for example, using a reducing agent such as sodium cyanoborohydride and the like, in a solvent that does not adversely influence the reaction.

The amount of the reducing agent to be used is preferably about 1 to about 20 mol per 1 mol of compound (VI-2).

Examples of the solvent that does not adversely influence the reaction include acetic acid and the like; ethers such as diethyl ether, tetrahydrofuran, dioxane and the like; halogenated hydrocarbons such as chloroform, dichloromethane and the like; amides such as N,N-dimethylformamide and the like, and the like. These solvents may be used in a mixture at an appropriate ratio.

The reaction temperature is generally about −80 to about 150° C., preferably about 0 to about 80° C.

The reaction time is generally about 0.5 to about 40 hr.

[Step 2]

In this step, compound (XV) can be produced from compound (XIV).

This reaction is carried out according to a method known per se, for example, using potassium thiocyanate, bromine, potassium hydroxide and iodomethane, in a solvent that does not adversely influence the reaction.

The amount of the pyridine to be used is preferably about 0.01 to about 20 mol per 1 mol of compound (XIV).

The amount of the bromine to be used is preferably about 1 to about 20 mol per 1 mol of compound (XIV).

The amount of the potassium hydroxide to be used is preferably about 1 to about 20 mol per 1 mol of compound (XIV).

The amount of the iodomethane to be used is preferably about 1 to about 20 mol per 1 mol of compound (XIV).

Examples of the solvent that does not adversely influence the reaction include water; alcohols such as ethanol, methanol, isopropanol and the like, and the like. These solvents may be used in a mixture at an appropriate ratio.

The reaction temperature is generally about −80 to about 150° C., preferably about −20 to about 120° C.

The reaction time is generally about 0.5 to about 40 hr.

[Step 3]

In this step, compound (XVI) can be produced from compound (XV).

This reaction is carried out according to a method known per se, for example, using di-tert-butyl dicarbonate in the presence of a base such as triethylamine and the like, in a solvent that does not adversely influence the reaction.

The amount of the di-tert-butyl dicarbonate to be used is preferably about 1 to about 20 mol per 1 mol of compound (XV).

The amount of the base to be used is preferably about 1 to about 20 mol per 1 mol of compound (XV).

Examples of the solvent that does not adversely influence the reaction include ethers such as diethyl ether, tetrahydrofuran, dioxane and the like; halogenated hydrocarbons such as chloroform, dichloromethane and the like, and the like. These solvents may be used in a mixture at an appropriate ratio.

The reaction temperature is generally about −80 to about 150° C., preferably about −20 to about 120° C.

The reaction time is generally about 0.5 to about 40 hr.

[Step 4]

In this step, compound (XVII) can be produced from compound (XVI).

This reaction is carried out according to a method known per se, for example, using a oxidant such as m-chloroperbenzoic acid and the like, in a solvent that does not adversely influence the reaction.

The amount of the oxidant to be used is preferably about 2 to about 20 mol per 1 mol of compound (XVI).

Examples of the solvent that does not adversely influence the reaction include ethyl acetate; halogenated hydrocarbons such as chloroform, dichloromethane and the like, and the like. These solvents may be used in a mixture at an appropriate ratio.

The reaction temperature is generally about −80 to about 150° C., preferably about −20 to about 120° C.

The reaction time is generally about 0.5 to about 40 hr.

[Step 5]

In this step, compound (V-2) can be produced from compound (XVII).

This reaction is carried out according to a method known per se, for example, in the presence of an acid such as trifluoroacetic acid, 4N hydrochloric acid-ethyl acetate solution and the like, in a solvent that does not adversely influence the reaction.

The amount of the acid to be used is preferably about 1 to about 50 mol per 1 mol of compound (XVII).

Examples of the solvent that does not adversely influence the reaction include ethyl acetate; ethers such as tetrahydrofuran, dioxane and the like; alcohols such as ethanol, methanol, isopropanol and the like, and the like.

The reaction temperature is generally about −80 to about 150° C., preferably about 0 to about 80° C.

The reaction time is generally about 0.5 to about 40 hr.

Compound (I-12) which is compound (I) wherein $A^1$ is $NR^{4c}$ and $R^{4c}$ is a trifluoromethyl group, can be produced, for example, according to the following Method G.

[Method G]

(I-10)

Step 1

(I-11)

Step 2

-continued (I-12)

wherein each symbol is as defined above.

[Step 1]

In this step, compound (I-11) can be produced from compound (I-10).

This reaction is carried out according to a method known per se, for example, using carbon disulfide and methyl iodide in the presence of a base, in a solvent that does not adversely influence the reaction.

Examples of the base include n-butyllithium, lithium diisopropylamide and the like.

The amount of the base to be used is preferably about 1 to about 20 mol per 1 mol of compound (I-10).

The amount of the carbon disulfide to be used is preferably about 1 to about 20 mol per 1 mol of compound (I-10).

The amount of the methyl iodide to be used is preferably about 1 to about 20 mol per 1 mol of compound (I-10).

Examples of the solvent that does not adversely influence the reaction include ethers such as diethyl ether, tetrahydrofuran and the like; hexane and the like. These solvents may be used in a mixture at an appropriate ratio.

The reaction temperature is generally about −80 to about 150° C., preferably about −20 to about 120° C.

The reaction time is generally about 0.5 to about 40 hr.

[Step 2]

In this step, compound (I-12) can be produced from compound (I-11).

This reaction is carried out according to a method known per se, for example, using tetrabutylammonium dihydrogentrifluoride and N-bromosuccinimide, in a solvent that does not adversely influence the reaction.

The amount of the tetrabutylammonium dihydrogentrifluoride to be used is preferably about 1 to about 20 mol per 1 mol of compound (I-11).

The amount of the N-bromosuccinimide to be used is preferably about 1 to about 20 mol per 1 mol of compound (I-11).

Examples of the solvent that does not adversely influence the reaction include halogenated hydrocarbons such as chloroform, dichloromethane and the like; aromatic hydrocarbons such as benzene, toluene, xylene and the like, and the like. These solvents may be used in a mixture at an appropriate ratio.

The reaction temperature is generally about −80 to about 150° C., preferably about −80 to about 50° C.

The reaction time is generally about 0.5 to about 40 hr.

Compound (I-10) used as a starting material compound in the above-mentioned Method G can be carried out, for example, according to the above-mentioned Methods A to D or a method analogous thereto.

Compound (I-14), (I-15), (I-16), (I-17), (I-18) and (I-19), which are compound (I) wherein $A^1$ is O can be produced, for example, according to the following Method H.

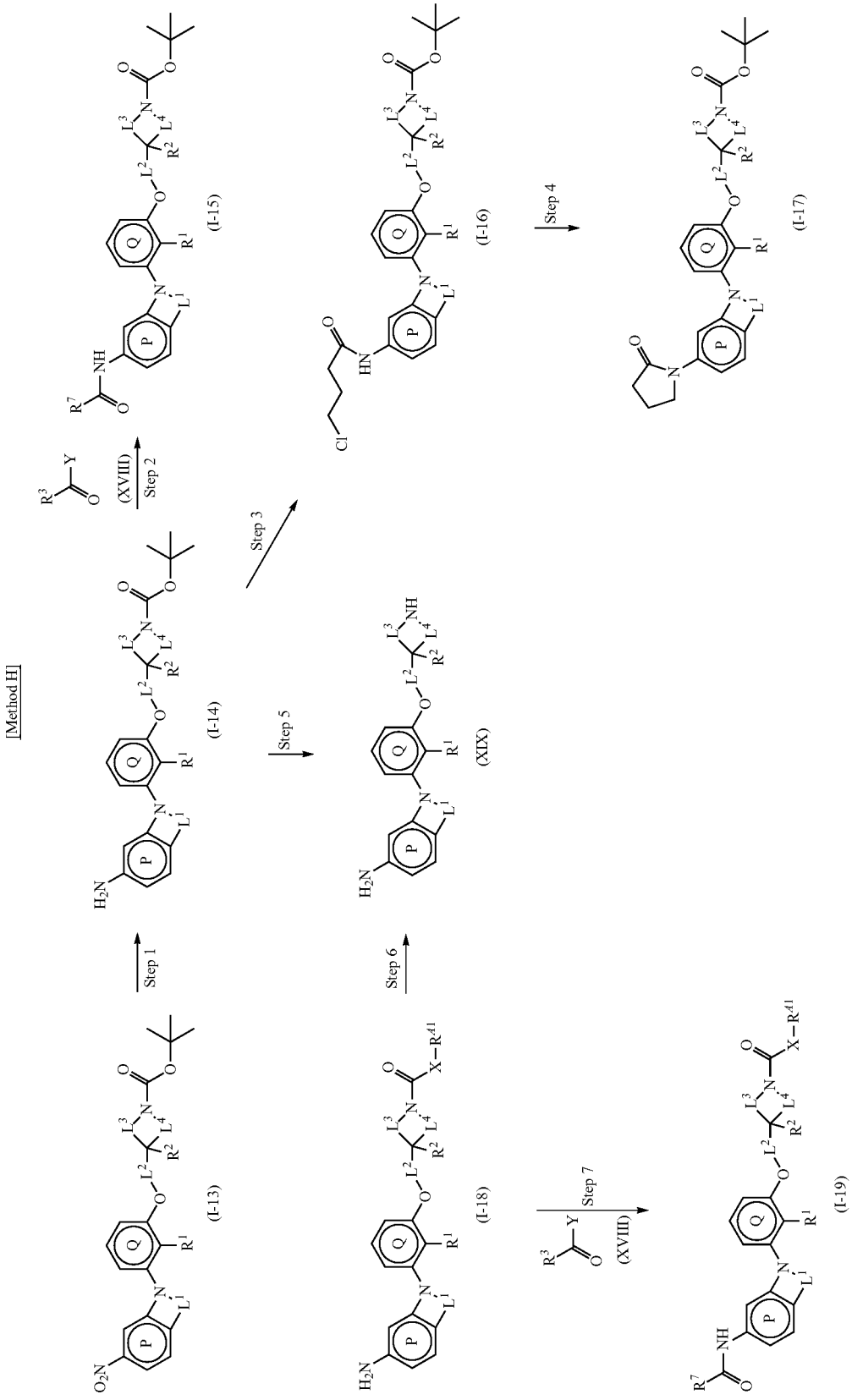

wherein
X is O or S,
Y is Cl or OH,
$R^7$ is
(1) a $C_{1-6}$ alkyl group optionally substituted by 1 to 3 substituents selected from a halogen atom, a hydroxy group and a $C_{1-6}$ alkoxy group,
(2) a $C_{1-6}$ alkoxy group optionally substituted by 1 to 3 halogen atoms,
(3) an amino group optionally mono- or di-substituted by $C_{1-6}$ alkyl group(s) optionally substituted by 1 to 3 halogen atoms, or
(4) a non-aromatic heterocyclic group,
and other symbols are as defined above.

[Step 1]

In this step, compound (I-14) can be produced from compound (I-13).

This reaction is carried out according to a conventional method, in the presence of a metal catalyst and a hydrogen source, in a solvent that does not adversely influence the reaction.

Examples of the metal catalyst include palladium-carbon and the like.

The amount of the metal catalyst to be used is generally 0.001 to 1000 mol, preferably 0.01 to 100 mol, per 1 mol of compound (I-13).

Examples of the hydrogen source include hydrogen gas, formic acid amine salts, hydrazine and the like.

Examples of the solvent that does not adversely influence the reaction include ethers such as tetrahydrofuran and the like; alcohols such as methanol, ethanol and the like, water and the like. These solvents may be used in a mixture at an appropriate ratio.

The reaction temperature is generally about −100 to about 150° C., preferably about −10 to about 100° C.

The reaction time is generally about 0.5 to about 20 hr.

[Step 2]

In this step, compound (I-15) can be produced from compound (I-14) and compound (XVIII).

When compound (XVIII) is an acid chloride (Y═Cl), this reaction is carried out according to a method known per se, for example, in the presence of a base such as triethylamine and the like, in a solvent that does not adversely influence the reaction.

Examples of compound (XVIII) include acetoxyacetyl chloride, methoxyacetyl chloride and the like.

The amount of compound (XVIII) to be used is preferably about 1 to about 10 mol per 1 mol of compound (I-14).

Examples of the base include triethylamine, diisopropylethylamine and the like.

The amount of the base to be used is preferably about 1 to about 20 mol per 1 mol of compound (I-14).

Examples of the solvent that does not adversely influence the reaction include ethers such as tetrahydrofuran, dioxane, dimethoxyethane and the like; halogenated hydrocarbons such as chloroform, dichloromethane and the like, acetonitrile and the like. These solvents may be used in a mixture at an appropriate ratio.

The reaction temperature is generally about −100 to about 150° C., preferably about −10 to about 100° C.

The reaction time is generally about 0.5 to about 20 hr.

When compound (XVIII) is a carboxylic acid (Y═OH), this reaction is carried out according to a method known per se, for example, using a condensing agent in a solvent that does not adversely influence the reaction.

Examples of compound (XVIII) include (R)-(+)-tetrahydrofuran-2-carboxylic acid, (S)-(−)-tetrahydrofuran-2-carboxylic acid and the like.

The amount of compound (XVIII) to be used is preferably about 1 to about 10 mol per 1 mol of compound (I-14).

Examples of the condensing agent include 2-(7-aza-1H-benzotriazol-1-yl)-1,1,3,3-tetramethyluronium hexafluorophosphate, 1-ethyl-3-(3-dimethylaminopropyl)-carbodiimide hydrochloride, 4-(4,6-dimethoxy-1,3,5-triazin-2-yl)-4-methylmorpholinium chloride hydrate and the like.

The amount of the condensing agent to be used is preferably about 1 to about 20 mol per 1 mol of compound (I-14).

Examples of the solvent that does not adversely influence the reaction include ethers such as tetrahydrofuran, dioxane and the like; amides such as N,N-dimethylformamide and the like; acetonitrile and the like. These solvents may be used in a mixture at an appropriate ratio.

The reaction temperature is generally about −80 to about 150° C., preferably about 0 to about 120° C.

Compound (XVIII) used as a starting material compound can be produced according to a method known per se.

[Step 3]

In this step, compound (I-16) can be produced from compound (I-14).

This reaction is carried out according to a method known per se, for example, in the presence of 4-chlorobutyryl chloride and a base such as triethylamine and the like, in a solvent that does not adversely influence the reaction.

The amount of the 4-chlorobutyryl chloride to be used is preferably about 1 to about 10 mol per 1 mol of compound (I-14).

Examples of the base include triethylamine, diisopropylethylamine and the like.

The amount of the base to be used is preferably about 1 to about 20 mol per 1 mol of compound (I-14). Examples of the solvent that does not adversely influence the reaction include ethers such as tetrahydrofuran, dioxane, dimethoxyethane and the like; halogenated hydrocarbons such as chloroform, dichloromethane and the like, acetonitrile, propionitrile and the like. These solvents may be used in a mixture at an appropriate ratio.

The reaction temperature is generally about −100 to about 150° C., preferably about −10 to about 100° C.

The reaction time is generally about 0.5 to about 20 hr.

[Step 4]

In this step, compound (I-17) can be produced from compound (I-16).

This reaction is carried out according to a method known per se, for example, in the presence of a base such as sodium hydride and the like, in a solvent that does not adversely influence the reaction.

Examples of the base include sodium hydride, tert-butoxy sodium and the like.

The amount of the base to be used is preferably about 1 to about 10 mol per 1 mol of compound (I-16).

Examples of the solvent that does not adversely influence the reaction include ethers such as diethyl ether, tetrahydrofuran, dioxane and the like; amides such as N,N-dimethylformamide, N,N-dimethylacetamide, N-methylpyrrolidone and the like, and the like. These solvents may be used in a mixture at an appropriate ratio.

The reaction temperature is generally about −80 to about 150° C., preferably about 0 to about 80° C.

The reaction time is generally about 0.5 to about 40 hr.

[Step 5]

In this step, compound (XIX) can be produced from compound (I-14).

This reaction is carried out according to a method known per se, for example, in the presence of an acid such as trifluoroacetic acid, 4N hydrochloric acid-ethyl acetate solution and the like, in a solvent that does not adversely influence the reaction.

The amount of the acid to be used is preferably about 1 to about 50 mol per 1 mol of compound (I-14).

Examples of the solvent that does not adversely influence the reaction include ethyl acetate; ethers such as tetrahydrofuran, dioxane and the like; alcohols such as ethanol, methanol, isopropanol and the like, and the like.

The reaction temperature is generally about −80 to about 150° C., preferably about 0 to about 80° C.

The reaction time is generally about 0.5 to about 40 hr.

[Step 6]

In this step, compound (I-18) can be produced from compound (XIX).

This reaction is carried out in the presence of a chlorothiocarbonate or chlorocarbonate corresponding to $R^{41}$, and a base such as triethylamine and the like, in a solvent that does not adversely influence the reaction.

Examples of the chlorothiocarbonate or chlorocarbonate corresponding to $R^{41}$ include S-isopropyl chlorothiocarbonate, isopropyl chlorocarbonate and the like.

The amount of the chlorothiocarbonate or chlorocarbonate corresponding to $R^{41}$ to be used is preferably about 1 to about 10 mol per 1 mol of compound (XIX).

Examples of the base include triethylamine, diisopropylethylamine and the like.

The amount of the base to be used is preferably about 1 to about 20 mol per 1 mol of compound (XIX).

Examples of the solvent that does not adversely influence the reaction include ethers such as tetrahydrofuran, dioxane, dimethoxyethane and the like; halogenated hydrocarbons such as chloroform, dichloromethane and the like, acetonitrile, propionitrile and the like. These solvents may be used in a mixture at an appropriate ratio.

The reaction temperature is generally about −100 to about 150° C., preferably about −10 to about 100° C.

The reaction time is generally about 0.5 to about 20 hr.

[Step 7]

In this step, compound (I-19) can be produced from compound (I-18) and compound (XVIII).

This reaction is carried out according to the above-mentioned Step 2.

Compound (I-13) used as a starting material compound in the above-mentioned Method H can be produced, for example, according to the above-mentioned Method B to Method D or a method analogous thereto.

Compound (I-21), which is compound (I) wherein $A^1$ is O, and having a hydroxyacetylamino group is present on ring P can be produced, for example, according to the following Method I.

[Method I]

wherein each symbol is as defined above.

In this step, compound (I-21) can be produced from compound (I-20).

This reaction is carried out according to a method known per se, for example, in the presence of a base, in a solvent that does not adversely influence the reaction.

Examples of the base include alkali metal hydroxides such as sodium hydroxide, potassium hydroxide, lithium hydroxide and the like, and the like. These bases may be used in the form of an aqueous solution having an appropriate concentration.

The amount of the base to be used is preferably about 1 to about 20 mol per 1 mol of compound (I-20).

Examples of the solvent that does not adversely influence the reaction include ethers such as tetrahydrofuran, dioxane and the like; alcohols such as ethanol, methanol and the like; water and the like. These solvents may be used in a mixture at an appropriate ratio.

The reaction temperature is generally about −80 to about 150° C., preferably about 0 to about 120° C.

The reaction time is generally about 0.5 to about 40 hr.

Compound (I-20) used as a starting material compound in the above-mentioned Method I can be produced, for example, according to the above-mentioned Method B, Method H or a method analogous thereto.

Compounds (I-23), (I-24) and (I-25) can be produced, for example, according to the following Method J.

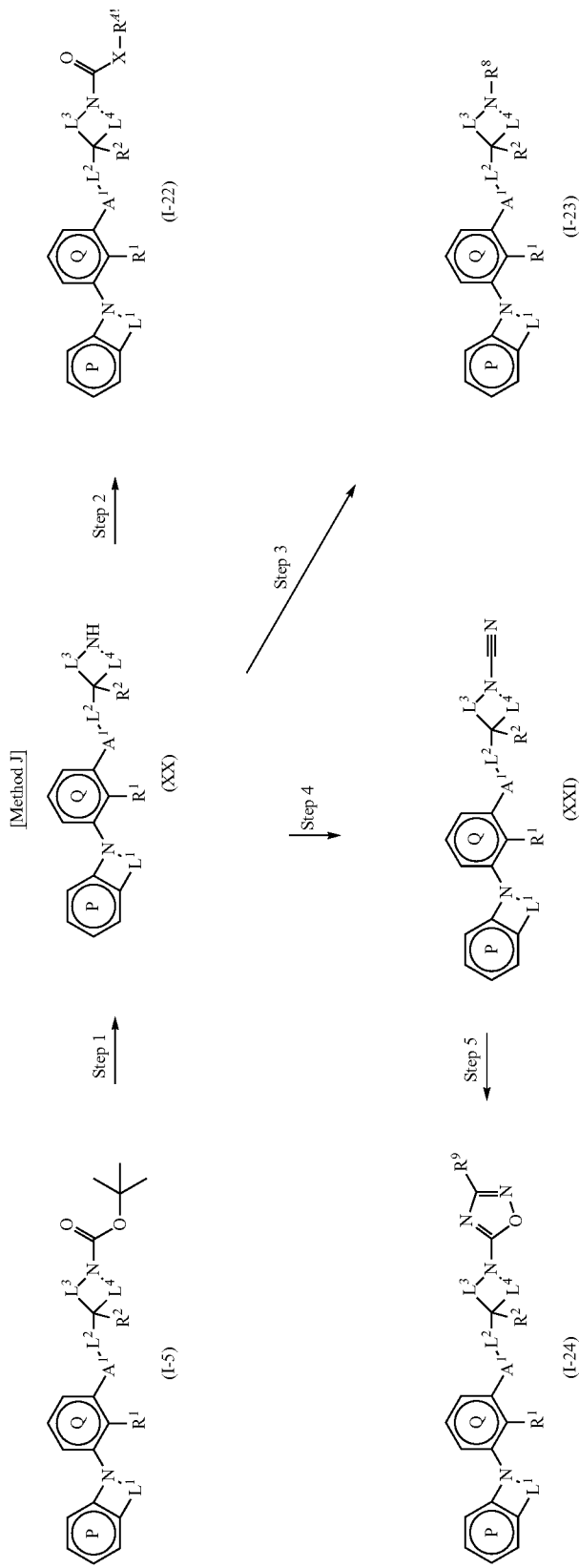

wherein
X is O or S,
$R^9$ is an optionally substituted 5- or 6-membered aromatic ring group,
$R^9$ is
(1) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s);
(2) a $C_{3-10}$ cycloalkyl group;
(3) a $C_{1-6}$ alkoxy group optionally substituted by 1 to 3 substituents selected from
  (a) a halogen atom,
  (b) a carboxy group,
  (c) a $C_{1-6}$ alkoxy group,
  (d) a $C_{1-6}$ alkoxy-carbonyl group optionally substituted by 1 to 3 $C_{6-14}$ aryl groups,
  (e) an amino group optionally mono- or di-substituted by substituent(s) selected from a $C_{1-6}$ alkyl group and $C_{1-6}$ alkoxy-carbonyl group,
  (f) a heterocyclic group, and
  (g) a $C_{3-10}$ cycloalkyl group; or
(4) a non-aromatic heterocyclic group optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
and other symbols are as defined above.

[Step 1]

In this step, compound (XX) can be produced from compound (I-5).

This reaction is carried out according to the above-mentioned Method H, Step 5.

[Step 2]

In this step, compound (I-22) can be produced from compound (XX).

This reaction is carried out in the presence of a chlorothiocarbonate or chlorocarbonate corresponding to $R^{41}$, and a base such as triethylamine and the like, in a solvent that does not adversely influence the reaction.

This reaction is carried out according to the above-mentioned Method H, Step 6.

[Step 3]

In this step, compound (I-23) can be produced from compound (XX).

This reaction can also be carried out according to a method known per se, for example, a method to be performed in the presence of a halide corresponding to $R^8$ and a base such as cesium carbonate and the like.

Examples of the halide corresponding to $R^8$ include 2-chloro-5-propylpyrimidine, 2-chloro-5-ethylpyrimidine, 2-chloro-5-methylpyrimidine, 2-chloro-5-methoxypyrimidine and the like.

The amount of the halide corresponding to $R^8$ to be used is preferably about 1 to about 20 mol per 1 mol of compound (XX).

The amount of the base to be used is preferably about 1 to about 20 mol per 1 mol of compound (XX).

Examples of the solvent that does not adversely influence the reaction include amides such as 1-methyl-2-pyrrolidone, N,N-dimethylformamide and the like, and the like.

The reaction temperature is generally about −80 to about 150° C., preferably about 0 to about 150° C.

The reaction time is generally about 0.5 to about 90 hr.

[Step 4]

In this step, compound (XXI) can be produced from compound (XX).

This reaction is carried out according to a method known per se, for example, in the presence of cyano bromide and a base such as sodium hydrogen carbonate and the like, in a solvent that does not adversely influence the reaction.

The amount of the cyano bromide to be used is preferably about 1 to about 20 mol per 1 mol of compound (XX).

Examples of the base include alkali metal salts such as sodium hydrogen carbonate and the like, and the like.

The amount of the base to be used is preferably about 1 to about 20 mol per 1 mol of compound (XX).

Examples of the solvent that does not adversely influence the reaction include water; ethers such as tetrahydrofuran, dioxane and the like, and the like. These solvents may be used in a mixture at an appropriate ratio.

The reaction temperature is generally about −80 to about 150° C., preferably about −20 to about 120° C.

The reaction time is generally about 0.5 to about 40 hr.

[Step 5]

In this step, compound (I-24) can be produced from compound (XXI).

This reaction is carried out according to a method known per se, for example, a method wherein the reaction is carried out in the presence of a substituted imidamide corresponding to $R^9$ and 1.0M zinc chloride-diethyl ether solution, in a solvent that does not adversely influence the reaction, after which the reaction is carried out in the presence of concentrated hydrochloric acid, in a solvent that does not adversely influence the reaction and the like.

Examples of the substituted imidamide corresponding to $R^9$ include N'-hydroxy-2-methylpropanimidamide, (2R)—N'-hydroxytetrahydrofuran-2-carboximidamide, (1Z)—N'-hydroxy-2,2-dimethylpropanimidamide, N'-hydroxycyclopropane-carboximidamide, (1Z)—N'-hydroxypropanimidamide, (1Z)—N'-hydroxy-2-methoxyethanimidamide, (1Z)—N'-hydroxyethanimidamide and the like.

The amount of the substituted imidamide corresponding to $R^9$ to be used is preferably about 1 to about 20 mol per 1 mol of compound (XXI).

The amount of the 1.0M zinc chloride-diethyl ether solution to be used is preferably about 1 to about 20 mol per 1 mol of compound (XXI).

Examples of the solvent that does not adversely influence the reaction include water; ethyl acetate; ethers such as tetrahydrofuran, dioxane and the like; alcohols such as ethanol, methanol, isopropanol and the like; amides such as 1-methyl-2-pyrrolidone, N,N-dimethylformamide and the like; ethers such as tetrahydrofuran, dioxane and the like; alcohols such as ethanol, methanol and the like; water and the like.

These solvents may be used in a mixture at an appropriate ratio.

The reaction temperature is generally about −80 to about 150° C., preferably about 0 to about 150° C.

The reaction time is generally about 0.5 to about 40 hr.

The amount of the concentrated hydrochloric acid to be used is preferably about 10 to about 1000 mol per 1 mol of compound (XXI).

Examples of the solvent that does not adversely influence the reaction include water; alcohols such as ethanol and the like, and the like. These solvents may be used in a mixture at an appropriate ratio.

The reaction temperature is generally about −80 to about 150° C., preferably about 30 to about 150° C.

The reaction time is generally about 0.5 to about 40 hr.

In each of the above-mentioned reactions, when the starting compound has an amino group, a carboxyl group, a hydroxy group, a carbonyl group or a mercapto group as a substituent, a protecting group generally used for peptide chemistry etc. may be introduced into these groups, and the object compound can be obtained by removing, as necessary, the protecting groups after the reaction.

Examples of the amino-protecting group include a formyl group, a $C_{1-6}$ alkyl-carbonyl group, a $C_{1-6}$ alkoxy-carbonyl group, benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{2-6}$ alkyl group, a $C_{1-6}$ alkoxy group and a nitro group.

Examples of the carbonyl-protecting group include a cyclic acetal (e.g., 1,3-dioxane), an acyclic acetal (e.g., di-$C_{1-6}$ alkylacetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The above-mentioned protecting groups can be removed by a method known per se, for example, the method described in Protective Groups in Organic Synthesis, John Wiley and Sons (1980) and the like. Specifically, a method using an acid, a base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be mentioned.

The compound obtained by each of the above-mentioned production methods can be isolated and purified by known means such as concentration, concentration under reduced pressure, solvent extraction, crystallization, recrystallization, phase transfer, chromatography and the like. Each starting compound used for each of the above-mentioned production methods can be isolated and purified by known means similar to those mentioned above. Such starting compounds may also be used as the starting materials for the next step, without isolation and directly in the form of a reaction mixture.

When compound (I) contains an optical isomer, a stereoisomer, a positional isomer or a rotamer, these are also encompassed in compound (I). Each of them can be obtained as a single product by a synthesis method and a separation method known per se. For example, when compound (I) contains an optical isomer, the optical isomer resolved from the compound is also encompassed in compound (I).

Compound (I) may be a crystal.

The crystal of compound (I) (hereinafter sometimes to be abbreviated as the crystal of the present invention) can be produced by crystallization by subjecting compound (I) to a crystallization method known per se.

In the present specification, the melting point means, for example, a melting point measured using a trace melting point measurement device (Yanaco, MP-500D or Buchi, B-545) or DSC (differential scanning calorimetry) (SEIKO, EXSTAR6000) and the like.

In general, the melting point sometimes varies depending on the measurement device, measurement conditions and the like. The crystal in the present specification may show a value different from the melting point described in the present specification as long as it is within the general error range.

The crystal of the present invention is superior in the physicochemical properties (e.g., melting point, solubility, stability) and biological properties (e.g., in vivo kinetics (absorbability, distribution, metabolism, excretion), and efficacy expression), and is extremely useful as a medicament Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

The medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

A pharmaceutical composition can be produced by a method conventionally used in the technical field of pharmaceutical preparation, for example, the method described in the Japanese Pharmacopoeia and the like.

While the content of the compound of the present invention in the pharmaceutical composition varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

Examples of the sugar coating base include sucrose. It may be used in combination with one or more kinds selected from talc, precipitated calcium carbonate, gelatin, gum arabic, pullulan, carnauba wax and the like.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity and the like) and a few side effects. Therefore, it can be used as an agent for the prophylaxis or treatment or a diagnostic of various diseases in a mammal (e.g., human, bovine, horse, dog, cat, monkey, mouse, rat) as mentioned below.

The compound of the present invention has a superior GPR119 agonist action.

Since a GPR119 agonist activates GPR119 expressed in pancreatic B cells and promotes insulin secretion, as well as activates GPR119 expressed in the intestine and promotes glucagon-like peptide-1 (GLP-1) secretion, the compound of the present invention exhibits a hypoglycemic action, an insulin secretagogue action, a GLP-1 secretagogue action and a pancreatic B cell protective action. Moreover, the compound of the present invention may have a glucose-dependent insulinotropic polypeptide (GIP) secretagogue action, a peptide YY (PYY) secretagogue action, a food ingestion suppressive action, and a glucagon secretion suppressive action.

The compound of the present invention can be used as a GPR119 agonist.

The compound of the present invention can be used as a prophylactic or therapeutic agent for pathology and diseases involving GPR119.

The compound of the present invention can be used as, for example, an agent for the prophylaxis or treatment of diabetes (e.g., type 1 diabetes, type 2 diabetes, gestational diabetes, obese diabetes), an insulin secretagogue, a GLP-1 secretion promoter, a pancreatic B cell protector, a GIP secretion promoter, a PYY secretion promoter, an agent for the prophylaxis or treatment of impaired glucose tolerance (IGT), and an agent for preventing progression from impaired glucose tolerance to diabetes.

The compound of the present invention can be used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, hypo-HDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (according to the criteria of diagnosis reported in the Japan Society for the Study of Obesity in 2005, and the like for the Japanese population, metabolic syndrome meets two out of three cutpoints of waist circumference of 85 cm or above for male and 90 cm or above for female, systolic blood pressure 130 or above or diastolic blood pressure 85 mmHg or above, neutral triglyceride 150 mg/dl or above or HDLc less than 40 mg/dl, and fasting blood sugar level (venous plasma glucose level 110 mg/dl or above, and the like.

For diagnostic criteria of diabetes, Japan Diabetes Society reported diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO in 1998 reported diagnostic criteria of diabetes.

According to the report of ADA, diabetes is a condition showing diabetes-like symptoms (polyuria, polydipsia, overeating, overwork, body weight decrease, blurred vision, growth disorder), as well as any of a non-fasting blood glucose level (glucose concentration of venous plasma) of not less than 200 mg/dl, a fasting blood glucose level (glucose concentration of venous plasma) of not less than 126 mg/dl, and a 75 g oral glucose tolerance test 2 h level (glucose concentration of venous plasma) of not less than 200 mg/dl. According to the report of WHO, diabetes is a condition showing a fasting blood glucose level (glucose concentration of intravenous plasma) of not less than 126 mg/dl or a 75 g oral glucose tolerance test 2 hr level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention can also be used, for example, as an agent for the prophylaxis or treatment of cognitive impairment, osteoporosis, cachexia (e.g., is carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), insulin resistance syndrome, syndrome X, hyperinsulinemia, sensory abnormality in hyperinsulinemia, tumor (e.g., leukemia, breast cancer, prostate cancer, skin cancer), irritable bowel syndrome, acute or chronic diarrhea, inflammatory disease (e.g., arteriosclerosis (e.g., atherosclerosis), rheumatoid arthritis, spondylitis deformans, osteoarthritis, lumbago, gout, postoperative or posttraumatic inflammation, swelling, neuralgia, pharyngolaryngitis, cystitis, hepatitis (including nonalcoholic steatohepatitis), pneumonia, pancreatitis, inflammatory colitis, ulcerative colitis, chronic obstructive pulmonary diseases (COPD)), visceral obesity syndrome, foot ulcer, sepsis, psoriasis and the like.

In addition, the compound of the present invention can also be used for the improvement and the like of symptoms such as abdominal pain, nausea, vomiting, upper abdominal uncomfortableness and the like, which are associated with peptic ulcer, acute or chronic gastritis, biliary dyskinesia, cholecystitis and the like.

Since the compound of the present invention has a pancreatic β cell protective action, it can be used for improving prognosis of pancreatic islet transplantation.

The compound of the present invention can also be used for reduction of visceral fat, suppression of accumulation of visceral fat, improvement of sugar metabolism, improvement of lipid metabolism, insulin sensitizing, suppression of oxidative LDL production, improvement of lipoprotein metabolism, improvement of coronary metabolism, prophylaxis or treatment of cardiovascular complications, prophylaxis or treatment of heart failure complications, decrease of blood remnant, prophylaxis or treatment of anovulation, prophylaxis or treatment of hirsutism, the prophylaxis or treatment of hyperandrogenism and the like.

The compound of the present invention can also be used for secondary prevention or suppression of progression of the above-mentioned various diseases (e.g., cardiovascular events such as myocardial infarction and the like).

While the dose of the compound of the present invention varies depending on the subject of administration, administration route, target disease, symptom and the like, for example, for oral administration to an adult diabetic patient, it is generally about 0.01 to 100 mg/kg body weight, preferably 0.05 to 30 mg/kg body weight, further preferably 0.1 to 10 mg/kg body weight for one dose, particularly preferably 0.3 to 5 mg/kg body weight for one dose, which is desirably administered once to 3 times a day.

The compound of the present invention can be used in combination with drugs such as a therapeutic agent for diabetes, a therapeutic agent for diabetic complications, a therapeutic agent for hyperlipidemia, an antihypertensive agent, an antiobestic agent, a diuretic, a chemotherapeutic agent, an immunotherapeutic agent; an antithrombotic agent, a therapeutic agent for osteoporosis, an antidementia agent, an erectile dysfunction improver, a therapeutic agent for pollakiuria or urinary incontinence, a therapeutic agent for dysuria and the like (hereinafter to be referred to as a concomitant drug). These concomitant drugs may be low-molecular-weight compounds or high-molecular-weight proteins, polypeptides, antibodies or vaccines etc.

The timing of administration of the compound of the present invention and a combination drug is not limited. These may be simultaneously administered to an administration subject or administered in a staggered manner.

The mode of administration is not particularly limited, as long as the compound of the present invention and a concomitant drug are combined. Examples of such administration mode include
(1) administration of a single preparation obtained by simultaneous formulation of the compound of the present invention and a concomitant drug,
(2) simultaneous administration by the same administration route of two kinds of preparations obtained by separate formulation of the compound of the present invention and a concomitant drug,
(3) staggered administration by the same administration route of two kinds of preparations obtained by separate formulation of the compound of the present invention and a concomitant drug,
(4) simultaneous administration by different administration routes of two kinds of preparations obtained by separate formulation of the compound of the present invention and a concomitant drug,
(5) staggered administration by different administration routes of two kinds of preparations obtained by separate formulation of the compound of the present invention and a concomitant drug, such as administration in the order of the compound of the present invention and a concomitant drug, or in the reversed order, and the like.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [e.g., sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO 2004/041266, WO 2004/106276, WO 2005/063729, WO 2005/063725, WO 2005/087710, WO 2005/095338, WO 2007/013689 or WO 2008/001931), GLP-1 receptor agonists [e.g., GLP-1, GLP-1MR, Liraglutide, Exenatide, AVE-0010, BIM-51077, Aib(8, 35)hGLP-1(7,37)NH$_2$, CJC-1131, Albiglutide], amylin agonists (e.g., pramlintide), phosphotyrosine phosphatase inhibitors (e.g., sodium vanadate), gluconeogenesis inhibitors (e.g., glycogen phosphorylase inhibitors glucose-6-phosphatase inhibitors, glucagon antagonists, FBPase inhibitors), SGLT2(sodium-glucose cotransporter 2)inhibitors (e.g., Dapagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO 2006/112549, WO 2007/028135, WO 2008/047821, WO 2008/050821, WO 2008/136428 or WO 2008/156757), GIP (Glucose-dependent insulinotropic peptide), GPR119 agonist (e.g., PSN821, MBX-2982, APD597), FGF21, FGF analogue and the like.

Examples of the therapeutic agents for diabetic complications include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF, neurotrophic factors and increasing drugs thereof (e.g., 4-(4-chlorophenyl)-2-(2-methyl-1-imidazolyl)-5-[3-(2-methylphenoxy)propyl]oxazole) described in WO01/14372, a compound described in WO 2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, Pregabalin), serotonin noradrenaline re-uptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like.

Examples of the therapeutic agent for hyperlipidemia include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., a compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterols (e.g., soysterol), γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil etc.), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol etc.), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoAcarboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFκ inhibitory (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and pig; human GLP-1 preparations genetically synthesized using Escherichia coli or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine and pig; human FGF21 preparations genetically synthesized using Escherichia coli or yeast; fragments or derivatives of FGF21)), anorexigenic agents (e.g., P-57) and the like.

Examples of the diuretics include xanthine derivatives (e.g., theobromine sodium salicylate, theobromine calcium salicylate etc.), thiazide preparations (e.g., ethiazide, cyclopenthiazide, trichloromethiazide, hydrochlorothiazide, hydroflumethiazide, benzylhydrochlorothiazide, penflutizide, poly5thiazide, methyclothiazide etc.), antialdosterone preparations (e.g., spironolactone, triamterene etc.), carbonic anhydrase inhibitors (e.g., acetazolamide etc.), chlorobenzenesulfonamide agents (e.g., chlortalidone, mefruside, indapamide etc.), azosemide, isosorbide, ethacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and derivatives thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agent include heparins (e.g., heparin sodium, heparin calcium, sodium enoxaparin, sodium dalteparin), warfarins (e.g., potassium warfarin), anti-thrombin drugs (e.g., aragatroban), dabigatran, FXa inhibitors (e.g., rivaroxaban, apixaban, edoxaban, YM150, compounds described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agents include tacrine, donepezil, rivastigmine, galanthamine and the like.

Examples of the erectile dysfunction improvers include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

In addition, examples of the combination drug include drugs having a cachexia-improving action established in animal models and clinical situations, such as cyclooxygenase inhibitors (e.g., indometacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like.

As the combination drug, moreover, nerve regeneration promoter drugs (e.g., Y-128, VX-853, prosaptide), antidepressants (e.g., desipramine, amitriptyline, imipramine), antiepileptic drugs (e.g., lamotrigine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin), α2 receptor agonists (e.g., clonidine), topical analgesics (e.g., capsaicin), antianxiety drugs (e.g., benzodiazepine), dopamine agonists (e.g., apomorphine), midazolam, ketoconazole and the like can also be mentioned.

The combination drug is preferably insulin preparation, insulin sensitizer, dipeptidyl peptidase IV inhibitor, α-glucosidase inhibitor, biguanide, insulin secretagogue (preferably sulfonylurea), GLP-1 receptor agonist and the like.

Two or more kinds of the above-mentioned combination drugs may be used in an appropriate combination.

When the compound of the present invention is used in combination with a combination drug, the amount thereof can be reduced within a safe range: in consideration of counteraction of these agents. Particularly, the dose of an insulin sensitizer, dipeptidyl peptidase IV inhibitor, α-glucosidase inhibitor, biguanide, an insulin secretagogue and GLP-1 receptor agonist can be reduced as compared with the normal dose. Therefore, an adverse effect which may be caused by these agents can be prevented safely. In addition, the dose of the therapeutic agent for diabetic complications, therapeutic agent for hyperlipidemia and antihypertensive agent can be reduced whereby an adverse effect which may be caused by these agents can be prevented effectively.

EXAMPLES

The present invention is explained in detail in the following by referring to Reference Examples, Examples, Experimental Examples and Formulation Examples, which are not to be construed as limitative, and the invention may be changed within the scope of the present invention.

In the following Reference Examples and Examples, "%" means, unless otherwise specified, mol/mol % for the yield and wt % for others; and "room temperature" means, unless otherwise specified, 1-30° C.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

Abbreviations used in the present specification mean the following:
s: singlet
d: doublet
t: triplet
q: quartet
dd: double doublet
dt: double triplet
m: multiplet
br: broad
J: coupling constant
Hz: hertz
CDCl$_3$: deuterated chloroform
DMA: dimethylacetamide
THF: tetrahydrofuran
NMP: 1-methyl-2-pyrrolidone
DMF: N,N-dimethylformamide
DMSO: dimethyl sulfoxide $^1$H-NMR (proton nuclear magnetic resonance spectrum) was measured by Fourier-transform type NMR. For the analysis, ACD/SpecManager (trade name) and the like were used. Peaks with very mild protons such as hydroxy group, an amino group and the like are not described.

MS (mass spectrum) was measured by LC/MS (liquid chromatography mass spectrometer). As the ionization method, ESI (ElectroSpray Ionization) method, or APCI (Atomospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxy group (—OH), a peak after elimination of H$_2$O may be observed as a fragment ion. In the case of a salt, a molecular ion peak or fragment ion peak of free form is generally observed.

Reference Example 1 tert-butyl 4-(4-chloro-7H-pyrrolo[2,3-d]pyrimidin-7-yl)piperidine-1-carboxylate

To a mixture cooled to 0° C. in an ice bath of 4-chloro-7H-pyrrolo[2,3-d]pyrimidine (6.40 g, 41.7 mmol), tert-butyl 4-hydroxypiperidine-1-carboxylate (25.2 g, 125 mmol), triphenylphosphine (21.9 g, 83.5 mmol), and tetrahydrofuran (500 mL) was added dropwise diethyl azodicarboxylate (40% toluene solution, 36.3 g, 83.4 mmol). The reaction mixture was stirred at room temperature for 10 hr. The reaction mixture was concentrated, and the residue was purified by silica gel column chromatography (hexane-ethyl acetate 91:9-67:33, v/v) and crystallized from hexane-diisopropyl ether to give the title compound (11.5 g, yield 82%) as colorless crystals.

$^1$H-NMR (300 MHz, CDCl$_3$) δ: 1.50 (s, 9H), 1.84-2.11 (m, 4H), 2.89-3.00 (m, 2H), 4.26-4.41 (m, 2H), 4.81-4.94 (m, 1H), 6.64 (d, J=3.8 Hz, 1H), 7.30 (d, J=3.8 Hz, 1H), 8.63 (s, 1H).

Reference Example 2 isopropyl 4-hydroxypiperidine-1-carboxylate

To a mixture cooled to 0° C. in an ice bath of 4-hydroxypiperidine (19.0 g, 188 mmol), triethylamine (25.4 g, 251 mmol), and ethyl acetate (250 mL) was added dropwise isopropyl chlorocarbonate (27.6 g, 225 mmol). The reaction mixture was stirred at room temperature for 12 hr. The reaction mixture was washed successively with 2N hydrochloric acid, aqueous potassium carbonate solution and saturated brine, dried over anhydrous magnesium sulfate and filtered. The filtrate was concentrated to give the title compound (30.3 g, yield 86%) as a colorless oil.

$^1$H-NMR (300 MHz, CDCl$_3$) δ: 1.24 (d, J=6.4 Hz, 6H), 1.40-1.55 (m, 2H), 1.78-1.94 (m, 2H), 3.00-3.15 (m, 2H), 3.77-3.97 (m, 3H), 4.83-4.99 (m, 1H).

Reference Example 3

1-methylethyl 4-(4-chloro-7H-pyrrolo[2,3-d]pyrimidin-7-yl)piperidine-1-carboxylate In the same manner as in Reference Example 1, the title compound was obtained from 4-chloro-7H-pyrrolo[2,3-d]pyrimidine and isopropyl 4-hydroxypiperidine-1-carboxylate obtained in Reference Example 2.

$^1$H-NMR (300 MHz, CDCl$_3$) δ: 1.28 (d, J=6.4 Hz, 6H), 1.85-2.12 (m, 4H), 2.99 (t, J=12.6 Hz, 2H), 4.31-4.47 (m, 2H), 4.82-5.03 (m, 2H), 6.64 (d, J=3.8 Hz, 1H), 7.30 (d, J=3.8 Hz, 1H), 8.63 (s, 1H).

Reference Example 4 tert-butyl 4-(4-chloro-1H-pyrrolo[2,3-b]pyridin-1-yl)piperidine-1-carboxylate

In the same manner as in Reference Example 1, the title compound was obtained from 4-chloro-1H-pyrrolo[2,3-b]pyridine and tert-butyl 4-hydroxypiperidine-1-carboxylate.

$^1$H-NMR (300 MHz, CDCl$_3$) δ: 1.50 (s, 9H), 1.80-2.11 (m, 4H), 2.87-3.05 (m, 2H), 4.18-4.46 (m, 2H), 4.87-5.00 (m, 1H), 6.59 (d, J=3.4 Hz, 1H), 7.10 (d, J=4.9 Hz, 1H), 7.31 (d, J=3.4 Hz, 1H), 8.19 (d, J=4.9 Hz, 1H).

Reference Example 5

1-methylethyl 4-(4-chloro-6-methyl-7H-pyrrolo[2,3-d]pyrimidin-7-yl)piperidine-1-carboxylate In the same manner as in Reference Example 1, the title compound was obtained from 4-chloro-6-methyl-7H-pyrrolo[2,3-d]pyrimidine and isopropyl 4-hydroxypiperidine-1-carboxylate.

$^1$H-NMR (300 MHz, CDCl$_3$) δ: 1.29 (d, J=6.4 Hz, 6H), 1.76-1.86 (m, 2H), 2.51 (s, 3H), 2.67-2.93 (m, 4H), 4.32-4.55 (m, 3H), 4.90-5.04 (m, 1H), 6.33 (s, 1H), 8.52 (s, 1H).

Reference Example 6 tert-butyl 4-{4-bromo-1H-indazol-1-yl}piperidine-1-carboxylate

In the same manner as in Reference Example 1, the title compound was obtained from 4-bromo-1H-indazole and tert-butyl 4-hydroxypiperidine-1-carboxylate.

$^1$H-NMR (300 MHz, CDCl$_3$) δ: 1.49 (s, 9H), 1.95-2.06 (m, 2H), 2.14-2.32 (m, 2H), 2.89-3.05 (m, 2H), 4.24-4.39 (m, 2H), 4.46-4.59 (m, 1H), 7.19-7.33 (m, 2H), 7.39 (d, J=8.3 Hz, 1H), 8.01 (s, 1H).

Reference Example 7

2,3-dihydro-1H-indole-5-carbonitrile

To a solution (5 mL) cooled to 0° C. in an ice bath of 1H-indole-5-carbonitrile (640 mg, 4.50 mmol) in acetic acid was added sodium cyanotrihydroborate (848 mg, 13.5 mmol). The reaction mixture was stirred at room temperature for 5 hr and diluted with water. The mixture was basified with 8N aqueous sodium hydroxide solution and extracted with ethyl acetate. The organic layer was extracted with 1N hydrochloric acid and the aqueous layer was again basified with 8N aqueous sodium hydroxide solution and extracted with ethyl acetate. The organic layer was washed with saturated brine, dried over anhydrous magnesium sulfate and filtered. The filtrate was concentrated. The residue was crystallization from ethyl acetate to give the title compound as pale-yellow crystals (213 mg, yield 33%).

$^1$H-NMR (300 MHz, CDCl$_3$) δ: 3.06 (t, J=8.5 Hz, 2H), 3.67 (t, J=8.7 Hz, 2H), 3.83 (br s, 1H), 6.45-6.59 (m, 1H), 7.24-7.33 (m, 2H).

Reference Example 8 methyl 1-(7-{1-[(1-methylethoxy)carbonyl]piperidin-4-yl}-7H-pyrrolo[2,3-d]pyrimidin-4-yl)-1H-indole-5-carboxylate To a mixture of methyl 1H-indole-5-carboxylate (1.26 g, 7.20 mmol), 1-methylethyl 4-(4-chloro-7H-pyrrolo[2,3-d]pyrimidin-7-yl)piperidine-1-carboxylate (1.60 g, 5.00 mmol) obtained in Reference Example 3, and N,N-dimethylformamide (15 mL) was added sodium hydride (60%, oil, 332 mg, 8.30 mmol), and the mixture was stirred at 50° C. for 16 hr. The reaction mixture was allowed to cool to room temperature, water was added thereto, and the mixture was extracted with ethyl acetate. The organic layer was washed with saturated brine, dried over anhydrous magnesium sulfate and filtered. The filtrate was concentrated. The residue was subjected to silica gel column chromatography (hexane-ethyl acetate 100:0-40:60, v/v) and crystallized from hexane-ethyl acetate to give the title compound (1.59 g, yield 49%) as colorless crystals.

$^1$H-NMR (300 MHz, CDCl$_3$) δ: 1.18-1.38 (m, 6H), 1.85-2.24 (m, 4H), 3.03 (t, J=12.4 Hz, 2H), 3.96 (s, 3H), 4.34-4.51 (m, 2H), 4.85-5.14 (m, 2H), 6.74 (d, J=3.4 Hz, 1H), 6.89 (d, J=3.4 Hz, 1H), 7.34 (d, J=3.4 Hz, 1H), 7.83-8.16 (m, 2H), 8.34-8.63 (m, 2H), 8.84 (s, 1H).

Reference Example 9 tert-butyl (3S)-3-[(4-chloro-7H-pyrrolo[2,3-d]pyrimidin-7-yl)methyl]pyrrolidine-1-carboxylate In the same manner as in Reference Example 1, the title compound was obtained from 4-chloro-7H-pyrrolo[2,3-d]pyrimidine and tert-butyl (3S)-3-(hydroxymethyl)pyrrolidine-1-carboxylate.

$^1$H-NMR (300 MHz, CDCl$_3$) δ: 1.45 (s, 9H), 1.51-1.82 (m, 1H), 1.79-2.02 (m, 1H), 2.50-2.95 (m, 1H), 2.95-3.24 (m, 1H), 3.23-3.76 (m, 3H), 4.18-4.56 (m, 2H), 6.63 (br s, 1H), 7.23 (d, J=3.8 Hz, 1H), 8.63 (s, 1H).

Reference Example 10 tert-butyl (3R)-3-[(4-chloro-7H-pyrrolo[2,3-d]pyrimidin-7-yl)methyl]pyrrolidine-1-carboxylate In the same manner as in Reference Example 1, the title compound was obtained from 4-chloro-7H-pyrrolo[2,3-d]pyrimidine and tert-butyl (3R)-3-(hydroxymethyl)pyrrolidine-1-carboxylate.

$^1$H-NMR (300 MHz, CDCl$_3$) δ: 1.45 (s, 9H), 1.60-1.82 (m, 1H), 1.94 (td, J=12.2, 7.2 Hz, 1H), 2.49-2.97 (m, 1H), 3.00-3.23 (m, 1H), 3.22-3.38 (m, 1H), 3.37-3.73 (m, 2H), 4.18-4.54 (m, 2H), 6.63 (br s, 1H), 7.22 (d, J=3.4 Hz, 1H), 8.63 (s, 1H).

Reference Example 11 tert-butyl 3-[(4-chloro-7H-pyrrolo[2,3-d]pyrimidin-7-yl)methyl]azetidine-1-carboxylate In the same manner as in Reference Example 1, the title compound was obtained from 4-chloro-7H-pyrrolo[2,3-d]pyrimidine and tert-butyl 3-(hydroxymethyl)azetidine-1-carboxylate.

$^1$H-NMR (300 MHz, CDCl$_3$) δ: 1.43 (s, 9H), 2.87-3.25 (m, 1H), 3.75 (dd, J=8.9, 5.1 Hz, 2H), 3.87-4.11 (m, 2H), 4.49 (d, J=7.5 Hz, 2H), 6.63 (d, J=3.8 Hz, 1H), 7.23 (d, J=3.8 Hz, 1H), 8.64 (s, 1H).

Reference Example 12 benzyl 4-(4-chloro-7H-pyrrolo[2,3-d]pyrimidin-7-yl)azepane-1-carboxylate

In the same manner as in Reference Example 1, the title compound was obtained from 4-chloro-7H-pyrrolo[2,3-d]pyrimidine and benzyl 4-hydroxyazepane-1-carboxylate.

$^1$H-NMR (300 MHz, CDCl$_3$) δ: 1.77-2.34 (m, 6H), 3.05-3.50 (m, 1H), 3.51-3.79 (m, 2H), 3.80-4.05 (m, 1H), 4.62-5.01 (m, 1H), 5.19 (s, 2H), 6.43-6.79 (m, 1H), 7.18 (d, J=3.8 Hz, 1H), 7.32-7.60 (m, 5H), 8.61 (s, 1H).

Reference Example 13 tert-butyl 3-(4-chloro-7H-pyrrolo[2,3-d]pyrimidin-7-yl)pyrrolidine-1-carboxylate A mixture of 4-chloro-7H-pyrrolo[2,3-d]pyrimidine (1.01 g, 6.58 mmol), tert-butyl 3-{[(4-methylphenyl)sulfonyl]oxy}pyrrolidine-1-carboxylate (2.70 g, 7.91 mmol) and potassium carbonate (3.64 g, 26.34 mmol) in dimethyl sulfoxide (15 mL) was stirred at 80° C. overnight. The reaction mixture was allowed to cool to room temperature, water was added thereto, and the resulting solid was removed by filtration. The filtrate was extracted with ethyl acetate. The organic layer was washed with saturated brine, dried over anhydrous magnesium sulfate and filtered. The filtrate was concentrated. The obtained residue was subjected to silica gel column chromatography (hexane-ethyl acetate 95:5-60:40, v/v) and crystallized from hexane-ethyl acetate to give the title compound (953 mg, yield 45%) as colorless crystals.

$^1$H-NMR (300 MHz, CDCl$_3$) δ: 1.49 (br s, 9H), 2.08-2.38 (m, 1H), 2.37-2.62 (m, 1H), 3.15-3.87 (m, 3H), 3.83-4.09 (m, 1% H), 5.25-5.69 (m, 1H), 6.65 (d, J=3.8 Hz, 1H), 7.28 (br s, 1H), 8.64 (s, 1H).

Reference Example 14

1-methylethyl 4-[(6-chloropyrimidin-4-yl)oxy]piperidine-1-carboxylate

To a mixture of 4,6-dichloropyrimidine (1.58 g, 10.7 mmol) and isopropyl 4-hydroxypiperidine-1-carboxylate (2.01 g, 10.7 mmol) obtained in Reference Example 2 in N,N-dimethylformamide (50 mL) was added under ice-cooling sodium hydride (60%, oil, 450 mg, 11.3 mmol), and the mixture was stirred at room temperature overnight. Water was added to the reaction mixture, and the mixture was extracted with ethyl acetate. The organic layer was washed with saturated brine, dried over anhydrous magnesium sulfate and filtered. The filtrate was concentrated. The obtained residue was subjected to silica gel column chromatography (hexane-ethyl acetate 95:5-60:40, v/v) to give the title compound (2.15 g, yield 67%) as a white solid. Crystallization from hexane-ethyl acetate gave white crystals.

$^1$H-NMR (300 MHz, CDCl$_3$) δ: 1.25 (d, J=6.4 Hz, 6H), 1.63-1.87 (m, 2H), 1.86-2.22 (m, 2H), 3.12-3.44 (m, 2H), 3.67-4.02 (m, 2H), 4.70-5.11 (m, 1H), 5.33 (tt, J=7.9, 3.8 Hz, 1H), 6.76 (s, 1H), 8.55 (s, 1H).

Reference Example 15 methyl 1-(6-chloropyrimidin-4-yl)-2,3-dihydro-1H-indole-5-carboxylate

A mixture of methyl 2,3-dihydro-1H-indole-5-carboxylate (5.19 g), 4,6-dichloropyrimidine (4.37 g), and ethanol (50 mL) was stirred overnight with heating under reflux, and concentrated under reduced pressure. To the residue were added saturated aqueous sodium hydrogen carbonate solution and ethyl acetate, and the mixture was stirred for 30 min. Insoluble materials were collected by filtration to give the title compound (5.87 g, 69%) as a white solid.

$^1$H-NMR (300 MHz, CDCl$_3$) δ: 3.32 (t, J=8.7 Hz, 2H), 3.91 (s, 3H), 4.08 (t, J=8.7 Hz, 2H), 6.66 (s, 1H), 7.90 (s, 1H), 7.95 (d, J=8.5 Hz, 1H), 8.46 (d, J=8.5 Hz, 1H), 8.64 (s, 1H).

Reference Example 16 methyl 1-[6-(piperidin-4-yloxy)pyrimidin-4-yl]-2,3-dihydro-1H-indole-5-carboxylate To a suspension of sodium hydride (oil, 60%, 2.51 g) in N,N-dimethylformamide (100 mL) was added a solution of tert-butyl 4-hydroxypiperidine-1-carboxylate (12.6 g) in N,N-dimethylformamide (10 mL) at 0° C., and the mixture was stirred for 1 hr. The mixture was transferred, with a cannula, to a suspension of methyl 1-(6-chloropyrimidin-4-yl)-2,3-dihydro-1H-indole-5-carboxylate (9.08 g) synthesized in Reference Example 15 in N,N-dimethylformamide (100 mL), and the mixture was stirred at room temperature for 3 hr. To the reaction mixture was added saturated aqueous ammonium chloride solution, and the mixture was extracted with ethyl acetate. The extract was washed with saturated brine, dried over magnesium sulfate, and concentrated under reduced pressure. The residue was purified by silica gel column chromatography (30-70% ethyl acetate/hexane) to give a colorless oil. To a mixture of the obtained oil, tetrahydrofuran (200 mL) and ethanol (200 mL) was added 4N aqueous lithium hydroxide solution (20 mL), and the mixture was stirred for 3 hr with heating under reflux, and concentrated under reduced pressure. The residue was suspended in water (200 mL), 1N hydrochloric acid (80 mL) was added thereto at 0° C., and the mixture was extracted with a mixed solvent of ethyl acetate and tetrahydrofuran. The extract was washed with saturated brine, dried over magnesium sulfate, and concentrated under reduced pressure. The residue was washed with diisopropyl ether to give a white solid (9.71 g). To a solution of the obtained solid (8.12 g) in N,N-dimethylformamide (150 mL) were added methyl iodide (2.63 mL) and potassium carbonate (5.83 g), and the mixture was stirred at 50° C. for 3 hr. Water was added to the reaction mixture, and the mixture was extracted with ethyl acetate. The extract was washed with saturated brine, dried over magnesium sulfate, and concentrated under reduced pressure to give a pale-yellow is solid (7.69 g). To a solution of the obtained solid (6.19 g) in tetrahydrofuran (50 mL) was added 4N hydrochloric acid-ethyl acetate solution (20 mL) and the mixture was stirred for 1 hr, and concentrated under reduced pressure. To the residue was added 10% hydrochloric acid-methanol solution (50 mL) and the mixture was stirred at room temperature for 1 hr. Insoluble materials were collected by filtration to give hydrochloride (4.29 g) of the title compound as a white solid.

$^1$H-NMR (300 MHz, DMSO-$d_6$) δ: 1.84-2.03 (m, 2H), 2.09-2.25 (m, 2H), 3.00-3.20 (m, 2H), 3.20-3.35 (m, 4H), 3.81 (s, 3H), 4.06 (t, J=8.5 Hz, 2H), 5.23-5.39 (m, 1H), 6.24 (s, 1H), 7.78 (s, 1H), 7.81 (d, J=8.7 Hz, 1H), 8.44 (d, J=8.7 Hz, 1H), 8.53 (s, 1H), 9.02-9.34 (m, 2H).

Reference Example 17

1-(6-chloropyrimidin-4-yl)-5-(methylsulfonyl)-2,3-dihydro-1H-indole

A mixture of 4,6-dichloropyrimidine (4.1 g, 27.5 mmol), 5-(methylsulfonyl)-2,3-dihydro-1H-indole (5.0 g, 25.0 mmol), and ethanol (160 mL) was heated under reflux for 4 hr. The reaction mixture was concentrated, aqueous sodium hydrogen carbonate solution was added thereto, and the resulting solid was washed with water and dried under reduced pressure to give the title compound (5.5 g, yield 71%) as colorless crystals.

$^1$H-NMR (300 MHz, DMSO-$d_6$) δ: 3.17 (s, 3H), 3.24-3.37 (m, 2H), 4.16 (t, J=8.7 Hz, 2H), 7.09 (s, 1H), 7.73-7.85 (m, 2H), 8.57 (d, J=9.4 Hz, 1H), 8.68 (s, 1H).

Reference Example 18

5-(methylsulfonyl)-1-[6-(piperidin-4-yloxy)pyrimidin-4-yl]-2,3-dihydro-1H-indole To a solution of tert-butyl 4-hydroxypiperidine-1-carboxylate (20.8 g, 103 mmol) in tetrahydrofuran (200 mL) was added sodium hydride (60%, oil, 4.12 g, 103 mmol), and the mixture was stirred at room temperature for 2 hr. 1-(6-Chloropyrimidin-4-yl)-5-(methylsulfonyl)-2,3-dihydro-1H-indole (8.0 g, 25.8 mmol) obtained in Reference Example 17 was added thereto, and the mixture was stirred at 50° C. for 2 hr. Water was added to the reaction mixture, and the mixture was extracted with ethyl acetate. The organic layer was washed with saturated brine, dried over anhydrous magnesium sulfate and filtered. The filtrate was concentrated. The residue was subjected to silica gel column chromatography (hexane-ethyl acetate 80:20-50:50, v/v), and crystallized from hexane-ethyl acetate to give a colorless solid (6.17 g). A mixture of the obtained colorless solid (6.17 g), 4N hydrochloric acid-ethyl acetate solution (15 mL, 60 mmol), ethyl acetate (100 mL), and methanol (100 mL) was stirred at room temperature for 16 hr. The reaction mixture was concentrated, 1N aqueous sodium hydroxide solution was added thereto, and the mixture was extracted with ethyl acetate. The organic layer was washed with saturated brine, dried over anhydrous magnesium sulfate and filtered. The filtrate was concentrated. The residue was crystallized from ethyl acetate to give the title compound as colorless crystals (4.56 g, yield 47%).

MS (ESI+): 375.

Reference Example 19

(1Z)-(2R)—N'-hydroxytetrahydrofuran-2-carboximidamide

A mixture of (R)-tetrahydrofuran-2-carbonitrile (5.0 g, 636 mmol), 50% hydroxylamine solution (14 mL, 206 mmol), and ethanol (30 mL) was heated under reflux for 1 day. The reaction mixture was concentrated, toluene was added thereto, and the remaining water was removed by azeotropic distillation under reduced pressure. To the residue was added ethyl acetate, and the mixture was dried over anhydrous magnesium sulfate and filtered. The filtrate was concentrated to give the title compound as a colorless oil (6.5 g, yield 97%).

$^1$H-NMR (300 MHz, CDCl$_3$) δ: 1.78-2.23 (m, 4H), 3.71-4.09 (m, 2H), 4.24-4.52 (m, 1H), 4.86 (br. s., 2H), 7.92 (br. s., 1H).

Reference Example 20

(1Z)—N'-hydroxy-2,2-dimethylpropanimidamide

A mixture of trimethylacetonitrile (41.9 g, 504 mmol), 50% hydroxylamine solution (100 ml, 1512 mmol), and ethanol (200 mL) was heated under reflux for 16 hr. The reaction mixture was concentrated, toluene was added thereto, and the remaining water was removed by azeotropic distillation under reduced pressure. To the residue was added ethyl acetate, and the mixture was dried over anhydrous magnesium sulfate and filtered. The filtrate was concentrated. The residue was crystallized from ethyl acetate to give the title compound as colorless crystals (58.5 g, yield quant.).

$^1$H-NMR (300 MHz, CDCl$_3$) δ: 1.19 (s, 9H), 4.60 (br. s., 2H), 8.22 (br. s., 1H).

Reference Example 21

(1Z)—N'-hydroxycyclopropanecarboximidamide

A mixture of cyclopropanecarbonitrile (42.7 g, 636 mmol), 50% hydroxylamine solution (100 mL, 1512 mmol), and ethanol (200 mL) was heated under reflux for 16 hr. The reaction mixture was concentrated, toluene was added thereto, and the remaining water was removed by azeotropic distillation under reduced pressure. To the residue was added ethyl acetate, and the mixture was dried over anhydrous magnesium sulfate and filtered. The filtrate was concentrated. The residue was subjected to silica gel column chromatography (hexane-ethyl acetate 50:50-0:100, v/v) and the solvent was concentrated to give the title compound (45 g, yield 71%) as a colorless oil.

$^1$H-NMR (300 MHz, CDCl$_3$) δ: 0.56-0.89 (m, 4H), 1.46 (tt, J=8.1, 5.5 Hz, 1H), 4.57 (br. s., 2H), 8.72 (br. s., 1H).

Reference Example 22

(1Z)—N'-hydroxypropanimidamide

A mixture of propanenitrile (20.0 g, 363 mmol), 50% hydroxylamine solution (100 mL, 1512 mmol), and ethanol (200 mL) was heated under reflux for 16 hr. The reaction mixture was concentrated, toluene was added thereto, and the remaining water was removed by azeotropic distillation under reduced pressure. To the residue was added ethyl acetate, and the mixture was dried over anhydrous magnesium sulfate and filtered. The filtrate was concentrated to give the title compound as a colorless oil (29.0 g, yield 91%).

$^1$H-NMR (300 MHz, CDCl$_3$) δ: 1.14 (t, 3H), 2.18 (q, J=7.8 Hz, 2H), 4.65 (br. s., 2H), 9.06 (br. s., 1H).

Reference Example 23

(1Z)—N'-hydroxy-2-methoxyethanimidamide

A mixture of methoxyacetonitrile (23 g, 324 mmol), 50% hydroxylamine solution (100 mL, 1512 mmol), and ethanol (200 mL) was heated under reflux for 16 hr. The reaction mixture was concentrated, toluene was added thereto, and the remaining water was removed by azeotropic distillation under reduced pressure. To the residue was added ethyl acetate, and the mixture was dried over anhydrous magnesium sulfate and filtered. The filtrate was concentrated to give the title compound as a colorless oil (32 g, yield 95%).

$^1$H-NMR (300 MHz, CDCl$_3$) δ: 3.35 (s, 3H), 3.95 (s, 2H), 4.93 (br. s., 2H), 8.56 (br. s., 1H).

Reference Example 24

1-(6-chloropyrimidin-4-yl)-5-nitro-2,3-dihydro-1H-indole

A mixture of 4,6-dichloropyrimidine (25 g, 168 mmol), 5-nitro-2,3-dihydro-1H-indole (25.0 g, 152 mmol), and ethanol (500 mL) was heated under reflux for 16 hr. The reaction mixture was concentrated, the residue was partitioned between 1N aqueous sodium hydroxide solution and ethyl acetate, and the organic layer was dried under reduced pressure to give the title compound (35 g, yield 83%) as pale-yellow crystals.

$^1$H-NMR (300 MHz, DMSO-d$_6$) δ: 3.33 (t, J=8.5 Hz, 2H), 3.96-4.34 (m, 2H), 7.16 (s, 1H), 8.09-8.28 (m, 2H), 8.56 (d, J=9.0 Hz, 1H), 8.72 (s, 1H).

Reference Example 25

1-{1-[6-(piperidin-4-yloxy)pyrimidin-4-yl]-2,3-dihydro-1H-indol-5-yl}pyrrolidin-2-one A mixture of tert-butyl 4-{[6-(5-amino-2,3-dihydro-1H-indol-1-yl)pyrimidin-4-yl]oxy}piperidine-1-carboxylate (823 mg, 2.0 mmol) obtained in Example 44, 4-chlorobutyryl chloride (310 mg, 2.2 mmol), triethylamine (418 μL, 3.0 mmol), and tetrahydrofuran (50 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated to give a colorless solid. The obtained colorless solid was dissolved in N,N-dimethylformamide (20 mL), sodium hydride (60%, oil, 120 mg, 3.0 mmol) was added thereto, and the mixture was stirred at room temperature for 6 hr. Water was added to the reaction mixture, and the mixture was extracted with ethyl acetate. The organic layer was washed with saturated brine, dried over anhydrous magnesium sulfate and filtered. The filtrate was concentrated to give a solid. A mixture of the obtained solid (863 mg), 4N hydrochloric acid-ethyl acetate solution (10 ml, 40 mmol), ethyl acetate (50 mL), and methanol (50 mL) was stirred at room temperature for 16 hr. The reaction mixture was concentrated, 1N aqueous sodium hydroxide solution was added thereto, and the mixture was extracted with ethyl acetate. The organic layer was washed with saturated brine, dried over anhydrous magnesium sulfate and filtered. The filtrate was concentrated. The residue was crystallized from ethyl acetate to give the title compound as colorless crystals (620 mg, yield 74%).

MS (ESI+): 380.

Reference Example 26

(2R)—N-{1-[6-(piperidin-4-yloxy)pyrimidin-4-yl]-2,3-dihydro-1H-indol-5-yl}tetrahydrofuran-2-carboxamide hydrochloride A mixture of tert-butyl 4-{[6-(5-{[(2R)-tetrahydrofuran-2-ylcarbonyl]amino}-2,3-dihydro-1H-indol-1-yl)pyrimidin-4-yl]oxy}piperidine-1-carboxylate (1.1 g, 2.16 mmol) obtained in Example 49, 4N hydrochloric acid-ethyl acetate solution (5 mL, 20 mmol), and ethyl acetate (50 mL) was stirred at room temperature for 16 hr. The reaction mixture was concentrated, and the residue was crystallized from ethyl acetate to give the title compound as colorless crystals (950 mg, yield 99%).

MS (ESI+): 410.

Reference Example 27

(2S)—N-{1-[6-(piperidin-4-yloxy)pyrimidin-4-yl]-2,3-dihydro-1H-indol-5-yl}tetrahydrofuran-2-carboxamide hydrochloride A mixture of tert-butyl 4-{[6-(5-{[(2S)-tetrahydrofuran-2-ylcarbonyl]amino}-2,3-dihydro-1H-indol-1-yl)pyrimidin-4-yl]oxy}piperidine-1-carboxylate (600 mg, 1.18 mmol) obtained in Example 50, 4N hydrochloric acid-ethyl acetate solution (5 mL, 20 mmol), and ethyl acetate (25 mL) was stirred at room temperature for 16 hr. The reaction mixture was concentrated, and the residue was crystallized from ethyl acetate to give the title compound as colorless crystals (521 mg, yield 99%).

MS (ESI+): 410.

Reference Example 28

2-oxo-2-({1-[6-(piperidin-4-yloxy)pyrimidin-4-yl]-2,3-dihydro-1H-indol-5-yl}amino)ethyl acetate hydrochloride A mixture of tert-butyl 4-{[6-(5-amino-2,3-dihydro-1H-indol-1-yl)pyrimidin-4-yl]oxy}piperidine-1-carboxylate (3.0 g, 7.29 mmol) obtained in Example 44, acetoxyacetyl chloride (1.3 g, 9.5 mmol), triethylamine (1.39 mL, 10.0 mmol), and tetrahydrofuran (200 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated to give an oil. A mixture of the obtained oil, 4N hydrochloric acid-ethyl acetate solution (10 mL, 40 mmol), and ethyl acetate (200 mL) was stirred at room temperature for 16 hr. The reaction mixture was concentrated, and the residue was crystallized from ethyl acetate to give the title compound as colorless crystals (3.17 g, yield 97%).

MS (ESI+): 412.

Reference Example 29

1-[6-(piperidin-4-yloxy)pyrimidin-4-yl]-2,3-dihydro-1H-indol-5-amine

A mixture of tert-butyl 4-{[6-(5-amino-2,3-dihydro-1H-indol-1-yl)pyrimidin-4-yl]oxy}piperidine-1-carboxylate (3.0 g, 7.29 mmol) obtained in Example 44, 4N hydrochloric acid-ethyl acetate solution (10 ml, 40 mmol), ethyl acetate (150 mL), and methanol (100 mL) was stirred at room temperature for 16 hr. The reaction mixture was concentrated, 1N aqueous sodium hydroxide solution was added thereto, and the mixture was extracted with ethyl acetate. The organic layer was washed with saturated brine, dried over anhydrous magnesium sulfate and filtered. The filtrate was concentrated. The residue was crystallized from ethyl acetate to give the title compound as colorless crystals (2.2 g, yield 97%).

MS (ESI+): 312.

Reference Example 30

7-fluoro-5-(methylsulfonyl)-2,3-dihydro-1H-indole hydrochloride (A) 7-fluoro-2,3-dihydro-1H-indole To a solution of 7-fluoroindole (20.0 g, 148 mmol) in is acetic acid (60 mL) was added sodium cyanoborohydride (18.7 g, 298 mmol) by small portions, and the mixture was stirred at room temperature for 2 hr. The reaction mixture was added to 2M aqueous sodium hydroxide solution (1500 mL), and the mixture was extracted with dichloromethane. The extract was washed with saturated brine, dried over anhydrous magnesium sulfate, and concentrated under reduced pressure. The residue was purified by silica gel column chromatography (ethyl acetate:hexane=40:60-100:0) to give the title compound (20.0 g, yield 99%).

$^1$H-NMR (300 MHz, CDCl$_3$) δ: 3.08 (t, J=8.4 Hz, 2H), 3.62 (t, J=8.4 Hz, 2H), 6.62-6.66 (m, 1H), 6.78-6.83 (m, 1H), 6.90 (dd, J=7.6, 0.4 Hz, 1H).

(B) 7-fluoro-5-(methylsulfanyl)-2,3-dihydro-1H-indole

A solution of potassium thiocyanate (14 g, 144 mmol) in methanol (150 mL) was cooled in ice-bath under nitrogen atmosphere, bromine (3.8 mL, 74.2 mmol) was added dropwise thereto, and the mixture was stirred for 15 hr. To the reaction mixture was added a solution of 7-fluoro-2,3-dihydro-1H-indole (9.0 g, 65.6 mmol) in methanol (100 mL), and the mixture was stirred at room temperature for 3 hr. To the reaction mixture was slowly added dropwise a solution of potassium hydroxide (18.4 g, 328 mmol) in water (120 mL) at 43° C. or below, and the mixture was stirred for 30 min. The reaction mixture was cooled to 10° C., iodomethane (4.1 mL, 65.8 mmol) was added and the mixture was stirred at room temperature for 30 min. The reaction mixture was concentrated under reduced pressure, water was added thereto, and the mixture was extracted with dichloromethane. The extract was dried and concentrated under reduced pressure, and the residue was purified by silica gel column chromatography (petroleum ether:dichloromethane=2:1-1:1) to give the title compound (2.8 g, yield 23%).

$^1$H-NMR (300 MHz, CDCl$_3$) δ: 2.42 (s, 3H), 3.05 (t, J=8.4 Hz, 2H), 3.62 (t, J=8.4 Hz, 2H), 6.85 (d, J=10.8 Hz, 1H), 6.93 (s, 1H).

(C) tert-butyl 7-fluoro-5-(methylsulfonyl)-2,3-dihydro-1H-indole-1-carboxylate

To a solution of 7-fluoro-5-(methylsulfanyl)-2,3-dihydro-1H-indole (4.4 g, 24.0 mmol) in dichloromethane (30 mL) were added di-tert-butyl bicarbonate (6.6 g, 30 mmol) and triethylamine (4.3 mL, 30.9 mmol), and the mixture was stirred at room temperature for 48 hr. To the reaction mixture was added saturated aqueous sodium hydrogen carbonate, and the mixture was extracted with ethyl acetate. The extract was washed successively with 1 M hydrochloric acid, saturated aqueous sodium hydrogen carbonate and saturated brine, dried over anhydrous magnesium sulfate, and concentrated under reduced pressure. The residue was dissolved in dichloromethane (60 mL), m-chloroperbenzoic acid (65%, 8.8 g, 33.1 mmol) was added thereto under ice-cooling, and the mixture was stirred for 1 hr. To the reaction mixture was added 10% aqueous sodium sulfite solution, and the mixture was extracted with dichloromethane. The extract was successively washed with aqueous sodium carbonate solution and saturated brine, dried over anhydrous sodium sulfate, and concentrated under reduced pressure. The residue was purified by silica gel column chromatography (ethyl acetate:hexane=1:10-40:60) to give the title compound (4.1 g, yield 54%) as a white powder.

$^1$H-NMR (300 MHz, CDCl$_3$) δ: 1.53 (s, 9H), 3.04 (s, 3H), 3.15 (t, J=8.4 Hz, 2H), 4.14 (t, J=8.4 Hz, 2H), 7.26 (s, 1H), 7.52 (s, 1H).

(D) 7-fluoro-5-(methylsulfonyl)-2,3-dihydro-1H-indole hydrochloride

To a solution of tert-butyl 7-fluoro-5-(methylsulfonyl)-2,3-dihydro-1H-indole-1-carboxylate (4.1 g, 13.0 mmol) in ethyl acetate (20 mL) was added 5 M hydrogen chloride/ethyl acetate (40 mL) solution, and the mixture was stirred at room temperature for 3 hr. The precipitated solid was collected by filtration and washed with ethyl acetate/diisopropyl ether to give the title compound (3.1 g, yield 95%) as a white powder.

MS (ESI+): 216.

Reference Example 31

1-(6-chloropyrimidin-4-yl)-7-fluoro-5-(methylsulfonyl)-2,3-dihydro-1H-indole To 7-fluoro-5-(methylsulfonyl)-2,3-dihydro-1H-indole hydrochloride (18 g, 71.5 mmol) obtained in Reference Example 30 was added 1N aqueous sodium hydroxide solution, and the mixture was extracted with ethyl acetate. The organic layer was washed with saturated brine, dried over anhydrous magnesium sulfate and filtered. The filtrate was concentrated and the residue was crystallized from ethyl acetate to give 7-fluoro-5-(methylsulfonyl)-2,3-dihydro-1H-indole (14.4 g, 67.0 mmol). A mixture of the obtained 7-fluoro-5-(methylsulfonyl)-2,3-dihydro-1H-indole (14.4 g, 67.0 mmol), 4,6-dichloropyrimidine (25.0 g, 168 mmol), and ethanol (300 mL) was heated under reflux for 16 hr. The reaction mixture was concentrated, 1N aqueous sodium hydroxide solution was added thereto, and the mixture was extracted with ethyl acetate. The organic layer was washed with saturated brine, dried over anhydrous magnesium sulfate and filtered. The filtrate was concentrated. The residue was subjected to silica gel column chromatography (hexane-ethyl acetate 80:20-40:60, v/v) and crystallized from hexane-ethyl acetate to give the title compound (16 g, yield 73%) as colorless crystals.

$^1$H-NMR (300 MHz, CDCl$_3$) δ: 2.98-3.15 (m, 3H), 3.29 (t, J=8.3 Hz, 2H), 4.35-4.50 (m, 2H), 6.04-6.87 (m, 1H), 7.51-7.71 (m, 2H), 8.45-8.71 (m, 1H).

Reference Example 32

7-fluoro-5-(methylsulfonyl)-1-[6-(piperidin-4-yloxy)pyrimidin-4-yl]-2,3-dihydro-1H-indole To a solution of tert-butyl 4-hydroxypiperidine-1-carboxylate (24.0 g, 120 mmol) in tetrahydrofuran (500 mL) was added sodium hydride (60%, oil, 4.8 g, 120 mmol) at 0° C., and the mixture was stirred at room temperature for 2 hr. 1-(6-Chloropyrimidin-4-yl)-7-fluoro-5-(methylsulfonyl)-2,3-dihydro-1H-indole (10.0 g, 30.5 mmol) obtained in Reference Example 31 was added thereto, and the mixture was stirred at room temperature for 4 hr. Water was added to the reaction mixture, and the mixture was extracted with ethyl acetate. The organic layer was washed with saturated brine, dried over anhydrous magnesium sulfate and filtered. The filtrate was concentrated. The residue was subjected to silica gel column chromatography (hexane-ethyl acetate 80:20-50:50-25:75, v/v) and crystallized from hexane-ethyl acetate to give a colorless solid (12.0 g). A mixture of the obtained solid (12.0 g), 4N hydrochloric acid-ethyl acetate solution (30 ml, 120 mmol), and ethyl acetate (500 mL) was stirred at room temperature for 16 hr. The reaction mixture was concentrated, 1N aqueous sodium hydroxide solution was added thereto, and the mixture was extracted with ethyl acetate. The organic layer was washed with saturated brine, dried over anhydrous magnesium sulfate and filtered. The filtrate was concentrated. The residue was crystallized from ethyl acetate to give the title compound as colorless crystals (9.1 g, yield 76%).

MS (ESI+): 393.

Reference Example 33

(1Z)-(2R)—N'-hydroxytetrahydrofuran-2-carboximidamide

A mixture of (2R)-tetrahydrofuran-2-carbonitrile (5.0 g, 51.5 mmol), 50% hydroxylamine solution (14 mL, 206 mmol), and ethanol (30 mL) was heated under reflux for one day. The reaction mixture was concentrated, toluene was added thereto, and the remaining water was removed by azeotropic distillation under reduced pressure. To the residue was added ethyl acetate, and the mixture was dried over anhydrous magnesium sulfate and filtered. The filtrate was concentrated to give the title compound as a colorless oil (6.5 g, yield 97%).

$^1$H-NMR (300 MHz, CDCl$_3$) δ: 1.78-2.23 (m, 4H), 3.71-4.09 (m, 2H), 4.24-4.52 (m, 1H), 4.86 (br. s., 2H), 7.92 (br. s., 1H).

Reference Example 34

6-[5-(methylsulfonyl)-2,3-dihydro-1H-indol-1-yl]-N-(piperidin-4-yl)-N-(trifluoromethyl)pyrimidin-4-amine tert-Butyl 4-([(methylsulfanyl)carbonothioyl]{6-[5-(methylsulfonyl)-2,3-dihydro-1H-indol-1-yl]pyrimidin-4-yl}amino)piperidine-1-carboxylate (15.8 g, 10.5 mmol) obtained in the below-mentioned Reference Example 35 and tetrabutylammonium dihydrogentrifluoride (5.91 g, 52.4 mmol) were mixed in dichloromethane (30 mL), N-bromosuccinimide (7.46 g, 41.9 mmol) was added at room temperature and the mixture was stirred at the same temperature for 5 hr. Ethyl acetate and aqueous sodium hydroxide solution were added thereto, and the organic layer was washed with water and saturated brine, dried over sodium sulfate, and concentrated under reduced pressure. The obtained residue was purified by silica gel column chromatography [eluent; hexane:ethyl acetate=6:4 (volume ratio)→hexane:ethyl acetate=1:9 (volume ratio)]. The obtained solid was dissolved in a mixed solvent of ethyl acetate (20 mL)-methanol (20 mL), hydrogen chloride-ethyl acetate solution (4.0 M, 10 mL) was added thereto, and the mixture was stirred at room temperature for 17 hr. The reaction solution was concentrated under reduced pressure, and the residue was dissolved in water, and the solution was basified with aqueous sodium hydroxide solution. The mixture was extracted with ethyl acetate, and the organic layer was washed with water and saturated brine, dried over sodium sulfate, and concentrated under reduced pressure. The obtained residue was purified by NH silica gel column chromatography [eluent; ethyl acetate→ethyl acetate:methanol=17:3 (volume ratio)]. The obtained solid was purified by HPLC [CHIRALPAK AD LF001, eluent; ethanol:DEA=1000:1 (volume ratio)] to give the title compound (507 mg, yield 11%) as a white solid.

$^1$H-NMR (300 MHz, CDCl$_3$) δ: 1.26 (t, J=7.2 Hz, 1H), 1.94 (dd, J=11.7, 2.3 Hz, 2H), 2.17 (qd, J=12.3, 4.3 Hz, 2H), 2.77 (td, J=12.4, 2.1 Hz, 2H), 3.04 (s, 3H), 3.20-3.39 (m, 4H), 4.12 (t, J=8.7 Hz, 2H), 4.61 (tt, J=11.9, 3.4 Hz, 1H), 6.27 (d, J=1.1 Hz, 1H), 7.73 (d, J=1.5 Hz, 1H), 7.80 (dd, J=8.7, 1.9 Hz, 1H), 8.56 (d, J=8.7 Hz, 1H), 8.63 (d, J=1.1 Hz, 1H).

Reference Example 35 tert-butyl 4-([(methylsulfanyl)carbonothioyl]{6-[5-(methylsulfonyl)-2,3-dihydro-1H-indol-1-yl]pyrimidin-4-yl}amino)piperidine-1-carboxylate tert-Butyl 4-({6-[5-(methylsulfonyl)-2,3-dihydro-1H-indol-1-yl]pyrimidin-4-yl}amino)piperidine-1-carboxylate (8.32 g, 17.6 mmol) obtained in the below-mentioned Example 19 was dissolved in THF (500 mL), n-BuLi hexane solution (1.6 M, 13.2 ml, 21.1 mmol) was added thereto dropwise under a nitrogen atmosphere at 0° C., and the mixture was stirred at the same temperature for 1 hr. Carbon disulfide (1.59 mL, 26.4 mmol) was added thereto at 0° C., and the mixture was stirred from 0° C. to room temperature for 7 hr. Methyl iodide (3.28 mL, 52.7 mmol) was added thereto, and the mixture was stirred from 0° C. to room temperature for 63 hr. Water was added to the reaction solution and the aqueous layer was partitioned and extracted with ethyl acetate. The organic layers were combined, and washed with saturated brine, dried over sodium sulfate, and concentrated under reduced pressure. The obtained residue was purified by silica gel column chromatography [eluent; hexane:ethyl acetate=6:4 (volume ratio)→hexane:ethyl acetate=1:9 (volume ratio)] to give the title compound (5.91 g, yield 60%) as a yellow amorphous solid.

$^1$H-NMR (300 MHz, CDCl$_3$) δ: 1.41 (s, 9H), 1.49 (dd, J=12.5, 4.5 Hz, 2H), 2.10 (d, J=12.1 Hz, 2H), 2.60 (s, 3H), 2.82 (t, J=13.0 Hz, 2H), 3.07 (s, 3H), 3.38 (t, J=8.5 Hz, 2H), 4.07-4.29 (m, 4H), 5.54 (tt, J=11.9, 3.6 Hz, 1H), 6.57 (d, J=0.8 Hz, 1H), 7.79 (d, J=1.5 Hz, 1H), 7.86 (dd, J=8.5, 2.1 Hz, 1H), 8.65 (d, J=8.7 Hz, 1H), 8.90 (d, J=1.1 Hz, 1H).

Reference Example 36

4-({6-[7-fluoro-5-(methylsulfonyl)-2,3-dihydro-1H-indol-1-yl]pyrimidin-4-yl}oxy)piperidine-1-carbonitrile To a mixture of 7-fluoro-5-(methylsulfonyl)-1-[6-(piperidin-4-yloxy)pyrimidin-4-yl]-2,3-dihydro-1H-indole (3.0 g, 7.64 mmol) obtained in Reference Example 32, sodium hydrogen carbonate (2.02 g, 24 mmol), water (50 mL), and tetrahydrofuran (150 mL) was added cyano bromide (1.08 g, 10.2 mmol) at 0° C., and the mixture was stirred at room temperature for 16 hr. To the reaction mixture was added aqueous sodium hydrogen carbonate solution, and the mixture was extracted with ethyl acetate. The organic layer was washed with saturated brine, dried over anhydrous magnesium sulfate and filtered. The filtrate was concentrated. The residue was crystallized from ethyl acetate to give the title compound as colorless crystals (2.7 g, yield 85%).

MS (ESI+): 418.

Example 1 tert-butyl 4-{4-[5-(methylsulfonyl)-2,3-dihydro-1H-indol-1-yl]-7H-pyrrolo[2,3-d]pyrimidin-7-yl}piperidine-1-carboxylate

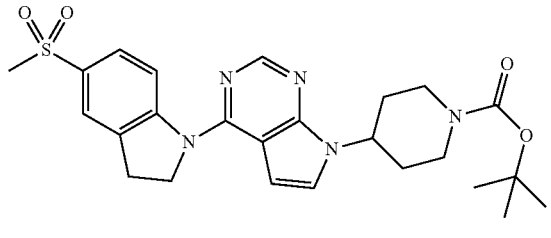 [SMILES: CC(C)(C)OC(=O)N1CCC(n2ccc3c(N4CCc5cc(S(C)(=O)=O)ccc54)ncnc32)CC1]

To a mixture of 5-(methylsulfonyl)-2,3-dihydro-1H-indole (97 mg, 0.49 mmol), tert-butyl 4-(4-chloro-7H-pyrrolo[2,3-d]pyrimidin-7-yl)piperidine-1-carboxylate (150 mg, 0.45 mmol) obtained in Reference Example 1, and N,N-dimethylformamide (5 mL) was added sodium hydride (60%, oil, 39 mg, 0.98 mmol), and the mixture was stirred at room temperature for 0.5 hr, and at 50° C. for 5 hr. The reaction mixture was allowed to cool to room temperature, water was added thereto, and the mixture was extracted with ethyl acetate. The organic layer was washed with saturated brine, dried over anhydrous magnesium sulfate and filtered. The filtrate was concentrated. The residue was crystallized from ethyl acetate to give the title compound as colorless crystals (163 mg, yield 74%).

$^1$H-NMR (300 MHz, DMSO-$d_6$) δ: 1.44 (s, 9H), 1.83-2.01 (m, 4H), 2.83-3.06 (m, 2H), 3.16 (s, 3H), 3.32-3.40 (m, 2H), 4.08-4.21 (m, 2H), 4.62 (t, J=8.7 Hz, 2H), 4.76-4.92 (m, 1H), 6.80 (d, J=3.8 Hz, 1H), 7.62 (d, J=3.8 Hz, 1H), 7.72-7.78 (m, 2H), 8.45 (s, 1H), 8.69 (d, J=9.1 Hz, 1H).

Example 2

1-methylethyl 4-{4-[5-(methylsulfonyl)-2,3-dihydro-1H-indol-1-yl]-7H-pyrrolo[2,3-d]pyrimidin-7-yl}piperidine-1-carboxylate

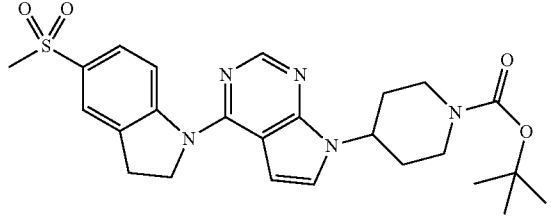 [SMILES: CC(C)(C)OC(=O)N1CCC(n2ccc3c(N4CCc5cc(S(C)(=O)=O)ccc54)ncnc32)CC1]

In the same manner as in Example 1, the title compound was obtained from 5-(methylsulfonyl)-2,3-dihydro-1H-indole and 1-methylethyl 4-(4-chloro-7H-pyrrolo[2,3-d]pyrimidin-7-yl)piperidine-1-carboxylate obtained in Reference Example 3.

$^1$H-NMR (300 MHz, DMSO-$d_6$) δ: 1.22 (d, J=6.4 Hz, 6H), 1.84-2.03 (m, 4H), 2.91-3.10 (m, 3H), 3.13-3.18 (m, 3H), 3.35 (t, J=8.7 Hz, 2H), 4.08-4.23 (m, 2H), 4.62 (t, J=8.7 Hz, 1H), 4.74-4.95 (m, 2H), 6.80 (d, J=3.8 Hz, 1H), 7.62 (d, J=3.8 Hz, 1H), 7.71-7.78 (m, 2H), 8.45 (s, 1H), 8.70 (d, J=9.1 Hz, 1H).

Example 3 tert-butyl 4-{4-[5-(methylsulfonyl)-2,3-dihydro-1H-indol-1-yl]-1H-pyrrolo[2,3-b]pyridin-1-yl}piperidine-1-carboxylate

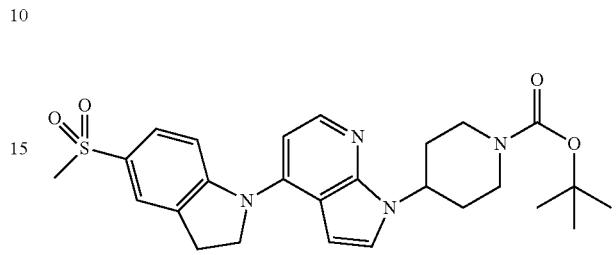

A mixture of 5-(methylsulfonyl)-2,3-dihydro-1H-indole (106 mg, 0.54 mmol), tert-butyl 4-(4-chloro-1H-pyrrolo[2,3-b]pyridin-1-yl)piperidine-1-carboxylate (150 mg, 0.45 mmol) obtained in Reference Example 4,2-dicyclohexylphosphino-2',4',6'-triisopropyl-1,1'-biphenyl (21 mg, 0.045 mmol), tris(dibenzylideneacetone)dipalladium(O) (20 mg, 0.022 mmol), and tert-butanol (7 mL) was stirred under a nitrogen atmosphere at 100° C. for 3 hr. The reaction mixture was allowed to cool to room temperature and concentrated. The residue was subjected to silica gel column chromatography (hexane-ethyl acetate 50:50-1:99, v/v) and crystallized from hexane-ethyl acetate to give the title compound (184 mg, yield 83%) as colorless crystals.

$^1$H-NMR (300 MHz, DMSO-$d_6$) δ: 1.44 (s, 9H), 1.87-1.98 (m, 4H), 2.88-3.05 (m, 2H), 3.13 (s, 3H), 3.25 (t, J=8.5 Hz, 2H), 4.06-4.22 (m, 2H), 4.32 (t, J=8.5 Hz, 2H), 4.84-4.96 (m, 1H), 6.38 (d, J=3.8 Hz, 1H), 7.00-7.07 (m, 2H), 7.59-7.66 (m, 2H), 7.71 (d, J=1.9 Hz, 1H), 8.17 (d, J=5.3 Hz, 1H).

Example 4

1-methylethyl 4-{4-[6-(methylsulfonyl)-3,4-dihydroquinolin-1(2H)-yl]-1H-pyrrolo[2,3-b]pyridin-1-yl}piperidine-1-carboxylate

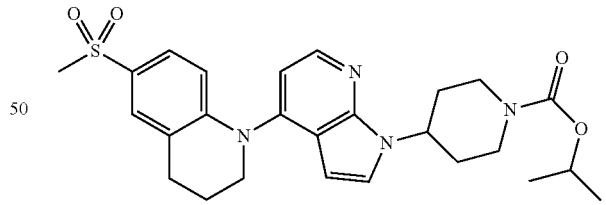

A mixture of 6-(methylsulfonyl)-1,2,3,4-tetrahydroquinoline (113 mg, 0.54 mmol), tert-butyl 4-(4-chloro-1H-pyrrolo[2,3-b]pyridin-1-yl)piperidine-1-carboxylate (150 mg, 0.45 mmol) obtained in Reference Example 4,2-dicyclohexylphosphino-2',4',6'-triisopropyl-1,1'-biphenyl (21 mg, 0.045 mmol), tris(dibenzylideneacetone)dipalladium(O) (20 mg, 0.022 mmol), and tert-butanol (7 mL) was stirred under a nitrogen atmosphere at 100° C. for 3 hr. The reaction mixture was allowed to cool to room temperature, and concentrated. The residue was subjected to silica gel column chromatography (hexane-ethyl acetate 50:50-1:99, v/v) to give an oil. The oil was dissolved in methanol (4 mL), 4N hydrochloric acid-ethyl acetate solution (1 mL) was added thereto, and the mixture was stirred at room temperature for 4 hr. The reaction mixture was concentrated, and tetrahydrofuran (7 mL) and triethylamine (0.376 mL, 2.68 mmol) were added to the residue. Further, isopropyl chlorocarbonate (82 mg, 0.67 mmol) was added dropwise thereto, and the mixture was stirred at room temperature for 12 hr. To the reaction mixture was added aqueous sodium hydrogen carbonate solution, and the mixture was extracted with ethyl acetate. The organic layer was washed with saturated brine, dried over anhydrous magnesium sulfate and filtered. The filtrate was concentrated. The residue was crystallized from hexane-ethyl acetate to give the title compound as colorless crystals (90 mg, yield 41%).

$^1$H-NMR (300 MHz, CDCl$_3$) δ: 1.28 (d, J=6.4 Hz, 6H), 1.84-1.98 (m, 2H), 2.05-2.19 (m, 4H), 2.93-3.08 (m, 7. H), 3.83-3.89 (m, 2H), 4.31-4.44 (m, 2H), 4.88-5.05 (m, 2H), 6.11 (d, J=3.8 Hz, 1H), 6.76 (d, J=8.7 Hz, 1H), 6.93 (d, J=5.3 Hz, 1H), 7.18 (d, J=3.8 Hz, 1H), 7.44 (dd, J=8.7, 2.3 Hz, 1H), 7.64 (d, J=2.3 Hz, 1H), 8.30 (d, J=5.3 Hz, 1H).

Example 5

1-methylethyl 4-{6-methyl-4-[5-(methylsulfonyl)-2,3-dihydro-1H-indol-1-yl]-7H-pyrrolo[2,3-d]pyrimidin-7-yl}piperidine-1-carboxylate

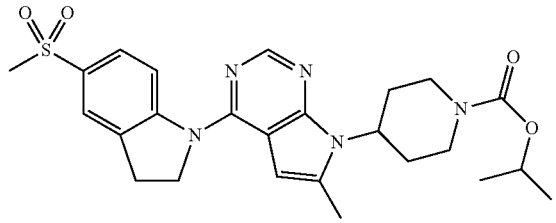 [SMILES: Cc1cc2c(N3CCc4cc(S(C)(=O)=O)ccc43)ncnc2n1C1CCN(C(=O)OC(C)C)CC1]

In the same manner as in Example 1, the title compound was obtained from 5-(methylsulfonyl)-2,3-dihydro-1H-indole and 1-methylethyl 4-(4-chloro-6-methyl-7H-pyrrolo[2,3-d]pyrimidin-7-yl)piperidine-1-carboxylate obtained in Reference Example 5.

$^1$H-NMR (300 MHz, CDCl$_3$) δ: 1.29 (d, J=5.7 Hz, 6H), 1.77-1.90 (m, 2H), 2.50 (s, 3H), 2.58-2.73 (m, 2H), 2.85-2.97 (m, 2H), 3.04 (s, 3H), 3.33 (t, J=8.7 Hz, 2H), 4.29-4.73 (m, 5H), 4.92-5.03 (m, 1H), 6.32 (s, 1H), 7.70-7.82 (m, 2H), 8.47 (s, 1H), 8.51 (d, J=8.7 Hz, 1H).

Example 6

1-methylethyl 4-{4-[5-(methylsulfonyl)-2,3-dihydro-1H-indol-1-yl]-1H-indazol-1-yl}piperidine-1-carboxylate

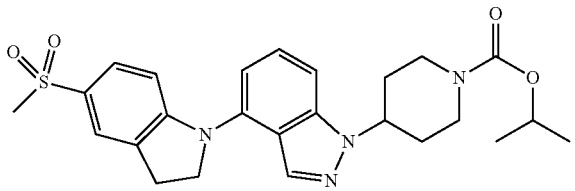 [SMILES: CC(C)OC(=O)N1CCC(n2ncc3c(N4CCc5cc(S(C)(=O)=O)ccc54)cccc32)CC1]

In the same manner as in Example 4, the title compound was obtained from 5-(methylsulfonyl)-2,3-dihydro-1H-indole and tert-butyl 4-[4-bromo-1H-indazol-1-yl]piperidine-1-carboxylate obtained in Reference Example 6.

$^1$H-NMR (300 MHz, CDCl$_3$) δ: 1.28 (d, J=6.4 Hz, 6H), 2.00-2.11 (m, 2H), 2.16-2.34 (m, 2H), 2.94-3.08 (m, 5H), 3.29 (t, J=8.5 Hz, 2H), 4.25 (t, J=8.5 Hz, 2H), 4.31-4.45 (m, 2H), 4.54-4.67 (m, 1H), 4.89-5.02 (m, 1H), 6.81 (d, J=8.3 Hz, 1H), 7.00 (d, J=7.2 Hz, 1H), 7.23-7.28 (m, 1H), 7.34-7.41 (m, 1H), 7.58-7.64 (m, 1H), 7.69 (s, 1H), 7.89 (s, 1H).

Example 7

1-methylethyl 4-[4-(5-nitro-2,3-dihydro-1H-indol-1-yl)-7H-pyrrolo[2,3-d]pyrimidin-7-yl]piperidine-1-carboxylate

To a mixture of 5-nitro-2,3-dihydro-1H-indole (328 mg, 2.00 mmol), 1-methylethyl 4-(4-chloro-7H-pyrrolo[2,3-d]pyrimidin-7-yl)piperidine-1-carboxylate (323 mg, 1.00 mmol) obtained in Reference Example 3, and N,N-dimethylformamide (10 ml) was added potassium carbonate (830 mg, 6.01 mmol), and the mixture was stirred at 100° C. for 2 days. The reaction mixture was allowed to cool to room temperature, water was added thereto, and the mixture was extracted with ethyl acetate. The organic layer was washed with saturated brine, dried over anhydrous magnesium sulfate and filtered. The filtrate was concentrated. The residue was crystallized from ethyl acetate to give the title compound as yellow crystals (175 mg, yield 39%).

$^1$H-NMR (300 MHz, CDCl$_3$) δ: 1.28 (d, J=6.0 Hz, 6H), 1.82-1.99 (m, 2H), 2.02-2.16 (m, 2H), 2.91-3.08 (m, 2H), 3.38 (t, J=8.7 Hz, 2H), 4.29-4.46 (m, 2H), 4.65 (t, J=8.7 Hz, 2H), 4.87-5.02 (m, 2H), 6.65 (d, J=3.8 Hz, 1H), 7.16 (d, J=3.8 Hz, 1H), 8.08 (s, 1H), 8.17 (dd, J=9.0, 2.3 Hz, 1H), 8.57 (s, 1H), 8.62 (d, J=9.4 Hz, 1H).

Example 8

1-methylethyl 4-[4-(5-cyano-2,3-dihydro-1H-indol-1-yl)-7H-pyrrolo[2,3-d]pyrimidin-7-yl]piperidine-1-carboxylate

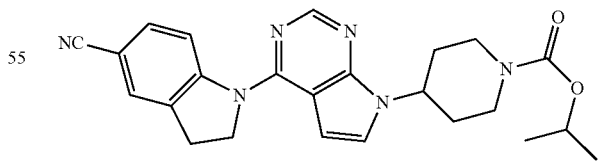

In the same manner as in Example 1, the title compound was obtained from 2,3-dihydro-1H-indole-5-carbonitrile obtained in Reference Example 7 and 1-methylethyl 4-(4-chloro-7H-pyrrolo[2,3-d]pyrimidin-7-yl)piperidine-1-carboxylate obtained in Reference Example 3.

$^1$H-NMR (300 MHz, CDCl$_3$) δ: 1.28 (d, J=6.1 Hz, 6H), 1.77-2.15 (m, 4H), 2.91-3.10 (m, 2H), 3.33 (t, J=8.5 Hz, 2H), 4.24-4.49 (m, 2H), 4.59 (t, J=8.7 Hz, 2H), 4.85-5.03 (m, 2H), 6.63 (d, J=3.4 Hz, 1H), 7.14 (d, J=3.8 Hz, 1H), 7.45 (s, 1H), 7.53 (d, J=8.3 Hz, 1H), 8.53 (s, 1H), 8.62 (d, J=8.7 Hz, 1H).

Example 9

1-methylethyl 4-[4-(5-bromo-2,3-dihydro-1H-indol-1-yl)-7H-pyrrolo[2,3-d]pyrimidin-7-yl]piperidine-1-carboxylate

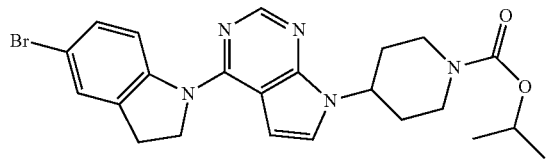 [SMILES: CC(C)OC(=O)N1CCC(n2ccc3c(N4CCc5cc(Br)ccc54)ncnc32)CC1]

In the same manner as in Example 1, the title compound was obtained from 5-bromo-2,3-dihydro-1H-indole and 1-methylethyl 4-(4-chloro-7H-pyrrolo[2,3-d]pyrimidin-7-yl)piperidine-1-carboxylate obtained in Reference Example 3 obtained in Reference Example 3.

$^1$H-NMR (300 MHz, CDCl$_3$) δ: 1.28 (d, J=6.4 Hz, 6H), 1.79-1.96 (m, 2H), 2.01-2.13 (m, 2H), 2.99 (t, J=12.5 Hz, 2H), 3.29 (t, J=8.5 Hz, 2H), 4.27-4.45 (m, 2H), 4.53 (t, J=8.7 Hz, 2H), 4.83-5.05 (m, 2H), 6.62 (d, J=3.8 Hz, 1H), 7.08 (d, J=3.4 Hz, 1H), 7.30-7.39 (m, 2H), 8.38-8.52 (m, 2H).

Example 10

1-methylethyl 4-{4-[5-(2-oxopyrrolidin-1-yl)-2,3-dihydro-1H-indol-1-yl]-7H-pyrrolo[2,3-d]pyrimidin-7-yl}piperidine-1-carboxylate

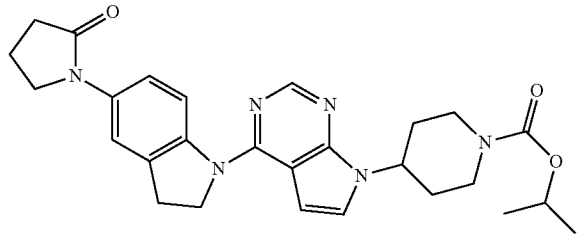 [SMILES: CC(C)OC(=O)N1CCC(n2ccc3c(N4CCc5cc(N6CCCC6=O)ccc54)ncnc32)CC1]

A mixture of 1-methylethyl 4-[4-(5-bromo-2,3-dihydro-1H-indol-1-yl)-7H-pyrrolo[2,3-d]pyrimidin-7-yl]piperidine-1-carboxylate (484 mg, 1.00 mmol) obtained in Example 9, pyrrolidin-2-one (102 mg, 1.20 mmol), cesium carbonate (456 mg, 1.40 mmol), (9,9-dimethyl-9H-xanthene-4,5-diyl)bis(diphenylphosphane) (17 mg, 0.030 mmol), tris(dibenzylideneacetone)dipalladium(O) (9.2 mg, 0.010 mmol), and toluene (10 mL) was stirred under a nitrogen atmosphere at 110° C. for 30 hr. The reaction mixture was allowed to cool to room temperature, and concentrated. The residue was subjected to silica gel column chromatography (ethyl acetate-methanol 100:0-90:10, v/v) and crystallized from hexane-ethyl acetate to give the title compound (117 mg, yield 24%) as colorless crystals.

$^1$H-NMR (300 MHz, CDCl$_3$) δ: 1.28 (d, J=6.0 Hz, 6H), 1.82-1.98 (m, 2H), 2.02-2.24 (m, 4H), 2.54-2.67 (m, 2H), 2.99 (t, J=12.2 Hz, 2H), 3.31 (t, J=8.5 Hz, 2H), 3.86 (t, J=7.2 Hz, 2H), 4.25-4.45 (m, 2H), 4.52 (t, J=8.5 Hz, 2H), 4.79-5.05 (m, 2H), 6.63 (d, J=3.8 Hz, 1H), 7.06 (d, J=3.8 Hz, 1H), 7.18 (dd, J=8.9, 2.4 Hz, 1H), 7.75 (d, J=1.9 Hz, 1H), 8.48 (s, 1H), 8.52 (d, J=8.7 Hz, 1H).

Example 11 methyl 1-(7-{1-[(1-methylethoxy)carbonyl]piperidin-4-yl}-7H-pyrrolo[2,3-d]pyrimidin-4-yl)-2,3-dihydro-1H-indole-5-carboxylate

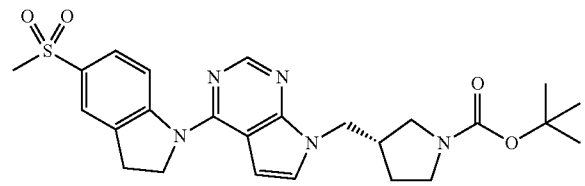 [SMILES: CC(C)(C)OC(=O)N1CC[C@H](Cn2ccc3c(N4CCc5cc(S(C)(=O)=O)ccc54)ncnc32)C1]

To a mixed solution of methyl 1-(7-{1-[(1-methylethoxy)carbonyl]piperidin-4-yl}-7H-pyrrolo[2,3-d]pyrimidin-4-yl)-1H-indole-5-carboxylate (200 mg, 0.43 mmol) obtained in Reference Example 8, methanol (20 mL), and tetrahydrofuran (5 mL) was added 10% palladium carbon (20 mg), and the mixture was stirred under 1 atm hydrogen atmosphere at 50° C. for 2 days. The catalyst was filtered off, and the filtrate was concentrated. The residue was subjected to silica gel column chromatography (hexane-ethyl acetate 100:0-50:50, v/v) and crystallized from hexane-ethyl acetate to give the title compound (150 mg, yield 75%) as colorless crystals.

$^1$H-NMR (300 MHz, CDCl$_3$) δ: 1.20-1.32 (m, 6H), 1.80-1.99 (m, 2H), 2.03-2.17 (m, 2H), 3.00 (t, J=12.5 Hz, 2H), 3.33 (t, J=8.5 Hz, 2H), 3.90 (s, 3H), 4.27-4.46 (m, 2H), 4.58 (t, J=8.7 Hz, 2H), 4.84-5.05 (m, 2H), 6.64 (d, J=3.8 Hz, 1H), 7.11 (d, J=3.8 Hz, 1H), 7.89 (s, 1H), 7.95 (dd, J=8.7, 1.9 Hz, 1H), 8.50-8.58 (m, 2H).

Example 12 tert-butyl (3S)-3-({4-[5-(methylsulfonyl)-2,3-dihydro-1H-indol-1-yl]-7H-pyrrolo[2,3-d]pyrimidin-7-yl}methyl)pyrrolidine-1-carboxylate In the same manner as in Example 1, the title compound was obtained from tert-butyl (3S)-3-[(4-chloro-7H-pyrrolo[2,3-d]pyrimidin-7-yl)methyl]pyrrolidine-1-carboxylate obtained in Reference Example 9 and 5-(methylsulfonyl)-2,3-dihydro-1H-indole.

$^1$H-NMR (300 MHz, CDCl$_3$) δ: 1.45 (s, 9H), 1.60-1.79 (m, 1H), 1.79-2.03 (m, 1H), 2.56-2.94 (m, 1H), 3.05 (s, 3H), 3.09-3.25 (m, 1H), 3.26-3.73 (m, 5H), 4.15-4.43 (m, 2H), 4.44-4.76 (m, 2H), 6.62 (br s, 1H), 7.06 (d, J=3.8 Hz, 1H), 7.76 (s, 1H), 7.82 (dd, J=8.5, 2.1 Hz, 1H), 8.54 (s, 1H), 8.66 (d, J=8.3 Hz, 1H).

Example 13 tert-butyl (3R)-3-({4-[5-(methylsulfonyl)-2,3-dihydro-1H-indol-1-yl]-7H-pyrrolo[2,3-d]pyrimidin-7-yl}methyl)pyrrolidine-1-carboxylate

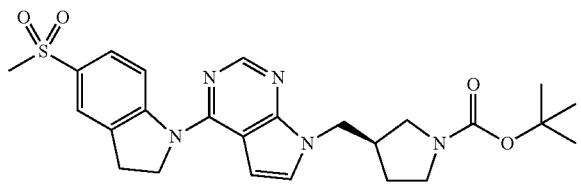 [SMILES: CC(C)(C)OC(=O)N1CC[C@@H](Cn2ccc3c(N4CCc5cc(S(C)(=O)=O)ccc54)ncnc32)C1]

In the same manner as in Example 1, the title compound was obtained from tert-butyl (3R)-3-[(4-chloro-7H-pyrrolo[2,3-d]pyrimidin-7-yl)methyl]pyrrolidine-1-carboxylate obtained in Reference Example 10 and 5-(methylsulfonyl)-2,3-dihydro-1H-indole.

$^1$H-NMR (300 MHz, CDCl$_3$) δ: 1.45 (s, 9H), 1.68 (dd, J=12.3, 7.8 Hz, 1H), 1.81-2.01 (m, 1H), 2.55-2.99 (m, 1H), 3.05 (s, 3H), 3.07-3.24 (m, 1H), 3.22-3.71 (m, 5H), 3.89-4.54 (m, 2H), 4.62 (t, J=8.7 Hz, 2H), 6.62 (br s, 1H), 7.06 (d, J=3.8 Hz, 1H), 7.76 (s, 1H), 7.82 (dd, J=8.7, 2.3 Hz, 1H), 8.54 (s, 1H), 8.66 (d, J=8.7 Hz, 1H).

Example 14 tert-butyl 3-({4-[5-(methylsulfonyl)-2,3-dihydro-1H-indol-1-yl]-7H-pyrrolo[2,3-d]pyrimidin-7-yl}methyl)azetidine-1-carboxylate

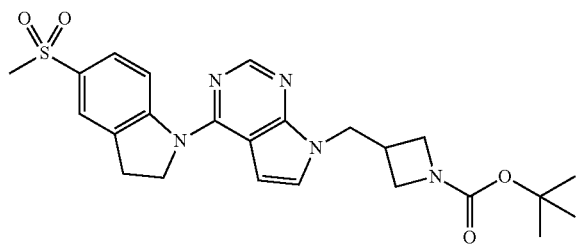 [SMILES: CC(C)(C)OC(=O)N1CC(Cn2ccc3c(N4CCc5cc(S(C)(=O)=O)ccc54)ncnc32)C1]

In the same manner as in Example 1, the title compound was obtained from 5-(methylsulfonyl)-2,3-dihydro-1H-indole and tert-butyl 3-[(4-chloro-7H-pyrrolo[2,3-d]pyrimidin-7-yl)methyl]azetidine-1-carboxylate obtained in Reference Example 11.

$^1$H-NMR (300 MHz, CDCl$_3$) δ: 1.44 (s, 9H), 3.05 (s, 3H), 3.07-3.25 (m, 1H), 3.38 (t, J=8.5 Hz, 2H), 3.77 (dd, J=8.7, 5.3 Hz, 2H), 4.01 (t, J=8.6 Hz, 2H), 4.47 (d, J=7.6 Hz, 2H), 4.62 (t, J=8.7 Hz, 2H), 6.62 (d, J=3.8 Hz, 1H), 7.08 (d, J=3.4 Hz, 1H), 7.76 (s, 1H), 7.82 (dd, J=8.7, 1.9 Hz, 1H), 8.55 (s, 1H), 8.67 (d, J=8.7 Hz, 1H).

Example 15 benzyl 4-{4-[5-(methylsulfonyl)-2,3-dihydro-1H-indol-1-yl]-7H-pyrrolo[2,3-d]pyrimidin-7-yl}azepane-1-carboxylate

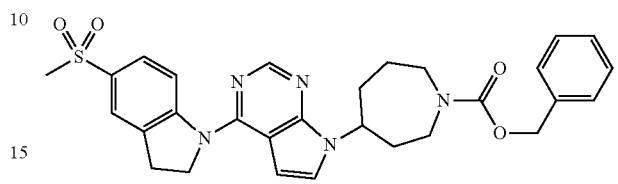

In the same manner as in Example 1, the title compound was obtained from 5-(methylsulfonyl)-2,3-dihydro-1H-indole and benzyl 4-(4-chloro-7H-pyrrolo[2,3-d]pyrimidin-7-yl)azepane-1-carboxylate obtained in Reference Example 12.

$^1$H-NMR (300 MHz, CDCl$_3$) δ: 1.68-2.46 (m, 6H), 3.05 (s, 3H), 3.17-3.44 (m, 3H), 3.45-4.05 (m, 3H), 4.36-4.74 (m, 2H), 4.72-5.06 (m, 1H), 5.19 (s, 2H), 6.28-6.75 (m, 1H), 6.94-7.21 (m, 1H), 7.28-7.50 (m, 5H), 7.75 (s, 1H), 7.81 (dd, J=8.5, 2.1 Hz, 1H), 8.54 (s, 1H), 8.65 (d, J=8.7 Hz, 1H).

Example 16 tert-butyl 4-{4-[5-(methylsulfonyl)-2,3-dihydro-1H-indol-1-yl]-7H-pyrrolo[2,3-d]pyrimidin-7-yl}azepane-1-carboxylate

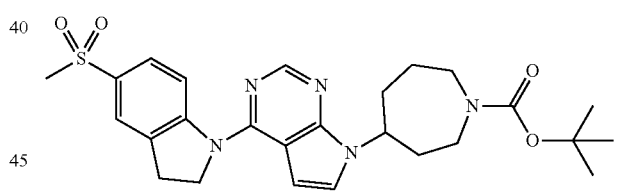

To a mixed solution of benzyl 4-{4-[5-(methylsulfonyl)-2,3-dihydro-1H-indol-1-yl]-7H-pyrrolo[2,3-d]pyrimidin-7-yl}azepane-1-carboxylate (1.47 g) obtained in Example 15, di-tert-butyl bicarbonate (650 mg) and tetrahydrofuran (15 mL) was added 10% palladium carbon (800 mg), and the mixture was stirred for under 1 atm hydrogen atmosphere at room temperature for 18 hr. The catalyst was filtered off, and the filtrate was concentrated. The residue was subjected to silica gel column chromatography (hexane-ethyl acetate 95:5-0:100, v/v), and the obtained residue was washed with hexane-diisopropyl ether-diethyl ether to give the title compound (194 mg, yield 26%) as a colorless solid.

$^1$H-NMR (300 MHz, CDCl$_3$) δ: 1.51 (s, 9H), 1.73-2.38 (m, 6H), 3.05 (s, 3H), 3.11-3.31 (m, 1H), 3.37 (t, J=8.5 Hz, 2H), 3.41-4.17 (m, 3H), 4.62 (t, J=8.7 Hz, 2H), 4.72-5.23 (m, 1H), 6.62 (br s, 1H), 7.14 (t, J=3.8 Hz, 1H), 7.75 (s, 1H), 7.81 (dd, J=8.5, 2.1 Hz, 1H), 8.54 (s, 1H), 8.65 (d, J=8.7 Hz, 1H).

Example 17 tert-butyl 3-{4-[5-(methylsulfonyl)-2,3-dihydro-1H-indol-1-yl]-7H-pyrrolo[2,3-d]pyrimidin-7-yl}pyrrolidine-1-carboxylate

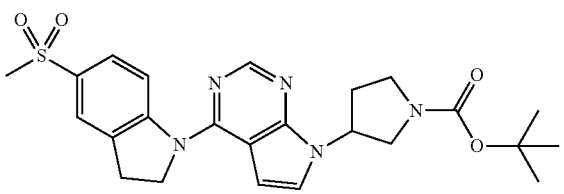 [SMILES: CC(C)(C)OC(=O)N1CCC(n2ccc3c(N4CCc5cc(S(C)(=O)=O)ccc54)ncnc32)C1]

In the same manner as in Example 1, the title compound was obtained from 5-(methylsulfonyl)-2,3-dihydro-1H-indole and tert-butyl 3-(4-chloro-7H-pyrrolo[2,3-d]pyrimidin-7-yl)pyrrolidine-1-carboxylate obtained in Reference Example 13.

$^1$H-NMR (300 MHz, CDCl$_3$) δ: 1.49 (br s, 9H), 2.19-2.35 (m, 1H), 2.35-2.58 (m, 1H), 3.05 (s, 3H), 3.38 (t, J=8.7 Hz, 2H), 3.46-3.72 (m, 3H), 3.92 (dd, J=11.7, 6.8 Hz, 1H), 4.62 (t, J=8.7 Hz, 2H), 5.52 (br s, 1H), 6.65 (d, J=3.4 Hz, 1H), 7.12 (d, J=3.8 Hz, 1H), 7.76 (s, 1H), 7.82 (dd, J=8.5, 2.1 Hz, 1H), 8.55 (s, 1H), 8.67 (d, 1H).

Example 18

1-methylethyl 4-({6-[5-(methylsulfonyl)-2,3-dihydro-1H-indol-1-yl]pyrimidin-4-yl}oxy)piperidine-1-carboxylate

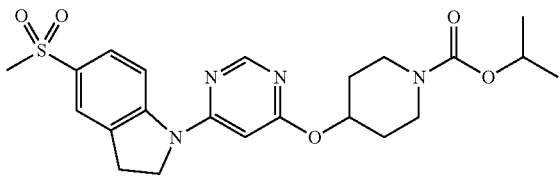 [SMILES: CC(C)OC(=O)N1CCC(Oc2cc(N3CCc4cc(S(C)(=O)=O)ccc43)ncn2)CC1]

A mixture of 5-(methylsulfonyl)-2,3-dihydro-1H-indole (105 mg, 0.532 mmol), 1-methylethyl 4-[(6-chloropyrimidin-4-yl)oxy]piperidine-1-carboxylate (150 mg, 0.500 mmol) obtained in Reference Example 14, 2,8,9-tris(2-methylpropyl)-2,5,8,9-tetraaza-1-phosphabicyclo[3.3.3]undecane (8 μL, 0.023 mmol), palladium(II) acetate (5.0 mg, 0.022 mmol), and sodium tert-butoxide (125 mg, 1.30 mmol) in tetrahydrofuran (5 mL) was stirred with heating under reflux overnight. The reaction mixture was allowed to cool to room temperature, water was added to the reaction mixture, and the mixture was extracted with ethyl acetate. The organic layer was washed with saturated brine, dried over anhydrous magnesium sulfate and filtered. The filtrate was concentrated. The obtained residue was subjected to silica gel column chromatography (hexane-ethyl acetate 85:15-75:25, v/v) and crystallized from hexane-ethyl acetate to give the title compound as white crystals (55 mg, yield 24%).

$^1$H-NMR (300 MHz, CDCl$_3$) δ: 1.26 (d, J=6.1 Hz, 6H), 1.62-1.88 (m, 2H), 1.85-2.20 (m, 2H), 3.04 (s, 3H), 3.16-3.49 (m, 4H), 3.70-3.96 (m, 2H), 4.07 (t, J=8.7 Hz, 2H), 4.94 (spt, J=6.2 Hz, 1H), 5.33 (tt, J=7.9, 3.9 Hz, 1H), 5.98 (s, 1H), 7.72 (s, 1H), 7.79 (dd, J=8.7, 1.9 Hz, 1H), 8.51 (s, 1H), 8.57 (d, J=8.7 Hz, 1H).

Example 19 tert-butyl 4-({6-[5-(methylsulfonyl)-2,3-dihydro-1H-indol-1-yl]pyrimidin-4-yl}amino)piperidine-1-carboxylate

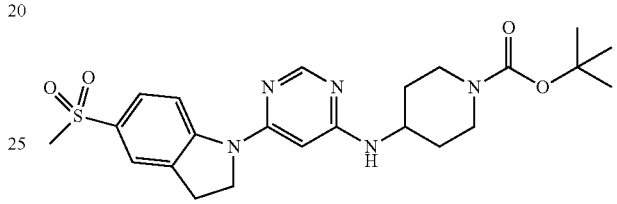

A mixture of tert-butyl 4-aminopiperidine-1-carboxylate (10.0 g, 50 mmol), 1-(6-chloropyrimidin-4-yl)-5-(methylsulfonyl)-2,3-dihydro-1H-indole (11.0 g, 35.6 mmol) obtained in Reference Example 17, 2-dicyclohexylphosphino-2',4',6'-triisopropyl-1,1'-biphenyl (1.91 g, 4.0 mmol), tris(dibenzylideneacetone)dipalladium(0) (1.83 g, 2.0 mmol), cesium carbonate (23.4 g, 72 mmol), and toluene (150 mL) was stirred under a nitrogen atmosphere at 110° C. for 16 hr. The reaction mixture was allowed to cool to room temperature, water was added thereto, and the mixture was extracted with ethyl acetate. The organic layer was washed with saturated brine, dried over anhydrous magnesium sulfate and filtered. The filtrate was concentrated. The residue was subjected to silica gel column chromatography (hexane-ethyl acetate 70:30-20:80, v/v) and crystallized from hexane-ethyl acetate to give the title compound (7.1 g, yield 42%) as colorless crystals.

$^1$H-NMR (300 MHz, CDCl$_3$) δ: 1.31-1.56 (m, 11H), 1.94-2.14 (m, 2H), 2.90-3.11 (m, 5H), 3.27 (t, J=8.7 Hz, 2H), 3.77-3.96 (m, 1H), 3.97-4.20 (m, 4H), 4.73 (d, J=7.9 Hz, 1H), 5.56 (s, 1H), 7.69 (s, 1H), 7.75 (dd, J=8.7, 1.9 Hz, 1H), 8.36 (s, 1H), 8.52 (d, J=8.7 Hz, 1H).

Example 20 tert-butyl 4-[(6-{5-[(2-hydroxyethyl)(methyl)carbamoyl]-2,3-dihydro-1H-indol-1-yl}pyrimidin-4-yl)oxy]piperidine-1-carboxylate

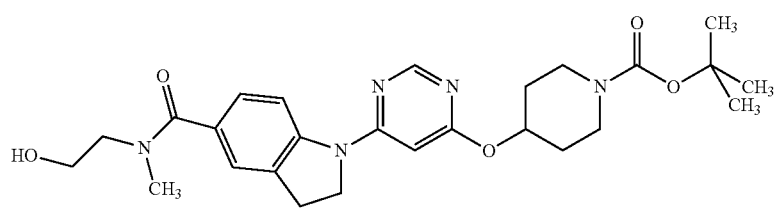 [SMILES: CN(CCO)C(=O)c1ccc2c(c1)CCN2c1cc(OC2CCN(C(=O)OC(C)(C)C)CC2)ncn1]

To a mixture of 1-(6-{[1-(tert-butoxycarbonyl)piperidin-4-yl]oxy}pyrimidin-4-yl)-2,3-dihydro-1H-indole-5-carboxylic acid (890 mg) obtained in the below-mentioned Example 74, N,N-dimethylformamide (20 mL), and isopropanol (20 mL) were added 2-(methylamino)ethanol (243 µL) and 4-(4,6-dimethoxy-1,3,5-triazin-2-yl)-4-methylmorpholinium chloride hydrate (842 mg), and the mixture was stirred at 50° C. overnight. Water was added to the reaction mixture, and the mixture was extracted with ethyl acetate. The extract was washed with saturated aqueous sodium hydrogen carbonate solution and saturated brine, dried over magnesium sulfate, and concentrated under reduced pressure. The residue was purified by silica gel column chromatography (50-100% ethyl acetate/hexane, thereafter 0-10% methanol/ethyl acetate) to give a white solid. The obtained solid was further purified by reversed-phase HPLC preparative (column: YMC manufactured by CombiPrep Pro C18RS (100×30 mmI. D., S-5 µm, 8 nm); eluent: 20-100% acetonitrile/distillation water (containing 0.1% trifluoroacetic acid)) to give a white solid. The obtained solid was washed with 50% ethyl acetate/hexane to give the title compound (235 mg) as a white solid.

¹H-NMR (300 MHz, CDCl₃) δ: 1.48 (s, 9H), 1.65-1.80 (m, 2H), 1.93-2.06 (m, 2H), 3.11 (s, 3H), 3.20-3.35 (m, 4H), 3.60-3.95 (m, 6H), 4.01 (t, J=8.7 Hz, 2H), 5.24-5.37 (m, 1H), 5.94 (s, 1H), 7.29-7.42 (m, 2H), 8.39 (d, J=8.3 Hz, 1H), 8.48 (s, 1H).

Example 21

1-(6-{[1-(5-ethylpyrimidin-2-yl)piperidin-4-yl]oxy}pyrimidin-4-yl)-N-(2-hydroxyethyl)-N-methyl-2,3-dihydro-1H-indole-5-carboxamide

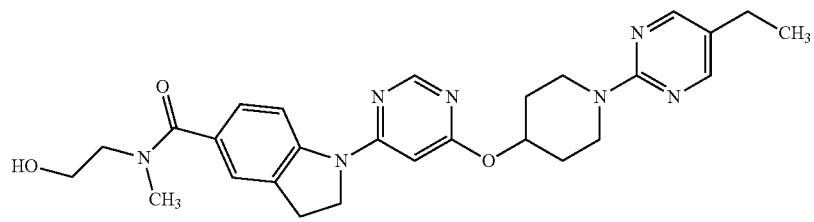 [SMILES: CCc1cnc(N2CCC(Oc3cc(N4CCc5cc(C(=O)N(C)CCO)ccc54)ncn3)CC2)nc1]

A mixture of tert-butyl 4-[(6-{5-[(2-hydroxyethyl)(methyl)carbamoyl]-2,3-dihydro-1H-indol-1-yl}pyrimidin-4-yl)oxy]piperidine-1-carboxylate (274 mg) synthesized in Example 20 and trifluoroacetic acid (5 mL) was stirred at room temperature for 1 hr, and concentrated under reduced pressure. To the residue was added saturated aqueous sodium hydrogen carbonate solution, and the solution was adjusted to pH 10 with 1N aqueous sodium hydroxide solution and extracted with ethyl acetate. The extract was dried over magnesium sulfate, and concentrated under reduced pressure to give a colorless oil. To a solution of the obtained oil in 1-methyl-2-pyrrolidone (5 mL) were added 2-chloro-5-ethylpyrimidine (52.0 µL) and cesium carbonate (186 mg) and the mixture was stirred at 80° C. overnight. Water was added to the reaction mixture, and the mixture was extracted with ethyl acetate. The extract was washed with saturated brine, dried over magnesium sulfate, and concentrated under reduced pressure. The residue was purified by silica gel column chromatography (50-100% ethyl acetate/hexane, thereafter 0-10% methanol/ethyl acetate) to give a white solid. The obtained solid was washed with 50% ethyl acetate/hexane to give the title compound (44.3 mg) as a white solid.

¹H-NMR (300 MHz, CDCl₃) δ: 1.20 (t, J=7.6 Hz, 3H), 1.73-1.87 (m, 2H), 2.03-2.16 (m, 2H), 2.47 (q, J=7.6 Hz, 2H), 3.11 (s, 3H), 3.25 (t, J=8.6 Hz, 2H), 3.51-3.77 (m, 4H), 3.82-3.93 (m, 2H), 4.01 (t, J=8.6 Hz, 2H), 4.23-4.35 (m, 2H), 5.34-5.46 (m, 1H), 5.96 (s, 1H), 7.30-7.40 (m, 2H), 8.19 (s, 2H), 8.39 (d, J=8.3 Hz, 1H), 8.50 (s, 1H).

Example 22 methyl 1-(6-{[1-(5-ethylpyrimidin-2-yl)piperidin-4-yl]oxy}pyrimidin-4-yl)-2,3-dihydro-1H-indole-5-carboxylate

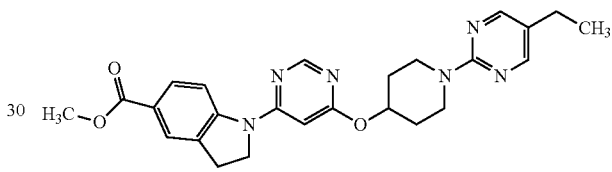

To a solution of methyl 1-[6-(piperidin-4-yloxy)pyrimidin-4-yl]-2,3-dihydro-1H-indole-5-carboxylate hydrochloride (1.00 g) synthesized in Reference Example 16 in 1-methyl-2-pyrrolidone (20 mL) were added 2-chloro-5-ethylpyrimidine (626 µL) and cesium carbonate (3.32 g) and the mixture was stirred at 80° C. overnight. Water was added to the reaction mixture and the mixture was extracted with a mixed solvent of ethyl acetate and tetrahydrofuran. The extract was washed with saturated brine, dried over magnesium sulfate, and concentrated under reduced pressure. The residue was washed with 50% ethyl acetate/hexane to give the title compound (570 mg, 48%) as a pale-yellow solid.

¹H-NMR (300 MHz, CDCl₃) δ: 1.20 (t, J=7.7 Hz, 3H), 1.71-1.88 (m, 2H), 2.02-2.17 (m, 2H), 2.47 (q, J=7.7 Hz, 2H), 3.27 (t, J=8.7 Hz, 2H), 3.51-3.64 (m, 2H), 3.89 (s, 3H), 4.03 (t, J=8.7 Hz, 2H), 4.22-4.36 (m, 2H), 5.33-5.47 (m, 1H), 5.98 (s, 1H), 7.85 (s, 1H), 7.92 (d, J=8.5 Hz, 1H), 8.18 (s, 2H), 8.41 (d, J=8.5 Hz, 1H), 8.51 (s, 1H).

Example 23

1-(6-{[1-(5-ethylpyrimidin-2-yl)piperidin-4-yl]oxy}pyrimidin-4-yl)-N-(1-hydroxypropan-2-yl)-2,3-dihydro-1H-indole-5-carboxamide

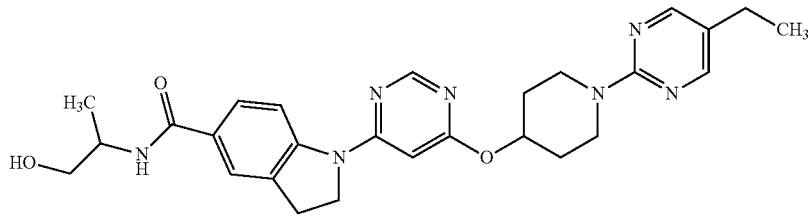 [SMILES: CCc1cnc(N2CCC(Oc3cc(N4CCc5cc(C(=O)NC(C)CO)ccc54)ncn3)CC2)nc1]

To a mixture of 1-(6-{[1-(5-ethylpyrimidin-2-yl)piperidin-4-yl]oxy}pyrimidin-4-yl)-2,3-dihydro-1H-indole-5-carboxylic acid (125 mg) obtained in the below-mentioned Example 75, N,N-dimethylformamide (5 mL), and isopropanol (5 mL) were added 2-amino-1-propanol (44.6 µL) and 4-(4,6-dimethoxy-1,3,5-triazin-2-yl)-4-methylmorpholinium chloride hydrate (128 mg), and the mixture was stirred at 80° C. overnight. Water was added to the reaction mixture, and the mixture was extracted with ethyl acetate. The extract was washed with saturated brine, dried over magnesium sulfate, and concentrated under reduced pressure. The residue was purified by NH-silica gel column chromatography (0-5% methanol/ethyl acetate) to give a white solid. The obtained solid was washed with 50% ethyl acetate/hexane to give the title compound (65.9 mg, 47%) as a white solid.

$^1$H-NMR (300 MHz, CDCl$_3$) δ: 1.20 (t, J=7.6 Hz, 3H), 1.30 (d, J=6.8 Hz, 3H), 1.68-1.87 (m, 2'H), 2.02-2.16 (m, 2H), 2.47 (q, J=7.6 Hz, 2H), 2.93 (dd, J=6.1, 4.9 Hz, 1H), 3.26 (t, J=8.6 Hz, 2H), 3.51-3.71 (m, 3H), 3.75-3.85 (m, 1H), 4.02 (t, J=8.6 Hz, 2H), 4.21-4.35 (m, 3H), 5.35-5.46 (m, 1H), 5.96 (s, 1H), 6.20 (d, J=6.8 Hz, 1H), 7.60 (dd, J=8.6, 1.7 Hz, 1H), 7.64-7.68 (m, 1H), 8.19 (s, 2H), 8.41 (d, J=8.6 Hz, 1H), 8.51 (s, 1H).

Example 24

1-(6-{[1-(5-ethylpyrimidin-2-yl)piperidin-4-yl]oxy}pyrimidin-4-yl)-N-(1-hydroxy-2-methylpropan-2-yl)-2,3-dihydro-1H-indole-5-carboxamide

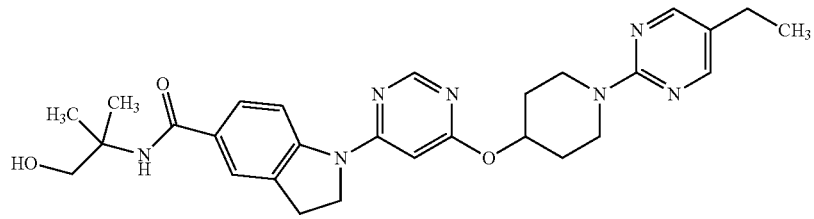 [SMILES: CCc1cnc(N2CCC(Oc3cc(N4CCc5cc(C(=O)NC(C)(C)CO)ccc54)ncn3)CC2)nc1]

To a mixture of 1-(6-{[1-(5-ethylpyrimidin-2-yl)piperidin-4-yl]oxy}pyrimidin-4-yl)-2,3-dihydro-1H-indole-5-carboxylic acid (125 mg) obtained in the below-mentioned Example 75, N,N-dimethylformamide (5 mL), and isopropanol (5% mL) were added 2-amino-2-methyl-1-propanol (53.4 µL) and 4-(4,6-dimethoxy-1,3,5-triazin-2-yl)-4-methylmorpholinium chloride hydrate (128 mg) and the mixture was stirred at 80° C. overnight. Water was added to the reaction mixture, and the mixture was extracted with ethyl acetate. The extract was washed with saturated brine, dried over magnesium sulfate, and concentrated under reduced pressure. The residue was purified by NH-silica gel column chromatography (0-5% methanol/ethyl acetate) to give a white solid. The obtained solid was washed with 50% ethyl acetate/hexane to give the title compound (32.7 mg, 23%) as a white solid.

$^1$H-NMR (300 MHz, CDCl$_3$) δ: 1.20 (t, J=7.8 Hz, 3H), 1.42 (s, 6H), 1.72-1.88 (m, 2H), 2.02-2.16 (m, 2H), 2.47 (q, J=7.8 Hz, 2H), 3.26 (t, J=8.7 Hz, 2H), 3.50-3.64 (m, 2H), 3.70 (d, J=6.3 Hz, 2H), 4.02 (t, J=8.7 Hz, 2H), 4.23-4.35 (m, 2H), 4.95 (t, J=6.3 Hz, 1H), 5.34-5.46 (m, 1H), 5.97 (s, 1H), 6.08 (s, 1H), 7.55 (dd, J=8.6, 2.1 Hz, 1H), 7.61-7.64 (m, 1H), 8.19 (s, 2H), 8.41 (d, J=8.6 Hz, 1H), 8.51 (s, 1H).

Example 25

1-(6-{[1-(5-ethylpyrimidin-2-yl)piperidin-4-yl]oxy}pyrimidin-4-yl)-N-(2-methoxyethyl)-N-methyl-2,3-dihydro-1H-indole-5-carboxamide

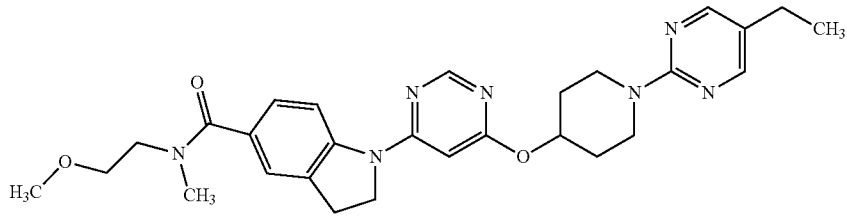 [SMILES: CCc1cnc(N2CCC(Oc3cc(N4CCc5cc(C(=O)N(C)CCOC)ccc54)ncn3)CC2)nc1]

To a mixture of 1-(6-{[1-(5-ethylpyrimidin-2-yl)piperidin-4-yl]oxy}pyrimidin-4-yl)-2,3-dihydro-1H-indole-5-carboxylic acid (150 mg) obtained in the below-mentioned Example 75, N-(2-methoxyethyl)methylamine (54.1 µL), and N,N-dimethylformamide (10 mL) were added O-(7-azabenzotriazol-1-yl)-N,N,N',N'-tetramethyluronium hexafluorophosphate (192 mg) and N-ethyldiisopropylamine (87.8 µL), and the mixture was stirred at room temperature for 1 day. Water was added to the reaction mixture, and the mixture was extracted with ethyl acetate. The extract was washed with saturated brine, dried over magnesium sulfate, and concentrated under reduced pressure. The residue was purified by silica gel column chromatography (50-100% ethyl acetate/hexane, thereafter 0-10% methanol/ethyl acetate) to give a white solid. The obtained solid was washed with 50% ethyl acetate/hexane to give the title compound (45.1 mg, 26%) as a white solid.

$^1$H-NMR (300 MHz, CDCl$_3$) δ: 1.20 (t, J=7.6 Hz, 3H), 1.71-1.87 (m, 2H), 2.02-2.16 (m, 2H), 2.47 (q, J=7.6 Hz, 2H), 3.10 (s, 3H), 3.24 (t, J=8.7 Hz, 2H), 3.36 (br s, 3H), 3.49-3.74 (m, 6H), 4.00 (t, J=8.7 Hz, 2H), 4.22-4.34 (m, 2H), 5.33-5.46 (m, 1H), 5.95 (s, 1H), 7.24-7.34 (m, 2H), 8.19 (s, 2H), 8.36 (d, J=8.3 Hz, 1H), 8.49 (s, 1H).

Example 26

1-(6-{[1-(5-ethylpyrimidin-2-yl)piperidin-4-yl]oxy}pyrimidin-4-yl)-N-(tetrahydrofuran-3-yl)-2,3-dihydro-1H-indole-5-carboxamide

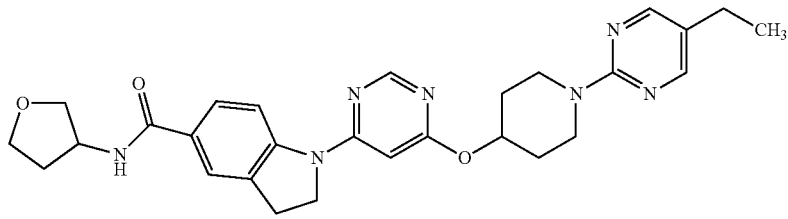 [SMILES: CCc1cnc(N2CCC(Oc3cc(N4CCc5cc(C(=O)NC6CCOC6)ccc54)ncn3)CC2)nc1]

To a mixture of 1-(6-{[1-(5-ethylpyrimidin-2-yl)piperidin-4-yl]oxy}pyrimidin-4-yl)-2,3-dihydro-1H-indole-5-carboxylic acid (150 mg) obtained in the below-mentioned Example 75, 3-aminotetrahydrofuran (42.9 µL), and N,N-dimethylformamide (10 mL) were added O-(7-azabenzotriazol-1-yl)-N,N,N',N'-tetramethyluronium hexafluorophosphate (192 mg) and N-ethyldiisopropylamine (87.8 µL), and the mixture was stirred at room temperature for 1 day. Water was added to the reaction mixture, and the mixture was extracted with a mixed solution of ethyl acetate and tetrahydrofuran. The extract was washed with saturated brine, dried over magnesium sulfate, and concentrated under reduced pressure. The residue was washed with 50% ethyl acetate/hexane to give the title compound (150 mg, 87%) as a white solid.

$^1$H-NMR (300 MHz, CDCl$_3$) δ: 1.20 (t, J=7.6 Hz, 3H), 1.72-2.00 (m, 3H), 2.04-2.16 (m, 2H), 2.29-2.43 (m, 1H), 2.47 (q, J=7.6 Hz, 2H), 3.27 (t, J=8.5 Hz, 2H), 3.50-3.64 (m, 2H), 3.76-3.96 (m, 3H), 3.97-4.07 (m, 3H), 4.23-4.35 (m, 2H), 4.67-4.80 (m, 1H), 5.34-5.46 (m, 1H), 5.97 (s, 1H), 6.19 (d, J=7.2 Hz, 1H), 7.58 (dd, J=8.5, 1.5 Hz, 1H), 7.65 (d, J=1.5 Hz, 1H), 8.19 (s, 2H), 8.41 (d, J=8.5 Hz, 1H), 8.51 (s, 1H).

Example 27

[1-(6-{[1-(5-ethylpyrimidin-2-yl)piperidin-4-yl]oxy}pyrimidin-4-yl)-2,3-dihydro-1H-indol-5-yl](morpholin-4-yl)methanone

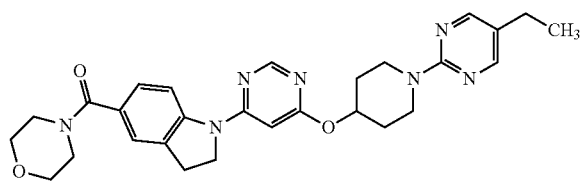 [SMILES: CCc1cnc(N2CCC(Oc3cc(N4CCc5cc(C(=O)N6CCOCC6)ccc54)ncn3)CC2)nc1]

To a mixture of 1-(6-{[1-(5-ethylpyrimidin-2-yl)piperidin-4-yl]oxy}pyrimidin-4-yl)-2,3-dihydro-1H-indole-5-carboxylic acid (150 mg) obtained in the below-mentioned Example 75, morpholine (44.1 μL), and N,N-dimethylformamide (10 mL) were added 0-(7-azabenzotriazol-1-yl)-N,N,N',N'-tetramethyluronium hexafluorophosphate (192 mg) and N-ethyldiisopropylamine (87.8 μL), and the mixture was stirred at room temperature for 1 day. Water was added to the reaction mixture and the mixture was extracted with a mixed solution of ethyl acetate and tetrahydrofuran. The extract was washed with saturated brine, dried over magnesium sulfate, and concentrated under reduced pressure. The residue was washed with 50% ethyl acetate/hexane to give the title compound (118 mg, 68%) as a white solid.

$^1$H-NMR (300 MHz, CDCl$_3$) δ: 1.20 (t, J=7.5 Hz, 3H), 1.72-1.87 (m, 2H), 2.03-2.16 (m, 2H), 2.47 (q, J=7.5 Hz, 2H), 3.26 (t, J=8.6 Hz, 2H), 3.51-3.78 (m, 10H), 4.01 (t, J=8.6 Hz, 2H), 4.23-4.35 (m, 2H), 5.35-5.45 (m, 1H), 5.95 (s, 1H), 7.23-7.29 (m, 1H), 7.30-7.34 (m, 1H), 8.19 (s, 2H), 8.39 (d, J=8.3 Hz, 1H), 8.50 (s, 1H).

Example 28 methyl 1-[6-({1-[3-(1-methylethyl)-1,2,4-oxadiazol-5-yl]piperidin-4-yl}oxy)pyrimidin-4-yl]-2,3-dihydro-1H-indole-5-carboxylate

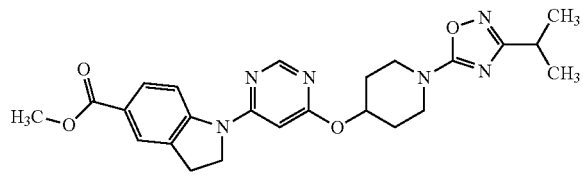 [SMILES: COC(=O)c1ccc2c(c1)CCN2c1cc(OC2CCN(c3nc(C(C)C)no3)CC2)ncn1]

To a suspension of methyl 1-[6-(piperidin-4-yloxy)pyrimidin-4-yl]-2,3-dihydro-1H-indole-5-carboxylate hydrochloride (1.00 g) synthesized in Reference Example 16 in N,N-dimethylformamide (40 mL) were added cyano bromide (451 mg) and sodium hydrogen carbonate (716 mg), and the mixture was stirred at room temperature overnight. Water was added to the reaction mixture and the mixture was extracted with a mixed solvent of ethyl acetate and tetrahydrofuran. The extract was washed with saturated brine, dried over magnesium sulfate, and concentrated under reduced pressure to give a white solid. To a mixture of the obtained solid, (1Z)—N'-hydroxy-2-methylpropanimidamide (349 mg), ethyl acetate (20 ml), and tetrahydrofuran (20 mL) was added a solution (3.42 mL) of 1.0M zinc chloride in diethyl ether, and the mixture was stirred with heating under reflux for 4 hr. Insoluble materials were collected by filtration, and washed with ethyl acetate to give a white solid. To a suspension of the obtained solid in methanol (40 mL) was added concentrated hydrochloric acid (2.00 mL), and the mixture was stirred overnight with heating under reflux, and concentrated under reduced pressure. To the residue was added saturated aqueous sodium hydrogen carbonate solution, and the mixture was extracted with a mixed solvent of ethyl acetate and tetrahydrofuran. The extract was washed with saturated brine, dried over magnesium sulfate, and concentrated under reduced pressure. The residue was washed with 50% ethyl acetate/hexane to give the title compound (741 mg, 62%) as a white solid.

$^1$H-NMR (300 MHz, CDCl$_3$) δ: 1.30 (d, J=7.1 Hz, 6H), 1.83-1.99 (m, 2H), 2.03-2.18 (m, 2H), 2.82-2.98 (m, 1H), 3.27 (t, J=8.6 Hz, 2H), 3.52-3.66 (m, 2H), 3.81-3.97 (m, 5H), 4.03 (t, J=8.6 Hz, 2H), 5.34-5.46 (m, 1H), 5.98 (s, 1H), 7.86 (s, 1H), 7.92 (d, J=8.5 Hz, 1H), 8.41 (d, J=8.5 Hz, 1H), 8.50 (s, 1H).

Example 29

N-[1-(3-cyclopropyl-1,2,4-oxadiazol-5-yl)piperidin-4-yl]-6-[5-(methylsulfonyl)-2,3-dihydro-1H-indol-1-yl]-N-(trifluoromethyl)pyrimidin-4-amine

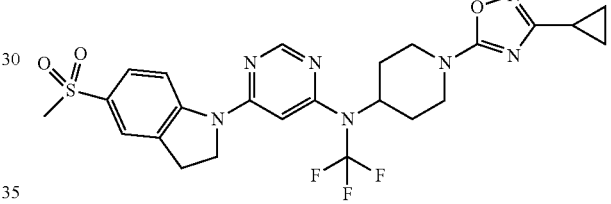

6-[5-(Methylsulfonyl)-2,3-dihydro-1H-indol-1-yl]-N-(piperidin-4-yl)-N-(trifluoromethyl)pyrimidin-4-amine (60.0 mg, 0.136 mmol) obtained in Reference Example 34 and sodium hydrogen carbonate (34.3 mg, 0.408 mmol) were dissolved in a mixed solvent of THF (3.0 mL)-water (1.0 mL), cyano bromide (21.6 mg, 0.234 mmol) was added thereto at 0° C., and the mixture was stirred at 0° C.-room temperature for 14 hr. The reaction solution was diluted with a mixed solvent of THF-ethyl acetate, and aqueous sodium hydrogen carbonate solution was added thereto. The organic layer was washed with water and saturated brine, dried over sodium sulfate, and concentrated under reduced pressure. The obtained residue and (1Z)—N'-hydroxycyclopropanecarboximidamide (20.4 mg, 0.204 mmol) obtained in Reference Example 21 were suspended in a mixed solvent of THF (10 mL)-ethyl acetate (10 mL). Zinc chloride-diethyl ether solution (1.0 M, 0.204 mL, 0.204 mmol) was added thereto, and the mixture was stirred with heating under reflux for 4 hr. The reaction solution was concentrated under reduced pressure, to the obtained residue were added ethanol (6.0 mL) and concentrated hydrochloric acid (0.10 mL), and the mixture was stirred at 70° C. for 40 hr. After cooling to room temperature, the mixture was concentrated under reduced pressure, and the obtained residue was partitioned between aqueous sodium hydrogen carbonate solution and ethyl acetate. The organic layer was washed with water and saturated brine, dried over sodium sulfate, and concentrated under reduced pressure. The obtained residue was purified by silica gel column chromatography [eluent; hexane:ethyl acetate=6:4 (volume ratio)→ethyl acetate], and the obtained solid was washed with diisopropyl ether and dried under reduced pressure to give the title compound (10.1 mg, yield 14%) as a white solid.

$^1$H-NMR (300 MHz, CDCl$_3$) δ: 0.91-1.01 (m, 4H), 1.81-1.93 (m, 1H), 1.93-2.03 (m, 2H), 2.22 (qd, J=12.1, 4.7 Hz, 2H), 3.04 (s, 3H), 3.14 (td, J=12.9, 2.5 Hz, 2H), 3.33 (t, J=8.7 Hz, 2H), 4.07-4.18 (m, 2H), 4.25 (dt, J=13.4, 2.2 Hz, 2H), 4.74 (tt, J=12.3, 3.4 Hz, 1H), 6.27 (d, J=1.1 Hz, 1H), 7.74 (d, J=1.5 Hz, 1H), 7.80 (dd, J=8.5, 2.1 Hz, 1H), 8.57 (d, J=8.7 Hz, 1H), 8.61 (d, J=0.8 Hz, 1H).

Example 30

N-(2-hydroxyethyl)-N-methyl-1-[6-({1-[3-(1-methylethyl)-1,2,4-oxadiazol-5-yl]piperidin-4-yl}oxy)pyrimidin-4-yl]-2,3-dihydro-1H-indole-5-carboxamide

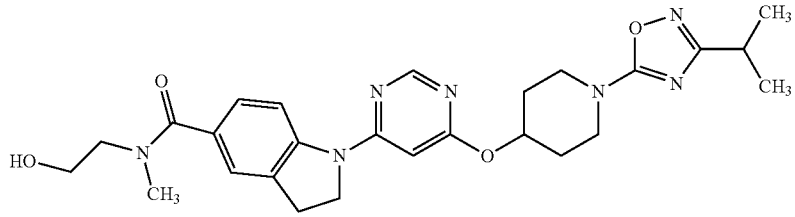 [SMILES: CC(C)c1noc(N2CCC(Oc3cc(N4CCc5cc(C(=O)N(C)CCO)ccc54)ncn3)CC2)n1]

To a suspension of 1-[6-({1-[3-(1-methylethyl)-1,2,4-oxadiazol-5-yl]piperidin-4-yl}oxy)pyrimidin-4-yl]-2,3-dihydro-1H-indole-5-carboxylic acid (200 mg) obtained in the below-mentioned Example 76 in isopropanol (20 mL) were added 2-(methylamino)ethanol (71.3 μL) and 4-(4,6-dimethoxy-1,3,5-triazin-2-yl)-4-methylmorpholinium chloride hydrate (247 mg), and the mixture was stirred with heating under reflux overnight. Water was added to the reaction mixture, and the mixture was extracted with ethyl acetate. The extract was washed with saturated brine, dried over magnesium sulfate, and concentrated under reduced pressure. The residue was purified by silica gel column chromatography (50-100% ethyl acetate/hexane, thereafter 0-10% methanol/ethyl acetate) to give a white solid. The obtained solid was washed with 50% ethyl acetate/hexane to give the title compound (171 mg, 76%) as a white solid.

$^1$H-NMR (300 MHz, CDCl$_3$) δ: 1.29 (d, J=6.8 Hz, 6H), 1.83-1.98 (m, 2H), 2.03-2.17 (m, 2H), 2.81-2.98 (m, 1H), 3.11 (s, 3H), 3.26 (t, J=8.7 Hz, 2H), 3.52-3.77 (m, 5H), 3.82-3.95 (m, 4H), 4.01 (t, J=8.7 Hz, 2H), 5.35-5.45 (m, 1H), 5.96 (s, 1H), 7.33 (d, J=8.3 Hz, 1H), 7.37 (s, 1H), 8.39 (d, J=8.3 Hz, 1H), 8.48 (s, 1H).

Example 31

N-(2-methoxyethyl)-N-methyl-1-[6-({1-[3-(1-methylethyl)-1,2,4-oxadiazol-5-yl]piperidin-4-yl}oxy)pyrimidin-4-yl]-2,3-dihydro-1H-indole-5-carboxamide

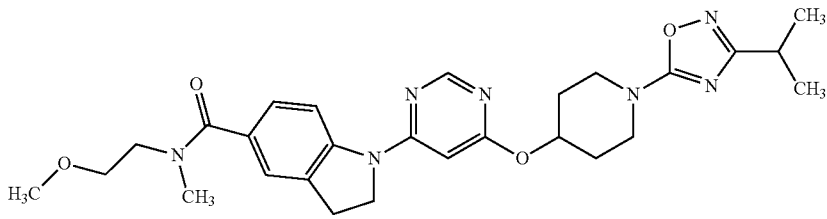 [SMILES: COCCN(C)C(=O)c1ccc2c(c1)CCN2c1cc(OC2CCN(c3nc(C(C)C)no3)CC2)ncn1]

To a mixture of 1-[6-({1-[3-(1-methylethyl)-1,2,4-oxadiazol-5-yl]piperidin-4-yl}oxy)pyrimidin-4-yl]-2,3-dihydro-1H-indole-5-carboxylic acid (200 mg) obtained in the below-mentioned Example 76, N-(2-methoxyethyl)methylamine (71.5 μL), and N,N-dimethylformamide (20 mL) were added 0-(7-azabenzotriazol-1-yl)-N,N,N',N'-tetramethyluronium hexafluorophosphate (253 mg) and N-ethyldiisopropylamine (116 μL), and the mixture was stirred at room temperature overnight. Water was added to the reaction mixture, and the mixture was extracted with ethyl acetate. The extract was washed with saturated brine, dried over magnesium sulfate, and concentrated under reduced pressure. The residue was purified by silica gel column chromatography (50-100% ethyl acetate/hexane, thereafter 0-10% methanol/ethyl acetate) to give a white solid. The obtained solid was washed with 30% ethyl acetate/hexane to give the title compound (36.5 mg, 16%) as a white solid.

$^1$H-NMR (300 MHz, CDCl$_3$) δ: 1.29 (d, J=6.8 Hz, 6H), 1.82-1.98 (m, 2H), 2.03-2.17 (m, 2H), 2.82-2.98 (m, 1H), 3.10 (s, 3H), 3.25 (t, J=8.7 Hz, 2H), 3.36 (br s, 3H), 3.45-3.77 (m, 6H), 3.83-3.95 (m, 2H), 4.00 (t, J=8.7 Hz, 2H), 5.34-5.45 (m, 1H), 5.95 (s, 1H), 7.26-7.35 (m, 2H), 8.36 (d, J=8.3 Hz, 1H), 8.47 (s, 1H).

Example 32

N-{1-[3-(1-methylethyl)-1,2,4-oxadiazol-5-yl]piperidin-4-yl}-6-[5-(methylsulfonyl)-2,3-dihydro-1H-indol-1-yl]-N-(trifluoromethyl)pyrimidin-4-amine

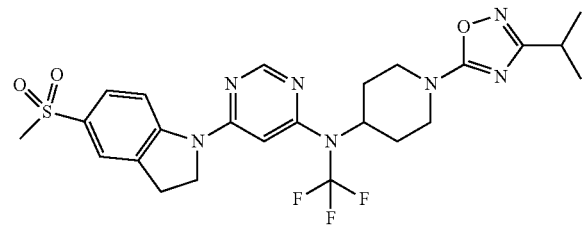 [SMILES: CC(C)c1noc(N2CCC(N(c3cc(N4CCc5cc(S(C)(=O)=O)ccc54)ncn3)C(F)(F)F)CC2)n1]

6-[5-(Methylsulfonyl)-2,3-dihydro-1H-indol-1-yl]-N-(piperidin-4-yl)-N-(trifluoromethyl)pyrimidin-4-amine (60.0 mg, 0.136 mmol) obtained in Reference Example 34 and sodium hydrogen carbonate (34.3 mg, 0.408 mmol) were dissolved in a mixed solvent of THF (3.0 mL)-water (1.0 mL), cyano bromide (21.6 mg, 0.234 mmol) was added thereto at 0° C., and the mixture was stirred at 0° C.-room temperature for 14 hr. The reaction solution was diluted with a mixed solvent of THF-ethyl acetate, and aqueous sodium hydrogen carbonate solution was added thereto. The organic layer was washed with water and saturated brine, dried over sodium sulfate, and concentrated under reduced pressure. The obtained residue and (1Z)—N'-hydroxy-2-methylpropanimidamide (20.8 mg, 0.204 mmol) were suspended in a mixed solvent of THF (10 mL)-ethyl acetate (10 mL). Zinc chloride-diethyl ether solution (1.0 M, 0.204 mL, 0.204 mmol) was added thereto, and the mixture was heated under reflux for 4 hr. The reaction solution was concentrated under reduced pressure, to the obtained residue were added ethanol (6.0 mL) and concentrated hydrochloric acid (0.10 mL) and the mixture was stirred at 70° C. for 40 hr. After cooling to room temperature, the mixture was concentrated under reduced pressure, and the obtained residue was partitioned between aqueous sodium hydrogen carbonate solution and ethyl acetate. The organic layer was washed with water and saturated brine, dried over sodium sulfate, and concentrated under reduced pressure. The obtained residue was purified by silica gel column chromatography [eluent; hexane:ethyl acetate=6:4 (volume ratio)→ethyl acetate] and the obtained solid was washed with diisopropyl ether and dried under reduced pressure to give the title compound (2.3 mg, yield 3%) as a white solid.

$^1$H-NMR (300 MHz, CDCl$_3$) δ: 1.29 (d, J=6.8 Hz, 6H), 1.99 (d, J=9.8 Hz, 2H), 2.15-2.34 (m, 1H), 2.90 (dt, J=13.9, 6.8 Hz, 1H), 3.05 (s, 3H), 3.17 (td, J=12.8, 2.3 Hz, 3H), 3.33 (t, J=8.5 Hz, 2H), 4.12 (t, J=8.7 Hz, 2H), 4.21-4.35 (m, 2H), 4.68-4.83 (m, 1H), 6.27 (d, J=1.5 Hz, 1H), 7.74 (d, J=1.5 Hz, 1H), 7.77-7.84 (m, 1H), 8.57 (d, J=8.7 Hz, 1H), 8.62 (d, J=0.8 Hz, 1H).

Example 33

1-(6-{[1-(5-ethylpyrimidin-2-yl)piperidin-4-yl]oxy}pyrimidin-4-yl)-5-(methylsulfonyl)-2,3-dihydro-1H-indole

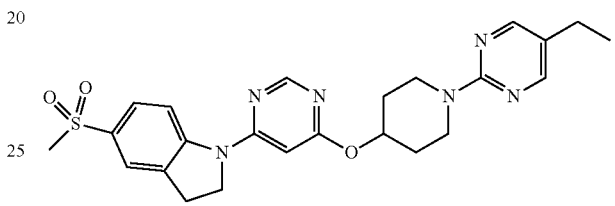

A mixture of 5-(methylsulfonyl)-1-[6-(piperidin-4-yloxy)pyrimidin-4-yl]-2,3-dihydro-1H-indole (250 mg, 0.67 mmol) obtained in Reference Example 18, 2-chloro-5-ethylpyrimidine (143 mg, 1.0 mmol), cesium carbonate (326 mg, 1.0 mmol), and 1-methyl-2-pyrrolidone (3 mL) was stirred at 80° C. for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (265 mg, yield 82%).

$^1$H-NMR (300 MHz, DMSO-d$_6$) δ: 1.13 (t, J=7.6 Hz, 3H), 1.53-1.74 (m, 2H), 1.95-2.14 (m, 2H), 2.44 (q, J=7.6 Hz, 2H), 3.15 (s, 3H), 3.24-3.31 (m, 2H), 3.37-3.54 (m, 2H), 4.09 (t, J=8.7 Hz, 2H), 4.20-4.38 (m, 2H), 5.28-5.43 (m, 1H), 6.23 (s, 1H), 7.66-7.82 (m, 2H), 8.26 (s, 2H), 8.48-8.65 (m, 2H).

Example 34

5-(methylsulfonyl)-1-(6-{[1-(5-propylpyrimidin-2-yl)piperidin-4-yl]oxy}pyrimidin-4-yl)-2,3-dihydro-1H-indole

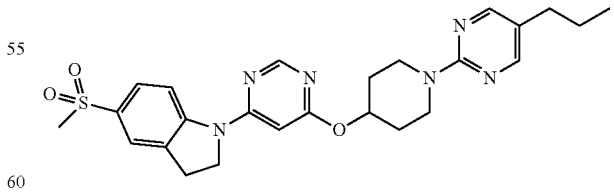

A mixture of 5-(methylsulfonyl)-1-[6-(piperidin-4-yloxy)pyrimidin-4-yl]-2,3-dihydro-1H-indole (350 mg, 0.93 mmol) obtained in Reference Example 18, 2-chloro-5-propylpyrimidine (235 mg, 1.0 mmol), cesium carbonate (652 mg, 2.0 mmol), and 1-methyl-2-pyrrolidone (3 mL) was stirred at 80° C. for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (350 mg, yield 76%).

$^1$H-NMR (300 MHz, DMSO-$d_6$) δ: 0.88 (t, J=7.4 Hz, 3H), 1.43-1.74 (m, 4H), 1.96-2.15 (m, 2H), 2.38 (t, J=7.4 Hz, 2H), 3.15 (s, 3H), 3.22-3.32 (m, 2H), 3.38-3.54 (m, 2H), 4.09 (t, J=8.7 Hz, 2H), 4.19-4.35 (m, 2H), 5.36 (tt, J=8.3, 4.0 Hz, 1H), 6.23 (s, 1H), 7.67-7.80 (m, 2H), 8.23 (s, 2H), 8.48-8.62 (m, 2H).

Example 35

S-(1-methylethyl)4-({6-[5-(methylsulfonyl)-2,3-dihydro-1H-indol-1-yl]pyrimidin-4-yl}oxy)piperidine-1-carbothioate

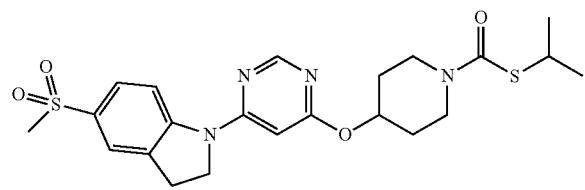 [SMILES: CC(C)SC(=O)N1CCC(Oc2cc(N3CCc4cc(S(C)(=O)=O)ccc43)ncn2)CC1]

A mixture of 5-(methylsulfonyl)-1-[6-(piperidin-4-yloxy)pyrimidin-4-yl]-2,3-dihydro-1H-indole (150 mg, 0.4 mmol) is obtained in Reference Example 18, S-isopropyl chlorothioformate (111 mg, 0.8 mmol), triethylamine (139 μL, 1.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (180 mg, yield 94%).

$^1$H-NMR (300 MHz, DMSO-$d_6$) δ: 1.28 (d, J=6.8 Hz, 6H), 1.53-1.71 (m, 2H), 1.94-2.10 (m, 2H), 3.15 (s, 3H), 3.22-3.40 (m, 4H), 3.48 (quin, J=6.9 Hz, 1H), 3.61-3.98 (m, 2H), 4.08 (t, J=8.9 Hz, 2H), 5.25-5.40 (m, 1H), 6.23 (s, 1H), 7.67-7.79 (m, 2H), 8.54 (t, J=4.7 Hz, 2H).

Example 36

S-tert-butyl 4-({6-[5-(methylsulfonyl)-2,3-dihydro-1H-indol-1-yl]pyrimidin-4-yl}oxy)piperidine-1-carbothioate

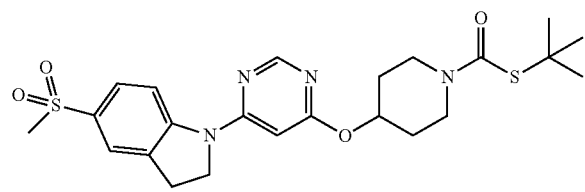 [SMILES: CC(C)(C)SC(=O)N1CCC(Oc2cc(N3CCc4cc(S(C)(=O)=O)ccc43)ncn2)CC1]

A mixture of 5-(methylsulfonyl)-1-[6-(piperidin-4-yloxy)pyrimidin-4-yl]-2,3-dihydro-1H-indole (200 mg, 0.53 mmol) obtained in Reference Example 18, S-tert-butyl chlorothioformate (122 mg, 0.8 mmol), triethylamine (139 μL, 1.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated. The residue was crystallized from ethyl acetate to give the title compound as colorless crystals (260 mg, yield 100%).

$^1$H-NMR (300 MHz, DMSO-$d_6$) δ: 1.46 (s, 9H), 1.53-1.71 (m, 2H), 1.90-2.11 (m, 2H), 3.15 (s, 3H), 3.21-3.42 (m, 4H), 3.77 (br. s., 2H), 4.08 (t, J=8.7 Hz, 2H), 5.22-5.40 (m, 1H), 6.23 (s, 1H), 7.67-7.81 (m, 2H), 8.54 (t, J=4.5 Hz, 2H).

Example 37

S-propyl 4-({6-[5-(methylsulfonyl)-2,3-dihydro-1H-indol-1-yl]pyrimidin-4-yl}oxy)piperidine-1-carbothioate

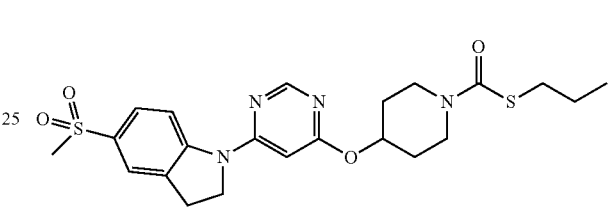

A mixture of 5-(methylsulfonyl)-1-[6-(piperidin-4-yloxy)pyrimidin-4-yl]-2,3-dihydro-1H-indole (150 mg, 0.4 mmol) obtained in Reference Example 18, S-propyl chlorothioformate (139 mg, 1.0 mmol), triethylamine (139 μL, 1.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (160 mg, yield 84%).

$^1$H-NMR (300 MHz, DMSO-$d_6$) δ: 0.92 (t, J=7.4 Hz, 3H), 1.19 (t, J=7.4 Hz, 1H), 1.45-1.73 (m, 4H), 1.90-2.10 (m, 2H), 2.82 (t, J=7.2 Hz, 2H), 3.02-3.12 (m, 1H), 3.15 (s, 3H), 3.21-3.47 (m, 4H), 4.08 (t, J=8.7 Hz, 2H), 5.24-5.43 (m, 1H), 6.23 (s, 1H), 7.66-7.82 (m, 2H), 8.48-8.61 (m, 2H).

Example 38

1-[6-({1-[3-(1-methylethyl)-1,2,4-oxadiazol-5-yl]piperidin-4-yl}oxy)pyrimidin-4-yl]-5-(methylsulfonyl)-2,3-dihydro-1H-indole

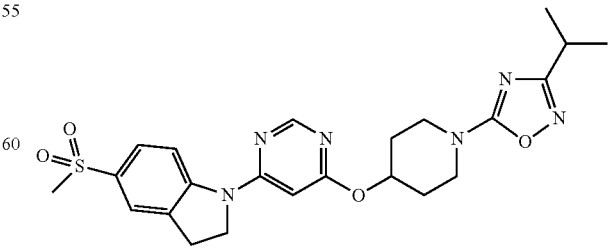

To a mixture of 5-(methylsulfonyl)-1-[6-(piperidin-4-yloxy)pyrimidin-4-yl]-2,3-dihydro-1H-indole (500 mg, 1.34 mmol) obtained in Reference Example 18, sodium hydrogen carbonate (344 mg, 4.1 mmol), water (10 mL), and tetrahydrofuran (30 mL) was added cyano bromide (191 mg, 1.8 mmol) at 0° C., and the mixture was stirred at room temperature for 16 hr. To the reaction mixture was added aqueous sodium hydrogen carbonate solution, and the mixture was extracted with ethyl acetate-tetrahydrofuran. The organic layer was washed with saturated brine, dried over anhydrous magnesium sulfate and filtered. The filtrate was concentrated. A mixture of the obtained residue, (1Z)—N'-hydroxy-2-methylpropanimidamide (204 mg, 2.0 mmol), zinc dichloride (1.0 M diethyl ether solution, 2 mL, 2.0 mmol), ethyl acetate (100 mL), and tetrahydrofuran (100 mL) was heated under reflux for 4 hr. The resulting solid was filtered, and washed with ethyl acetate. A mixture of the obtained solid, ethanol (300 mL), and 12M hydrochloric acid (1 mL) was stirred at 70° C. for 1 day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (560 mg, yield 86%).

$^1$H-NMR (300 MHz, DMSO-d$_6$) δ: 1.19 (d, J=6.8 Hz, 6H), 1.64-1.88 (m, 2H), 2.02-2.21 (m, 2H), 2.73-2.92 (m, 1H), 3.15 (s, 3H), 3.21-3.35 (m, 2H), 3.42-3.59 (m, 2H), 3.75-3.93 (m, 2H), 4.09 (t, J=8.7 Hz, 2H), 5.25-5.47 (m, 1H), 6.25 (s, 1H), 7.68-7.81 (m, 2H), 8.47-8.63 (m, 2H).

Example 39

1-(6-{[1-(3-tert-butyl-1,2,4-oxadiazol-5-yl)piperidin-4-yl]oxy}pyrimidin-4-yl)-5-(methylsulfonyl)-2,3-dihydro-1H-indole

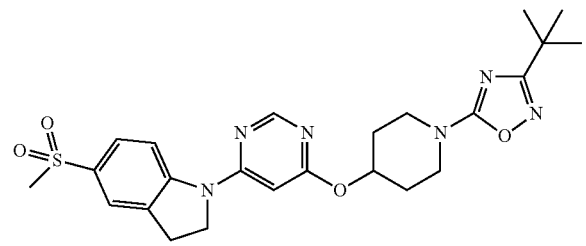 [SMILES: CC(C)(C)c1noc(N2CCC(Oc3cc(N4CCc5cc(S(C)(=O)=O)ccc54)ncn3)CC2)n1]

To a mixture of 5-(methylsulfonyl)-1-[6-(piperidin-4-yloxy)pyrimidin-4-yl]-2,3-dihydro-1H-indole (500 mg, 1.34 mmol) obtained in Reference Example 18, sodium hydrogen carbonate (344 mg, 4.1 mmol), water (10 mL), and tetrahydrofuran (30 mL) was added cyano bromide (191 mg, 1.8 mmol) at 0° C., and the mixture was stirred at room temperature for 16 hr. To the reaction mixture was added aqueous sodium hydrogen carbonate solution, and the mixture was extracted with ethyl acetate-tetrahydrofuran. The organic layer was washed with saturated brine, dried over anhydrous magnesium sulfate and filtered. The filtrate was concentrated. A mixture of the obtained residue, (1Z)—N'-hydroxy-2,2-dimethylpropanimidamide (232 mg, 2.0 mmol) obtained in Reference Example 20, zinc dichloride (1.0 M diethyl ether solution, 2 mL, 2.0 mmol), ethyl acetate (100 mL), and tetrahydrofuran (100 mL) was heated under reflux for 4 hr. The resulting solid was filtered, and washed with ethyl acetate. A mixture of the obtained solid, ethanol (300 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (485 mg, yield 73%).

$^1$H-NMR (300 MHz, DMSO-d$_6$) δ: 1.24 (s, 9H), 1.67-1.86 (m, 2H), 2.03-2.17 (m, 2H), 3.15 (s, 3H), 3.23-3.31 (m, 2H), 3.43-3.57 (m, 2H), 3.75-3.91 (m, 2H), 4.05-4.15 (m, 2H), 5.26-5.44 (m, 1H), 6.25 (s, 1H), 7.64-7.81 (m, 2H), 8.48-8.63 (m, 2H).

Example 40

1-(6-{[1-(3-cyclopropyl-1,2,4-oxadiazol-5-yl)piperidin-4-yl]oxy}pyrimidin-4-yl)-5-(methylsulfonyl)-2,3-dihydro-1H-indole

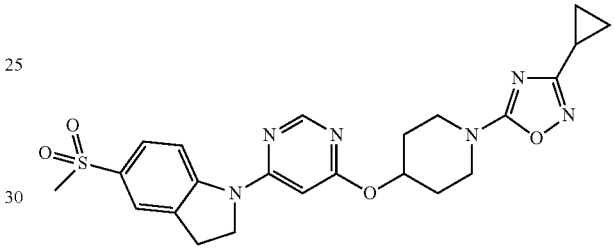

To a mixture of 5-(methylsulfonyl)-1-[6-(piperidin-4-yloxy)pyrimidin-4-yl]-2,3-dihydro-1H-indole (500 mg, 1.34 mmol) obtained in Reference Example 18, sodium hydrogen carbonate (344 mg, 4.1 mmol), water (10 mL), and tetrahydrofuran (30 mL) was added cyano bromide (191 mg, 1.8 mmol) at 0° C., and the mixture was stirred at room temperature for 16 hr. To the reaction mixture was added aqueous sodium hydrogen carbonate solution, and the mixture was extracted with ethyl acetate-tetrahydrofuran. The organic layer was washed with saturated brine, dried over anhydrous magnesium sulfate and filtered. The filtrate was concentrated. A mixture of the obtained residue, (1Z)—N'-hydroxycyclopropanecarboximidamide (200 mg, 2.0 mmol) obtained in Reference Example 21, zinc dichloride (1.0 M diethyl ether solution, 2 mL, 2.0 mmol), ethyl acetate (100 mL), and tetrahydrofuran (100 mL) was heated under reflux for 4 hr. The resulting solid was filtered, and washed with ethyl acetate. A mixture of the obtained solid, ethanol (300 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was subjected to silica gel column chromatography (hexane-ethyl acetate 50:50-0:100, v/v) and crystallized from hexane-ethyl acetate to give the title compound (380 mg, yield 59%) as colorless crystals.

$^1$H-NMR (300 MHz, DMSO-d$_6$) δ: 0.75-0.87 (m, 2H), 0.88-1.03 (m, 2H), 1.61-1.94 (m, 3H), 2.01-2.18 (m, 2H), 3.15 (s, 3H), 3.27 (t, J=8.7 Hz, 2H), 3.39-3.56 (m, 2H), 3.69-3.89 (m, 2H), 4.08 (t, J=8.7 Hz, 2H), 5.25-5.41 (m, 1H), 6.24 (s, 1H), 7.68-7.79 (m, 2H), 8.47-8.61 (m, 2H).

Example 41

1-(6-{[1-(3-ethyl-1,2,4-oxadiazol-5-yl)piperidin-4-yl]oxy}pyrimidin-4-yl)-5-(methylsulfonyl)-2,3-dihydro-1H-indole

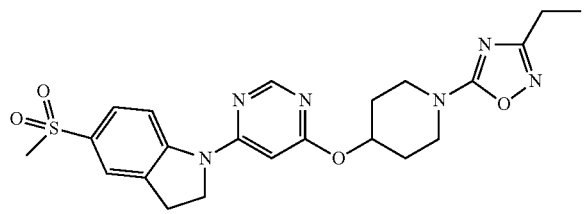 [SMILES: CCc1noc(N2CCC(Oc3cc(N4CCc5cc(S(C)(=O)=O)ccc54)ncn3)CC2)n1]

To a mixture of 5-(methylsulfonyl)-1-[6-(piperidin-4-yloxy)pyrimidin-4-yl]-2,3-dihydro-1H-indole (500 mg, 1.34 mmol) obtained in Reference Example 18, sodium hydrogen carbonate (344 mg, 4.1 mmol), water (10 mL), and tetrahydrofuran (30 mL) was added cyano bromide (191 mg, 1.8 mmol) at 0° C., and the mixture was stirred at room temperature for 16 hr. To the reaction mixture was added aqueous sodium hydrogen carbonate solution, and the mixture was extracted with ethyl acetate-tetrahydrofuran. The organic layer was washed with saturated brine, dried over anhydrous magnesium sulfate and filtered. The filtrate was concentrated. A mixture of the obtained residue, (1Z)—N'-hydroxypropanimidamide (176 mg, 2.0 mmol) obtained in Reference Example 22, zinc dichloride (1.0 M diethyl ether solution, 2 mL, 2.0 mmol), ethyl acetate (100 mL), and tetrahydrofuran (100 mL) was heated under reflux for 4 hr. The resulting solid was filtered, and washed with ethyl acetate. A mixture of the obtained solid, ethanol (300 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was subjected to silica gel column chromatography (hexane-ethyl acetate 50:50-0:100, v/v) and crystallized from hexane-ethyl acetate to give the title compound (460 mg, yield 73%) as colorless crystals.

$^1$H-NMR (300 MHz, DMSO-$d_6$) δ: 1.16 (t, J=7.6 Hz, 3H), 1.66-1.87% (m, 2H), 2.02-2.20 (m, 2H), 2.40-2.55 (m, 2H), 3.15 (s, 3H), 3.28 (t, J=8.7 Hz, 2H), 3.41-3.60 (m, 2H), 3.74-3.91 (m, 2H), 4.09 (t, J=8.9 Hz, 2H), 5.25-5.42 (m, 1H), 6.25 (s, 1H), 7.67-7.81 (m, 2H), 8.48-8.62 (m, 2H).

Example 42 tert-butyl 4-{[6-(5-nitro-2,3-dihydro-1H-indol-1-yl)pyrimidin-4-yl]oxy}piperidine-1-carboxylate

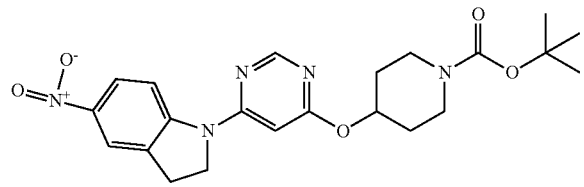 [SMILES: CC(C)(C)OC(=O)N1CCC(Oc2cc(N3CCc4cc([N+](=O)[O-])ccc43)ncn2)CC1]

To a solution of tert-butyl 4-hydroxypiperidine-1-carboxylate (23.3 g, 116 mmol) in tetrahydrofuran (300 mL) was added sodium hydride (60%, oil, 4.64 g, 116 mmol), and the mixture was stirred at room temperature for 1 hr. 1-(6-Chloropyrimidin-4-yl)-5-nitro-2,3-dihydro-1H-indole (8.0 g, 28.9 mmol) obtained in Reference Example 24 was added thereto, and the mixture was stirred at room temperature for 5 hr. Water was added to the reaction mixture, and the mixture was extracted with ethyl acetate. The organic layer was washed with saturated brine, dried over anhydrous magnesium sulfate and filtered. The filtrate was concentrated to give the title compound as yellow crystals (8.8 g, yield 69%).

$^1$H-NMR (300 MHz, DMSO-$d_6$) δ: 1.41 (s, 9H), 1.49-1.66 (m, 2H), 1.90-2.06 (m, 2H), 3.08-3.24 (m, 2H), 3.24-3.36 (m, 2H), 3.64-3.82 (m, 2H), 4.12 (t, J=8.7 Hz, 2H), 5.21-5.37 (m, 1H), 6.28 (s, 1H), 8.04-8.10 (m, 1H), 8.10-8.19 (m, 1H), 8.51 (d, J=9.1 Hz, 1H), 8.56 (s, 1H).

Example 43 tert-butyl 4-{[6-(5-amino-2,3-dihydro-1H-indol-1-yl}pyrimidin-4-yl]oxy)piperidine-1-carboxylate

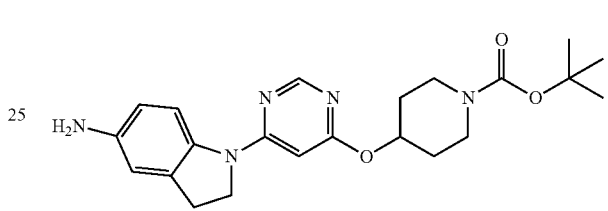

A mixture of tert-butyl 4-{[6-(5-nitro-2,3-dihydro-1H-indol-1-yl)pyrimidin-4-yl]oxy}piperidine-1-carboxylate (8.8 g, 20.0 mmol) obtained in Example 42, palladium carbon (500 mg), tetrahydrofuran (150 mL), and methanol (300 mL) was stirred under a hydrogen atmosphere (1 atm), and the mixture was stirred at room temperature for 16 hr. The reaction mixture was filtered, and the filtrate was concentrated to give the title compound as yellow crystals (8.44 g, yield quant.).

$^1$H-NMR (300 MHz, DMSO-$d_6$) δ: 1.41 (s, 9H), 1.46-1.65 (m, 2H), 1.84-2.03 (m, 2H), 2.98-3.25 (m, 4H), 3.63-3.78 (m, 2H), 3.86 (t, J=8.5 Hz, 2H), 4.79 (s, 2H), 5.11-5.31 (m, 1H), 5.91 (s, 1H), 6.38 (dd, J=8.5, 2.5 Hz, 1H), 6.49 (d, J=2.3 Hz, 1H), 8.03 (d, J=8.3 Hz, 1H), 8.34 (s, 1H).

Example 44 tert-butyl 4-[(6-{5-[(hydroxyacetyl)amino]-2,3-dihydro-1H-indol-1-yl}pyrimidin-4-yl)oxy]piperidine-1-carboxylate

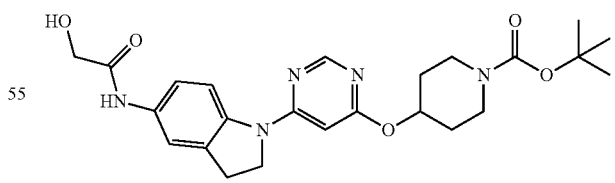

A mixture of tert-butyl 4-{[6-(5-amino-2,3-dihydro-1H-indol-1-yl)pyrimidin-4-yl]oxy}piperidine-1-carboxylate (150 mg, 0.36 mmol) obtained in Example 43, acetoxyacetyl chloride (137 mg, 1.0 mmol), triethylamine (139 μL, 1.0 mmol), and tetrahydrofuran (10 mL) was stirred at room temperature for 16 hr. To a reaction mixture were added 1N aqueous sodium hydroxide solution (5 mL) and methanol (5 mL), and the mixture was stirred at room temperature for 2 hr.

The reaction mixture was concentrated, water was added to the residue, and the mixture was extracted with ethyl acetate. The organic layer was washed with saturated brine, dried over anhydrous magnesium sulfate and filtered. The filtrate was concentrated to give the title compound as colorless crystals (150 mg, yield 89%).

$^1$H-NMR (300 MHz, DMSO-$d_6$) δ: 1.41 (s, 9H), 1.47-1.66 (m, 2H), 1.88-2.05 (m, 2H), 3.07-3.26 (m, 4H), 3.65-3.80 (m, 2H), 3.90-4.05 (m, 4H), 5.13-5.32 (m, 1H), 5.62 (t, J=5.9 Hz, 1H), 6.05 (s, 1H), 7.41 (dd, J=8.9, 2.1 Hz, 1H), 7.66 (s, 1H), 8.27 (d, J=9.1 Hz, 1H), 8.43 (s, 1H), 9.53 (s, 1H).

Example 45

S-(1-methylethyl) 4-({6-[5-(2-oxopyrrolidin-1-yl)-2,3-dihydro-1H-indol-1-yl]pyrimidin-4-yl}oxy)piperidine-1-carbothioate

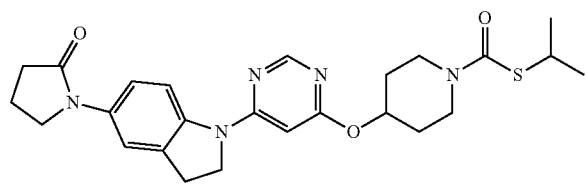 [SMILES: CC(C)SC(=O)N1CCC(Oc2cc(N3CCc4cc(N5CCCC5=O)ccc43)ncn2)CC1]

A mixture of 1-{1-[6-(piperidin-4-yloxy)pyrimidin-4-yl]-2,3-dihydro-1H-indol-5-yl}pyrrolidin-2-one (120 mg, 0.32 mmol) obtained in Reference Example 25, S-isopropyl chlorothioformate (97 mg, 0.7 mmol), triethylamine (139 μL, 1.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (120 mg, yield 78%).

$^1$H-NMR (300 MHz, DMSO-$d_6$) δ: 1.17 (t, J=7.2 Hz, 1H), 1.28 (d, J=6.8 Hz, 6H), 1.50-1.71 (m, 2H), 1.89-2.16 (m, 4H), 2.41-2.50 (m, 2H), 2.99-3.14 (m, 1H), 3.20 (t, J=8.5 Hz, 2H), 3.26-3.41 (m, 2H), 3.48 (quin, J=6.9 Hz, 1H), 3.80 (t, J=7.0 Hz, 2H), 3.98 (t, J=8.5 Hz, 2H), 5.22-5.38 (m, 1H), 6.07 (s, 1H), 7.35 (dd, J=8.9, 2.4 Hz, 1H), 7.61 (d, J=2.3 Hz, 1H), 8.32 (d, J=8.7 Hz, 1H), 8.45 (s, 1H).

Example 46

1-{1-[6-({1-[3-(1-methylethyl)-1,2,4-oxadiazol-5-yl]piperidin-4-yl}oxy)pyrimidin-4-yl]-2,3-dihydro-1H-indol-5-yl}pyrrolidin-2-one

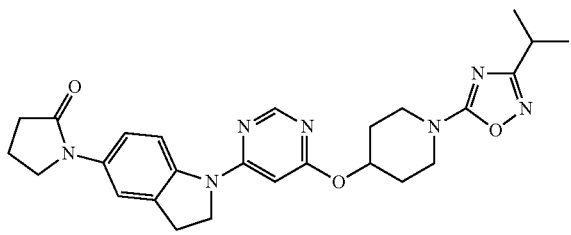 [SMILES: CC(C)c1noc(N2CCC(Oc3cc(N4CCc5cc(N6CCCC6=O)ccc54)ncn3)CC2)n1]

To a mixture of 1-{1-[6-(piperidin-4-yloxy)pyrimidin-4-yl]-2,3-dihydro-1H-indol-5-yl]pyrrolidin-2-one (500 mg, 1.32 mmol) obtained in Reference Example 25, sodium hydrogen carbonate (344 mg, 4.1 mmol), water (15 mL), and tetrahydrofuran (45 mL) was added cyano bromide (191 mg, 1.8 mmol) at 0° C., and the mixture was stirred at room temperature for 16 hr. To the reaction mixture was added aqueous sodium hydrogen carbonate solution, and the mixture was extracted with ethyl acetate-tetrahydrofuran. The organic layer was washed with saturated brine, dried over anhydrous magnesium sulfate and filtered. The filtrate was concentrated. A mixture of the obtained residue, (1Z)—N'-hydroxy-2-methylpropanimidamide (204 mg, 2.0 mmol), zinc dichloride (1.0 M diethyl ether solution, 2 mL, 2.0 mmol), ethyl acetate (100 mL), and tetrahydrofuran (100 mL) was heated under reflux for hr. The resulting solid was filtered, and washed with ethyl acetate. A mixture of the obtained solid, ethanol (300 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was subjected to silica gel column chromatography (hexane-ethyl acetate 80:20-0:100, v/v) and crystallized from hexane-ethyl acetate to give the title compound (270 mg, yield 42%) as colorless crystals.

$^1$H-NMR (300 MHz, DMSO-$d_6$) δ: 1.19 (d, J=6.8 Hz, 6H), 1.65-1.84 (m, 2H), 1.96-2.18 (m, 4H), 2.41-2.50 (m, 2H), 2.82 (quin, J=6.9 Hz, 1H), 3.20 (t, J=8.5 Hz, 2H), 3.41-3.59 (m, 2H), 3.73-3.90 (m, 4H), 3.98 (t, J=8.7 Hz, 2H), 5.23-5.39 (m, 1H), 6.09 (s, 1H), 7.35 (dd, J=8.7, 2.3 Hz, 1H), 7.61 (d, J=2.3 Hz, 1H), 8.32 (d, J=9.0 Hz, 1H), 8.46 (s, 1H).

Example 47 tert-butyl 4-[(6-{5-[(methoxyacetyl)amino]-2,3-dihydro-1H-indol-1-yl}pyrimidin-4-yl)oxy]piperidine-1-carboxylate

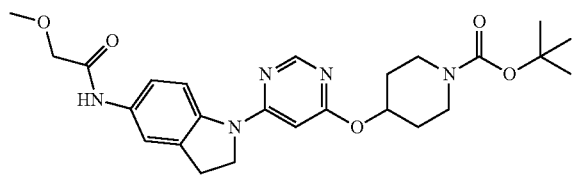 [SMILES: COCC(=O)Nc1ccc2c(c1)CCN2c1cc(OC2CCN(C(=O)OC(C)(C)C)CC2)ncn1]

A mixture of tert-butyl 4-{[6-(5-amino-2,3-dihydro-1H-indol-1-yl)pyrimidin-4-yl]oxy}piperidine-1-carboxylate (500 mg, 1.22 mmol) obtained in Example 43, methoxyacetyl chloride (217 mg, 2.0 mmol), triethylamine (418 μL, 3.0 mmol), and tetrahydrofuran (50 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated to give the title compound as colorless crystals (510 mg, yield 86%).

$^1$H-NMR (300 MHz, DMSO-$d_6$) δ: 1.41 (s, 9H), 1.47-1.68 (m, 2H), 1.88-2.06 (m, 2H), 3.04-3.25 (m, 4H), 3.37 (s, 3H), 3.63-3.80 (m, 2H), 3.89-4.03 (m, 4H), 5.14-5.32 (m, 1H), 6.04 (s, 1H), 7.37 (dd, J=8.9, 2.1 Hz, 1H), 7.62 (s, 1H), 8.27 (d, J=8.7 Hz, 1H), 8.43 (s, 1H), 9.63 (s, 1H).

Example 48 tert-butyl 4-{[6-(5-{[(2R)-tetrahydrofuran-2-ylcarbonyl]amino}-2,3-dihydro-1H-indol-1-yl)pyrimidin-4-yl]oxy}piperidine-1-carboxylate

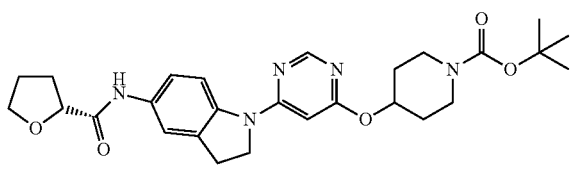

A mixture of tert-butyl 4-{[6-(5-amino-2,3-dihydro-1H-indol-1-yl)pyrimidin-4-yl]oxy}piperidine-1-carboxylate (1.0 g, 2.44 mmol) obtained in Example 43, (R)-(+)-tetrahydrofuran-2-carboxylic acid (464 mg, 4.0 mmol), 1-ethyl-3-(3-dimethylaminopropyl)-carbodiimide hydrochloride (958 mg, 5.0 mmol), 1-hydroxybenzotriazole monohydrate (766 mg, 5.0 mmol), triethylamine (836 µL, 6.0 mmol), and N,N-dimethylformamide (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated to give the title compound as colorless crystals (1.1 g, yield 88%).

$^1$H-NMR (300 MHz, DMSO-d$_6$) δ: 1.41 (s, 9H), 1.46-1.66 (m, 2H), 1.78-2.06 (m, 5H), 2.09-2.26 (m, 1H), 3.02-3.26 (m, 4% H), 3.64-3.77 (m, 2H), 3.77-3.89 (m, 1H), 3.90-4.08 (m, 3H), 4.29-4.43 (m, 1H), 5.16-5.32 (m, 1H), 6.05 (s, 1H), 7.40 (dd, J=8.7, 2.3 Hz, 1H), 7.64 (d, J=1.5 Hz, 1H), 8.27 (d, J=9.1 Hz, 1H), 8.43 (s, 1H), 9.55 (s, 1H).

Example 49 tert-butyl 4-{[6-(5-{[(2S)-tetrahydrofuran-2-ylcarbonyl]amino}-2,3-dihydro-1H-indol-1-yl)pyrimidin-4-yl]oxy}piperidine-1-carboxylate

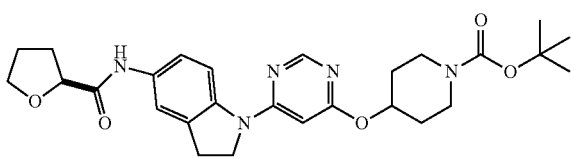

A mixture of tert-butyl 4-{[6-(5-amino-2,3-dihydro-1H-indol-1-yl)pyrimidin-4-yl]oxy}piperidine-1-carboxylate (500 mg, 1.22 mmol) obtained in Example 43, (S)-(−)-tetrahydrofuran-2-carboxylic acid (232 mg, 2.0 mmol), 1-ethyl-3-(3-dimethylaminopropyl)-carbodiimide hydrochloride (479 mg, 2.5 mmol), 1-hydroxybenzotriazole monohydrate (383 mg, 2.5 mmol), triethylamine (418 µL, 3.0 mmol), and N,N-dimethylformamide (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated to give the title compound as colorless crystals (621 mg, yield 100%).

$^1$H-NMR (300 MHz, DMSO-d$_6$) δ: 1.41 (s, 9H), 1.46-1.66 (m, 2H), 1.77-2.06 (m, 5H), 2.11-2.26 (m, 1H), 3.06-3.25 (m, 4H), 3.64-3.77 (m, 2H), 3.77-3.88 (m, 1H), 3.91-4.07 (m, 3H), 4.31-4.42 (m, 1H), 5.15-5.33 (m, 1H), 6.05 (s, 1H), 7.40 (dd, J=8.7, 2.3 Hz, 1H), 7.64 (d, J=1.5 Hz, 1H), 8.27 (d, J=9.1 Hz, 1H), 8.43 (s, 1H), 9.55 (s, 1H).

Example 50

S-(1-methylethyl)4-{[6-(5-{[(2R)-tetrahydrofuran-2-ylcarbonyl]amino}-2,3-dihydro-1H-indol-1-yl)pyrimidin-4-yl]oxy}piperidine-1-carbothioate

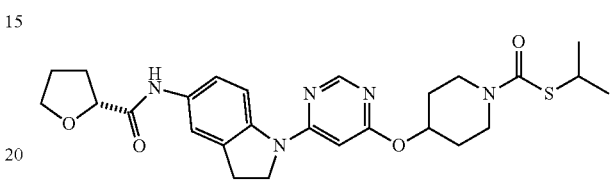

A mixture of (2R)—N-{1-[6-(piperidin-4-yloxy)pyrimidin-4-yl]-2,3-dihydro-1H-indol-5-yl}tetrahydrofuran-2-carboxamide hydrochloride (490 mg, 1.1 mmol) obtained in Reference Example 26, S-isopropyl chlorothioformate (236 mg, 1.7 mmol), triethylamine (558 µL, 4.0 mmol), and tetrahydrofuran (50 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (400 mg, yield 71%).

$^1$H-NMR (300 MHz, DMSO-d$_6$) δ: 1.18 (t, J=7.4 Hz, 1H), 1.28 (d, J=6.8 Hz, 6H), 1.50-1.70 (m, 2H), 1.79-1.93 (m, 2H), 1.93-2.07 (m, 2H), 2.10-2.27 (m, 1H), 2.99-3.23 (m, 3H), 3.26-3.39 (m, 2H), 3.41-3.56 (m, 1H), 3.61-3.89 (m, 2H), 3.90-4.07 (m, 3H), 4.30-4.42 (m, 1H), 5.19-5.37 (m, 1H), 6.05 (s, 1H), 7.40 (dd, J=8.7, 2.3 Hz, 1H), 7.64 (d, J=1.9 Hz, 1H), 8.27 (d, J=8.7 Hz, 1H), 8.44 (s, 1H), 9.55 (s, 1H).

Example 51 isopropyl 4-{[6-(5-{[(2R)-tetrahydrofuran-2-ylcarbonyl]amino}-2,3-dihydro-1H-indol-1-yl)pyrimidin-4-yl]oxy}piperidine-1-carboxylate

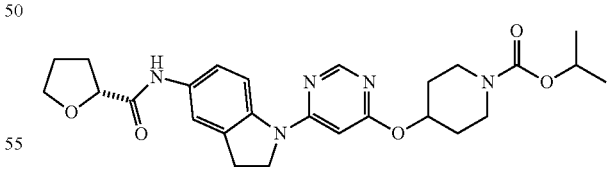

A mixture of (2R)—N-{1-[6-(piperidin-4-yloxy)pyrimidin-4-yl]-2,3-dihydro-1H-indol-5-yl}tetrahydrofuran-2-carboxamide hydrochloride (250 mg, 0.56 mmol) obtained in Reference Example 26, isopropyl chlorocarbonate (123 mg, 1.0 mmol), triethylamine (279 µL, 2.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (170 mg, yield 61%).

$^1$H-NMR (300 MHz, DMSO-$d_6$) δ: 1.19 (d, J=6.4 Hz, 6H), 1.48-1.68 (m, 2H), 1.77-2.07 (m, 5H), 2.10-2.30 (m, 1H), 3.11-3.29 (m, 4H), 3.67-3.89 (m, 3H), 3.89-4.05 (m, 3H), 4.28-4.42 (m, 1H), 4.78 (quin, J=6.3 Hz, 1H), 5.17-5.33 (m, 1H), 6.04 (s, 1H), 7.40 (dd, J=8.9, 2.1 Hz, 1H), 7.60-7.69 (m, 1H), 8.26 (d, J=8.7 Hz, 1H), 8.43 (s, 1H), 9.54 (s, 1H).

Example 52

S-(1-methylethyl) 4-{[6-(5-{[(2S)-tetrahydrofuran-2-ylcarbonyl]amino}-2,3-dihydro-1H-indol-1-yl)pyrimidin-4-yl]oxy}piperidine-1-carbothioate

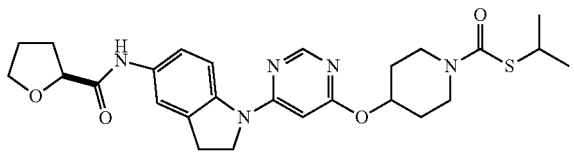

A mixture of (2S)—N-{1-[6-(piperidin-4-yloxy)pyrimidin-4-yl]-2,3-dihydro-1H-indol-5-yl}tetrahydrofuran-2-carboxamide hydrochloride (300 mg, 0.67 mmol) obtained in Reference Example 27, S-isopropyl chlorothioformate (208 mg, 1.5 mmol), triethylamine (418 µL, 3.0 mmol), and tetrahydrofuran (15 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (190 mg, yield 55%).

$^1$H-NMR (300 MHz, DMSO-$d_6$) δ: 1.22-1.36 (m, 7H), 1.50-1.71 (m, 2H), 1.77-2.08 (m, 5H), 2.11-2.25 (m, 1H), 3.17 (t, J=8.3 Hz, 2H), 3.25-3.39 (m, 2H), 3.40-3.56 (m, 1H), 3.64-3.89 (m, 2H), 3.89-4.10 (m, 3H), 4.31-4.42 (m, 1H), 5.21-5.38 (m, 1H), 6.05 (s, 1H), 7.40 (dd, J=8.9, 2.1 Hz, 1H), 7.64 (d, J=1.9 Hz, 1H), 8.27 (d, J=8.7 Hz, 1H), 8.43 (s, 1H), 9.55 (s, 1H).

Example 53 isopropyl 4-{[6-(5-{[(2S)-tetrahydrofuran-2-ylcarbonyl]amino}-2,3-dihydro-1H-indol-1-yl)pyrimidin-4-yl]oxy}piperidine-1-carboxylate

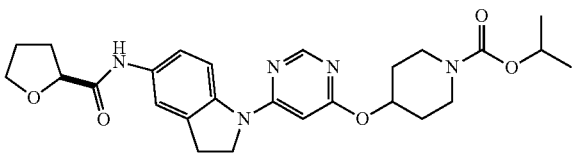

A mixture of (2S)—N-{1-[6-(piperidin-4-yloxy)pyrimidin-4-yl]-2,3-dihydro-1H-indol-5-yl}tetrahydrofuran-2-carboxamide hydrochloride (300 mg, 0.67 mmol) obtained in Reference Example 27, isopropyl chlorocarbonate (184 mg, 1.5 mmol), triethylamine (418 µL, 3.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (190 mg, yield 57%), $^1$H-NMR (300 MHz, DMSO-$d_6$) δ: 1.19 (d, J=6.0 Hz, 6H), 1.47-1.68 (m, 2H), 1.78-2.05 (m, 5H), 2.10-2.26 (m, 1H), 3.08-3.28 (m, 4H), 3.67-3.88 (m, 3H), 3.90-4.07 (m, 3H), 4.30-4.42 (m, 1H), 4.68-4.90 (m, 1H), 5.17-5.35 (m, 1H), 6.05 (s, 1H), 7.40 (dd, J=8.9, 2.1 Hz, 1H), 7.57-7.68 (m, 1H), 8.27 (d, J=9.1 Hz, 1H), 8.43 (s, 1H), 9.55 (s, 1H).

Example 54

S-(1-methylethyl) 4-[(6-{5-[(hydroxyacetyl)amino]-2,3-dihydro-1H-indol-1-yl}pyrimidin-4-yl)oxy]piperidine-1-carbothioate

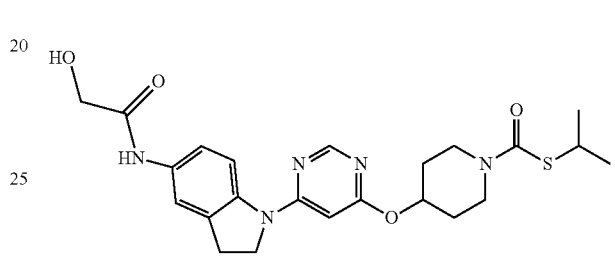

A mixture of 2-oxo-2-({1-[6-(piperidin-4-yloxy)pyrimidin-4-yl]-2,3-dihydro-1H-indol-5-yl}amino)ethyl acetate hydrochloride (1.5 g, 3.35 mmol) obtained in Reference Example 28, S-isopropyl chlorothioformate (610 mg, 4.4 mmol), triethylamine (1.39 mL, 10.0 mmol), and tetrahydrofuran (150 mL) was stirred at room temperature for 16 hr. To the reaction mixture were added 1N aqueous sodium hydroxide solution and methanol, and the mixture was stirred at room temperature for 2 hr. The reaction mixture was concentrated, water was added to the residue, and the mixture was extracted with ethyl acetate. The organic layer was washed with saturated brine, dried over anhydrous magnesium sulfate and filtered. The filtrate was concentrated to give the title compound as colorless crystals (1.1 g, yield 70%).

$^1$H-NMR (300 MHz, DMSO-$d_6$) δ: 1.28 (d, J=6.8 Hz, 6H), 1.51-1.70 (m, 2H), 1.92-2.09 (m, 2H), 3.18 (t, J=8.3 Hz, 2H), 3.26-3.40 (m, 2H), 3.48 (quin, J=6.9 Hz, 1H), 3.57-4.09 (m, 6H), 5.21-5.38 (m, 1H), 5.63 (t, J=5.9 Hz, 1H), 6.05 (s, 1H), 7.41 (dd, J=8.9, 2.1 Hz, 1H), 7.66 (s, 1H), 8.27 (d, J=9.1 Hz, 1H), 8.43 (s, 1H), 9.53 (s, 1H).

Example 55 isopropyl 4-[(6-{5-[(hydroxyacetyl)amino]-2,3-dihydro-1H-indol-1-yl}pyrimidin-4-yl)oxy]piperidine-1-carboxylate

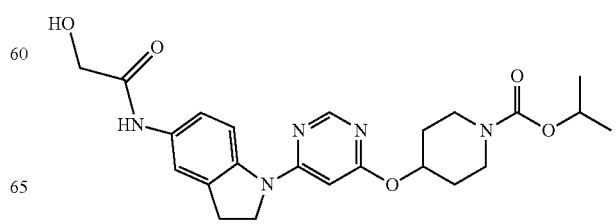

A mixture of 2-oxo-2-({1-[6-(piperidin-4-yloxy)pyrimidin-4-yl]-2,3-dihydro-1H-indol-5-yl}amino)ethyl acetate hydrochloride (300 mg, 0.67 mmol) obtained in Reference Example 28, isopropyl chlorocarbonate (126 mg, 1.0 mmol), triethylamine (418 μL, 3.0 mmol), and tetrahydrofuran (15 mL) was stirred at room temperature for 16 hr. To the reaction mixture were added 1N aqueous sodium hydroxide solution (3 mL) and methanol (4 mL), and the mixture was stirred at room temperature for 2 hr. The reaction mixture was concentrated, water was added to the residue, and the mixture was extracted with ethyl acetate. The organic layer was washed with saturated brine, dried over anhydrous magnesium sulfate and filtered. The filtrate was concentrated to give the title compound as colorless crystals (190 mg, yield 62%).

$^1$H-NMR (300 MHz, DMSO-$d_6$) δ: 1.19 (d, J=6.0 Hz, 6H), 1.47-1.67 (m, 2H), 1.87-2.06 (m, 2H), 3.08-3.29 (m, 4H), 3.65-3.83 (m, 2H), 3.88-4.05 (m, 4H), 4.68-4.88 (m, 1H), 5.15-5.36 (m, 1H), 5.63 (t, J=5.9 Hz, 1H), 6.05 (s, 1H), 7.41 (dd, J=9.1, 1.9 Hz, 1H), 7.66 (s, 1H), 8.27 (d, J=8.7 Hz, 1H), 8.43 (s, 1H), 9.53 (s, 1H).

Example 56

N-[1-(6-{[1-(5-ethylpyrimidin-2-yl)piperidin-4-yl]oxy}pyrimidin-4-yl)-2,3-dihydro-1H-indol-5-yl]-2-hydroxyacetamide

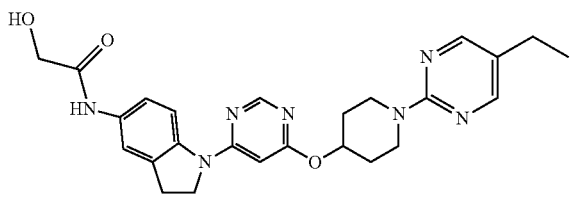 [SMILES: CCc1cnc(N2CCC(Oc3cc(N4CCc5cc(NC(=O)CO)ccc54)ncn3)CC2)nc1]

A mixture of 2-oxo-2-({1-[6-(piperidin-4-yloxy)pyrimidin-4-yl]-2,3-dihydro-1H-indol-5-yl}amino)ethyl acetate hydrochloride (500 mg, 1.12 mmol) obtained in Reference Example 28, 2-chloro-5-ethylpyrimidine (159 mg, 1.12 mmol), cesium carbonate (730 mg, 2.24 mmol), and 1-methyl-2-pyrrolidone (3 mL) was stirred at 80° C. for 16 hr. To the reaction mixture were added 1N aqueous sodium hydroxide solution (3 mL), tetrahydrofuran (4 mL) and methanol (4 mL), and the mixture was stirred at room temperature for 2 hr. The reaction mixture was concentrated, water was added to the residue, and the mixture was extracted with ethyl acetate. The organic layer was washed with saturated brine, dried over anhydrous magnesium sulfate and filtered. The filtrate was concentrated and the residue was subjected to silica gel column chromatography (hexane-ethyl acetate 50:50-0:100, v/v) and crystallized from hexane-ethyl acetate to give the title compound (196 mg, yield 37%) as colorless crystals.

$^1$H-NMR (300 MHz, DMSO-$d_6$) δ: 1.13 (t, J=7.6 Hz, 3H), 1.52-1.70 (m, 2H), 1.97-2.14 (m, 2H), 2.43 (q, J=7.6 Hz, 2H), 3.18 (t, J=8.5 Hz, 2H), 3.37-3.54 (m, 2H), 3.89-4.04 (m, 4H), 4.19-4.37 (m, 2H), 5.24-5.43 (m, 1H), 5.63 (t, J=6.0 Hz, 1H), 6.05 (s, 1H), 7.41 (dd, J=8.7, 1.9 Hz, 1H), 7.66 (s, 1H), 8.19-8.34 (m, 3H), 8.44 (s, 1H), 9.53 (s, 1H).

Example 57 isopropyl 4-{[6-(5-amino-2,3-dihydro-1H-indol-1-yl)pyrimidin-4-yl]oxy}piperidine-1-carboxylate

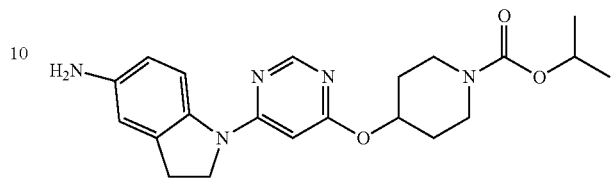

A mixture of 1-[6-(piperidin-4-yloxy)pyrimidin-4-yl]-2,3-dihydro-1H-indol-5-amine (1.0 g, 3.2 mmol) obtained in Reference Example 29, isopropyl chlorocarbonate (349 mg, 2.85 mmol), triethylamine (976 μL, 7.0 mmol), and tetrahydrofuran (50 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was subjected to silica gel column chromatography (hexane-ethyl acetate 0:100, v/v) and crystallized from hexane-ethyl acetate to give the title compound (940 mg, yield 74%) as colorless crystals.

$^1$H-NMR (300 MHz, DMSO-$d_6$) δ: 1.19 (d, J=6.4 Hz, 6H), 1.45-1.67 (m, 2H), 1.86-2.05 (m, 2H), 3.06 (t, J=8.5 Hz, 2H), 3.20 (t, J=10.0 Hz, 2H), 3.64-3.81 (m, 2H), 3.86 (t, J=8.5 Hz, 2H), 4.70-4.90 (m, 3H), 5.14-5.30 (m, 1H), 5.91 (s, 1H), 6.38 (dd, J=8.7, 2.3 Hz, 1H), 6.49 (d, J=2.3 Hz, 1H), 8.03 (d, J=8.3 Hz, 1H), 8.34 (s, 1H).

Example 58

S-(1-methylethyl)4-{[6-(5-amino-2,3-dihydro-1H-indol-1-yl)pyrimidin-4-yl]oxy}piperidine-1-carbothioate

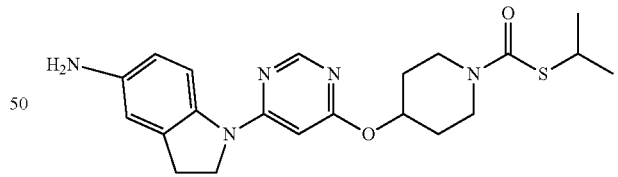

A mixture of 1-[6-(piperidin-4-yloxy)pyrimidin-4-yl]-2,3-dihydro-1H-indol-5-amine (1.0 g, 3.2 mmol) obtained in Reference Example 29, S-isopropyl chlorothioformate (395 mg, 2.85 mmol), triethylamine (976 μL, 7.0 mmol), and tetrahydrofuran (50 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was subjected to silica gel column chromatography (hexane-ethyl acetate 0:100, v/v) and crystallized from hexane-ethyl acetate to give the title compound (1.1 g, yield 83%) as colorless crystals.

¹H-NMR (300 MHz, DMSO-d₆) δ: 1.13-1.39 (m, 7H), 1.49-1.69 (m, 2H), 1.99 (dd, J=6.6, 4.0 Hz, 2H), 3.06 (t, J=8.5 Hz, 2H), 3.23-3.39 (m, 2H), 3.48 (quin, J=6.8 Hz, 1H), 3.58-4.01 (m, 4H), 4.79 (s, 1H), 5.18-5.36 (m, 1H), 5.92 (s, 1H), 6.38 (dd, J=8.7, 2.3 Hz, 1H), 6.49 (d, J=1.9 Hz, 1H), 8.03 (d, J=8.7 Hz, 1H), 8.34 (s, 1H).

Example 59 isopropyl 4-[(6-{5-[(methoxyacetyl)amino]-2,3-dihydro-1H-indol-1-yl}pyrimidin-4-yl)oxy]piperidine-1-carboxylate

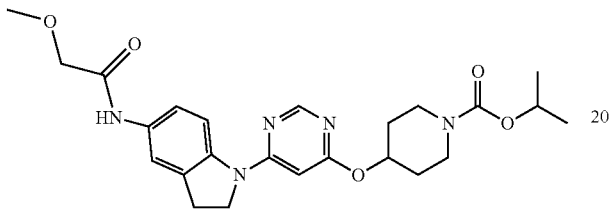

A mixture of isopropyl 4-{[6-(5-amino-2,3-dihydro-1H-indol-1-yl)pyrimidin-4-yl]oxy}piperidine-1-carboxylate (250 mg, 0.63 mmol) obtained in Example 57, methoxyacetyl chloride (109 mg, 1.0 mmol), triethylamine (279 μL, 2.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated to give the title compound as colorless crystals (260 mg, yield 88%).

¹H-NMR (300 MHz, DMSO-d₆) δ: 1.19 (d, J=6.4 Hz, 6H), 1.47-1.69 (m, 2H), 1.89-2.06 (m, 2H), 3.03-3.29 (m, 4H), 3.37 (s, 3H), 3.65-3.84 (m, 2H), 3.87-4.16 (m, 4H), 4.78 (quin, J=6.2 Hz, 1H), 5.15-5.35 (m, 1H), 6.05 (s, 1H), 7.37 (dd, J=8.9, 2.1 Hz, 1H), 7.63 (d, J=1.9 Hz, 1H), 8.27 (d, J=8.7 Hz, 1H), 8.43 (s, 1H), 9.64 (s, 1H).

Example 60

S-(1-methylethyl) 4-[(6-{5-[(methoxyacetyl)amino]-2,3-dihydro-1H-indol-1-yl}pyrimidin-4-yl)oxy]piperidine-1-carbothioate

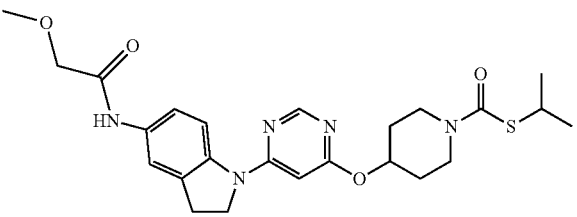 [SMILES: COCC(=O)Nc1ccc2c(c1)CCN2c1cc(OC2CCN(C(=O)OC(C)C)CC2)ncn1]

A mixture of S-(1-methylethyl) 4-{[6-(5-amino-2,3-dihydro-1H-indol-1-yl)pyrimidin-4-yl]oxy}piperidine-1-carbothioate (250 mg, 0.63 mmol) obtained in Example 58, methoxyacetyl chloride (109 mg, 1.0 mmol), triethylamine (279 μL, 2.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated to give the title compound as colorless crystals (250 mg, yield 86%).

¹H-NMR (300 MHz, DMSO-d₆) δ: 1.28 (d, J=6.8 Hz, 6H), 1.51-1.71 (m, 2H), 1.90-2.10 (m, 2H), 3.18 (t, J=8.5 Hz, 2H), 3.25-3.40 (m, 5H), 3.48 (quin, J=6.9 Hz, 1H), 3.57-4.16 (m, 6% H), 5.20-5.40 (m, 1H), 6.06 (s, 1H), 7.37 (dd, J=8.9, 2.1 Hz, 1H), 7.57-7.68 (m, 1H), 8.27 (d, J=8.7 Hz, 1H), 8.43 (s, 1H), 9.64 (s, 1H).

Example 61

S-methyl 4-({6-[5-(methylsulfonyl)-2,3-dihydro-1H-indol-1-yl]pyrimidin-4-yl}oxy)piperidine-1-carbothioate

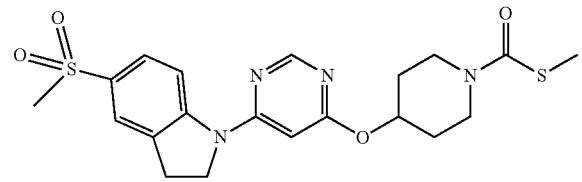 [SMILES: CSC(=O)N1CCC(Oc2cc(N3CCc4cc(S(C)(=O)=O)ccc43)ncn2)CC1]

A mixture of 5-(methylsulfonyl)-1-[6-(piperidin-4-yloxy)pyrimidin-4-yl]-2,3-dihydro-1H-indole (340 mg, 0.91 mmol) obtained in Reference Example 18, methyl chlorothioformate (133 mg, 1.2 mmol), triethylamine (279 μL, 2.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (390 mg, yield 97%).

¹H-NMR (300 MHz, DMSO-d₆) δ: 1.49-1.75 (m, 2H), 1.93-2.11 (m, 2H), 2.26 (s, 3H), 3.15 (s, 3H), 3.21-3.49 (m, 4H), 3.65-3.96 (m, 2H), 4.09 (t, J=8.7 Hz, 2H), 5.25-5.43 (m, 1H), 6.24 (s, 1H), 7.62-7.81 (m, 2H), 8.47-8.62 (m, 2H).

Example 62

S-(1-methylethyl) 4-({6-[7-fluoro-5-(methylsulfonyl)-2,3-dihydro-1H-indol-1-yl]pyrimidin-4-yl}oxy)piperidine-1-carbothioate

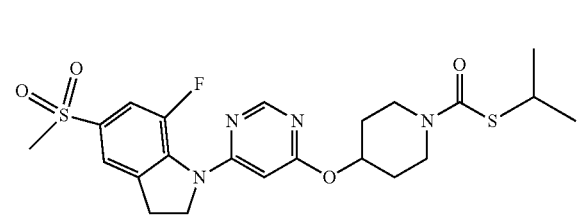 [SMILES: CC(C)SC(=O)N1CCC(Oc2cc(N3CCc4cc(S(C)(=O)=O)cc(F)c43)ncn2)CC1]

A mixture of 7-fluoro-5-(methylsulfonyl)-1-[6-(piperidin-4-yloxy)pyrimidin-4-yl]-2,3-dihydro-1H-indole (250 mg, 0.64 mmol) obtained in Reference Example 32, S-isopropyl chlorothioformate (139 mg, 1.0 mmol), triethylamine (279 μL, 2.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (240 mg, yield 76%).

$^1$H-NMR (300 MHz, DMSO-d$_6$) δ: 1.11-1.23 (m, 1H), 1.28 (d, J=6.8 Hz, 6H), 1.50-1.73 (m, 2H), 1.90-2.09 (m, 2H), 3.16-3.41 (m, 7H), 3.47 (quin, J=6.9 Hz, 1H), 3.56-3.91 (m, 1H), 4.27 (t, J=8.3 Hz, 2H), 5.22-5.38 (m, 1H), 6.29 (d, J=2.6 Hz, 1H), 7.59-7.72 (m, 2H), 8.46 (s, 1H).

Example 63

S-methyl 4-({6-[7-fluoro-5-(methylsulfonyl)-2,3-dihydro-1H-indol-1-yl]pyrimidin-4-yl}oxy)piperidine-1-carbothioate

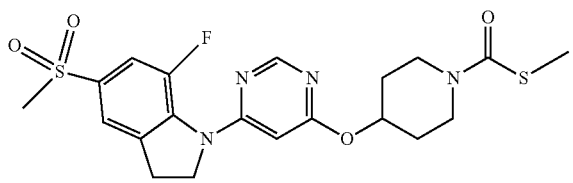 [SMILES: CSC(=O)N1CCC(Oc2cc(N3CCc4cc(S(C)(=O)=O)cc(F)c43)ncn2)CC1]

A mixture of 7-fluoro-5-(methylsulfonyl)-1-[6-(piperidin-4-yloxy)pyrimidin-4-yl]-2,3-dihydro-1H-indole (410 mg, 1.05 mmol) obtained in Reference Example 32, methyl chlorothioformate (155 mg, 1.4 mmol), triethylamine (279 μL, 2.0 mmol), and tetrahydrofuran (10 mL) was stirred at room temperature for 16 hr. Water was added to the reaction mixture, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (430 mg, yield 88%).

$^1$H-NMR (300 MHz, DMSO-d$_6$) δ: 1.53-1.73 (m, 2H), 1.91-2.11 (m, 2H), 2.25 (s, 3H), 3.15-3.30 (m, 5H), 3.31-3.50 (m, 2H), 3.59-3.93 (m, 2H), 4.27 (t, J=8.3 Hz, 2H), 5.24-5.39 (m, 1H), 6.29 (d, J=2.6 Hz, 1H), 7.58-7.73 (m, 2H), 8.46 (s, 1H).

Example 64

7-fluoro-1-[6-({1-[3-(1-methylethyl)-1,2,4-oxadiazol-5-yl]piperidin-4-yl}oxy)pyrimidin-4-yl]-5-(methylsulfonyl)-2,3-dihydro-1H-indole

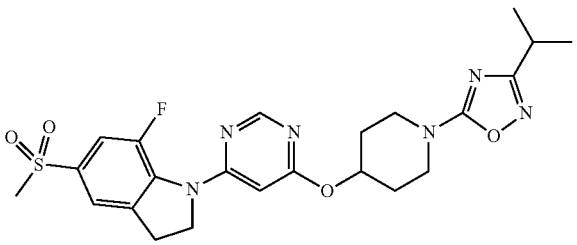 [SMILES: CC(C)c1noc(N2CCC(Oc3cc(N4CCc5cc(S(C)(=O)=O)cc(F)c54)ncn3)CC2)n1]

A mixture of 4-({6-[7-fluoro-5-(methylsulfonyl)-2,3-dihydro-1H-indol-1-yl]pyrimidin-4-yl}oxy)piperidine-1-carbonitrile (500 mg, 1.2 mmol) obtained in Reference Example 39, (1Z)—N'-hydroxy-2-methylpropanimidamide (204 mg, 2.0 mmol), zinc dichloride (1.0 M diethyl ether solution, 2 mL, 2.0 mmol), ethyl acetate (100 mL), and tetrahydrofuran (100 mL) was heated under reflux for 4 hr. The resulting solid was filtered, and washed with ethyl acetate. A mixture of the obtained solid, ethanol (150 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (420 mg, yield 70%).

$^1$H-NMR (300 MHz, DMSO-d$_6$) δ: 1.19 (d, J=7.2 Hz, 6H), 1.63-1.88 (m, 2H), 1.98-2.15 (m, 2H), 2.82 (quin, J=7.0 Hz, 1H), 3.14-3.31 (m, 5H), 3.42-3.61 (m, 2H), 3.71-3.92 (m, 2H), 4.28 (t, J=8.3 Hz, 2H), 5.22-5.40 (m, 1H), 6.30 (d, J=2.6 Hz, 1H), 7.57-7.74 (m, 2H), 8.47 (s, 1H).

Example 65

1-(6-{[1-(3-ethyl-1,2,4-oxadiazol-5-yl)piperidin-4-yl]oxy}pyrimidin-4-yl)-7-fluoro-5-(methylsulfonyl)-2,3-dihydro-1H-indole

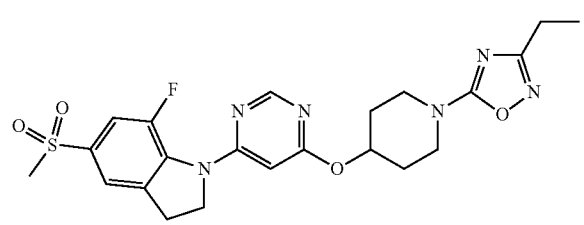 [SMILES: CCc1noc(N2CCC(Oc3cc(N4CCc5cc(S(C)(=O)=O)cc(F)c54)ncn3)CC2)n1]

A mixture of 4-({6-[7-fluoro-5-(methylsulfonyl)-2,3-dihydro-1H-indol-1-yl]pyrimidin-4-yl}oxy)piperidine-1-carbonitrile (500 mg, 1.2 mmol) obtained in Reference Example 39, (1Z)—N'-hydroxypropanimidamide (176 mg, 2.0 mmol) obtained in Reference Example 22, zinc dichloride (1.0 M diethyl ether solution, 2 mL, 2.0 mmol), ethyl acetate (100 mL), and tetrahydrofuran (100 mL) was heated under reflux for 4 hr. The resulting solid was filtered, and washed with ethyl acetate. A mixture of the obtained solid, ethanol (150 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (420 mg, yield 72%).

$^1$H-NMR (300 MHz, DMSO-d$_6$) δ: 1.16 (t, J=7.6 Hz, 3H), 1.66-1.87 (m, 2H), 2.00-2.16 (m, 2H), 2.41-2.50 (m, 2H), 3.15-3.32 (m, 5H), 3.43-3.59 (m, 2H), 3.73-3.89 (m, 2H), 4.28 (t, J=8.3 Hz, 2H), 5.23-5.39 (m, 1H), 6.31 (d, J=2.6 Hz, 1H), 7.58-7.73 (m, 2H), 8.47 (s, 1H).

Example 66

7-fluoro-1-[6-({1-[3-(methoxymethyl)-1,2,4-oxadiazol-5-yl]piperidin-4-yl}oxy)pyrimidin-4-yl]-5-(methylsulfonyl)-2,3-dihydro-1H-indole

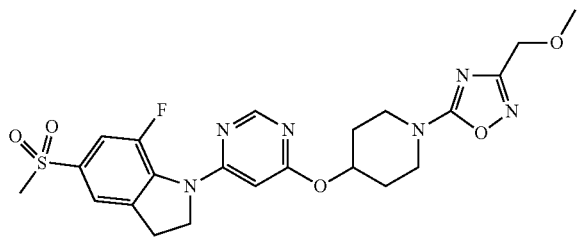 [SMILES: COCc1noc(N2CCC(Oc3cc(N4CCc5cc(S(C)(=O)=O)cc(F)c54)ncn3)CC2)n1]

A mixture of 4-({6-[7-fluoro-5-(methylsulfonyl)-2,3-dihydro-1H-indol-1-yl]pyrimidin-4-yl}oxy)piperidine-1-carbonitrile (500 mg, 1.2 mmol) obtained in Reference Example 39, (1Z)—N'-hydroxy-2-methoxyethanimidamide (208 mg, 2.0 mmol) obtained in Reference Example 23, zinc dichloride (1.0 M diethyl ether solution, 2 mL, 2.0 mmol), ethyl acetate (100 ml), and tetrahydrofuran (100 mL) was heated under reflux for 4 hr. The resulting solid was filtered, and washed with ethyl acetate. A mixture of the obtained solid, ethanol (150 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (440 mg, yield 73%).

$^1$H-NMR (300 MHz, DMSO-$d_6$) δ: 1.68-1.87 (m, 2H), 2.01-2.21 (m, 2H), 3.20-3.29 (m, 5H), 3.31 (s, 3H), 3.44-3.63 (m, 2H), 3.73-3.91 (m, 2H), 4.21-4.35 (m, 4H), 5.23-5.40 (m, 1H), 6.31 (d, J=2.6 Hz, 1H), 7.56-7.75 (m, 2H), 8.47 (s, 1H).

Example 67

7-fluoro-1-(6-{[1-(3-methyl-1,2,4-oxadiazol-5-yl)piperidin-4-yl]oxy}pyrimidin-4-yl)-5-(methylsulfonyl)-2,3-dihydro-1H-indole

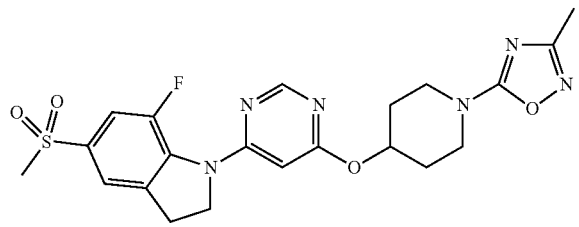 [SMILES: Cc1noc(N2CCC(Oc3cc(N4CCc5cc(S(C)(=O)=O)cc(F)c54)ncn3)CC2)n1]

A mixture of 4-({6-[7-fluoro-5-(methylsulfonyl)-2,3-dihydro-1H-indol-1-yl]pyrimidin-4-yl}oxy)piperidine-1-carbonitrile (500 mg, 1.2 mmol) obtained in Reference Example 39, (1Z)—N'-hydroxyethanimidamide (148 mg, 2.0 mmol), zinc dichloride (1.0 M diethyl ether solution, 2 mL, 2.0 mmol), ethyl acetate (100 mL), and tetrahydrofuran (100 mL) was heated under reflux for 4 hr. The resulting solid was filtered, and washed with ethyl acetate. A mixture of the obtained solid, ethanol (150 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (400 mg; yield 70%).

$^1$H-NMR (300 MHz, DMSO-$d_6$) δ: 1.67-1.84 (m, 2H), 1.98-2.20 (m, 5H), 3.16-3.31 (m, 5H), 3.42-3.59 (m, 2H), 3.70-3.90 (m, 2H), 4.27 (t, J=8.3 Hz, 2H), 5.24-5.41 (m, 1H), 6.30 (d, J=2.6 Hz, 1H), 7.58-7.73 (m, 2H), 8.47 (s, 1H).

Example 68

7-fluoro-5-(methylsulfonyl)-1-{6-[(1-{3-[(2R)-tetrahydrofuran-2-yl]-1,2,4-oxadiazol-5-yl}piperidin-4-yl)oxy]pyrimidin-4-yl}-2,3-dihydro-1H-indole

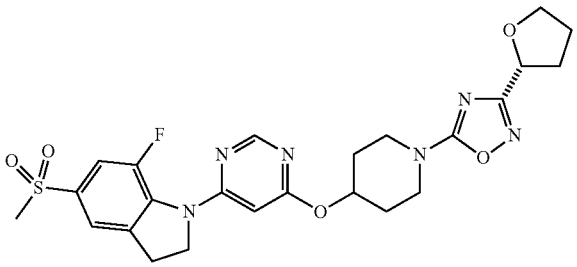

A mixture of 4-({6-[7-fluoro-5-(methylsulfonyl)-2,3-dihydro-1H-indol-1-yl]pyrimidin-4-yl}oxy)piperidine-1-carbonitrile (500 mg, 1.2 mmol) obtained in Reference Example 39, (1Z)-(2R)—N'-hydroxytetrahydrofuran-2-carboximidamide (260 mg, 2.0 mmol) obtained in Reference Example 33, zinc dichloride (1.0 M diethyl ether solution, 2 mL, 2.0 mmol), ethyl acetate (100 mL), and tetrahydrofuran (100 mL) was heated under reflux for 4 hr. The resulting solid was filtered, and washed with ethyl acetate. A mixture of the obtained solid, ethanol (150 mL), and 12M hydrochloric acid (1 mL) was stirred at 70° C. for one day. The reaction mixture was allowed to cool to room temperature, and concentrated. To the residue was added aqueous sodium hydrogen carbonate solution, and the mixture was extracted with ethyl acetate. The organic layer was washed with saturated brine, dried over anhydrous magnesium sulfate and filtered. The filtrate was concentrated and the residue was crystallized from ethyl acetate to give the title compound as colorless crystals (270 mg, yield 51%).

$^1$H-NMR (300 MHz, DMSO-$d_6$) δ: 1.66-2.28 (m, 8H), 3.18-3.31 (m, 5H), 3.43-3.62 (m, 2H), 3.70-3.93 (m, 4H), 4.28 (t, J=8.3 Hz, 2H), 4.69-4.84 (m, 1H), 5.21-5.42 (m, 1H), 6.31 (d, J=2.6 Hz, 1H), 7.55-7.73 (m, 2H), 8.47 (s, 1H).

Example 69

N-[1-(5-ethylpyrimidin-2-yl)piperidin-4-yl]-6-[5-(methylsulfonyl)-2,3-dihydro-1H-indol-1-yl]-N-(trifluoromethyl)pyrimidin-4-amine

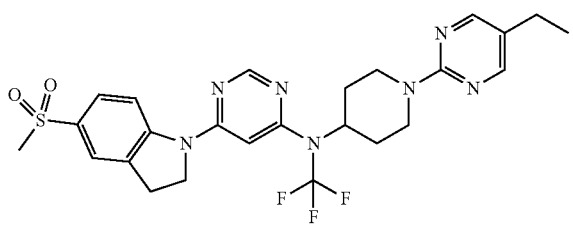 [SMILES: CCc1cnc(N2CCC(N(c3cc(N4CCc5cc(S(C)(=O)=O)ccc54)ncn3)C(F)(F)F)CC2)nc1]

6-[5-(Methylsulfonyl)-2,3-dihydro-1H-indol-1-yl]-N-(piperidin-4-yl)-N-(trifluoromethyl)pyrimidin-4-amine (65.0 mg, 0.147 mmol) obtained in Reference Example 34 and 2-chloro-5-ethylpyrimidine (84.0 mg, 0.589 mmol) were dissolved in NMP (3.0 mL), cesium carbonate (192 mg, 0.589 mmol) was added, and the mixture was stirred at 70° C. for 73 hr. After cooling to room temperature, the mixture was diluted with ethyl acetate, and water was added thereto. The organic layer was washed with water and saturated brine, dried over sodium sulfate, and concentrated under reduced pressure. The obtained residue was purified by silica gel column chromatography [eluent; hexane:ethyl acetate=7:3 (volume ratio)→hexane:ethyl acetate=3:7 (volume ratio)], and the obtained solid was suspended in diisopropyl ether. The precipitate was collected by filtration, washed with diisopropyl ether and dried under reduced pressure to give the title compound (28.2 mg, yield 35%) as a white solid.

$^1$H-NMR (300 MHz, CDCl$_3$) δ: 1.20 (t, 3H), 1.92-2.04 (m, 2H), 2.04-2.22 (m, 2H), 2.48 (q, J=7.6 Hz, 2H), 2.86-3.01 (m, 2H), 3.04 (s, 3H), 3.26-3.39 (m, 2H), 4.12 (t, J=8.7 Hz, 2H), 4.70-4.97 (m, 3H), 6.28 (d, J=1.1 Hz, 1H), 7.73 (d, J=1.5 Hz, 1H), 7.80 (dd, J=8.7, 1.9 Hz, 1H), 8.18 (s, 2H), 8.56 (d, J=8.7 Hz, 1H), 8.62 (d, J=1.1 Hz, 1H).

Example 70

1-methylethyl 4-[{6-[5-(methylsulfonyl)-2,3-dihydro-1H-indol-1-yl]pyrimidin-4-yl}(trifluoromethyl)amino]piperidine-1-carboxylate

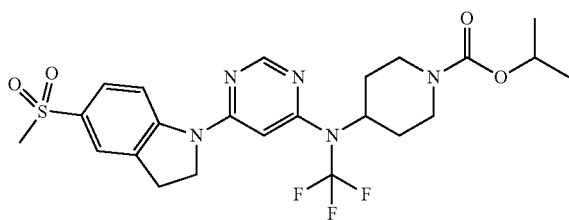 [SMILES: CC(C)OC(=O)N1CCC(N(c2cc(N3CCc4cc(S(C)(=O)=O)ccc43)ncn2)C(F)(F)F)CC1]

6-[5-(Methylsulfonyl)-2,3-dihydro-1H-indol-1-yl]-N-(piperidin-4-yl)-N-(trifluoromethyl)pyrimidin-4-amine (45.0 mg, 0.102 mmol) obtained in Reference Example 34 was suspended in THF (5.0 mL), triethylamine (20.6 mg, 0.204 mmol) and isopropyl chloroformate (0.023 mL, 0.20 mmol) were added thereto at room temperature, and the mixture was stirred at the same temperature for 19 hr. To the reaction solution was added aqueous sodium hydrogen carbonate solution, and the mixture was extracted with ethyl acetate. The organic layer was washed with water and saturated brine, dried over sodium sulfate, and concentrated under reduced pressure. The obtained residue was purified by silica gel column chromatography [eluent; hexane:ethyl acetate=7:3 (volume ratio)→hexane:ethyl acetate=1:9 (volume ratio)] and the obtained solid was suspended in diisopropyl ether. The precipitate was collected by filtration, washed with diisopropyl ether and dried under reduced pressure to give the title compound (46.0 mg, yield 86%) as a white solid.

$^1$H-NMR (300 MHz, CDCl$_3$) δ: 1.26 (d, J=6.4 Hz, 6H), 1.82-1.95 (m, 2H), 1.97-2.17 (m, 2H), 2.74-2.91 (m, 2H), 3.04 (s, 3H), 3.32 (t, J=9.1 Hz, 2H), 4.06-4.17 (m, 2H), 4.20-4.39 (m, 2H), 4.68 (t, J=12.3 Hz, 1H), 4.93 (quin, J=6.2 Hz, 1H), 6.26 (d, J=1.1 Hz, 1H), 7.73 (d, J=1.5 Hz, 1H), 7.80 (dd, J=8.5, 2.1 Hz, 1H), 8.56 (d, J=8.7 Hz, 1H), 8.62 (d, J=0.8 Hz, 1H).

Example 71

S-(1-methylethyl) 4-[{6-[5-(methylsulfonyl)-2,3-dihydro-1H-indol-1-yl]pyrimidin-4-yl}(trifluoromethyl)amino]piperidine-1-carbothioate

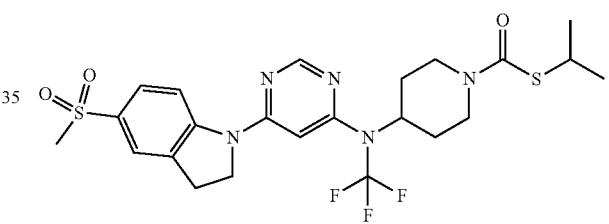

6-[5-(Methylsulfonyl)-2,3-dihydro-1H-indol-1-yl]-N-(piperidin-4-yl)-N-(trifluoromethyl)pyrimidin-4-amine (55.0 mg, 0.125 mmol) obtained in Reference Example 34 was suspended in THF (10 mL), triethylamine (0.035 mL, 0.25 mmol) and S-isopropyl chlorothioformate (0.037 mL, 0.25 mmol) were added at room temperature, and the mixture was stirred at the same temperature for 18 hr. To the reaction solution was added aqueous sodium hydrogen carbonate solution, and the mixture was extracted with ethyl acetate. The organic layer was washed with water and saturated brine, dried over sodium sulfate, and concentrated under reduced pressure. The obtained residue was purified by silica gel column chromatography [eluent; hexane:ethyl acetate=7:3 (volume ratio)→hexane:ethyl acetate=4:6 (volume ratio)], and the obtained solid was suspended in diisopropyl ether. The precipitate was collected by filtration, washed with diisopropyl ether and dried under reduced pressure to give the title compound (58.3 mg, yield 86%) as a white solid.

$^1$H-NMR (300 MHz, CDCl$_3$) δ: 1.36 (d, J=6.8 Hz, 6H), 1.87-2.01 (m, 2H), 2.01-2.20 (m, 2H), 2.89 (br. s., 2H), 3.04 (s, 3H), 3.33 (t, J=8.5 Hz, 2H), 3.63 (dt, J=13.9, 6.8 Hz, 1H), 3.90-4.86 (m, 5H), 6.26 (d, J=1.1 Hz, 1H), 7.74 (d, J=1.5 Hz, 1H), 7.80 (dd, J=8.7, 2.3 Hz, 1H), 8.56 (d, J=8.7 Hz, 1H), 8.61 (d, J=0.8 Hz, 1H).

Example 72

N-[1-(5-methoxypyrimidin-2-yl)piperidin-4-yl]-6-[5-(methylsulfonyl)-2,3-dihydro-1H-indol-1-yl]-N-(trifluoromethyl)pyrimidin-4-amine

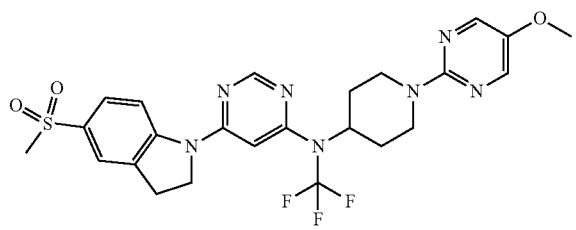 [SMILES: COc1cnc(N2CCC(N(c3cc(N4CCc5cc(S(C)(=O)=O)ccc54)ncn3)C(F)(F)F)CC2)nc1]

6-[5-(Methylsulfonyl)-2,3-dihydro-1H-indol-1-yl]-N-(piperidin-4-yl)-N-(trifluoromethyl)pyrimidin-4-amine (100 mg, 0.227 mmol) obtained in Reference Example 34 and 2-chloro-5-methoxypyrimidine (131 mg, 0.906 mmol) were dissolved in NMP (5.0 mL). Cesium carbonate (295 mg, 0.906 mmol) was added thereto, and the mixture was stirred at 80° C. for 74 hr. After cooling to room temperature, the mixture was diluted with ethyl acetate, and water was added thereto. The organic layer was washed with water and saturated brine, dried over sodium sulfate, and concentrated under reduced pressure. The obtained residue was purified by silica gel column chromatography [eluent; hexane:ethyl acetate=6:4 (volume ratio)→hexane:ethyl acetate=2:8 (volume ratio)], and the obtained solid was suspended in diisopropyl ether. The precipitate was collected by filtration, washed with diisopropyl ether and dried under reduced pressure to give the title compound (17.8 mg, yield 14%) as a white solid.

$^1$H-NMR (300 MHz, CDCl$_3$) δ: 1.90-2.03 (m, 2H), 2.04-2.24 (m, 2H), 2.93 (t, J=12.7 Hz, 2H), 3.04 (s, 3H), 3.32 (t, J=8.7 Hz, 2H), 3.81 (s, 3H), 4.12 (t, J=8.9 Hz, 2H), 4.69-4.88 (m, 3H), 6.24-6.31 (m, 1H), 7.73 (d, J=1.1 Hz, 1H), 7.80 (dd, J=8.7, 1.9 Hz, 1H), 8.10 (s, 2H), 8.56 (d, J=8.7 Hz, 1H), 8.62 (d, J=1.1 Hz, 1H).

Example 73

N-[1-(5-methylpyrimidin-2-yl)piperidin-4-yl]-6-[5-(methylsulfonyl)-2,3-dihydro-1H-indol-1-yl]-N-(trifluoromethyl)pyrimidin-4-amine

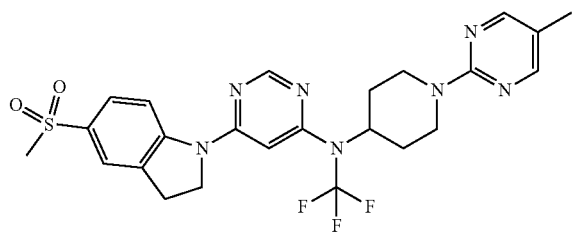 [SMILES: Cc1cnc(N2CCC(N(c3cc(N4CCc5cc(S(C)(=O)=O)ccc54)ncn3)C(F)(F)F)CC2)nc1]

6-[5-(Methylsulfonyl)-2,3-dihydro-1H-indol-1-yl]-N-(piperidin-4-yl)-N-(trifluoromethyl)pyrimidin-4-amine (65.0 mg, 0.147 mmol) obtained in Reference Example 34 and 2-chloro-5-methoxypyrimidine (75.7 mg, 0.589 mmol) were dissolved in NMP (3.0 mL). Cesium carbonate (192 mg, 0.589 mmol) was added thereto, and the mixture was stirred at 70° C. for 73 hr. After cooling to room temperature, the mixture was diluted with ethyl acetate, and water was added thereto. The organic layer was washed with water and saturated brine, dried over sodium sulfate, and concentrated under reduced pressure. The obtained residue was purified by silica gel column chromatography [eluent; hexane:ethyl acetate=6:4 (volume ratio)→hexane:ethyl acetate=2:8 (volume ratio)], and the obtained solid was suspended in diisopropyl ether. The precipitate was collected by filtration, washed with diisopropyl ether and dried under reduced pressure to give the title compound (31.3 mg, yield 40%) as a white solid.

$^1$H-NMR (300 MHz, CDCl$_3$) δ: 1.90-2.02 (m, 2H), 2.02-2.21 (m, 5H), 2.86-3.00 (m, 2H), 3.04 (s, 3H), 3.32 (t, J=8.5 Hz, 2H), 4.11 (t, J=8.7 Hz, 2H), 4.71-4.95 (m, 3H), 6.27 (s, 1H), 7.73 (d, J=1.5 Hz, 1H), 7.80 (dd, J=8.7, 1.9 Hz, 1H), 8.16 (s, 2H), 8.56 (d, J=8.7 Hz, 1H), 8.62 (d, J=0.8 Hz, 1H).

Example 74

1-(6-{[1-(tert-butoxycarbonyl)piperidin-4-yl]oxy}pyrimidin-4-yl)-2,3-dihydro-1H-indole-5-carboxylic acid

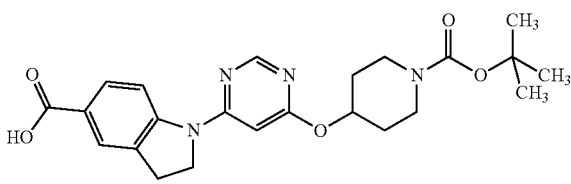 [SMILES: CC(C)(C)OC(=O)N1CCC(Oc2cc(N3CCc4cc(C(=O)O)ccc43)ncn2)CC1]

To a mixture of methyl 1-(6-chloropyrimidin-4-yl)-2,3-dihydro-1H-indole-5-carboxylate (4.37 g) synthesized in Reference Example 15, tert-butyl 4-hydroxypiperidine-1-carboxylate (7.61 g), and N,N-dimethylformamide (100 mL) was added at 0° C. sodium hydride (oil, 60%, 1.51 g) by small portions, and the mixture was stirred at room temperature for 5 hr. To the reaction mixture was added saturated aqueous ammonium chloride solution, and the mixture was extracted with ethyl acetate. The extract was washed with saturated brine, dried over magnesium sulfate, and concentrated under reduced pressure. The residue was purified by silica gel column chromatography (30-70% ethyl acetate/hexane) to give a pale-yellow oil. To a mixture of the obtained oil, tetrahydrofuran (50 mL), and ethanol (50 mL) was added 1N aqueous sodium hydroxide solution (50 mL), and the mixture was stirred with heating under reflux for 5 hr, and concentrated under reduced pressure. The residue was dissolved in water (100 mL), 1N hydrochloric acid (50 mL) was added thereto, and the mixture was extracted with ethyl acetate. The extract was washed with saturated brine, dried over magnesium sulfate, and concentrated under reduced pressure. The residue was washed with diisopropyl ether to give the title compound (3.54 g) as a white solid. The obtained title compound contained 1-(6-methoxypyrimidin-4-yl)-2,3-dihydro-1H-indole-5-carboxylic acid as impurity at a ratio of 1:1.

$^1$H-NMR (300 MHz, DMSO-d$_6$) δ: 1.41 (s, 9H), 1.48-1.65 (m, 2H), 1.88-2.05 (m, 2H), 3.07-3.30 (m, 4H), 3.64-3.80 (m, 2H), 4.00-4.12 (m, 2H), 5.19-5.33 (m, 1H), 6.18 (s, 1H), 7.76 (s, 1H), 7.79 (d, J=8.7 Hz, 1H), 8.43 (d, J=8.7 Hz, 1H), 8.51 (s, 1H), 12.54 (br s, 1H).

Example 75

1-(6-{[1-(5-ethylpyrimidin-2-yl)piperidin-4-yl]oxy}pyrimidin-4-yl)-2,3-dihydro-1H-indole-5-carboxylic acid

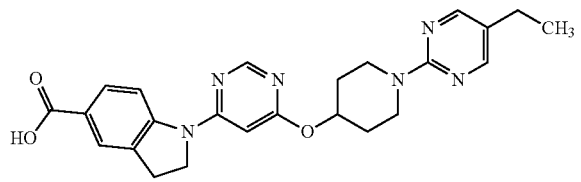 [SMILES: CCc1cnc(N2CCC(Oc3cc(N4CCc5cc(C(=O)O)ccc54)ncn3)CC2)nc1]

To a mixture of methyl 1-(6-{[1-(5-ethylpyrimidin-2-yl)piperidin-4-yl]oxy}pyrimidin-4-yl)-2,3-dihydro-1H-indole-5-carboxylate (912 mg) synthesized in Example 22, tetrahydrofuran (50 mL), and ethanol (50 mL) was added 1N aqueous sodium hydroxide solution (30 mL), and the mixture was stirred with heating under reflux for 2.5 hr. The reaction mixture was concentrated under reduced pressure, and to a suspension of the residue in water (60 mL) was added at 0° C. 1N hydrochloric acid (30 mL), and the mixture was extracted with a mixed solvent of ethyl acetate and tetrahydrofuran. The extract was washed with saturated brine, dried over magnesium sulfate, and concentrated under reduced pressure. The residue was washed with 50% ethyl acetate/hexane to give the title compound (690 mg, 78%) as a white solid.

$^1$H-NMR (300 MHz, DMSO-d6) δ: 1.13 (t, J=7.6 Hz, 3H), 1.54-1.72 (m, 2H), 1.97-2.14 (m, 2H), 2.43 (q, J=7.6 Hz, 2H), 3.18-3.29 (m, 2H), 3.37-3.51 (m, 2H), 4.05 (t, J=8.7 Hz, 2H), 4.20-4.36 (m, 2H), 5.28-5.43 (m, 1H), 6.19 (s, 1H), 7.76 (s, 1H), 7.79 (d, J=8.8 Hz, 1H), 8.25 (s, 2H), 8.43 (d, J=8.8 Hz, 1H), 8.52 (s, 1H), 12.54 (s, 1H).

Example 76

1-[6-({1-[3-(1-methylethyl)-1,2,4-oxadiazol-5-yl]piperidin-4-yl}oxy)pyrimidin-4-yl]-2,3-dihydro-1H-indole-5-carboxylic acid

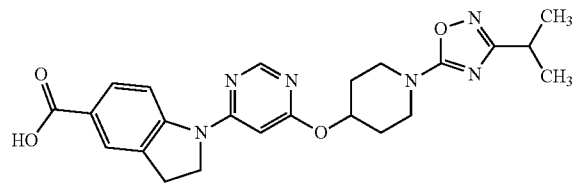 [SMILES: CC(C)c1noc(N2CCC(Oc3cc(N4CCc5cc(C(=O)O)ccc54)ncn3)CC2)n1]

To a mixture of methyl 1-[6-({1-[3-(1-methylethyl)-1,2,4-oxadiazol-5-yl]piperidin-4-yl}oxy)pyrimidin-4-yl]-2,3-dihydro-1H-indole-5-carboxylate (695 mg) synthesized in Example 29, tetrahydrofuran (20 mL), and ethanol (20 mL) was added 1N aqueous sodium hydroxide solution (10 mL), and the mixture was stirred with heating under reflux for 5 hr, and concentrated under reduced pressure. To a suspension of the residue in water (20 mL) was added at 0° C. 1N hydrochloric acid (10 mL), and the mixture was extracted with a mixed solvent of ethyl acetate and tetrahydrofuran. The extract was washed with saturated brine, dried over magnesium sulfate, and concentrated under reduced pressure. The residue was washed with 50% ethyl acetate/hexane to give the title compound (609 mg, 90%) as a white solid.

$^1$H-NMR (300 MHz, CDCl$_3$) δ: 1.30 (d, J=7.2 Hz, 6H), 1.83-1.99 (m, 2H), 2.04-2.17 (m, 2H), 2.83-2.98 (m, 1H), 3.29 (t, J=8.8 Hz, 2H), 3.53-3.65 (m, 2H), 3.84-3.96 (m, 2H), 4.05 (t, J=8.8 Hz, 2H), 5.35-5.47 (m, 1H), 6.01 (s, 1H), 7.92 (d, J=1.5 Hz, 1H), 8.01 (dd, J=8.7, 1.5 Hz, 1H), 8.45 (d, J=8.7 Hz, 1H), 8.52 (s, 1H).

Experimental Example 1

Evaluation of Human GPR119 Agonist Activity with Increase of Intracellular Camp Concentration as Index (1) Construction of Expression Plasmid of Human GPR119 Gene Using High Fidelity RNA PCR Kit (Takara Bio Inc.), human GPR119 gene was cloned by PCR using cDNA library synthesized from human brain mRNA (Clontech) as a template and synthetic DNA having the following sequence. Primer 1 and Primer 2 were is prepared by adding cleavage sites for Sal I and Nhe I based on the base sequence information of human GPR119 gene.

(SEQ ID NO: 1)
Primer 1: 5'-GCGTCGACATGGAATCATCTTTCTCATTTGG-3'

(SEQ ID NO: 2)
Primer 2: 5'-GCGCTAGCTTAGCCATCAAACTCTGAGCT-3'

PCR was performed using Pyrobest DNA polymerase (Takara Bio Inc.). The obtained PCR product was cloned to pUC118 (Takara Bio Inc.), and the base sequence was continued and digested with restriction enzymes Sal I, Nhe I. The obtained DNA fragment was inserted into an animal cell expression vector pAKKO-111H (plasmid same as pAKKO-1.111H described in Biochem. Biophys. Acta, Hinuma, S. et al., 1219, 251-259 (1994)) similarly digested with Sal I, Nhe I, whereby an expression plasmid pAKKO-111H/hGPR119 was prepared.

(2) Construction of Reporter Plasmid

Zeocin resistance gene was cloned by PCR using plasmid pcDNA3.1/Zeo (Invitrogen) as a template, synthetic DNA having the following sequences wherein cleavage sites for restriction enzymes Sal I and BamH I are added to before and after a region containing SV40 Ori and a region containing SV40pA, which are located at the upstream and downstream of Zeocin resistance gene of this plasmid, as a primer set, and KOD polymerase (TOYOBO).

(SEQ ID NO: 3)
Zeocin-U: 5'-GGATCCAGGCAGGCAGAAGTATG-3'

(SEQ ID NO: 4)
Zeocine-L: 5'-GTCGACAGACATGATAAGATACATTGATG-3'

The obtained PCR product was inserted into pCR-BluntII (Invitrogen). A fragment containing a Zeocine resistance gene obtained by digesting the plasmid with restriction enzymes Sal I and BamH I was inserted into plasmid pGL3 (R2.2)-Basic Vector (promega) similarly digested with Sal I and Bam HI to give Zeocin resistance plasmid pGL3(R2.2)/Zeocin-Basic Vector.

A reporter plasmid containing 4 cAMP responsive elements (CRE) connected in tandem was prepared using the following 5'-terminal phosphorylated synthetic DNA.

CRE-Upper:
(SEQ ID NO: 5)
5'-CAGCCTGACGTCAGAGAGCCTGACGTCAGAGAGCCTGACGTCAGAG

AGCCTGACGTCAGAGTCGACAGCGGAGACTCTAGAGGGTATATAAGCT

T-3'

CRE-Lower:
(SEQ ID NO: 6)
5'-AGCTTATATACCCTCTAGAGTCTCCGCTGTCGACTCTGACGTCAGG

CTCTCTGACGTCAGGCTCTCTGACGTCAGGCTCTCTGACGTCAGGCTGG

TACC-3'

First, a DNA fragment containing a CRE sequence obtained by annealing CRE-Upper and CRE-Lower and elongating with KOD polymerase was inserted into pCR-BluntII to give pCR-BluntII-CRE. A fragment cleaved from pCR-BluntII-CRE with restriction enzymes Kpn I and Hind III was inserted into pGL3(R2.2)/Zeocin-Basic Vector similarly digested with Kpn I and Hind III to give reporter plasmid pGL3(R2.2)/Zeocin-CRE-luc.
(3) Introduction of Human GPR119 Gene and Reporter Gene into CHO(dhfr-) Cells and Acquirement of Expressing Cell CHO(dhfr-) cells in MEMα (minimum essential medium alpha) (Nikken bio medical laboratory) medium containing 10% fetal bovine serum, 100 U/mL penicillin and 100 μg/mL streptomycin (Invitrogen) were detached by a treatment with trypsin-EDTA (ethylenediaminetetraacetic acid) (Invitrogen), the cells were washed with PBS (Phosphate-buffered saline), centrifuged (1000 rpm, 5 min) and suspended in PBS at a cell density of $1 \times 10^7$ cells/mL. Then, DNA was introduced into the cell by a gene pulser (Bio-Rad) under the following conditions. That is, $1 \times 10^7$ cells, plasmid pGL3 (R2.2)/Zeocin-CRE-luc (15 μg), which was obtained in (2) and linearized with BssH II, and pAKKO-111H (5 μg) were added in a 0.4 cm gap cuvette, and the mixture was electroporated at voltage 250 mV, capacitance 950 μF. The cells were placed in the above-mentioned medium, cultured for 24 hr, and the cells were detached and centrifuged. The cells were diluted to 250 cells/well, plated in a 96 well plate (Corning) and cultivated in a $CO_2$ incubator at 37° C. to give a transformant. Then, forskolin was added to the obtained transformant and a strain (CRE-luc/CHO(dhfr-) cell) that induces luciferase expression was selected.

Then, according to a method similar to the above-mentioned method, plasmid pAKKO-111H/hGPR119 (15 μg) obtained in (1) and pcDNA3.1 (Invitrogen) (5 μg) were added to $1 \times 10^7$ CRE-luc/CHO(dhfr-) cells, and the mixture was electroporated at voltage 250 mV, capacitance 950 μF. After culture in the same manner as in the above, the cells were suspended in a medium containing Geneticin (Wako Pure Chemical Industries, Ltd., 500 μg/mL), diluted to 250 cells/well, plated in a 96 well plate, and cultivated in a $CO_2$ incubator at 37° C. to give a Geneticin resistance transformant. Then, N-[4-(methylsulfonyl)phenyl]-5-nitro-6-{4-[4-(trifluoromethoxy)phenoxy]piperidin-1-yl}pyrimidin-4-amine was added to the obtained transformant and a strain (hGPR119/CRE-luc/CHO(dhfr-) cell) that induces luciferase expression was selected.
(4) Reporter Assay hGPR119/CRE-luc/CHO (dhfr-) cells were sown on a 384 well white plate (NUNC) at $1 \times 10^4$ cells/well and cultured overnight in an MEMα (minimum essential medium alpha) medium containing 10% fetal bovine serum, 100 U/mL penicillin, 100 μg/mL streptomycin and 500 μg/mL Geneticin in a $CO_2$ incubator at 37° C. The cells were washed once with an assay buffer (MEMα medium containing 20 mM HEPES (2-[4-(2-hydroxyethyl)-1-piperazinyl]ethanesulfonic acid) (pH 7.4) (Invitrogen), 0.1% bovine serum albumin (Sigma Ltd.), 100 U/mL penicillin, 100 μg/mL streptomycin), and incubated in an assay buffer (40 μL) containing 1 μM test compound in a $CO_2$ incubator at 37° C. for 2 hr. The assay buffer was removed from each well, Steady-Glo (Promega) diluted 2-fold with HBSS (Hanks' balanced salt solution) was added by 25 μL, and the mixture was shaken under shading. After 30 min, luciferase activity was measured by Envision (PerkinElmer). The GPR119 agonist activity was calculated using luciferase activity in the presence of 10 μM N-[4-(methylsulfonyl)phenyl]-5-nitro-6-{4-[4-(trifluoromethoxy)phenoxy]piperidin-1-yl}pyrimidin-4-amine as 100%, and luciferase activity when DMSO was added instead of a test compound as 0%, and increase of intracellular cAMP concentration as an index. The results are shown in Table 1.

TABLE 1

| test compound (Example No.) | GPR119 agonist activity (%) at 1 μM concentration |
| --- | --- |
| 1 | 62 |
| 3 | 87 |
| 7 | 96 |
| 10 | 93 |
| 12 | 84 |
| 14 | 82 |
| 16 | 77 |
| 18 | 74 |
| 20 | 88 |
| 21 | 80 |
| 23 | 79 |
| 27 | 77 |
| 30 | 78 |
| 31 | 80 |
| 32 | 92 |
| 33 | 74 |
| 35 | 82 |
| 36 | 87 |
| 38 | 79 |
| 41 | 85 |
| 45 | 75 |
| 46 | 80 |
| 50 | 85 |
| 51 | 83 |
| 54 | 82 |
| 55 | 84 |
| 56 | 75 |
| 59 | 77 |
| 60 | 81 |
| 61 | 85 |
| 62 | 83 |
| 64 | 77 |
| 69 | 98 |
| 70 | 83 |
| 71 | 82 |
| 72 | 77 |
| 73 | 88 |

As shown in Table 1, the compound of the present invention has a superior GPR119 agonist action.

Experimental Example 2

A hypoglycemic action of the compound of the present invention was examined in an oral glucose tolerance test (OGTT) using male Wistar fatty rats (WF rat, TAKEDA RABICS).

First, 22-week-old WF rats fasted overnight were divided into groups (6 per group), and blood samples were collected and used as plasma samples before drug administration (-60 min). Thereafter, 0.5% methylcellulose (control group) and a test compound was orally administered at 10 mg/kg. At 60 min after compound administration, each individual was loaded by oral administration of glucose at 1 g/kg, and the blood was drawn before glucose loading (0 min) and 10, 30, 60 and 120 min after loading. The plasma glucose concentration was measured using L type Waco Glu2 (Wako) and Hitachi automatic analyzer 7080 (Hitachi Instruments Service Co., Ltd.). The 0-120 min area under time curve ($AUC_{0-120min}$) and the decrease rate when the control group was 100% were calculated from the plasma glucose values measured. The results are shown in Table 2.

TABLE 2

| test compound (Example No.) | plasma glucose $AUC_{0-120\,min}$ (mg/dL × min) | blood glucose lowering rate (%) |
|---|---|---|
| control group | 32734.2 | — |
| 33 | 25073.3 | 23.4** |
| 35 | 25212.5 | 23.0** |
| 38 | 24612.5 | 24.8** |

**$p \leq 0.01$ (Dennett's multiple comparison test to control group)

As shown in Table 2, the compound of the present invention has a superior hypoglycemic action.

Formulation Example 1

Production of Capsule

| 1) compound of Example 1 | 30 mg |
|---|---|
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablets

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 30 g of 4) are kneaded with water, vacuum dried, and sieved. The sieved powder is mixed with 4) (14 g) and 5) (1 g), and the mixture is tableted by a tableting machine, whereby 1000 tablets containing 30 mg of the compound of Example 1 per tablet are obtained.

INDUSTRIAL APPLICABILITY

The compound of the present invention has a GPR119 agonist action, and is useful for the prophylaxis or treatment of diabetes, obesity and the like.

This application is based on patent application No. 61/202, 321 filed in USA, the contents of which are hereby incorporated in its entirety.

The invention claimed is:

1. A compound represented by the formula:

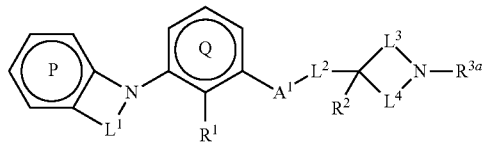

(Ia)

wherein ring P is a further substituted 6-membered aromatic ring;

ring Q is a further optionally substituted 6-membered aromatic ring;

$A^1$ is $CR^{4a}R^{4b}$ wherein $R^{4a}$ and $R^{4b}$ are each independently a hydrogen atom, an optionally substituted hydrocarbon group, an optionally substituted heterocyclic group or an optionally substituted hydroxy group, $NR^{4c}$ wherein $R^{4c}$ is a hydrogen atom or an optionally substituted hydrocarbon group, O, S, SO or $SO_2$;

$L^1$ is an optionally substituted $C_{1-5}$ alkylene group;

$L^2$ is a bond or an optionally substituted $C_{1-3}$ alkylene group;

$L^3$ and $L^4$ are each independently an optionally substituted $C_{1-3}$ alkylene group;

$R^1$ is (1) a hydrogen atom, a halogen atom, a cyano group, an optionally substituted hydrocarbon group, an optionally substituted heterocyclic group or an optionally substituted hydroxy group, or (2) when $A^1$ is $CR^{4a}R^{4b}$, $R^1$ and $R^{4a}$ and/or $R^{4b}$ in combination optionally form, together with the adjacent carbon atoms, an optionally substituted 4- to 8-membered ring, or (3) when $A^1$ is $Nr^{4c}$, $R^1$ and $R^{4c}$ in combination optionally form, together with the adjacent carbon atom and nitrogen atom, an optionally substituted 4- to 8-membered nitrogen-containing heterocycle;

$R^2$ is a hydrogen atom, a cyano group or an optionally substituted hydrocarbon group; and $R^{3a}$ is a group represented by the formula: $-CO-SR^{41}$ wherein $R^{41}$ is an optionally substituted hydrocarbon group or an optionally substituted heterocyclic group, or $R^{3a}$ is an optionally substituted 5- or 6-membered aromatic ring group, or a salt thereof.

2. The compound of claim 1, wherein $R^{3a}$ is an optionally substituted 5- or 6-membered aromatic ring group.

3. The compound of claim 1, wherein ring P is a benzene ring substituted by 1 to 3 substituents selected from (1) a halogen atom, (2) a $C_{1-6}$ alkylsulfonyl group, (3) a $C_{1-6}$ alkyl-carbonylamino group optionally substituted by 1 to 3 substituents selected from (i) a hydroxy group, and (ii) a $C_{1-6}$ alkoxy group, (4) a carbamoyl group optionally mono- or di-substituted by $C_{1-6}$ alkyl group(s) optionally substituted by hydroxy group(s), (5) a 5- or 6-membered non-aromatic heterocyclic group optionally substituted by 1 to 3 oxo groups, and (6) a 5- or 6-membered non-aromatic heterocyclylcarbonyl group.

4. The compound of claim 1, wherein ring Q is a pyrimidine ring.

5. The compound of claim 1, wherein $A^1$ is $NR^{4c}$ wherein $R^{4c}$ is a hydrogen atom or a $C_{1-6}$ alkyl group optionally substituted by 1 to 3 halogen atoms, or O.

6. The compound of claim 1, wherein $L^1$ is an ethylene group.

7. The compound of claim 1, wherein $L^3$ and $L^4$ are each independently an ethylene group.

8. The compound of claim 1, wherein $R^{3a}$ is
(1) a $C_{1-6}$ alkylthio-carbonyl group, or
(2) a 5- or 6-membered aromatic heterocyclic group optionally substituted by 1 to 3 substituents selected from
 (i) a halogen atom,
 (ii) a $C_{1-6}$ alkyl group,
 (iii) a $C_{1-6}$ alkoxy group, and
 (iv) a $C_{3-10}$ cycloalkyl group.

9. The compound of claim 1, wherein
ring P is a benzene ring substituted by 1 to 3 substituents selected from
(1) a halogen atom,
(2) a $C_{1-6}$ alkylsulfonyl group,
(3) a $C_{1-6}$ alkyl-carbonylamino group optionally substituted by 1 to 3 substituents selected from
 (i) a hydroxy group, and
 (ii) a $C_{1-6}$ alkoxy group,
(4) a carbamoyl group optionally mono- or di-substituted by $C_{1-6}$ alkyl group(s) optionally substituted by hydroxy group(s),
(5) a 5- or 6-membered non-aromatic heterocyclic group optionally substituted by 1 to 3 oxo groups, and
(6) a 5- or 6-membered non-aromatic heterocyclylcarbonyl group;

ring Q is a pyrimidine ring;

$A^1$ is $NR^{4c}$ wherein $R^{4c}$ is a hydrogen atom or a $C_{1-6}$ alkyl group optionally substituted by 1 to 3 halogen atoms, or O;

$L^1$ is an ethylene group;

$L^2$ is a bond;

$L^3$ and $L^4$ are each independently an ethylene group;

$R^1$ is a hydrogen atom;

$R^2$ is a hydrogen atom; and $R^{3a}$ is
(1) a $C_{1-6}$ alkylthio-carbonyl group, or
(2) a 5- or 6-membered aromatic heterocyclic group optionally substituted by 1 to 3 substituents selected from
 (i) a halogen atom,
 (ii) a $C_{1-6}$ alkyl group,
 (iii) a $C_{1-6}$ alkoxy group, and
 (iv) a $C_{3-10}$ cycloalkyl group.

10. 1-[6-({1-[3-(1-Methylethyl)-1,2,4-oxadiazol-5-yl]piperidin-4-yl}oxy)pyrimidin-4-yl]-5-(methylsulfonyl)-2,3-dihydro-1H-indole or a salt thereof.

11. S-(1-Methylethyl)4-[(6-{5-[(hydroxyacetyl)amino]-2,3-dihydro-1H-indol-1-yl}pyrimidin-4-yl)oxy]piperidine-1-carbothioate or a salt thereof.

12. 1-(6-{[1-(5-Ethylpyrimidin-2-yl)piperidin-4-yl]oxy}pyrimidin-4-yl)-5-(methylsulfonyl)-2,3-dihydro-1H-indole or a salt thereof.

13. A pharmaceutical composition comprising a compound of claim 1 or a salt thereof and a pharmacologically acceptable carrier.

14. A method for treatment of diabetes in a mammal, which comprises administering an effective amount of the compound of claim 1 or a salt thereof to the mammal.

* * * * *

UNITED STATES PATENT AND TRADEMARK OFFICE
CERTIFICATE OF CORRECTION

PATENT NO. : 8,410,089 B2
APPLICATION NO. : 13/201536
DATED : April 2, 2013
INVENTOR(S) : Kentaro Rikimaru Page 1 of 1

It is certified that error appears in the above-identified patent and that said Letters Patent is hereby corrected as shown below:

In the Claims:

Column 176, Claim 11, lines 24-26, please change "S-(1-Methylethyl)4-[(6-{5-[(hydroxyacetyl)amino]-2,3-dihydro-1H-indol-1-yl}pyrimidin-4-yl)oxy]piperidine-1-carbothioate" *to* -- S-(1-Methylethyl) 4-[(6-{5-[(hydroxyacetyl)amino]-2,3-dihydro-1H-indol-1-yl}pyrimidin-4-yl)oxy]piperidine-1-carbothioate --.

Signed and Sealed this
Thirteenth Day of August, 2013

Teresa Stanek Rea
*Acting Director of the United States Patent and Trademark Office*

SEQUENCE LISTING

```
<160> NUMBER OF SEQ ID NOS: 6

<210> SEQ ID NO 1
<211> LENGTH: 31
<212> TYPE: DNA
<213> ORGANISM: Artificial
<220> FEATURE:
<223> OTHER INFORMATION: primer 1

<400> SEQUENCE: 1
gcgtcgacat ggaatcatct ttctcatttg g                           31

<210> SEQ ID NO 2
<211> LENGTH: 29
<212> TYPE: DNA
<213> ORGANISM: Artificial
<220> FEATURE:
<223> OTHER INFORMATION: primer 2

<400> SEQUENCE: 2
gcgctagctt agccatcaaa ctctgagct                              29

<210> SEQ ID NO 3
<211> LENGTH: 23
<212> TYPE: DNA
<213> ORGANISM: Artificial
<220> FEATURE:
<223> OTHER INFORMATION: Zeocin-U (primer)
```

```
<400> SEQUENCE: 3
ggatccaggc aggcagaagt atg                                        23

<210> SEQ ID NO 4
<211> LENGTH: 29
<212> TYPE: DNA
<213> ORGANISM: Artificial
<220> FEATURE:
<223> OTHER INFORMATION: Zeocine-L (primer)

<400> SEQUENCE: 4
gtcgacagac atgataagat acattgatg                                  29

<210> SEQ ID NO 5
<211> LENGTH: 95
<212> TYPE: DNA
<213> ORGANISM: Artificial
<220> FEATURE:
<223> OTHER INFORMATION: CRE-Upper

<400> SEQUENCE: 5
cagcctgacg tcagagagcc tgacgtcaga gagcctgacg tcagagagcc tgacgtcaga 60
gtcgacagcg gagactctag agggtatata agctt                           95

<210> SEQ ID NO 6
<211> LENGTH: 99
<212> TYPE: DNA
<213> ORGANISM: Artificial
<220> FEATURE:
<223> OTHER INFORMATION: CRE-Lower

<400> SEQUENCE: 6
agcttatata ccctctagag tctccgctgt cgactctgac gtcaggctct ctgacgtcag 60
gctctctgac gtcaggctct ctgacgtcag gctggtacc                       99
```